United States Patent
Schlessinger et al.

(10) Patent No.: US 10,745,490 B2
(45) Date of Patent: Aug. 18, 2020

(54) ANTI-ERBB ANTIBODIES AND METHODS OF USE THEREOF

(71) Applicants: Celldex Therapeutics, Inc., Hampton, NJ (US); Yale University, New Haven, CT (US)

(72) Inventors: Joseph Schlessinger, Woodbridge, CT (US); Diego Alvarado, Madison, CT (US); Sangwon Lee, Branford, CT (US)

(73) Assignees: Celldex Therapeutics, Inc., Hampton, NJ (US); Yale University, New Haven, CT (US)

(*) Notice: Subject to any disclaimer, the term of this patent is extended or adjusted under 35 U.S.C. 154(b) by 457 days.

(21) Appl. No.: 15/302,342

(22) PCT Filed: Apr. 10, 2015

(86) PCT No.: PCT/US2015/025311
§ 371 (c)(1),
(2) Date: May 5, 2017

(87) PCT Pub. No.: WO2015/157634
PCT Pub. Date: Oct. 15, 2015

(65) Prior Publication Data
US 2017/0240648 A1    Aug. 24, 2017

Related U.S. Application Data

(60) Provisional application No. 61/978,783, filed on Apr. 11, 2014.

(51) Int. Cl.
C07K 16/32 (2006.01)
A61K 39/395 (2006.01)
G01N 33/74 (2006.01)
A61K 39/00 (2006.01)

(52) U.S. Cl.
CPC ........ *C07K 16/32* (2013.01); *A61K 39/39558* (2013.01); *G01N 33/74* (2013.01); *A61K 2039/505* (2013.01); *C07K 2299/00* (2013.01); *C07K 2317/30* (2013.01); *C07K 2317/31* (2013.01); *C07K 2317/34* (2013.01); *C07K 2317/53* (2013.01); *C07K 2317/55* (2013.01); *C07K 2317/56* (2013.01); *C07K 2317/565* (2013.01); *C07K 2317/76* (2013.01); *C07K 2317/92* (2013.01); *G01N 2333/82* (2013.01)

(58) Field of Classification Search
None
See application file for complete search history.

(56) References Cited

U.S. PATENT DOCUMENTS

| | | |
|---|---|---|
| 5,183,884 A | 2/1993 | Kraus et al. |
| 5,480,968 A | 1/1996 | Kraus et al. |
| 5,804,968 A | 9/1998 | Richard et al. |
| 5,820,859 A | 10/1998 | Kraus et al. |
| 5,916,755 A | 6/1999 | Kraus et al. |
| 5,968,511 A | 10/1999 | Akita et al. |
| 6,639,060 B1 | 10/2003 | Kraus et al. |
| 6,716,598 B2 | 4/2004 | Blank et al. |
| 6,870,034 B2 | 3/2005 | Breece et al. |
| 7,097,840 B2 | 8/2006 | Erickson et al. |
| 7,125,680 B2 | 10/2006 | Singer et al. |
| 7,247,301 B2 | 7/2007 | van de Winkel et al. |
| 7,285,649 B2 | 10/2007 | Akita et al. |
| 7,323,553 B2 | 1/2008 | Fahrner et al. |
| 7,332,580 B2 | 2/2008 | Adams et al. |
| 7,332,585 B2 | 2/2008 | Adams et al. |
| 7,354,584 B2 | 4/2008 | Reed et al. |
| 7,390,632 B2 | 6/2008 | Maihle et al. |
| 7,402,397 B2 | 7/2008 | Chan-Hui et al. |
| 7,485,704 B2 | 2/2009 | Fahrner et al. |
| 7,527,789 B2 | 5/2009 | Loibner et al. |
| 7,591,994 B2 | 9/2009 | Govindan et al. |
| 7,625,558 B2 | 12/2009 | Greene et al. |
| 7,662,374 B2 | 2/2010 | Greene et al. |
| 7,825,127 B2 | 2/2010 | Ohta et al. |
| 7,705,130 B2 | 4/2010 | Rothe et al. |
| 7,718,384 B2 | 5/2010 | Maihle et al. |
| 7,744,882 B2 | 6/2010 | Maihle et al. |
| 7,829,297 B2 | 11/2010 | Spector et al. |
| 7,846,440 B2 | 12/2010 | Schoeberl et al. |
| 7,919,098 B2 | 4/2011 | Zhou |
| 7,981,418 B2 | 7/2011 | Amler et al. |

(Continued)

FOREIGN PATENT DOCUMENTS

| | | |
|---|---|---|
| EP | 2067792 A2 | 6/2009 |
| JP | 2005504044 A | 2/2005 |

(Continued)

OTHER PUBLICATIONS

"A Phase 1 Dose Escalation Study of AV-203, an ERBB3 Inhibitory Antibody, in Subjects With Advanced Solid Tumors," ClinicalTrials. gov, accessed at http://www.clinicaltrials.gov/ct2/show/NCT01603979?term=AV-203&rank=1, accessed on Jul. 24, 2012, 4 pages.

"A Phase 1 Study to Evaluate the Safety and Pharmacokinetics of KTN3379 in Adult Subjects With Advanced Tumors," ClinicalTrials. gov, accessed at http://www.clinicaltrials.gov/ct2/show/study/NCT02014909?term=3379&rank=1, accessed on Oct. 7, 2014, 4 pages.

"Phase I Study of LJM716 in Combination With Trastuzumab in Patients With HER2 Overexpressing Metastatic Breast Cancer," ClinicalTrials.gov, accessed at http://clinicaltrials.gov/ct2/show/NCT01602406, accessed on Jul. 17, 2012, 4 pages.

(Continued)

*Primary Examiner* — Lei Yao
(74) *Attorney, Agent, or Firm* — Jones Day

(57) ABSTRACT

Provided herein are compositions, methods and uses involving antibodies that bind to ErbB, a receptor tyrosine kinase, and modulate the activity of ErbB. Also provided are uses and methods for treating disorders, such as cancer, by administering to subject an antibody that binds to ErbB.

12 Claims, 17 Drawing Sheets
Specification includes a Sequence Listing.

(56) References Cited

U.S. PATENT DOCUMENTS

| | | | |
|---|---|---|---|
| 8,124,085 B2 | 2/2012 | Nielsen et al. |
| 8,163,287 B2 | 4/2012 | Sliwkowski et al. |
| 8,333,964 B2 | 12/2012 | Agus et al. |
| 8,362,215 B2 | 1/2013 | Keyt et al. |
| 8,580,263 B2 | 11/2013 | Adams et al. |
| 8,592,152 B2 | 11/2013 | Mass et al. |
| 8,691,232 B2 | 4/2014 | Derynck et al. |
| 8,771,695 B2 | 7/2014 | Rothe et al. |
| 9,220,775 B2 | 12/2015 | Chowdhury et al. |
| 10,040,857 B2 | 8/2018 | Chowdhury et al. |
| 2003/0105057 A1 | 6/2003 | Fu et al. |
| 2004/0057950 A1 | 3/2004 | Waksal et al. |
| 2004/0063140 A1 | 4/2004 | Kraus et al. |
| 2004/0082510 A1 | 4/2004 | Ullrich et al. |
| 2004/0096436 A1 | 5/2004 | Carson et al. |
| 2004/0106161 A1 | 6/2004 | Bossenmaier et al. |
| 2004/0116330 A1 | 6/2004 | Naito et al. |
| 2004/0138160 A1 | 7/2004 | Naito et al. |
| 2004/0197332 A1 | 10/2004 | Ullrich et al. |
| 2004/0213791 A1 | 10/2004 | Bander et al. |
| 2004/0229293 A1 | 11/2004 | Chan Hui et al. |
| 2004/0229299 A1 | 11/2004 | Badal et al. |
| 2004/0229380 A1 | 11/2004 | Chan Hui et al. |
| 2004/0229494 A1 | 11/2004 | Chan Hui et al. |
| 2005/0101618 A1 | 5/2005 | Connell et al. |
| 2005/0147612 A1 | 7/2005 | Yayon et al. |
| 2006/0067947 A1 | 3/2006 | Yagita et al. |
| 2006/0148694 A1 | 7/2006 | Ullrich et al. |
| 2007/0009972 A1 | 1/2007 | Chao et al. |
| 2007/0059806 A1 | 3/2007 | Amon et al. |
| 2008/0138349 A1 | 6/2008 | Stavenhagen et al. |
| 2008/0153098 A1 | 6/2008 | Rimm et al. |
| 2008/0187948 A1 | 8/2008 | Chan-Hui et al. |
| 2008/0187966 A1 | 8/2008 | Simmons et al. |
| 2008/0206231 A1 | 8/2008 | Clinton et al. |
| 2008/0255027 A1 | 10/2008 | Moya et al. |
| 2009/0092617 A1 | 4/2009 | Bock et al. |
| 2009/0155259 A1 | 6/2009 | Derynck et al. |
| 2009/0214576 A1 | 8/2009 | Bacus et al. |
| 2009/0258005 A1 | 10/2009 | Gill et al. |
| 2009/0275633 A1 | 11/2009 | Esteller et al. |
| 2010/0004232 A1 | 1/2010 | Berdini et al. |
| 2010/0047829 A1 | 2/2010 | Rothe et al. |
| 2010/0056761 A1 | 3/2010 | Schoeberl et al. |
| 2010/0104586 A1 | 4/2010 | Tressler et al. |
| 2010/0196265 A1 | 8/2010 | Adams et al. |
| 2010/0255010 A1 | 10/2010 | Fuh et al. |
| 2010/0266584 A1 | 10/2010 | Schoeberl et al. |
| 2010/0310557 A1 | 12/2010 | Keyt et al. |
| 2011/0020327 A1 | 1/2011 | Moya et al. |
| 2011/0027296 A1 | 2/2011 | Navarro et al. |
| 2011/0033482 A1 | 2/2011 | Ullrich et al. |
| 2011/0039300 A1 | 2/2011 | Bayer et al. |
| 2011/0091473 A1 | 4/2011 | Golab et al. |
| 2011/0123523 A1 | 5/2011 | Schoeberl et al. |
| 2011/0171222 A1 | 7/2011 | Bossenmaier et al. |
| 2011/0229406 A1 | 9/2011 | Hettmann et al. |
| 2011/0229478 A1 | 9/2011 | Zhou et al. |
| 2011/0256154 A1 | 10/2011 | Vincent et al. |
| 2011/0280892 A1 | 11/2011 | Kinch et al. |
| 2012/0014957 A1 | 1/2012 | Ghayur et al. |
| 2012/0058122 A1 | 3/2012 | Rothe et al. |
| 2012/0107270 A1 | 5/2012 | Kaspar et al. |
| 2012/0107306 A1 | 5/2012 | Elis et al. |
| 2012/0156130 A1 | 6/2012 | Hettmann et al. |
| 2012/0201817 A1 | 8/2012 | Waksal |
| 2012/0225870 A1 | 9/2012 | Janne et al. |
| 2012/0328623 A1 | 12/2012 | Takahashi |
| 2013/0034548 A1 | 2/2013 | Moyo et al. |
| 2013/0039909 A1 | 2/2013 | Amler et al. |
| 2013/0084297 A1 | 4/2013 | Daly et al. |
| 2013/0156779 A1 | 6/2013 | Clarke et al. |
| 2013/0251703 A1 | 9/2013 | Elis et al. |
| 2016/0159913 A1 | 6/2016 | Chowdhury et al. |
| 2016/0237162 A1 | 8/2016 | Chowdhury et al. |

| | | | |
|---|---|---|---|
| 2017/0190788 A1 | 7/2017 | Lavallee et al. |
| 2018/0362443 A1 | 12/2018 | Lavallee et al. |
| 2019/0040143 A1 | 2/2019 | Chowdhury et al. |

FOREIGN PATENT DOCUMENTS

| | | | | |
|---|---|---|---|---|
| WO | WO 97/35885 | 10/1997 | | |
| WO | WO 00/78347 | 12/2000 | | |
| WO | WO 2007/077028 | 7/2007 | | |
| WO | WO 2008/081331 | 7/2008 | | |
| WO | WO 2008/100624 | 8/2008 | | |
| WO | WO 2008/119353 | 10/2008 | | |
| WO | WO 2009/052830 | 4/2009 | | |
| WO | WO 2009/082443 | 7/2009 | | |
| WO | WO 2009/126920 | 10/2009 | | |
| WO | WO 2009/157919 | 12/2009 | | |
| WO | WO 2010/054051 | 5/2010 | | |
| WO | WO 2010/097186 | 9/2010 | | |
| WO | WO 2010/108127 | 9/2010 | | |
| WO | WO 2010/127181 | 11/2010 | | |
| WO | WO 2010/129304 A2 | 11/2010 | | |
| WO | WO 2011/044311 | 4/2011 | | |
| WO | WO 2011/047180 | 4/2011 | | |
| WO | WO 2011/060206 | 5/2011 | | |
| WO | WO 2011/076683 A1 | 6/2011 | | |
| WO | WO 2011/136911 | 11/2011 | | |
| WO | WO 2011/153383 A1 | 12/2011 | | |
| WO | WO 2012/019024 | 2/2012 | | |
| WO | WO 2012/022814 | 2/2012 | | |
| WO | WO 2012/052230 A1 | 4/2012 | | |
| WO | WO 2012/059858 | 5/2012 | | |
| WO | WO 2012/125864 A2 | 9/2012 | | |
| WO | WO 2013/048883 A2 | 4/2013 | | |
| WO | WO 2013/071058 | 5/2013 | | |
| WO | WO2013/078191 | * | 5/2013 | |
| WO | WO 2013/078191 | 5/2013 | | |
| WO | WO-2013078191 A1 | * | 5/2013 | ....... A61K 39/39558 |
| WO | WO 2013/084147 | 6/2013 | | |
| WO | WO 2015/157634 | 10/2015 | | |

OTHER PUBLICATIONS

Addo-Yobo et al., 2006, "Paired overexpression of ErbB3 and Sox10 in pilocytic astrocytoma," J. Neuropathol. Exp. Neurol. 65:769-775.

Alimandi et al., 1995, "Cooperative signaling of ErbB3 and ErbB2 in neoplastic transformation and human mammary carcinomas," Oncogene 10:1813-1821.

Alvarado et al., 2014, "Structural basis for inhibition of ligand-dependent and -independent ErbB3 activation by KTN3379," Eur. J. Cancer 50(Suppl. 6):130, Poster 407. Board p. 187. Abstract. 26th EORTC-NCI-AACR Symposium on Molecular Targets and Cancer Therapeutics, Nov. 20, 2014.

Arteaga et al., 2012, "Treatment of HER2-positive breast cancer: current status and future perspectives," Nat. Rev. Clin. Oncol. 9: 16-32.

Aurisicchio et al., 2011, "Novel Anti-ErbB3 monoclonal antibodies show therapeutic efficacy in xenografted and spontaneous mouse tumors," J. Cell. Physiol. 227:3381-3388.

Baselga et al., 2009, "Novel anticancer targets: revisiting ERBB2 and discovering ERBB3," Nat. Rev. Cancer 9:463-475.

Beckman et al., 2007, "Antibody Constructs in Cancer Therapy Protein Engineering Strategies to Improve Exposure in Solid Tumors," Cancer 109:170-179.

Burgess et al., 2003, "An Open-and-Shut Case? Recent Insights into the Activation of EGF/ErbB Receptors," Molecular Cell 12:541-552.

Campbell et al., 2010, "HER3 Comes of Age: New Insights into its Functions and Role in Signaling, Tumor Biology, and Cancer Therapy," Clin. Cancer Res. 16(5):1373-1383.

Carrasco et al., 2013, "MEDI3379, a human monoclonal antibody against HER3, suppresses HER3 activity and cell proliferation in both ligand-dependent and independent cancers," AACR Annual Meeting 2013 Apr. 6-10, 2013, Abstract No. 558. Poster.

(56) References Cited

OTHER PUBLICATIONS

Carrasco et al., 2013, "MEDI3379, a human monoclonal antibody against HER3, suppresses HER3 activity and cell proliferation in both ligand-dependent and independent cancers," AACR Annual Meeting 2013, Abstract No. 558, Presentation Time Sunday Apr. 7, 2013, 1:00 PM-5:00 PM, Poster Section 24, Poster Board No. 30. Abstract.
Cespedes et al., 2006, "Mouse models in oncogenesis and cancer therapy," Clin. Transl. Oncol. 8(5):318-329.
Chakraborty et al., 2007, "Identification of genes associated with tumorigenesis of retinoblastoma by microarray analysis," Genomics 90:344-353.
Cho et al., 2002, "Structure of the Extracellular Region of HER3 Reveals an Interdomain Tether," Science 297:1330-1333.
Defazio et al., 2000, "Expression of c-erbB receptors, heregulin and oestrogen receptor in human breast cell lines," Cancer 87:487-498.
Dennis, 2006, "Off by a whisker," Nature 442:739-741.
Engelman et al., 2005, "ErbB-3 mediates phosphoinositide 3-kinase activity in gefitinib-sensitive non-small cell lung cancer cell lines," Proc. Natl. Acad. Sci. USA 102:3788-3793.
Friess et al., 1995, "Enhanced erbB-3 expression in human pancreatic cancer correlates with tumor progression," Clin. Cancer Res. 1:1413-1420.
Fujimori et al., 1990, "A Modeling Analysis of Monoclonal Antibody Percolation Through Tumors: A Binding-Site Barrier," J. Nuc. Med. 31:1191-1198.
Garner et al., 2011, "Targeting cancer with a novel anti-HER3 antibody: An anti-HER3 antibody that stabilizes the inactive conformation inhibits both HER2 and ligand driven tumor growth," San Antonio Breast Cancer Symposium Dec. 6-10, 2011, S2-5. Presentation, Daily Slide Viewer.
Garner et al., 2011, "Targeting cancer with a novel anti-HER3 antibody: An anti-HER3 antibody that stabilizes the inactive conformation inhibits both HER2 and ligand driven tumor growth," San Antonio Breast Cancer Symposium Dec. 6-10, 2011, S2-5. Presentation, Photographs.
Garner et al., 2012, "LJM716: an anti-HER3 antibody that inhibits both HER2 and NRG driven tumor growth by trapping HER3 in the inactive conformation.," Proceedings of the 103rd Annual Meeting of the American Association for Cancer Research; Mar. 31-Apr. 4, 2012; Abstract nr 2733.
Gregory et al., 2005, "Heregulin-induced activation of HER2 and HER3 increases androgen receptor transactivation and CWR-R1 human recurrent prostate cancer cell growth," Clin. Cancer Res. 11:1704-1712.
Holbro et al., 2003, "The ErbB2/ErbB3 heterodimer functions as an oncogenic unit: ErbB2 requires ErbB3 to drive breast tumor cell proliferation," Proc. Natl. Acad. Sci. USA 100:8933-8938.
International Search Report, dated Apr. 15, 2013, for International Application No. PCT/US2012/066038, filed Nov. 20, 2012. 5 pages.
Jiang et al., 2012, "Advances in Targeting HER3 as an Anticancer Therapy," Chemotherapy Research and Practice 2012:817304, 9 pages.
Junttila et al., 2009, "Ligand-independent HER2/HER3/PI3K complex is disrupted by trastuzumab and is effectively inhibited by the PI3K inhibitor GDC-0941," Cancer Cell 15(5):429-440.
Kim et al., 1998, "Signal transduction by epidermal growth factor and heregulin via the kinase-deficient ErbB3 protein," Biochem J. 334:189-195.
Kraus et al., 1989, "Isolation and characterization of ERBB3, a third member of the ERBB/epidermal growth factor receptor family: evidence for overexpression in a subset of human mammary tumors," Proc. Natl. Acad. Sci. USA 86:9193-9197.
Kraus et al., 1993, "Demonstration of ligand-dependent signaling by the erbB-3 tyrosine kinase and its constitutive activation in human breast tumor cells," Proc. Natl. Acad. Sci. USA 90:2900-2904.
Ligon et al., 2015, "KTN3379 overcomes ErbB3 mediated resistance of BRaf/MEK inhibition in Braf mutated melanoma," AACR-NCI-EORTC International Conference. Abstract published Oct. 26, 2015.
Lorusso et al., 2013, "Phase I Study of U3-1287, a Fully Human Anti-HER3 Monoclonal Antibody, in Patients With Advanced Solid Tumors," Clin. Can. Res. 19(11):3078-3087. First published online Apr. 16, 2013.
Lorusso et al., 2014, "A phase 1 study of KTN3379, a human anti-ErbB3 monoclonal antibody in patients with advanced cancers," Eur. J. Cancer 50(Suppl. 6):71, Oral Presentation 210. Abstract. 26th EORTC-NCI-AACR Symposium on Molecular Targets and Cancer Therapeutics, Nov. 20, 2014.
Mills et al., 2010, "The Rebirth of a Phoenix: Ovarian Cancers are Addicted to ErbB3," Cancer Cell 17:217-218.
Naidu et al., 1998, "Expression of c-erbB3 protein in primary breast carcinomas," Br. J. Cancer 78:1385-1390.
Quinn et al., 1994, "c-erbB-3 protein expression in human breast cancer: comparison with other tumour variables and survival," Histopathology 25:247-252.
Rajkumar et al., 1993, "Expression of the c-erbB-3 protein in gastrointestinal tract tumours determined by monoclonal antibody RTJ1," J. Pathol. 170:271-278.
Roepstorff et al., 2008, "Endocytic downregulation of ErbB receptors: mechanisms and relevance in cancer," Histochem. Cell Biol. 129:563-578.
Rudnick et al., 2009, "Affinity and Avidity in Antibody-Based Tumor Targeting," Can. Biotherp. & Radiopharm. 24:155-162.
Sala et al., 2012, "An ErbB-3 antibody, MP-RM-1, inhibits tumor growth by blocking ligand-dependent and independent activation of ErbB-3/Akt signaling," Oncogene 31:1275-1286.
Sanidas et al., 1993, "Expression of the c-erbB-3 gene product in gastric cancer," Int. J. Cancer 54:935-940.
Schaefer et al., 2004, "Expression profiling of t(12;22) positive clear cell sarcoma of soft tissue cell lines reveals characteristic up-regulation of potential new marker genes including ERBB3," Cancer Res. 64:3395-3405.
Schaefer et al., 2006, "Constitutive activation of neuregulin/ERBB3 signaling pathway in clear cell sarcoma of soft tissue," Neoplasia 8:612-622.
Schaefer et al., 2011, "A Two-in-One Antibody against HER3 and EGFR Has Superior Inhibitory Activity Compared with Monospecific Antibodies," Cancer Cell 20:472-486.
Schlessinger, 2002, "Ligand-induced, receptor-mediated dimerization and activation of EGF receptor," Cell 110:669-672.
Schoeberl et al., 2009, "Therapeutically Targeting ErbB3: A Key Node in Ligand-Induced Activation of the ErbB Receptor—PI3K Axis," Science Signaling 2(77):ra31, 14 pages.
Schoeberl et al., 2010, "An ErbB3 Antibody, MM-121, Is Active in Cancers with Ligand-Dependent Activation," Cancer Res. 70(6):2485-2494.
Setiady et al., 2011, "huHER3-8, a novel humanized anti-HER3 antibody that inhibits exogeneous ligand-independent proliferation of tumor cells," AACR 102nd Annual Meeting, Abstract No. 4564, Presentation Time Tuesday, Apr. 5, 2011, 1:00 PM-5:00 PM, Poster Section 31, Poster Board No. 6. Abstract.
Setiady et al., 2011, "huHER3-8, a novel humanized anti-HER3 antibody that inhibits exogeneous ligand-independent proliferation of tumor cells," AACR 102nd Annual Meeting, Apr. 2-6, 2011, Abstract No. 4564. Poster.
Shintani et al., 1995, "Prognostic significance of ERBB3 overexpression in oral squamous cell carcinoma," Cancer Lett. 95:79-83.
Singer et al., 2001, "Identification of a Heregulin Binding Site in HER3 Extracellular Domain," J. Biol. Chem. 274:44266-44274.
Sithanandam et al., 2008, "The ERBB3 receptor in cancer and cancer gene therapy," Cancer Gene Therapy 15:413-448.
Sliwkowski et al., 1994, "Coexpression of erbB2 and erbB3 proteins reconstitutes a high affinity receptor for heregulin," J. Biol. Chem. 269:14661-14665.
Steiner et al., 2012, "MEDI3379, an antibody against HER3, is active in heregulin or HER2-driven human tumor models," 24th EORTC-NCI-AACR Symposium on Molecular Targets and Cancer Therapeutics, Nov. 6-9, 2012, Abstract No. 331. Poster.

(56) References Cited

OTHER PUBLICATIONS

Steiner et al., 2012, "MEDI3379, an Antibody Against HER3, is Active in Heregulin or HER2-driven Human Tumor Models," Eur. J. Cancer 48(Suppl. 6):101, Poster 331. Abstract.
Steiner et al., 2013, "Combined targeting of HER2 and HER3 inhibits tumor growth in both trastuzumab-sensitive and trastuzumab-resistant breast cancer models," AACR-NCI-EORTC International Conference on Molecular Targets and Cancer Therapeutics, Abstract A112, Presentation Time Sunday Oct. 20, 2013, 12:30 PM-3:00 PM. Abstract.
Steiner et al., 2013, "Combined targeting of HER2 and HER3 inhibits tumor growth in both trastuzumab-sensitive and trastuzumab-resistant breast cancer models," AACR-NCI-EORTC International Conference on Molecular Targets and Cancer Therapeutics, Oct. 19-23, 2013. Poster.
Talmadge et al., 2007, "Murine Models to Evaluate Novel and Conventional Therapeutic Strategies for Cancer," Am. J. Pathol 170(3):793-804.
Tanner et al., 2006, "ErbB-3 predicts survival in ovarian cancer," J. Clin. Oncol. 24:4317-4323.
Thurber et al., 2008, "Antibody tumor penetration: Transport opposed by systemic and antigen-mediated clearance," Adv. Drug Deliv. Rev. 60:1421-1434.
Turke et al., 2012, "MEK inhibition leads to PI3K/AKT activation by relieving a negative feedback on ERBB receptors," Cancer Res. 72(13):3228-3237.
Van Der Horst et al., 2005, "Anti-HER-3 Mabs Inhibit HER-3-Mediated Signaling in Breast Cancer Cell Lines Resistant to Anti-HER-2 Antibodies," Int. J. Cancer 115:519-527.
Vincent et al., 2011, "Functional characterization of a diverse set of ERBB3 inhibitory antibodies," AACR 102nd Annual Meeting, Abstract No. 628, Presentation Time Sunday Apr. 3, 2011, 1:00 PM-5:00 PM. Poster Section 27, Poster Board No. 2. Abstract.
Voskoglou-Nomikos, 2003, "Clinical Predictive Value of the in Vitro Cell Line, Human Xenograft, and Mouse Allograft Preclinical Cancer Models," Clin. Can. Res. 9:4227-4239.
Xiao et al., 2012, "MEDI3379, an antibody against HER3, is active in HER2-driven human breast tumor models," 35th annual San Antonio Breast Cancer Symposium (SABCS), Dec. 4-8, 2012. Poster.
Xiao et al., 2012, "MEDI3379, an antibody against HER3, is active in HER2-driven human breast tumor models," Cancer Res. 72(24 Suppl.):380s. CTRC-AACR San Antonio Breast Cancer Symposium, P4-07-05. Abstract.
Xue et al., 2006, "ErbB3-dependent motility and intravasation in breast cancer metastasis," Canc. Res. 66:1418-1426.
Yarden et al., 2001, "Untangling the ErbB signalling network," Nat. Rev. Mol. Cell. Biol. 2:127-137.
Aurisicchio et al., 2012, "The promise of anti-ErbB3 monoclonals as new cancer therapeutics," Oncotarget 3:744-758.
Baro et al., 2016, "Inhibition of heregulin-mediated ErbB3 signaling as a radiosensitization therapy for head and neck cancers," AACR Annual Meeting, Apr. 16-20, 2016, New Orleans, LA, meeting abstract published online on Mar. 16, 2016.
Baro et al., 2016, "Inhibition of heregulin-mediated ErbB3 signaling as a radiosensitization therapy for head and neck cancers," AACR Annual Meeting, Apr. 16-20, 2016, New Orleans, LA, poster presented on Apr. 19, 2016.
Dawson et al., 2007, "Ligand-induced structural transitions in ErbB receptor extracellular domains," Structure 15:942-954.
Falchook et al., 2016, "Safety, pharmacokinetics, pharmacodynamics, and antitumor activity in a Phase 1b study evaluating anti-ErbB3 antibody KTN3379 in adults with advanced tumors alone and with targeted therapies," ASCO Annual Meeting, Jun. 3-7, 2016, Chicago, IL, slides presented on Jun. 6, 2016.
Sala et al., 2013, "EV20, a novel anti-ErbB-3 humanized antibody, promotes ErbB-3 down-regulation and inhibits tumor growth in vivo," Transl. Oncolv. 6: 676-684.
Schlessinger, 2010, "Cell signaling by receptor tyrosine kinases," Cell 13;103:211-225.
Jaiswal et al., 2013, "Oncogenic ERBB3 mutations in human cancers," Cancer Cell 23:603-617.
Khan et al., 2016, "Dual targeting of HER3 and PIK3CA has potent antitumor effects in preclinical models of HNSCC," AACR Annual Meeting, Apr. 16-20, 2016, New Orleans, LA, meeting abstract published online on Mar. 16, 2016.
Khan et al., 2016, "Dual targeting of HER3 and PIK3CA has potent antitumor effects in preclinical models of HNSCC," AACR Annual Meeting, Apr. 16-20, 2016, New Orleans, LA, poster presented on Apr. 19, 2016.
Xiao et al., 2016, "A potent HER3 monoclonal antibody that blocks both ligand-dependent and -independent activities: differential impacts of PTEN status on tumor response," Mol. Cancer. Ther. 15:689-701.
Huang et al., 2010, "Recombinant immunotherapeutics: current state and perspectives regarding the feasibility and market," Appl. Microbiol. Biotechnol. 87(2):401-410.
Kugel III et al., 2014, "Function-blocking ERBB3 antibody inhibits the adaptive response to RAF inhibitor," Cancer Res. 75(15):4122-4132, published online on Jul. 14, 2014.
Fattore et al., 2015, "ErbB3 plays a key role in the early phase of establishment of resistance to BRAF and/or MEK inhibitors," J. Transl. Med. 13(Suppl 1):K3, published online on Jan. 15, 2015.
Oshima et al., 2012, "Autocrine epidermal growth factor receptor ligand production and cetuximab response in head and neck squamous cell carcinoma cell lines," J. Cancer Res. Clin. Oncol. 138:491-499, published online on Dec. 23, 2011.
Sun et al., 2014, "Reversible and adaptive resistance to BRAF(V600E) inhibition in melanoma," Nature 508(7494):118-122, published online on Mar. 26, 2014.
Lazrek et al., Mar. 2013, "Anti-HER3 domain 1 and 3 antibodies reduce tumor growth by hindering HER2/HER3 dimerization and AKT-induced MDM2, XIAP, and FoxO1 phosphorylation," Neoplasia 15(3):335-347.
Hsieh et al., Aug. 2007, "Targeting HER proteins in cancer therapy and the role of the non-target HER3," British Journal of Cancer 97(4):453-457, published online in Jul. 2007.
Baxevanis et al., Apr. 2008, "Antibody-based cancer therapy," Expert Opinion on Drug Discovery 3(4):441-452, published online in Mar. 2008.
Fundamental Immunology, 3rd Edition, William E. Paul, ed., pp. 292-295, Raven Press, New York, United States (1993).
Bendig, 1995, "Humanization of rodent monoclonal antibodies by CDR grafting," Methods: A Companion to Methods in Enzymology 8(2):83-93.
Portolano et al., Feb. 1993, "Lack of promiscuity in autoantigen-specific H and L chain combinations as revealed by human H and L chain 'roulette' ," The Journal of Immunology 150(3):880-887.
Rudikoff et al., Mar. 1982, "Single amino acid substitution altering antigen-binding specificity," Proceedings of the National Academy of Sciences USA 79(6):1979-1983.
Panka et al., May 1988, "Variable region framework differences result in decreased or increased affinity of variant anti-digoxin antibodies," Proceedings of the National Academy of Sciences USA 85(9):3080-2084.
MacCallum et al., Oct. 1996, "Antibody-antigen interactions: contact analysis and binding site topography," Journal of Molecular Biology 262(5):732-745.
De Pascalis et al., Sep. 2002, "Grafting of 'abbreviated' complementarity-determining regions containing specificity-determining residues essential for ligand contact to engineer a less immunogenic humanized monoclonal antibody," The Journal of Immunology 169(6):3076-3084.
Vajdos et al., Jul. 2002, "Comprehensive functional maps of the antigen-binding site of an anti-ErbB2 antibody obtained with shotgun scanning mutagenesis," Journal of Molecular Biology 320(2):415-428.
Klimka et al., Jul. 2000, "Human anti-CD30 recombinant antibodies by guided phage antibody selection using cell panning," British Journal of Cancer 83(2):252-260.
Beiboer et al., Feb. 2000, "Guided selection of a pan carcinoma specific antibody reveals similar binding characteristics yet structural divergence between the original murine antibody and its human equivalent," Journal of Molecular Biology 296(3):833-849.

(56) References Cited

OTHER PUBLICATIONS

Harris et al., Nov. 1993, "Assessing genetic heterogeneity in production cell lines: detection by peptide mapping of a low level Tyr to Gln sequence variant in a recombinant antibody," Biotechnology 1993 11(11):1293-1297.
Fattore et al., Jul. 2013, "Activation of an early feedback survival loop involving phospho-ErbB3 is a general response of melanoma cells to RAF/MEK inhibition and is abrogated by anti-ErbB3 antibodies," J. Transl. Med. 11:180.
Alvarado et al., Aug. 2015, "Association of ErbB/HER Biomarkers with Antitumor Activity of the anti-ErbB3/HER3 Monoclonal Antibody KTN3379 in SCCHN", Cancer Research, 75(15 Supplement): 1558.
International Search Report, dated Sep. 16, 2015, for International Application No. PCT/US2015/025311, filed Apr. 10, 2015, 4 pages.
Written Opinion of the International Searching Authority, dated Sep. 16, 2015, for International Application No. PCT/US2015/025311, filed Apr. 10, 2015, 6 pages.

* cited by examiner

A

B

```
ERBB3    272  PHNFV-VDQTSCVRACPPDKMEVDKNGLKMCEPCGGLCPKACEGTGSGSR--FQTVDSSN  328
EGFR     272  PRNYVVTDHGSCVRACGADSYEMEEDGVRKCKKCEGPCRKVCNGIGIGEFKDSLSINATN  331
ERBB4    269  PHNFV-VDSSSCVRACPSSKMEVEENGIKMCKPCTDICPKACDGIGTGSLMSAQTVDSSN  327

ERBB3    329  IDGFVNCTKILGNLDFLITGLNGDPWHKIPALDPEKLNVFRTVREITGYLNIQSWPPHMH  388
EGFR     332  IKHFKNCTSISGDLHILPVAFRGDSFTHTPPLDPQELDILKTVKEITGFLLIQAWPENRT  391
ERBB4    328  IDKFINCTKINGNLIFLVTGIHGDPYNAIEAIDPEKLNVFRTVREITGFLNIQSWPPNMT  387

ERBB3    389  NFSVFSNLTTIGGRSLYNRGFSLLIMKNLNVTSLGFRSLKEISAGRIYISANRQLCYHHS  448
EGFR     392  DLHAFENLEIIRGRTKQHGQFSLA-VVSLNITSLGLRSLKEISDGDVIISGNKNLCYANT  450
ERBB4    388  DFSVFSNLVTIGGRVLYS-GLSLLILKQQGITSLQFQSLKEISAGNIYITDNSNLCYYHT  446

ERBB3    449  LNWTKVLRGPTEERLDIK
EGFR     451  INWKKLFGTSGQKTKIIS
ERBB4    447  INWTTLFSTINQ-RIVIR
```

Fig. 14

```
   1  LEEKKVCQGT SNKLTQLGTF EDHFLSLQRM FNNCEVVLGN LEITYVQRNY DLSFLKTIQE
  61  VAGYVLIALN TVERIPLENL QIIRGNMYYE NSYALAVLSN YDANKTGLKE LPMRNLQEIL
 121  HGAVRFSNNP ALCNVESIQW RDIVSSDFLS NMSMDFQNHL GSCQKCDPSC PNGSCWGAGE
 181  ENCQKLTKII CAQQCSGRCR GKSPSDCCHN QCAAGCTGPR ESDCLVCRKF RDEATCKDTC
 241  PPLMLYNPTT YQMDVNPEGK YSFGATCVKK CPRNYVVTDH GSCVRACGAD SYEMEEDGVR
 301  KCKKCEGPCR KVCNGIGIGE FKDSLSINAT NIKHFKNCTS ISGDLHILPV AFRGDSFTHT
 361  PPLDPQELDI LKTVKEITGF LLIQAWPENR TDLHAFENLE IIRGRTKQHG QFSLAVVSLN
 421  ITSLGLRSLK EISDGDVIIS GNKNLCYANT INWKKLFGTS GQKTKIISNR GENSCKATGQ
 481  VCHALCSPEG CWGPEPRDCV SCRNVSRGRE CVDKCNLLEG EPREFVENSE CIQCHPECLP
 541  QAMNITCTGR GPDNCIQCAH YIDGPHCVKT CPAGVMGENN TLVWKYADAG HVCHLCHPNC
 601  TYGCTGPGLE GCPTNGPKIP SIATGMVGAL LLLLVVALGI GLFMRRRHIV RKRTLRRLLQ
 661  ERELVEPLTP SGEAPNQALL RILKETEFKK IKVLGSGAFG TVYKGLWIPE GEKVKIPVAI
 721  KELREATSPK ANKEILDEAY VMASVDNPHV CRLLGICLTS TVQLITQLMP FGCLLDYVRE
 781  HKDNIGSQYL LNWCVQIAKG MNYLEDRRLV HRDLAARNVL VKTPQHVKIT DFGLAKLLGA
 841  EEKEYHAEGG KVPIKWMALE SILHRIYTHQ SDVWSYGVTV WELMTFGSKP YDGIPASEIS
 901  SILEKGERLP QPPICTIDVY MIMVKCWMID ADSRPKFREL IIEFSKMARD PQRYLVIQGD
 961  ERMHLPSPTD SNFYRALMDE EDMDDVVDAD EYLIPQQGFF SSPSTSRTPL LSSLSATSNN
1021  STVACIDRNG LQSCPIKEDS FLQRYSSDPT GALTEDSIDD TFLPVPEYIN QSVPKRPAGS
1081  VQNPVYHNQP LNPAPSRDPH YQDPHSTAVG NPEYLNTVQP TCVNSTFDSP AHWAQKGSHQ
1141  ISLDNPDYQQ DFFPKEAKPN GIFKGSTAEN AEYLRVAPQS SEFIGA
```

Fig. 15

```
   1  SEVGNSQAVC  PGTLNGLSVT  GDAENQYQTL  YKLYERCEVV  MGNLEIVLTG  HNADLSFLQW
  61  IREVTGYVLV  AMNEFSTLPL  PNLRVVRGTQ  VYDGKFAIFV  MLNYNTNSSH  ALRQLRLTQL
 121  TEILSGGVYI  EKNDKLCHMD  TIDWRDIVRD  RDAEIVVKDN  GRSCPPCHEV  CKGRCWGPGS
 181  EDCQTLTKTI  CAPQCNGHCF  GPNPNQCCHD  ECAGGCSGPQ  DTDCFACRHF  NDSGACVPRC
 241  PQPLVYNKLT  FQLEPNPHTK  YQYGGVCVAS  CPHNFVVDQT  SCVRACPPDK  MEVDKNGLKM
 301  CEPCGGLCPK  ACEGTGSGSR  FQTVDSSNID  GFVNCTKILG  NLDFLITGLN  GDPWHKIPAL
 361  DPEKLNVFRT  VREITGYLNI  QSWPPHMHNF  SVFSNLTTIG  GRSLYNRGFS  LLIMKNLNVT
 421  SLGFRSLKEI  SAGRIYISAN  RQLCYHHSLN  WTKVLRGPTE  ERLDIKHNRP  RRDCVAEGKV
 481  CDPLCSSGGC  WGPGPGQCLS  CRNYSRGGVC  VTHCNFLNGE  PREFAHEAEC  FSCHPECQPM
 541  EGTATCNGSG  SDTCAQCAHF  RDGPHCVSSC  PHGVLGAKGP  IYKYPDVQNE  CRPCHENCTQ
 601  GCKGPELQDC  LGQTLVLIGK  THLTMALTVI  AGLVVIFMML  GGTFLYWRGR  RIQNKRAMRR
 661  YLERGESIEP  LDPSEKANKV  LARIFKETEL  RKLKVLGSGV  FGTVHKGVWI  PEGESIKIPV
 721  CIKVIEDKSG  RQSFQAVTDH  MLAIGSLDHA  HIVRLLGLCP  GSSLQLVTQY  LPLGSLLDHV
 781  RQHRGALGPQ  LLLNWGVQIA  KGMYYLEEHG  MVHRNLAARN  VLLKSPSQVQ  VADFGVADLL
 841  PPDDKQLLYS  EAKTPIKWMA  LESIHFGKYT  HQSDVWSYGV  TVWELMTFGA  EPYAGLRLAE
 901  VPDLLEKGER  LAQPQICTID  VYMVMVKCWM  IDENIRPTFK  ELANEFTRMA  RDPPRYLVIK
 961  RESGPGIAPG  PEPHGLTNKK  LEEVELEPEL  DLDLDLEAEE  DNLATTTLGS  ALSLPVGTLN
1021  RPRGSQSLLS  PSSGYMPMNQ  GNLGESCQES  AVSGSSERCP  RPVSLHPMPR  GCLASESSEG
1081  HVTGSEAELQ  EKVSMCRSRS  RSRSPRPRGD  SAYHSQRHSL  LTPVTPLSPP  GLEEEDVNGY
1141  VMPDTHLKGT  PSSREGTLSS  VGLSSVLGTE  EEDEDEEYEY  MNRRRRHSPP  HPPRPSSLEE
1201  LGYEYMDVGS  DLSASLGSTQ  SCPLHPVPIM  PTAGTTPDED  YEYMNRQRDG  GGPGGDYAAM
1261  GACPASEQGY  EEMRAFQGPG  HQAPHVHYAR  LKTLRSLEAT  DSAFDNPDYW  HSRLFPKANA
1321  QRT
```

Fig. 16

```
   1   QSVCAGTENK LSSLSDLEQQ YRALRKYYEN CEVVMGNLEI TSIEHNRDLS FLRSVREVTG
  61   YVLVALNQFR YLPLENLRII RGTKLYEDRY ALAIFLNYRK DGNFGLQELG LKNLTEILNG
 121   GVYVDQNKFL CYADTIHWQD IVRNPWPSNL TLVSTNGSSG CGRCHKSCTG RCWGPTENHC
 181   QTLTRTVCAE QCDGRCYGPY VSDCCHRECA GGCSGPKDTD CFACMNFNDS GACVTQCPQT
 241   FVYNPTTFQL EHNFNAKYTY GAFCVKKCPH NFVVDSSSCV RACPSSKMEV EENGIKMCKP
 301   CTDICPKACD GIGTGSLMSA QTVDSSNIDK FINCTKINGN LIFLVTGIHG DPYNAIEAID
 361   PEKLNVFRTV REITGFLNIQ SWPPNMTDFS VFSNLVTIGG RVLYSGLSLL ILKQQGITSL
 421   QFQSLKEISA GNIYITDNSN LCYYHTINWT TLFSTINQRI VIRDNRKAEN CTAEGMVCNH
 481   LCSSDGCWGP GPDQCLSCRR FSRGRICIES CNLYDGEFRE FENGSICVEC DPQCEKMEDG
 541   LLTCHGPGPD NCTKCSHFKD GPNCVEKCPD GLQGANSFIF KYADPDRECH PCHPNCTQGC
 601   NGPTSHDCIY YPWTGHSTLP QHARTPLIAA GVIGGLFILV IVGLTFAVYV RRKSIKKKRA
 661   LRRFLETELV EPLTPSGTAP NQAQLRILKE TELKRVKVLG SGAFGTVYKG IWVPEGETVK
 721   IPVAIKILNE TTGPKANVEF MDEALIMASM DHPHLVRLLG VCLSPTIQLV TQLMPHGCLL
 781   EYVHEHKDNI GSQLLLNWCV QIAKGMMYLE ERRLVHRDLA ARNVLVKSPN HVKITDFGLA
 841   RLLEGDEKEY NADGGKMPIK WMALECIHYR KFTHQSDVWS YGVTIWELMT FGGKPYDGIP
 901   TREIPDLLEK GERLPQPPIC TIDVYMVMVK CWMIDADSRP KFKELAAEFS RMARDPQRYL
 961   VIQGDDRMKL PSPNDSKFFQ NLLDEEDLED MMDAEEYLVP QAFNIPPPIY TSRARIDSNR
1021   SEIGHSPPPA YTPMSGNQFV YRDGGFAAEQ GVSVPYRAPT STIPEAPVAQ GATAEIFDDS
1081   CCNGTLRKPV APHVQEDSST QRYSADPTVF APERSPRGEL DEEGYMTPMR DKPKQEYLNP
1141   VEENPFVSRR KNGDLQALDN PEYHNASNGP PKAEDEYVNE PLYLNTFANT LGKAEYLKNN
1201   ILSMPEKAKK AFDNPDYWNH SLPPRSTLQH PDYLQEYSTK YFYKQNGRIR PIVAENPEYL
1261   SEFSLKPGTV LPPPPYRHRN TVV
```

Fig. 17

ANTI-ERBB ANTIBODIES AND METHODS OF USE THEREOF

This application claims the benefit of U.S. Provisional Application No. 61/978,783 filed on Apr. 11, 2014, which is hereby incorporated by reference in its entirety.

1. FIELD

Provided herein are compositions, methods and uses involving antibodies that specifically bind to an ErbB, e.g., ErbB3, and modulate the expression and/or activity of the ErbB, e.g., ErbB3, for treating disorders, such as cancer.

2. BACKGROUND

The epidermal growth factor receptor (EGFR) family of receptor tyrosine kinases (RTKs) has long been recognized as including important oncology targets. ErbB3, an EGFR family member, been recently recognized as an important player in solid tumor biology and has emerged as a key unaddressed target in oncology. EGFR (also designated ErbB1) and ErbB2, two related members of the family, are known to drive progression of a significant subset of human tumors when inappropriately activated. Antibody-based inhibitors (Erbitux®, Vectibix®, and Herceptin®) and small molecule tyrosine kinase inhibitors (Iressa®, Tarceva®, and Tykerb®) that target EGFR and ErbB2 have been approved by the FDA for the treatment of a variety of cancers including mammary carcinoma, lung cancers, colon cancer among other oncological indications.

Unlike the three other members of the EGFR family of RTKs, data indicate that ErbB3 is a pseudo kinase that functions as an obligate heterodimer with other ErbB receptors. ErbB3-related signaling has been identified as an important driver of tumor cell survival and growth as well as poor patient prognosis. In addition, signaling involving ErbB3 is utilized by a subset of tumors as an escape mechanism from therapies that target other ErbB receptors.

In tumors, ErbB3 is activated in one of three known manners. First, the Neuregulin 1 (Nrg1) and Neuregulin 2 (Nrg2) family of ligands stabilize a heterodimerization-competent conformation of ErbB3 that allows the receptor to signal by partnering either with ErbB2, or the ligand stimulated activated forms of EGFR or ErbB4. This requirement for ligand stimulation, however, can be bypassed in cases where ErbB2 is very highly overexpressed (such as in ~20% of breast and gastric cancers). Through mass-action, ErbB2 can force heterodimerization with ErbB3 in a ligand-independent manner to provide survival cues to tumor cells. Lastly, oncogenic mutations in ErbB3, which presumably relieve auto-inhibitory mechanisms, can result in increased basal receptor activity when its co-receptors are present. From a therapeutic perspective, a drug that targets ErbB3 would ideally interfere with all mechanisms of ErbB3 activation relevant in disease.

There is a need for therapies modulating ErbB3 to manage, treat or ameliorate conditions involving ErbB3 and/or abnormal ErbB3 signaling or abnormal ErbB3 expression.

3. SUMMARY

In one aspect, provided herein is an antibody(ies) or fragment(s) thereof that binds to the extracellular domain of an ErbB polypeptide, wherein binding of the antibody(ies) or fragment(s) thereof to the ErbB extracellular domain restricts the ErbB polypeptide to an auto-inhibited configuration and inhibits ligand-dependent and ligand-independent ErbB activation. In a specific embodiment, the ErbB polypeptide is an ErbB3 polypeptide, e.g., a human ErbB3 polypeptide. In another embodiment, the ErbB polypeptide is an ErbB1 (EGFR) or ErbB4 polypeptide, e.g., a human ErbB1 or ErbB4 polypeptide. In a particular embodiment, the antibody(ies) or antigen-binding fragment(s) inhibits ligand binding. In a specific embodiment, the antibody(ies) or antigen-binding fragment(s) is isolated.

The antibodies, antigen-binding fragments thereof and uses described herein, are based, in part, on the structural analysis, using X-ray crystallography and other techniques, of a 2C2 Fab in complex with the extracellular domain of human ErbB3. This analysis not only revealed a unique epitope binding region of the 2C2 antibody, but also led to the elucidation of a structural basis for the ability of the 2C2 antibody to inhibit ligand-dependent and ligand-independent activation of human ErbB3. Briefly, without wishing to be bound by any particular mechanism or theory, the data presented herein demonstrate that 2C2 binds to ErbB3 domain II and domain III, including the domain II/domain III hinge region, thereby succeeding in restricting ErbB3 to an auto-inhibited configuration by hindering a crucial conformational change required for both ligand-dependent and ligand-independent ErbB3 activation. Thus, presented herein is a specific structural region within ErbB3 that can be immunologically targeted to successfully inhibit both ligand-dependent and ligand-independent activation of ErbB3. Moreover, as also demonstrated herein, the general architecture of this important ErbB3 epitope and structural region is conserved among ErbB members. Thus, evidence is provided herein indicating that antibodies directed against particular regions of not only ErbB3 but also other ErbBs (e.g., ErbB1 (EGFR or HER1) and ErbB4 (HER4)), can be generated and utilized to inhibit ligand-dependent and ligand-independent activation.

In another aspect, provided herein is an antibody(ies) or fragment(s) thereof that binds to an ErbB extracellular domain, wherein the antibody(ies) or fragment(s) thereof binds to an ErbB epitope comprising at least one amino acid residue within the domain II/domain III hinge region of the ErbB, and inhibits ligand-dependent and ligand-independent ErbB activation. In a specific embodiment, the ErbB polypeptide is an ErbB3 polypeptide, e.g., a human ErbB3 polypeptide. In another embodiment, the ErbB polypeptide is ErbB1 or ErbB4, e.g., a human ErbB1 or ErbB4 polypeptide. In certain embodiments, the antibody(ies) or antigen-binding fragment(s) thereof binds to the ErbB extracellular domain with a $K_D$ of 200 pM or less. In a specific embodiment, the ligand is neuregulin 1 or neuregulin 2. In another embodiment, the epitope is a non-linear epitope. In a particular embodiment, the antibody(ies) or antigen-binding fragment(s) inhibits ligand binding. In a specific embodiment, the antibody(ies) or antigen-binding fragment(s) is isolated.

In another aspect, provided herein is an antibody(ies) or fragment(s) thereof that binds to an ErbB3 extracellular domain, wherein the antibody(ies) or fragment(s) thereof binds to an ErbB3 epitope comprising at least one, two, three or four amino acid residues within the domain II/domain III hinge region of the ErbB, and inhibits ligand-dependent and ligand-independent ErbB activation. In a specific embodiment, the antibody(ies) or fragment(s) thereof binds to an epitope comprising human ErbB3 amino acid residues 309, 310 and/or 311 within the ErbB3 domain II/domain III hinge region. In another specific embodiment, the antibody(ies) or fragment(s) thereof binds to an epitope comprising at least human ErbB3 amino acid residues 309, 310 and 311 within the ErbB3 domain II/domain III hinge region. In certain embodiments, the antibody(ies) or antigen-binding fragment(s) thereof binds to the ErbB3 extracellular domain with a $K_D$ of 200 pM or less. In some embodiments, the antibody(ies) or fragment(s) thereof binds to a full-length ErbB3 extracellular domain with at least 20% lower $k_{off}$ than the antibody or fragment thereof binds to an ErbB3-domain III polypeptide. In a specific embodiment, the ligand is neuregulin 1 or neuregulin 2. In another embodiment, the epitope is a non-linear epitope. In a particular embodiment, the antibody(ies) or antigen-binding fragment(s) inhibits ligand binding. In a specific embodiment, the antibody(ies) or antigen-binding fragment(s) is isolated.

In another aspect, provided herein is an antibody(ies) or fragment(s) thereof that binds to an ErbB extracellular domain, wherein the antibody(ies) or fragment(s) thereof binds to an ErbB epitope comprising at least one amino acid residue within domain II of the ErbB extracellular domain and at least one amino acid residue within domain III of the ErbB extracellular domain and inhibits ligand-dependent and ligand-independent ErbB activation. In a specific embodiment, the ErbB polypeptide is an ErbB3 polypeptide, e.g., a human ErbB3 polypeptide. In another embodiment, the ErbB polypeptide is ErbB1 or ErbB4, e.g., a human ErbB1 or ErbB4 polypeptide. In certain embodiments, the antibody(ies) or antigen-binding fragment(s) thereof binds to the ErbB extracellular domain with a $K_D$ of 200 pM or less. In a specific embodiment, the ligand is neuregulin 1 or neuregulin 2. In another embodiment, the epitope is a non-linear epitope. In a particular embodiment, the antibody(ies) or antigen-binding fragment(s) inhibits ligand binding. In a specific embodiment, the antibody(ies) or antigen-binding fragment(s) is isolated.

In another aspect, provided herein is an antibody(ies) or fragment(ies) thereof that binds to an epitope of ErbB3 comprising (i) at least one, two, three, or four amino acid residues selected from human ErbB3 amino acid residues 291, 292, 294, 299, and 309, and (ii) at least one, two, three, four, five, six, seven, eight, nine, ten, or more amino acid residues selected from human ErbB3 domain III, and inhibits ligand-dependent and ligand-independent ErbB3 activation. In certain embodiments, the antibody(ies) or antigen-binding fragment(s) thereof binds to the ErbB3 extracellular domain with a $K_D$ of 200 pM or less. In another embodiment, the epitope is a non-linear epitope. In a particular embodiment, the antibody(ies) or antigen-binding fragment(s) inhibits ligand binding. In a specific embodiment, the antibody(ies) or antigen-binding fragment(s) is isolated.

In another aspect, provided herein is an antibody(ies) or fragment(s) thereof that binds to an epitope of ErbB3 comprising (i) at least one, two, three, or four amino acid residues selected from human ErbB3 amino acid residues 291, 292, 294, 299, and 309 and (ii) at least one, two, three, four, five, six, seven, eight, nine, ten, or more amino acid residue selected from human ErbB3 amino acid residues 310, 311, 317-319, 337, 339, 373, 394, 402-408, 429, 431-433, 456-458, and 462, and inhibits ligand-dependent and ligand-independent ErbB3 activation. In certain embodiments, the antibody(ies) or antigen-binding fragment(s) thereof binds to the ErbB3 extracellular domain with a $K_D$ of 200 pM or less. In a specific embodiment, the ligand is neuregulin 1 or neuregulin 2. In another embodiment, the epitope is a non-linear epitope. In a particular embodiment, the antibody(ies) or antigen-binding fragment(s) inhibits ligand binding. In a specific embodiment, the antibody(ies) or antigen-binding fragment(s) is isolated.

In some embodiments, the antibody(ies) or fragment(s) thereof binds to a full-length ErbB3 extracellular domain, e.g., human ErbB3 extracellular domain, with at least 20% lower $k_{off}$ than the antibody or fragment thereof binds to an ErbB3 domain III polypeptide, e.g., human ErbB3 domain III polypeptide.

In another aspect, provided herein is an antibody(ies) or fragment(s) thereof that binds to ErbB3, e.g., human ErbB3, wherein the antibody or fragment thereof comprises:
(a) a variable heavy chain region (VH) complementarity determining region (CDR)1 comprising the following amino acid sequence: YYYMQ (SEQ ID NO: 6);
(b) a VH CDR2 comprising the following amino acid sequence: YIGX$_1$SGGX$_2$TNYADSVKG (SEQ ID NO: 24);
(c) a VH CDR3 comprising the following amino acid sequence: VGX$_3$GDAFDI (SEQ ID NO: 27);
(d) a variable light chain region (VL) CDR1 comprising the following amino acid sequence: X$_4$GX$_5$X$_6$SNIGX$_7$NYVS (SEQ ID NO: 30);
(e) a VL CDR2 comprising the following amino acid sequence: RNNQRPS (SEQ ID NO: 10); and
(f) a VL CDR3 comprising the following amino acid sequence: AAWDX$_8$SPPGEA (SEQ ID NO: 33);
wherein X$_1$ represents amino acid residues S or T; X$_2$ represents amino acid residues V, Q, T, S, or N; X$_3$ represents amino acid residues R, Q, L, M, I, W, or Y; X$_4$ represents amino acid residues S, N, D, E, Q, H, R or K; X$_5$ represents amino acid residues S, N, T, D, R, K, H, F, or Y; X$_6$ represents amino acid residues L, F, Y, M, or I; X$_7$ represents amino acid residues L or M; and X$_8$ represents amino acid residues D, N, or H. In specific embodiments, the antibody(ies) or antigen-binding fragment(s) thereof inhibits ligand-dependent and ligand-independent ErbB3 activation. In a specific embodiment, the ligand is neuregulin 1 or neuregulin 2. In certain embodiments, the antibody(ies) or antigen-binding fragment(s) thereof binds to the ErbB3 extracellular domain with a $K_D$ of 200 pM or less. In some embodiments, the antibody(ies) or fragment(s) thereof binds to a full-length ErbB3 extracellular domain with at least 20% lower $k_{off}$ than the antibody or fragment thereof binds to an ErbB3-domain III polypeptide. In a particular embodiment, the antibody(ies) or antigen-binding fragment(s) inhibits ligand binding. In a specific embodiment, the antibody(ies) or antigen-binding fragment(s) is isolated.

In another aspect, provided herein is an antibody(ies) or fragment(s) thereof that binds to ErbB3, e.g., human ErbB3, wherein the antibody or fragment thereof comprises:
(a) a variable heavy chain region (VH) complementarity determining region (CDR)1 comprising the following amino acid sequence: GFTFSYYYM (SEQ ID NO: 12);
(b) a VH CDR2 comprising the following amino acid sequence: GX$_1$SGG (SEQ ID NO: 25);
(c) a VH CDR3 comprising the following amino acid sequence: VGX$_2$GDAFDI (SEQ ID NO: 28);
(d) a variable light chain region (VL) CDR1 comprising the following amino acid sequence: X$_3$GX$_4$X$_5$SNIGX$_6$NYVS (SEQ ID NO: 31);
(e) a VL CDR2 comprising the following amino acid sequence: RNNQRPS (SEQ ID NO: 16); and
(f) a VL CDR3 comprising the following amino acid sequence: AAWDX$_7$SPGEA (SEQ ID NO: 34);
wherein X$_1$ represents amino acid residues S or T; X$_2$ represents amino acid residues R, Q, L, M, I, W, or Y; X$_3$ represents amino acid residues S, N, D, E, Q, H, R or K; X$_4$ represents amino acid residues S, N, T, D, R, K, H, F, or Y;

$X_5$ represents amino acid residues L, F, Y, M, or I; $X_6$ represents amino acid residues L or M; $X_7$ represents amino acid residues D, N, or H. In specific embodiments, the antibody(ies) or antigen-binding fragment(s) thereof inhibits ligand-dependent and ligand-independent ErbB3 activation. In a specific embodiment, the ligand is neuregulin 1 or neuregulin 2. In certain embodiments, the antibody(ies) or antigen-binding fragment(s) thereof binds to the ErbB3 extracellular domain with a $K_D$ of 200 pM or less. In some embodiments, the antibody(ies) or fragment(s) thereof binds to a full-length ErbB3 extracellular domain with at least 20% lower $k_{off}$ than the antibody or fragment thereof binds to an ErbB3-domain III polypeptide. In a particular embodiment, the antibody(ies) or antigen-binding fragment(s) inhibits ligand binding. In a specific embodiment, the antibody(ies) or antigen-binding fragment(s) is isolated.

In another aspect, provided herein is an antibody(ies) or fragment(s) thereof that binds to ErbB3, e.g., human ErbB3, wherein the antibody or fragment thereof comprises:
(a) a variable heavy chain region (VH) complementarity determining region (CDR)1 comprising the following amino acid sequence: GFTGSYYY (SEQ ID NO: 18);
(b) a VH CDR2 comprising the following amino acid sequence: IGX$_1$SGGX$_2$T (SEQ ID NO: 26);
(c) a VH CDR3 comprising the following amino acid sequence: ARVGX$_3$GDAFDI (SEQ ID NO: 29);
(d) a variable light chain region (VL) CDR1 comprising the following amino acid sequence: X$_4$SNIGX$_5$NY (SEQ ID NO: 32);
(e) a VL CDR2 comprising the following amino acid sequence: RNN (SEQ ID NO: 22); and
(f) a VL CDR3 comprising the following amino acid sequence: AAWDX$_6$SPPGEA (SEQ ID NO: 35);

wherein $X_1$ represents amino acid residues S or T; $X_2$ represents amino acid residues V, Q, T, S, or N; $X_3$ represents amino acid residues R, Q, L, M, I, W, or Y; $X_4$ represents amino acid residues L, F, Y, M, or I; $X_5$ represents amino acid residues L or M; $X_6$ represents amino acid residues D, N, or H. In specific embodiments, the antibody(ies) or antigen-binding fragment(s) thereof inhibits ligand-dependent and ligand-independent ErbB3 activation. In a specific embodiment, the ligand is neuregulin 1 or neuregulin 2. In certain embodiments, the antibody(ies) or antigen-binding fragment(s) thereof binds to the ErbB3 extracellular domain with a $K_D$ of 200 pM or less. In some embodiments, the antibody(ies) or fragment(s) thereof binds to a full-length ErbB3 extracellular domain with at least 20% lower $k_{off}$ than the antibody or fragment thereof binds to an ErbB3-domain III polypeptide. In a particular embodiment, the antibody(ies) or antigen-binding fragment(s) inhibits ligand binding. In a specific embodiment, the antibody(ies) or antigen-binding fragment(s) is isolated.

In another aspect, provided herein are compositions (e.g., pharmaceutical compositions) and kits comprising an antibody described herein or fragment thereof that binds ErbB. In a specific embodiment, the ErbB is ErbB1, e.g., human ErbB1. In another embodiment, the ErbB is ErbB3, e.g., human ErbB3. In another embodiment, the ErbB is ErbB4, e.g., human ErbB4.

In another aspect, provided herein are polynucleotides encoding an antibody described herein or fragment thereof that binds ErbB, vectors comprising the polynucleotides, and host cells comprising the polynucleotides or vectors. The host cells can be used to express an antibody described herein or fragment thereof that binds ErbB.

In certain embodiments, provided herein are methods for producing an antibody described herein or fragment thereof that binds ErbB. In a specific embodiment, the ErbB is ErbB1, e.g., human ErbB1. In another embodiment, the ErbB is ErbB3, e.g., human ErbB3. In another embodiment, the ErbB is ErbB4, e.g., human ErbB4.

In another aspect, provided herein are methods for treating a condition, disease or disorder associated with ErbB expression or ErbB-expressing cells, comprising administering to a subject in need thereof an antibody described herein or fragment thereof that binds ErbB. In a specific embodiment, provided herein are methods for treating a hyperproliferative disorder, comprising administering to a subject in need thereof an antibody described herein or fragment thereof that binds ErbB. In a specific embodiment, the ErbB is ErbB1, e.g., human ErbB1. In another embodiment, the ErbB is ErbB3 or ErbB4, e.g., human ErbB3 or ErbB4.

In another aspect, provided herein are methods for treating cancer comprising administering to a subject in need thereof an antibody described herein or fragment thereof that binds ErbB (e.g., human ErbB1, ErbB3 or ErbB4). In a specific embodiment, the cancer is a head and neck cancer, colorectal cancer, breast cancer, thyroid cancer, melanoma, gastric cancer, lung cancer, prostate cancer, neurofibromatosis, bladder cancer, ovarian cancer, pancreatic cancer or renal cancer. In another specific embodiment, the subject is a human containing an ErbB3 amino acid sequence comprising an amino acid substitution of V85M, A213V, P243H, and/or G265R.

In another aspect, provided herein are methods for treating cancer comprising: (a) obtaining a biological sample suspected of containing ErbB3 from a subject and determining whether the amino acid sequence of the ErbB3 comprises a T336I amino acid substitution; and (b) administering to the subject an antibody or antigen-binding fragment thereof described herein if the amino acid sequence of the ErbB3 in the biological sample does not comprise a T336I amino acid substitution.

In yet another aspect, provided herein are methods for treating cancer comprising: obtaining a biological sample suspected of containing ErbB3 from a subject and determining whether the amino acid sequence of the ErbB3 comprises a V85M, A213V, P243H, and/or G265R amino acid substitution; and (b) administering to the subject an antibody or antigen-binding fragment thereof described herein if the amino acid sequence of the ErbB3 in the biological sample comprises at least one such amino acid substitution.

In another aspect, provided herein are diagnostic methods using an antibody described herein or an antigen-binding fragment thereof that binds ErbB. In a specific embodiment, the ErbB is ErbB1, e.g., human ErbB1. In another embodiment, the ErbB is ErbB3, e.g., human ErbB3. In another embodiment, the ErbB is ErbB4, e.g., human ErbB4.

4. BRIEF DESCRIPTION OF THE FIGURES

FIG. 1 shows the proposed mechanism of ErbB3 action. ErbB3 normally exists in equilibrium between an auto-inhibited (tethered) state mediated by domain II/IV contacts, and an extended state. In healthy tissues and many cancer types, ErbB3 is activated by Neuregulin 1 or Neuregulin 2 (top panel), which cross-link domains I and III, and act to stabilize the receptor in its extended activated configuration. Upon ligand binding, exposure of a dimerization interface (primarily domain II) promotes heterodimerization of ErbB3 with ErbB2, or ligand-bound ErbB1 (EGFR; shown) or ErbB4. In a subset of tumors where ErbB2 is highly overexpressed, the requirement for ligand can be by-passed, and ErbB3 can undergo "forced" hetero-dimerization with ErbB2 through mass action. In either scenario, the activated complex signals primarily via the MAPK and AKT signaling pathways to promote cell proliferation and survival.

FIG. 2 depicts the apparent affinity of 2C2 for cell-surface expressed ErbB3. Fluorescently-labeled 2C2 was titrated on BaF3 cells engineered to express ErbB2 and ErbB3. The background-subtracted mean fluorescent intensity was plotted as a function of antibody concentration. Data were fit to a single-site binding isotherm, yielding an apparent $K_D$ of 80 pM.

FIG. 3 demonstrates that 2C2 binds primarily to domain III in ErbB3. The purified ErbB3 extracellular domain (ErbB3-ECD), and each of the four purified ErbB3 domains in isolation were coated on ELISA plates. The 2C2 was titrated onto antigen-coated plates, followed by incubation with a secondary HRP-conjugated anti-human antibody. The luminescent readout was plotted as a function of the log of 2C2 concentration and data were fitted to a four-parameter sigmoidal equation.

FIG. 4 presents a space-filling model depicting binding of 2C2 Fab to the side of ErbB3 domain III. The model demonstrates that 2C2 Fab binds to a unique epitope comprising ErbB3 domain III residues.

FIGS. 5A and 5B depict an overlay of 2C2 Fab-bound ErbB3-ECD with the model of tethered ErbB3-ECD. (A) Structure comparison between 2C2 Fab-bound ErbB3 ECD and the inactive ErbB3 ECD (PDB ID: 1M6B, Cho and Leahy, 2002, *Science* 297:1330-1333). 2C2 Fab is omitted for clarity. (B) The plot denotes root mean square deviation (RMSD) values by amino acid position.

FIG. 6 demonstrates that 2C2 inhibits Neuregulin binding to ErbB3. Fluorescently-labeled Neuregulin1-beta1 (Nrg-647) was titrated onto ErbB3-expressing BaF3 cells alone (circles), or after pre-incubation of the cells with 10 nM 2C2 (squares). Binding data (reported as the mean fluorescent intensity) were fit to a two-site binding isotherm.

FIG. 7 demonstrates that the Neuregulin binding site on ErbB3 D1 and D3 is not occluded by 2C2 Fab binding. 2C2 Fab binds to an epitope primarily within domain III that does not overlap with the Neuregulin binding site, as determined by superposition of domain III in ErbB3 with that of the ligand-bound ErbB4 structure (3U7U.pdb).

FIG. 8 demonstrates that both the 2C2 Fab heavy and light chains have a strong contribution to ErbB3 binding, with both the heavy and light chains making robust contributions to ErbB3 binding. The zoomed box highlights the amino acids in ErbB3 that contact 2C2 Fab.

FIGS. 9A and 9B demonstrates that 2C2 Fab makes contacts with the hinge connecting domain II with domain III (the domainII/domainIII hinge region). (A) The light chain of 2C2 Fab makes a string of contacts with the domain II/domain III hinge region and actively prevents the receptor from releasing itself from an auto-inhibited state. (B) Without being bound by any theory, the cartoon diagrams the natural conformational change, which 2C2 is believed to prevent.

FIGS. 10A and 10B demonstrates that 2C2 binds to both the ErbB3-ECD and purified domain III, but binds to the ErbB3-ECD with higher affinity than to purified domain III. The figures depict sensorgrams of increasing concentrations of the purified ErbB3 ECD (A) or ErbB3 domain III (B) flowed over a chip with immobilized 2C2 Fab.

FIG. 11 depicts sensorgrams of increasing concentrations of the ErbB3 ECD flowed over a chip with immobilized 2C2 Fab, immobilized S25H Fab antibody, or immobilized S23R Fab antibody. Both the S25H Fab antibody and the S23R Fab antibody exhibit enhanced binding affinity to ErbB3 relative to that of 2C2.

FIGS. 12A and 12B demonstrates that 2C2 binds to most recurring oncogenic mutations in the ErbB3 ectodomain. (A) The ability of each purified ErbB3 mutant to compete off binding of fluorescently-labeled 2C2 to cell surface expressed ErbB3 was measured. (B) The same experiment as shown in FIG. 12A was performed by solid-state ELISA. Each purified protein was immobilized on capture plates, and 2C2 was titrated. The amino acid residue number for each mutation corresponds to the amino acid numbering of the mature human protein, which does not include the signal sequence.

FIGS. 13A, 13B, and 13C show that the superimposition of the inactive crystal structures of EGFR (ErbB1), ErbB3 and ErbB4 reveals a similar epitope within ErbB1 and erbB4 that can be exploited using, for example, agents as described herein. (A) An overlay of the three receptors demonstrates that the general 2C2 Fab epitope architecture is conserved. (B) and (C) depict in white the equivalent binding epitopes in EGFR (ErbB1) and ErbB4 relative to ErbB3, respectively.

FIG. 14 depicts sequence alignment of mature EGFR (ErbB1), mature ErbB3, and mature ErbB4 centered around the amino acid sequence containing the 2C2 binding epitope.

FIG. 15 depicts an exemplary amino acid sequence of mature human ErbB1 (EGFR, SEQ ID NO: 1, corresponding to amino acids 25 to 1,210 of Genbank™ accession number NP_005219.2), wherein the underlined amino acid residues correspond to the ErbB1 extracellular domain.

FIG. 16 depicts an exemplary amino acid sequence of mature human ErbB3 (SEQ ID NO: 2, corresponding to amino acids 20 to 1,342 of Genbank™ accession number NP_001973.2), wherein the underlined amino acid residues correspond to the ErbB3 extracellular domain.

FIG. 17 depicts an exemplary amino acid sequence of mature human ErbB4 (SEQ ID NO: 3, corresponding to amino acids 26 to 1,308 of Genbank™ accession number NP_005226.1), wherein the underlined amino acid residues correspond to the ErbB4 extracellular domain.

Figure 1:
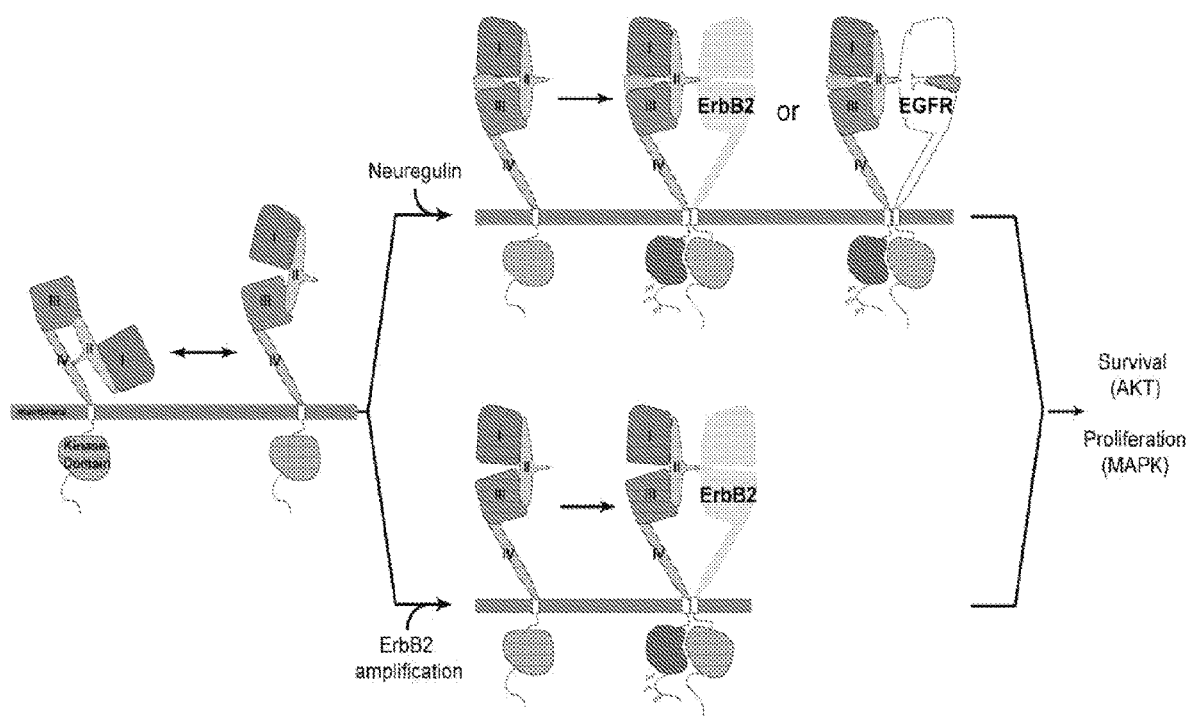

Table 30 provides a listing of the sequences described herein by SEQ ID NOs.

5. DETAILED DESCRIPTION

Provided herein are antibodies (e.g., monoclonal antibodies), and antigen-binding fragments thereof, that specifically bind to an ErbB polypeptide (e.g., an ECD of human ErbB) and modulate ErbB activity. For example, in one aspect, provided herein is an antibody(ies) or fragment(s) thereof that binds to the extracellular domain of an ErbB polypeptide, wherein binding of the antibody(ies) or fragment(s) thereof to the ErbB extracellular domain restricts the ErbB polypeptide to an auto-inhibited configuration and inhibits ligand-dependent and ligand-independent ErbB activation. In certain embodiments, the antibody(ies) or antigen-binding fragment(s) thereof binds to the ErbB extracellular domain with a $K_D$ of 200 pM or less. In a specific embodiment, the ErbB polypeptide is an ErbB3 polypeptide, e.g., a human ErbB3 polypeptide. In another embodiment, the ErbB polypeptide is an ErbB1 or ErbB4 polypeptide, e.g., a human ErbB1 or ErbB4 polypeptide. In a specific embodiment, the antibody(ies) or antigen-binding fragment(s) is isolated.

Also provided are isolated nucleic acids (polynucleotides), such as complementary DNA (cDNA), encoding such antibodies, and antigen-binding fragments thereof. Further provided are vectors (e.g., expression vectors) and cells (e.g., host cells) comprising nucleic acids (polynucleotides) encoding such antibodies or antigen-binding fragments thereof. Also provided are methods of making such antibodies. In other aspects, provided herein are methods and uses for modulating ErbB activity (e.g., inhibiting ErbB activity), and treating certain conditions, such as cancer. Related compositions (e.g., pharmaceutical compositions), kits, and diagnostic methods are also provided.

5.1 Antibodies

In one aspect, provided herein are antibodies (e.g., monoclonal antibodies, such as human, chimeric or humanized antibodies) and antigen-binding fragments thereof, which bind to ErbB and/or a fragment thereof (e.g., the extracellular domain of an ErbB polypeptide, for example, a human ErbB polypeptide) and inhibit ligand-dependent and ligand-independent ErbB activation. In a specific embodiment, the antibodies and antigen-binding fragments thereof provided herein bind to ErbB3 or a fragment thereof (e.g., the extracellular domain of an ErbB3 polypeptide, for example, a human ErbB3 polypeptide). In another specific embodiment, the antibodies and antigen-binding fragments thereof provided herein bind to EGFR and/or a fragment thereof (e.g., the extracellular domain of an EGFR polypeptide, for example, a human EGFR polypeptide. In another specific embodiment, the antibodies and antigen-binding fragments thereof provided herein bind to ErbB4 and/or a fragment thereof (e.g., the extracellular domain of an ErbB4 polypeptide, for example, a human ErbB4 polypeptide). In another specific embodiment, the antibodies and antigen-binding fragments thereof provided herein bind to (i) EGFR and/or a fragment thereof (e.g., the extracellular domain of an EGFR polypeptide, for example, a human EGFR polypeptide), and (ii) ErbB3 or a fragment thereof (e.g., the extracellular domain of an ErbB3 polypeptide, for example, a human ErbB3 polypeptide). In another specific embodiment, the antibodies and antigen-binding fragments thereof provided herein bind to (i) EGFR and/or a fragment thereof (e.g., the extracellular domain of an EGFR polypeptide, for example, a human EGFR polypeptide), and (ii) ErbB4 and/or a fragment thereof (e.g., the extracellular domain of an ErbB4 polypeptide, for example, a human ErbB4 polypeptide). In another specific embodiment, the antibodies and antigen-binding fragments thereof provided herein bind to (i) ErbB4 and/or a fragment thereof (e.g., the extracellular domain of an ErbB4 polypeptide, for example, a human ErbB4 polypeptide), and (ii) ErbB3 or a fragment thereof (e.g., the extracellular domain of an ErbB3 polypeptide, for example, a human ErbB3 polypeptide). In another specific embodiment, the antibodies and antigen-binding fragments thereof provided herein bind to (i) ErbB4 or a fragment thereof (e.g., the extracellular domain of an ErbB4 polypeptide, for example, a human ErbB4 polypeptide), (ii) ErbB3 or a fragment thereof (e.g., the extracellular domain of an ErbB3 polypeptide, for example, a human ErbB3 polypeptide), and (iii) EGFR and/or a fragment thereof (e.g., the extracellular domain of an EGFR polypeptide, for example, a human EGFR polypeptide). In other embodiments, the antibodies and antigen-binding fragments thereof provided herein specifically bind to EGFR. In certain embodiments, the antibodies and antigen-binding fragments thereof provided herein specifically bind to ErbB3. In other embodiments, the antibodies and antigen-binding fragments thereof provided herein specifically bind to ErbB4. In other embodiments, the antibodies and antigen-binding fragments thereof provided herein specifically bind to EGFR and ErbB3. In other embodiments, the antibodies and antigen-binding fragments thereof provided herein specifically bind to EGFR and ErbB4. In other embodiments, the antibodies and antigen-binding fragments thereof provided herein specifically bind to ErbB3 and ErbB4. In other embodiments, the antibodies and antigen-binding fragments thereof provided herein specifically bind to EGFR, ErbB3, and ErbB4. In specific embodiments, the antibodies or antigen-binding fragments thereof provided herein comprises one or more of the 2C2 amino acid mutations recited in Table 26, below, to enhance binding of the antibody or antigen binding fragment thereof to ErbB3. In specific embodiments, the antibodies or antigen-binding fragments thereof provided herein comprises one or more of the 2C2 amino acid mutations recited in Table 29, below, to enhance binding of the antibody or antigen binding fragment thereof to EGFR. In specific embodiments, the antibodies or antigen-binding fragments thereof provided herein comprises one or more of the 2C2 amino acid mutations recited in Table 29, below, to enhance binding of the antibody or antigen binding fragment thereof to ErbB4. In specific embodiments, the antibodies or antigen-binding fragments thereof provided herein comprises one or more of the 2C2 amino acid mutations recited in Table 29, below, to enhance binding of the antibody or antigen binding fragment thereof to EGFR and ErbB4. In specific embodiments, the antibodies and antigen-binding fragments thereof provided herein are isolated.

As used herein, the terms "antibody" and "immunoglobulin" and "Ig" are terms of art and can be used interchangeably and refer to a molecule with an antigen-binding site that binds an antigen. Unless specifically stated otherwise herein, the terms "antibody" and "immunoglobulin" and "Ig" do not refer to the 2C2 antibody, 2C2-YTE antibody, Clone 16 antibody, Clone 16 germlined antibody, 5H6 antibody, 8A3 antibody, 4H6 antibody, 6E3 antibody, 2B11 antibody, 2D1 antibody, 3A6 antibody, 4C4 antibody, 15D12.1 antibody, 15D12.2 antibody, 1A4 antibody, 3E1 antibody, or 2F10 antibody described in International Publication No. WO 2013/078191.

Antibodies can include, for example, monoclonal antibodies, recombinantly produced antibodies, monospecific antibodies, multispecific antibodies (including bispecific antibodies), human antibodies, humanized antibodies, chimeric antibodies, synthetic antibodies, tetrameric antibodies comprising two heavy chain and two light chain molecule, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv), camelized antibodies, affybodies, Fab fragments, F(ab') fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA or IgY), any class, (e.g., $IgG_1$, $IgG_2$, $IgG_3$, $IgG_4$, $IgA_1$ or $IgA_2$), or any subclass (e.g., $IgG_{2a}$ or $IgG_{2b}$) of immunoglobulin molecule. In certain embodiments, antibodies described herein are IgG antibodies, or a class (e.g., human $IgG_1$ or $IgG_4$) or subclass thereof.

As used herein, the term "monoclonal antibody" refers to an antibody obtained from a population of homogenous or substantially homogeneous antibodies. The term "monoclonal" is not limited to any particular method for making the antibody. Generally, a population of monoclonal antibodies can be generated by cells, a population of cells, or a cell line. In specific embodiments, a "monoclonal antibody," as used herein, is an antibody produced by a single cell (e.g., hybridoma or host cell producing a recombinant antibody), wherein the antibody binds to an ErbB epitope (e.g., an epitope of the extracellular domain of human ErbB) as determined, e.g., by ELISA or other antigen-binding or competitive binding assay known in the art or in the Examples provided herein. In particular embodiments, a monoclonal antibody can be a chimeric antibody, a human antibody, or a humanized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody). Monoclonal antibodies described herein can, for example, be made by the hybridoma method as described in Kohler et al.; Nature, 256:495 (1975) or can, e.g., be isolated from phage libraries using the techniques as described herein, for example. Other methods for the preparation of clonal cell lines and of monoclonal antibodies expressed thereby are well known in the art (see, for example, Chapter 11 in: *Short Protocols in Molecular Biology*, (2002) 5th Ed., Ausubel et al., eds., John Wiley and Sons, New York).

As used herein, the term "polyclonal antibodies" refers to an antibody population that includes a variety of different antibodies directed to the same and/or to different epitopes within an antigen or antigens. Methods for producing polyclonal antibodies are known in the art (see, for example, Chapter 11 in: *Short Protocols in Molecular Biology*, (2002) 5th Ed., Ausubel et al., eds., John Wiley and Sons, New York).

As used herein, an "antigen" is a moiety or molecule that contains an epitope, and, as such, also is bound by antibody. In a specific embodiment, the antigen, to which an antibody described herein binds, is ErbB (e.g., ErbB3, for example, a human ErbB3), or a fragment thereof, for example, an extracellular domain of ErbB (e.g., an ErbB3 extracellular domain, for example, a human ErbB3 extracellular domain).

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope can be determined by, e.g., X-ray diffraction crystallography studies, such as described in Section 6, infra, ELISA assays, hydrogen/deuterium exchange coupled with mass spectrometry (e.g., MALDI mass spectrometry), array-based oligo-peptide scanning assays, and/or mutagenesis mapping (e.g., site-directed mutagenesis mapping). In a specific embodiment, the epitope of an antibody or antigen-binding fragment thereof is determined using X-ray diffraction crystallography studies, such as described in Section 6, infra.

As used herein, the terms "antigen-binding domain," "antigen-binding region," "antigen-binding fragment," and similar terms refer to a portion of an antibody molecule which comprises the amino acid residues that confer on the antibody molecule its specificity for the antigen (e.g., the complementarity determining regions (CDR)). The antigen-binding region can be derived from any animal species, such as rodents (e.g., mouse, rat or hamster) and humans.

As used herein, the term "constant region" or "constant domain" refers to an antibody portion, e.g., a carboxyl terminal portion of a light and/or heavy chain which is not directly involved in binding of an antibody to antigen but which can exhibit various effector functions, such as interaction with the Fc receptor. The terms refer to a portion of an immunoglobulin molecule having a generally more conserved amino acid sequence relative to an immunoglobulin variable domain.

As used herein, the terms "variable region" or "variable domain" refer to a portion of an antibody, generally, a portion of a light or heavy chain, typically about the amino-terminal 110 to 120 amino acids in the mature heavy chain and about 90 to 100 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

As used herein, the term "heavy chain" when used in reference to an antibody can refer to any distinct types, e.g., alpha ($\alpha$), delta ($\delta$), epsilon ($\delta$), gamma ($\gamma$) and mu ($\mu$), based on the amino acid sequence of the constant domain, which give rise to IgA, IgD, IgE, IgG and IgM classes of antibodies, respectively, including subclasses of IgG, e.g., $IgG_1$, $IgG_2$, $IgG_3$ and $IgG_4$.

As used herein, the term "light chain" when used in reference to an antibody can refer to any distinct types, e.g., kappa ($\kappa$) of lambda ($\lambda$) based on the amino acid sequence of the constant domains. Light chain amino acid sequences are well known in the art. In specific embodiments, the light chain is a human light chain.

The terms "Kabat numbering," and like terms are recognized in the art and refer to a system of numbering amino acid residues in the heavy and light chain variable regions of an antibody, or an antigen-binding portion thereof. In certain aspects, the CDRs of an antibody can be determined according to the Kabat numbering system (see, e.g., Kabat et al. (1971) Ann. NY Acad. Sci. 190:382-391 and, Kabat et al. (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3).

In certain aspects, the CDRs of an antibody can be determined according to the Chothia numbering scheme, which refers to the location of immunoglobulin structural loops (see, e.g., Chothia and Lesk, 1987, J. Mol. Biol., 196:901-917; Al-Lazikani et al., 1997, J. Mol. Biol., 273: 927-948; Chothia et al., 1992, J. Mol. Biol., 227:799-817; Tramontano A et al., 1990, J. Mol. Biol. 215(1):175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain aspects, the CDRs of an antibody can be determined according to the IMGT numbering system as described in Lefranc, M.-P., 1999, The Immunologist, 7:132-136 and Lefranc, M.-P. et al., 1999, Nucleic Acids Res., 27:209-212. According to the IMGT numbering scheme, VH-CDRI is at positions 26 to 35, VH-CDR2 is at positions 51 to 57, VH-CDR3 is at positions 93 to 102, VL-CDRI is at positions 27 to 32, VL-CDR2 is at positions 50 to 52, and VL-CDR3 is at positions 89 to 97.

In certain aspects, the CDRs of an antibody can be determined according to MacCallum et al., 1996, J. Mol. Biol., 262:732-745. See also, e.g., Martin, A., "Protein Sequence and Structure Analysis of Antibody Variable Domains," in *Antibody Engineering*, Kontermann and Dübel, eds., Chapter 31, pp. 422-439, Springer-Verlag, Berlin (2001).

In certain aspects, the CDRs of an antibody can be determined according to the AbM numbering scheme, which refers AbM hypervariable regions which represent a compromise between the Kabat CDRs and Chothia structural loops, and are used by Oxford Molecular's AbM antibody modeling software.

As used herein, an "isolated" or "purified" antibody is substantially free of cellular material or other contaminating proteins from the cell or tissue source from which the antibody is derived, or substantially free of chemical precursors or other chemicals when chemically synthesized. In specific embodiments, the antibodies or antigen-binding fragments thereof described herein are isolated.

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, Biacore™, KinExA 3000 instrument (Sapidyne Instruments, Boise, Id.), or other assays known in the art. In a specific embodiment, molecules that immunospecifically bind to an antigen bind to the antigen with a $K_a$ that is at least 2 logs, 2.5 logs, 3 logs, 4 logs or greater than the $K_a$ when the molecules bind to another antigen.

In another specific embodiment, molecules that immunospecifically bind to an antigen do not cross react with other proteins under similar binding conditions. In another specific embodiment, molecules that immunospecifically bind to an antigen do not cross react with other non-ErbB proteins. In a specific embodiment, provided herein is an antibody or fragment thereof that binds to ErbB with higher affinity than to another unrelated antigen. In certain embodiments, provided herein is an antibody or fragment thereof that binds to a particular ErbB (e.g., ErbB3) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an anti-ErbB antibody described herein to an unrelated, non-ErbB protein is less than 10%, 15%, or 20% of the binding of the antibody to ErbB protein as measured by, e.g., a radioimmunoassay.

In a specific embodiment, provided herein is an antibody or fragment thereof that binds to a particular ErbB (e.g., ErbB3) with higher affinity than to another ErbB (e.g., ErbB1, ErbB2, or ErbB4). In certain embodiments, provided herein is an antibody or fragment thereof that binds to a particular ErbB (e.g., ErbB3) with a 5%, 10%, 15%, 20%, 25%, 30%, 35%, 40%, 45%, 50%, 55%, 60%, 65%, 70% or higher affinity than to another ErbB (e.g., ErbB1, ErbB2, or ErbB4) as measured by, e.g., a radioimmunoassay, surface plasmon resonance, or kinetic exclusion assay. In a specific embodiment, an antibody or fragment thereof described herein, which binds to a particular ErbB (e.g., ErbB3), will bind to another ErbB protein (e.g., ErbB1, ErbB2, or ErbB4) with less than 10%, 15%, or 20% of the binding of the antibody or fragment thereof to the particular ErbB protein as measured by, e.g., a radioimmunoassay, surface plasmon resonance, or kinetic exclusion assay.

In a specific embodiment, provided herein is an antibody or fragment thereof that binds to an ErbB3 with higher affinity than to another ErbB (e.g., ErbB1, ErbB2, or ErbB4). In certain embodiments, provided herein is an antibody or fragment thereof that binds to ErbB3 with a 5%, 10%, 15%, 20%, 25%, 30%, 35%, 40%, 45%, 50%, 55%, 60%, 65%, 70% or higher affinity than to another ErbB (e.g., ErbB1, ErbB2, or ErbB4) as measured by, e.g., a radioimmunoassay, surface plasmon resonance, or kinetic exclusion assay. In a specific embodiment, an antibody or fragment thereof described herein, which binds to ErbB3, will bind to another ErbB protein (e.g., ErbB1, ErbB2, or ErbB4) with less than 10%, 15%, or 20% of the binding of the antibody or fragment thereof to ErbB3 as measured by, e.g., a radioimmunoassay, surface plasmon resonance, or kinetic exclusion assay.

In a specific embodiment, provided herein is an antibody or fragment thereof that binds to an ErbB1 with higher affinity than to another ErbB (e.g., ErbB2, ErbB3, or ErbB4). In certain embodiments, provided herein is an antibody or fragment thereof that binds to ErbB3 with a 5%, 10%, 15%, 20%, 25%, 30%, 35%, 40%, 45%, 50%, 55%, 60%, 65%, 70% or higher affinity than to another ErbB (e.g., ErbB2, ErbB3, or ErbB4) as measured by, e.g., a radioimmunoassay, surface plasmon resonance, or kinetic exclusion assay. In a specific embodiment, an antibody or fragment thereof described herein, which binds to ErbB1, will bind to another ErbB protein (e.g., ErbB2, ErbB3, or ErbB4) with less than 10%, 15%, or 20% of the binding of the antibody or fragment thereof to ErbB1 as measured by, e.g., a radioimmunoassay, surface plasmon resonance, or kinetic exclusion assay.

In a specific embodiment, provided herein is an antibody or fragment thereof that binds to an ErbB4 with higher affinity than to another ErbB (e.g., ErbB1, ErbB2, or ErbB3). In certain embodiments, provided herein is an antibody or fragment thereof that binds to ErbB4 with a 5%, 10%, 15%, 20%, 25%, 30%, 35%, 40%, 45%, 50%, 55%, 60%, 65%, 70% or higher affinity than to another ErbB (e.g., ErbB1, ErbB2, or ErbB3) as measured by, e.g., a radioimmunoassay, surface plasmon resonance, or kinetic exclusion assay. In a specific embodiment, an antibody or fragment thereof described herein, which binds to ErbB4, will bind to another ErbB protein (e.g., ErbB1, ErbB2, or ErbB3) with less than 10%, 15%, or 20% of the binding of the antibody or fragment thereof to ErbB4 as measured by, e.g., a radioimmunoassay, surface plasmon resonance, or kinetic exclusion assay.

ErbB is a receptor tyrosine kinase of the EGFR family. As used herein, the terms "ErbB" or "ErbB receptor" or "ErbB polypeptide" refer to ErbB including, but not limited to, native ErbB, an isoform of ErbB, or an interspecies ErbB homolog of any ErbB other than ErbB2. In some embodiments, the term "ErbB" refers to epidermal growth factor receptor (EGFR; otherwise known as ErbB1 or HER1), ErbB3 (otherwise known as HER3), and/or ErbB4 (otherwise known as HER4). In certain embodiments, the term "ErbB" refers to EGFR and ErbB4. In a specific embodiment, the term "ErbB" refers to ErbB3. The ErbB can be from any animal species, including humans. In specific embodiments, the ErbB is a human ErbB.

ErbB is composed of an extracellular ligand-binding domain (ECD), a transmembrane domain, and an intracellular domain. The ErbB ECD can be further defined by domains I-IV (alternatively referred to as 1-4, respectively) and the domain II/domain III hinge region.

As used herein, the terms "ErbB1" or "ErbB1 receptor" or "ErbB1 polypeptide" refer to ErbB1 including, but not limited to, native ErbB1, an isoform of ErbB1, or an interspecies ErbB1 homolog of ErbB1. Native ErbB1 comprises an extracellular domain, which can be subdivided into domains I to IV, a transmembrane domain, and a cytoplasmic domain. GenBank™ accession numbers NM_005228.3, NM_201282.1, NM_201283.1 and NM_201284.1 provide exemplary human ErbB1 nucleic acid sequences. GenBank™ accession numbers NP_005219.2, NP_958439.1, NP_958440.1, and NP_958441.1 provide exemplary human ErbB1 amino acid sequences. GenBank™ accession number NP_997538.1 provides an exemplary murine ErbB1 amino acid sequence. In a specific embodiment, the ErbB1 is human ErbB1 (SEQ ID NO: 1). ErbB1 is also known as EGFR or HER1. An exemplary amino acid sequence of a mature human ErbB1 is provided in FIG. 15, see, also, Table 1, below. Unless otherwise specified herein, references to particular amino acid residues of ErbB1 correspond to the amino acid residues of the mature human form of ErbB1, set forth in FIG. 15 (SEQ ID NO: 1).

As used herein, the terms "ErbB3" or "ErbB3 receptor" or "ErbB3 polypeptide" refer to ErbB3 including, but not limited to, native ErbB3, an isoform of ErbB3, or an interspecies ErbB3 homolog of ErbB3. Native ErbB3 comprises an extracellular domain, which can be subdivided into domains I to IV, a transmembrane domain, and a cytoplasmic domain. GenBank™ accession number NM_001982.3 and NM_001005915.1 provides an exemplary human ErbB3 nucleic acid sequences. GenBank™ accession numbers NP_001973.2 and NP_001005915.1 provide exemplary human ErbB3 amino acid sequences. GenBank™ accession number NP_034283.1 provides an exemplary murine ErbB3 amino acid sequence. In a specific embodiment, the ErbB3 is human ErbB3 (SEQ ID NO: 2). ErbB3 is also known as HER3. An exemplary amino acid sequence of mature human ErbB3 is provided in FIG. 16, see, also, Table 1, below. Unless otherwise specified herein, references to particular amino acid residues of ErbB3 correspond to the amino acid residues of the mature human form of ErbB3, set forth in FIG. 16 (SEQ ID NO: 2).

As used herein, the terms "ErbB4" or "ErbB4 receptor" or "ErbB4 polypeptide" refer to ErbB1 including, but not limited to, native ErbB4, an isoform of ErbB4, or an interspecies ErbB4 homolog of ErbB4 Native ErbB4 comprises an extracellular domain, which can be subdivided into domains I to IV, a transmembrane domain, and a cytoplasmic domain. NM_005235.2 and NM_001042599.1 provides an exemplary human ErbB4 nucleic acid sequences. GenBank™ accession numbers NP_005226.1 and NP_001036064.1 provide exemplary human ErbB4 amino acid sequences. GenBank™ accession number NP_001036064.1 provides an exemplary murine ErbB4 amino acid sequence. In a specific embodiment, the ErbB4 is human ErbB4 (SEQ ID NO: 3). ErbB4 is also known as HER4. An exemplary amino acid sequence of mature human ErbB4 is provided in FIG. 17, see, also, Table 1, below. Unless otherwise specified herein, references to particular amino acid residues of ErbB4 correspond to the amino acid residues of the mature human form of ErbB4, set forth in FIG. 17 (SEQ ID NO: 3).

As used herein, the terms ErbB "hinge region" and "domain II/domain III hinge region" and analogous terms refer to the boundary between domains II and III of ErbB. Without being bound by any mechanism or theory, the ErbB hinge region is a key regulator of the receptor's ability to adopt an extended (and ligand-binding-competent) conformation. Further, without being bound by any mechanism or theory, the flexibility (or rigidity) imparted to ErbB is dependent, at least in part, upon the conformation of the domain II/domain III hinge region. In certain embodiments, the ErbB1 hinge region comprises amino mature ErbB1 acid residues 305-313 of human ErbB1. In specific embodiments, the ErbB3 hinge region comprises mature ErbB3 amino acid residues 304-312 of human ErbB3. In certain embodiments, the ErbB4 hinge region comprises mature ErbB4 amino acid residues 301-309 of human ErbB4. See, also, Table 1, below.

TABLE 1

|     |                | ErbB1   |          | ErbB3   |          | ErbB4   |          |
|-----|----------------|---------|----------|---------|----------|---------|----------|
|     |                | Mature  | Immature | Mature  | Immature | Mature  | Immature |
|     | Signal peptide |         | 1-24     |         | 1-19     |         | 1-25     |
| ECD | Domain I       | 1-182   | 25-206   | 1-182   | 20-201   | 1-180   | 26-205   |
|     | Domain II      | 183-311 | 207-335  | 183-309 | 202-328  | 181-307 | 206-332  |
|     | Domain III     | 312-503 | 336-527  | 310-502 | 329-521  | 308-499 | 333-524  |

TABLE 1-continued

| | ErbB1 | | ErbB3 | | ErbB4 | |
| --- | --- | --- | --- | --- | --- | --- |
| | Mature | Immature | Mature | Immature | Mature | Immature |
| Domain IV | 504-621 | 528-645 | 503-624 | 522-643 | 500-626 | 525-651 |
| Domain II/Domain III hinge region | 305-313 | 329-337 | 304-312 | 323-331 | 301-309 | 326-334 |
| Transmembrane domain | 622-644 | 646-668 | 625-645 | 644-664 | 627-650 | 652-675 |
| Intracellular domain | 645-1,186 | 669-1,210 | 646-1,323 | 665-1,342 | 651-1,283 | 676-1,308 |

As used herein, "ligand-dependent activation" refers to activation of a receptor by a ligand, e.g., activation of an ErbB by an ErbB ligand. In a specific embodiment, ErbB activation can be assessed by analyzing signal transduction pathways induced by the binding of a ligand to ErbB, for example, ErbB3. In a specific embodiment, the ligand is a member of the neuregulin family. In one embodiment, the neuregulin is neuregulin 1 or neuregulin 2, e.g., human neuregulin 1 or neuregulin 2. In a specific embodiment, the neuregulin is neuregulin 1β1. For example, the binding of ErbB1 to epidermal growth factor has been reported to induce the phosphorylation of MAPK, the phosphorylation of PI3K, and the phosphorylation AKT. The binding of ErbB1 to epidermal growth factor has also been reported to induce the nuclear import of MAPK, the nuclear import of AKT, and the nuclear import of STAT. The binding of ErbB1 to epidermal growth factor has also been reported to induce the binding of Grb2 to ErbB. The binding of ErbB3 to neuregulin has been reported to induce the phosphorylation of MAPK and phosphorylation of AKT. The binding of ErbB3 to neuregulin has also been reported to induce the nuclear import of MAPK and the nuclear import of AKT. The binding of ErbB3 to neuregulin has also been reported to induce the binding of Grb2 to ErbB. The binding of ErbB4 to neuregulin has been reported to induce the phosphorylation of MAPK, the phosphorylation of PI3K, and the phosphorylation of AKT. The binding of ErbB4 to neuregulin has also been reported to induce the nuclear import of MAPK and the nuclear import of AKT. The binding of ErbB4 to neuregulin has also been reported to induce the binding of Grb2 to ErbB. The phosphorylation of MAPK, PI3K, and AKT can be measured by assays described herein or those known to one of skill in the art, such as, e.g., western blot, radiolabeling, and phosphoimmunoprecipitations. Other assays that can be used to measure ligand-dependent activation include, for e.g., immunofluorescence to evaluate co-localization, co-immunoprecipitation, transcription reporter assays, subcellular fractionation and/or immunofluorescence to detect translocation of STAT, MAPK, and/or AKT into the nucleus, and cellular proliferation assays.

As used herein, "ligand-independent activation" refers to activation of ErbB in the absence of ligand, for example, activation of ErbB3 in the absence of ligand (e.g., in the absence of a neuregulin family member) in cells in which another receptor tyrosine kinase, such as, e.g., ErbB1, ErbB2, ErbB4, or Met, is overexpressed, or, for example, ligand-independent ErbB activation can be a result of activating mutations in ErbB heterodimers partners such as ErbB1, ErbB2, and ErbB3. Ligand-independent activation can be measured by assays described herein or those known to one of skill in the art, such as, e.g., phosphor-specific western blot, immunofluorescence to evaluate co-localization, co-immunoprecipitation, transcription reporter assays, subcellular fractionation and/or immunofluorescence to detect translocation of STAT, Erk, and/or AKT into the nucleus, phosphoimmunoprecipitations, and cellular proliferation assays.

As used herein, "neuregulin" refers to any member of the neuregulin family of proteins, such as, e.g., neuregulin-1, neuregulin-2. In some embodiments, "neuregulin" refers to "heregulin", another commonly utilized name for the neuregulin family of proteins. In a specific embodiment, "neuregulin" refers to neuregulin 1 and/or neuregulin 2. In a specific embodiment, "neuregulin" refers to one or more neuregulin-1 isoforms (such as, e.g., isoforms HRG-beta2b, HRG-gamma3, HRG-beta3b, ndf43b, HRG-gamma2, HRG-beta1d, HRG-beta1b, ndf43c, HRG-beta1c, ggf2, HRG-gamma, HRG-beta3, HRG-beta2, HRG-beta1, HRG-alpha, ndf43, and smdf, respectively). In a specific embodiment, "neuregulin" refers to one or more neuregulin-2 isoforms (such as, e.g., isoforms 1, 2, 3, 4, and 7). In a specific embodiment, "neuregulin" refers to neuregulin-1-beta. GenBank™ accession numbers NM_001160008.1, NM_001160007.1, NM_001160005.1, NM_001160004.1, NM_001160002.1, NM_001160001.1, NM_001159999.1, NM_001159996.1, NM_001159995.1, NM_013958.3, NM_013957.3, NM_013956.3, NM_004495.3, NM_013964.3, NM_013959.3, NM_013960.3, and NM_013962.2 provide exemplary human neuregulin 1 nucleic acid sequences. GenBank™ accession numbers NP_001153480.1, NP_001153479.1, NP_001153477.1, NP_001153476.1, NP_001153474.1, NP_001153473.1, NP_001153471.1, NP_001153468.1, NP_001153467.1, NP_039256.2, NP_004486.2, NP_039252.2, NP_039251.2, NP_039250.2, NP_039258.1, NP_039254.1, and NP_039253.1 provide exemplary human neuregulin 1 amino acid sequences. GenBank™ accession numbers NM_004883.2, NM_013981.3, NM_013982.2, NM_013983.2, and NM_001184935.1 provide exemplary human neuregulin 2 nucleic acid sequences. GenBank™ accession numbers NP_004874.1, NP_001159444.1, NP_053585.1, NP_053586.1, and NP_001171864.1 provides exemplary human neuregulin 2 amino acid sequences. In a particular embodiment, the neuregulin is a human Neuregulin. In a specific embodiment, the neuregulin is human neuregulin-1-beta1. In a particular embodiment, the neuregulin-1-beta1 has the following immature amino acid sequence:

(SEQ ID NO: 119)
MSERKEGRGKGKGKKKERGSGKKPESAAGSQSPALPPRLKEMKSQESAAG

SKLVLRCETSSEYSSLRFKWFKNGNELNRKNKPQNIKIQKKPGKSELRIN

KASLADSGEYMCKVISKLGNDSASANITIVESNEIITGMPASTEGAYVSS

ESPIRISVSTEGANTSSSTSTSTTGTSHLVKCAEKEKTFCVNGGECFMVK

DLSNPSRYLCKCPNEFTGDRCQNYVMASFYKHLGIEFMEAEELYQKRVLT

ITGICIALLVVGIMCVVAYCKTKKQRKKLHDRLRQSLRSERNNMMNIANG

PHHPNPPPENVQLVNQYVSKNVISSEHIVEREAETSFSTSHYTSTAHHST

TVTQTPSHSWSNGHTESILSESHSVIVMSSVENSRHSSPTGGPRGRLNGT

GGPRECNSFLRHARETPDSYRDSPHSERYVSAMTTPARMSPVDFHTPSSP

KSPPSEMSPPVSSMTVSMPSMAVSPFMEEERPLLLVTPPRLREKKFDHHP

QQFSSFHHNPAHDSNSLPASPLRIVEDEEYETTQEYEPAQEPVKKLANSR

RAKRTKPNGHIANRLEVDSNTSSQSSNSESETEDERVGEDTPFLGIQNPL

AASLEATPAFRLADSRTNPAGRFSTQEEIQARLSSVIANQDPIAV

As used herein, the term "inhibition" in the context of ligand-dependent ErbB activation refers to at least the partial inhibition of ligand-dependent ErbB activation, and in certain embodiments, the complete inhibition of ligand-dependent ErbB activation. In a specific embodiment, the term "inhibition" in the context of ligand-dependent ErbB activation refers to least 5%, 10%, 15%, 20%, 25%, 30%, 35%, 40%, 45%, 50%, 55%, 60%, 65%, 70%, 75%, 80%, 85%, 90%, 95%, 98%, or 99% inhibition of ligand-dependent ErbB activation as assessed by methods described herein or known to one of skill in the art, such as, e.g., proliferation assays and/or phosphorylation assays. In a specific embodiment, inhibition of ErbB activation is assessed by contacting a cell expressing ErbB with neuregulin and an antibody or fragment thereof described herein or a negative control (e.g., control IgG), and measuring the proliferation of cells as assessed by, for e.g., tritium thymidine incorporation, or the phosphorylation of a downstream signaling molecule, such as, AKT, as assessed by, for e.g., ELISA or western blot. In certain embodiments, inhibition of ErbB activation is assessed by contacting a cell expressing ErbB with neuregulin or a negative control for neuregulin (e.g. green fluorescent protein) and an antibody or fragment thereof described herein or a negative control (e.g., control IgG), and measuring the proliferation of cells as assessed by, for e.g., tritium thymidine incorporation, or the phosphorylation of a downstream signaling molecule, such as, AKT, as assessed by, for e.g., ELISA or western blot. In another specific embodiment, the term "inhibition" in the context of ligand-dependent ErbB activation refers to 5-10%, 5-15%, 15-25%, 25-35%, 35-45%, 45-55%, 55-65%, 65-75%, 75-85%, 85-95%, 95-98%, or by 95-100% inhibition of ligand-dependent ErbB activation as assessed by methods described herein or known to one of skill in the art, such as, e.g., proliferation assays and/or phosphorylation assays. For example, in a specific embodiment, inhibition of ErbB activation is assessed by contacting a cell expressing ErbB with neuregulin and an antibody or fragment thereof described herein or a negative control (e.g., control IgG), and measuring the proliferation of cells as assessed by, for e.g., tritium thymidine incorporation, or the phosphorylation of a downstream signaling molecule, such as, AKT, as assessed by, for e.g., ELISA or western blot. In certain embodiments, inhibition of ErbB activation is assessed by contacting a cell expressing ErbB with neuregulin or a negative control for neuregulin (e.g. green fluorescent protein) and an antibody or fragment thereof described herein or a negative control (e.g., control IgG), and measuring the proliferation of cells as assessed by, for e.g., tritium thymidine incorporation, or the phosphorylation of a downstream signaling molecule, such as, AKT, as assessed by, for e.g., ELISA or western blot. In another specific embodiment, the term "inhibition" in the context of ligand-dependent ErbB activation refers to at least 1.5 fold, 2 fold, 2.5 fold, 3 fold, 3.5 fold, 4 fold, 4.5 fold, 5 fold, 5.5 fold, 6 fold, 6.5 fold, 7 fold, 7.5 fold or 8 fold, or between 1.2-1.5 fold, 1.5-1.8 fold, 1.5-2 fold, 2.0-2.5 fold, 2.5-3.0 fold, 3.5-5.0 fold, or 5-10-fold inhibition of ligand-dependent ErbB activation as assessed by methods described herein or known to one of skill in the art, such as, e.g., proliferation assays and/or phosphorylation assays. For example, in a specific embodiment, inhibition of ErbB activation is assessed by contacting a cell expressing ErbB with neuregulin and an antibody or fragment thereof described herein or a negative control (e.g., control IgG), and measuring the proliferation of cells as assessed by, for e.g., tritium thymidine incorporation, or the phosphorylation of a downstream signaling molecule, such as, AKT, as assessed by, for e.g., ELISA or western blot. In certain embodiments, inhibition of ErbB activation is assessed by contacting a cell expressing ErbB with neuregulin or a negative control for neuregulin (e.g. green fluorescent protein) and an antibody or fragment thereof described herein or a negative control (e.g., control IgG), and measuring the proliferation of cells as assessed by, for e.g., tritium thymidine incorporation, or the phosphorylation of a downstream signaling molecule, such as, AKT, as assessed by, for e.g., ELISA or western blot.

In one aspect, provided herein is an antibody(ies) or fragment(s) thereof that specifically binds to the extracellular domain of an ErbB polypeptide, wherein binding of the antibody(ies) or fragment(s) thereof to the ErbB extracellular domain restricts the ErbB polypeptide to an auto-inhibited configuration. In certain embodiments, the antibody or antigen-binding fragment thereof is a human, humanized or chimeric antibody or antigen-binding fragment thereof. In a specific embodiment, the antibody or antigen-binding fragment thereof is a monoclonal antibody or antigen-binding fragment. In another specific embodiment, the antibody is a human, humanized or chimeric monoclonal antibody or antigen-binding fragment thereof. In certain embodiments, the antibody or antigen-binding fragment thereof is isolated.

In one embodiment, provided herein is an antibody(ies) or fragment(s) thereof that specifically binds to the extracellular domain of an ErbB3 polypeptide, wherein binding of the antibody(ies) or fragment(s) thereof to the ErbB3 extracellular domain restricts the ErbB3 polypeptide to an auto-inhibited configuration. In another embodiment, provided herein is an antibody or fragment thereof that specifically binds to the extracellular domain of an ErbB1 polypeptide, wherein binding of the antibody or fragment thereof to the ErbB1 extracellular domain restricts the ErbB1 polypeptide to an auto-inhibited configuration. In another embodiment, provided herein is an antibody or fragment thereof that specifically binds to the extracellular domain of an ErbB4 polypeptide, wherein binding of the antibody or fragment thereof to the ErbB4 extracellular domain restricts the ErbB4 polypeptide to an auto-inhibited configuration. In certain embodiments, the antibody or antigen-binding fragment thereof is a human, humanized or chimeric antibody or antigen-binding fragment thereof. In a specific embodiment, the antibody or antigen-binding fragment thereof is a monoclonal antibody or antigen-binding fragment. In another specific embodiment, the antibody is a human, humanized or chimeric monoclonal antibody or antigen-binding fragment thereof. In certain embodiments, the antibody or antigen-binding fragment thereof is isolated.

As used herein, the term "autoinhibited configuration," "auto-inhibited configuration" or "tethered state" refers to an ErbB arrangement that does not favor ligand binding. Without wishing to be bound by mechanism or theory, it is thought that an inactive ErbB arrangement is a configuration of the ErbB extracellular domain in which a specific loop of the ErbB domain II intramolecularly interacts with a specific loop of the ErbB domain IV, rendering the extracellular domain in a conformation in which the positions of the ErbB ligand binding domain I and III do not favor ligand binding.

In another aspect, provided herein is an antibody(ies) or fragment(s) thereof that binds to an ErbB extracellular domain, wherein the antibody(ies) or fragment(s) thereof binds to an ErbB epitope comprising at least one, two, three, four, five, six, seven, or eight amino acid residues, or 1 to 4, 2 to 4, 1 to 5, 2 to 6, 5 to 8, or 1 to 8, amino acid residues within the ErbB domain II/domain III hinge region, and inhibits ligand-dependent. In specific embodiments, the ErbB epitope is a non-linear epitope. In one embodiment, the ErbB is ErbB1, e.g., human ErbB1. In a particular embodiment, the ErbB is ErbB1 and the antibody or fragment thereof binds to an epitope comprising amino acid residue 310, amino acid residue 311, amino acid residue 312, amino acid residues 310 and 311, amino acid residues 311 and 312, or amino acid residues 310, 311, and 312 within the human ErbB1 domain II/domain III hinge region.

In another specific embodiment, the ErbB is ErbB3, e.g., human ErbB3. In a particular embodiment, the ErbB is ErbB3 and the antibody or fragment thereof binds to an epitope comprising amino acid residue 309, amino acid residue 310, amino acid residue 311, amino acid residues 309 and 310, amino acid residues 310 and 311, or amino acid residues 309, 310, and 311 within the human ErbB3 domain II/domain III hinge region.

In yet another embodiment, the ErbB is ErbB4, e.g., human ErbB4. In a particular embodiment, the ErbB is ErbB4 and the antibody or fragment thereof binds to an epitope comprising amino acid residue 306, amino acid residue 307, amino acid residue 308, amino acid residues 306 and 307, amino acid residues 307 and 308, or amino acid residues 306, 307, and 308 within the human ErbB4 domain II/domain III hinge region.

In a specific embodiment, the antibody or antigen-binding fragment thereof inhibits neuregulin-dependent ErbB activation, e.g., human neuregulin-dependent ErbB activation. In another specific embodiment, the antibody or antigen-binding fragment thereof inhibits neuregulin 1-dependent ErbB activation. In a particular embodiment, the neuregulin 1 is neuregulin 1β1. In another specific embodiment, the antibody or antigen-binding fragment thereof inhibits neuregulin 2-dependent ErbB activation. In certain embodiments, the antibody or antigen-binding fragment thereof is a human, humanized or chimeric antibody or antigen-binding fragment thereof. In a specific embodiment, the antibody or antigen-binding fragment thereof is a monoclonal antibody or antigen-binding fragment. In another specific embodiment, the antibody is a human, humanized or chimeric monoclonal antibody or antigen-binding fragment thereof. In certain embodiments, the antibody or antigen-binding fragment thereof is isolated.

In certain embodiments, an antibody or fragment thereof described herein binds to an ErbB extracellular domain with a dissociation rate constant ($k_{off}$) of $8.5 \times 10^{-5}$ s$^{-1}$ or less, $5 \times 10^{-5}$ s$^{-1}$ or less, $2.5 \times 10^{-5}$ s$^{-1}$ or less, $1 \times 10^{-5}$ s$^{-1}$ or less, $8.5 \times 10^{-6}$ s$^{-1}$ or less, $5 \times 10^{-6}$ s$^{-1}$ or less, $2.5 \times 10^{-6}$ s$^{-1}$ or less, $1 \times 10^{-6}$ s$^{-1}$ or less, $8.5 \times 10^{-7}$ s$^{-1}$ or less, $5 \times 10^{-7}$ s$^{-1}$ or less, $2.5 \times 10^{-7}$ s$^{-1}$ or less, $1 \times 10^{-7}$ s$^{-1}$ or less, $8.5 \times 10^{-8}$ s$^{-1}$ or less, $5 \times 10^{-8}$ s$^{-1}$ or less, $2.5 \times 10^{-8}$ s$^{-1}$ or less, $1 \times 10^{-8}$ s$^{-1}$ or less, $8.5 \times 10^{-9}$ s$^{-1}$ or less, $5 \times 10^{-9}$ s$^{-1}$ or less, $2.5 \times 10^{-9}$ s$^{-1}$ or less, or $1 \times 10^{-9}$ s$^{-1}$ or less. In some embodiments, an antibody or fragment thereof described herein binds to an ErbB extracellular domain with a $k_{off}$ of between $9.5 \times 10^{-5}$ s$^{-1}$ to $1 \times 10^{-9}$ s$^{-1}$, $8.5 \times 10^{-5}$ s$^{-1}$ to $1 \times 10^{-9}$ s$^{-1}$, $5 \times 10^{-5}$ s$^{-1}$ to $1 \times 10^{-9}$ s$^{-1}$, $9.5 \times 10^{-5}$ s$^{-1}$ to $1 \times 10^{-8}$ s$^{-1}$, $5 \times 10^{-5}$ s$^{-1}$ to $1 \times 10^{-8}$ s$^{-1}$, $9.5 \times 10^{-5}$ s$^{-1}$ to $1 \times 10^{-7}$ s$^{-1}$, $5 \times 10^{-5}$ s$^{-1}$ to $1 \times 10^{-7}$ s$^{-1}$, $9.5 \times 10^{-5}$ s$^{-1}$ to $5 \times 10^{-6}$ s$^{-1}$, or $9.5 \times 10^{-5}$ s$^{-1}$ to $1 \times 10^{-5}$ s$^{-1}$. In certain embodiments, the $k_{off}$ is determined using a monovalent antibody, such as a Fab fragment, as measured by, e.g., BIAcore™ surface plasmon resonance technology. In a particular embodiment, the $k_{off}$ is determined using an assay described in Section 6, infra.

In certain embodiments, an antibody or fragment thereof described herein binds to an ErbB extracellular domain with an association rate constant ($k_{on}$) of at least $10^5$ M$^{-1}$ s$^{-1}$, at least $5 \times 10^5$ M$^{-1}$ s$^{-1}$, at least $10^6$ M$^{-1}$ s$^{-1}$, at least $5 \times 10^6$ M$^{-1}$ s$^{-1}$, at least $10^7$ M$^{-1}$ s$^{-1}$, at least $5 \times 10^7$ M$^{-1}$ s$^{-1}$, at least $10^8$ M$^{-1}$ s$^{-1}$, at least $5 \times 10^8$ M$^{-1}$ s$^{-1}$ or at least $10^9$ M$^{-1}$ s$^{-1}$. In some embodiments, an antibody or fragment thereof described herein binds to an ErbB extracellular domain with a $k_{on}$ of between $1 \times 10^5$ M$^{-1}$ s$^{-1}$ to $5 \times 10^5$ M$^{-1}$ s$^{-1}$, $1 \times 10^5$ M$^{-1}$ s$^{-1}$ to $1 \times 10^6$ M$^{-1}$ s$^{-1}$, $1 \times 10^5$ M$^{-1}$ s$^{-1}$ to $5 \times 10^6$ M$^{-1}$ s$^{-1}$, $1 \times 10^5$ M$^{-1}$ s$^{-1}$ to $1 \times 10^7$ M$^{-1}$ s$^{-1}$, $1 \times 10^5$ M$^{-1}$ s$^{-1}$ to $5 \times 10^7$ M$^{-1}$ s$^{-1}$, $1 \times 10^5$ M$^{-1}$ s$^{-1}$ to $10^8$ M$^{-1}$ s$^{-1}$, $1 \times 10^5$ M$^{-1}$ s$^{-1}$ to $1 \times 10^9$ M$^{-1}$ s$^{-1}$, $1 \times 10^6$ M$^{-1}$ s$^{-1}$ to $1 \times 10^7$ M$^{-1}$ s$^{-1}$, $1 \times 10^6$ M$^{-1}$ s$^{-1}$ to $1 \times 10^8$ M$^{-1}$ s$^{-1}$, $1 \times 10^6$ M$^{-1}$ s$^{-1}$ to $1 \times 10^9$ M$^{-1}$ s$^{-1}$, $1 \times 10^7$ M$^{-1}$ s$^{-1}$ to $1 \times 10^8$ M$^{-1}$ s$^{-1}$, $1 \times 10^7$ M$^{-1}$ s$^{-1}$ to $1 \times 10^9$ M$^{-1}$ s$^{-1}$, $1 \times 10^8$ M$^{-1}$ s$^{-1}$ to $1 \times 10^9$ M$^{-1}$ s$^{-1}$. In certain embodiments, the $k_{on}$ is determined using a monovalent antibody, such as a Fab fragment, as measured by, e.g., BIAcore™ surface plasmon resonance technology. In a particular embodiment, the $k_{on}$ is determined using an assay described in Section 6, infra.

In certain embodiments, an antibody or fragment thereof described herein binds to an ErbB extracellular domain with a $K_D$ of less than 375 pM, 350 pM, 325 pM, 300 pM, 275 pM, 250 pM, 225 pM, 200 pM, 175 pM, 150 pM, 125 pM, 100 pM, 75 pM, 50 pM, 45 pM, 40 pM, or 35 pM. In some embodiments, an antibody or fragment thereof described herein binds to an ErbB extracellular domain with a $k_D$ of 375 pM, 350 pM, 325 pM, 300 pM, 275 pM, 250 pM, 225 pM, 200 pM, 175 pM, 150 pM, 125 pM, 100 pM, 75 pM, or 50 pM, or between 375 pM to 300 pM, 375 pM to 200 pM, 375 pM to 100 pM, 350 pM to 250 pM, 350 pM to 200 pM, 300 pM to 150 pM, 300 pM to 100 pM, 300 pM to 50 pM, 300 pM to 200 pM, 300 pM to 150 pM, 300 pM to 100 pM, 300 pM to 50 pM, 275 pM to 200 pM, 275 pM to 175 pM, 275 pM to 150 pM, 275 pM to 100 pM, 275 pM to 50 pM, 250 pM to 200 pM, 250 pM to 150 pM, 250 pM to 100 pM, 250 pM to 50 pM, 200 pM to 150 pM, 200 pM to 100 pM, 200 to 50 pM, 150 pM to 100 pM, 150 pM to 50 pM, 100 pM to 50 pM, 200 to 40 pM, 150 pM to 40 pM, 150 pM to 40 pM, or 100 pM to 35 pM. In certain embodiments, the $k_D$ is calculated as the quotient of $k_{off}/k_{on}$, and the $k_{on}$ and $k_{off}$ are determined using a monovalent antibody, such as a Fab fragment, as measured by, e.g., BIAcore™ surface plasmon resonance technology.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), equilibrium association constant ($K_A$), and $IC_{50}$. In certain aspects, inhibition by antibodies described herein (e.g., monoclonal antibody) or antigen-binding fragments thereof of ErbB ligand (e.g., neuregulin) binding to ErbB can be characterized by $IC_{50}$ values, which reflects the concentration of antibodies or antigen-binding fragments thereof achieving 50% inhibition of binding of ErbB ligand to ErbB. The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIAcore™ or Kinexa.

Affinity can be measured by common methods known in the art, including those described herein. For example, individual association ($k_{on}$) and dissociation ($k_{off}$) rate constants can be calculated from the resulting binding curves using the BIAevaluation software available through the vendor. Data are fit to a 1:1 binding model, which includes a term to correct for mass transport limited binding, should it be detected. From these rate constants, the apparent dissociation binding constant ($K_D$) for the interaction of the antibody (e.g., IgG) with the antigen (e.g., extracellular domain of ErbB) is calculated from the quotient of $k_{off}/k_{on}$. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

In a specific embodiment, an antibody or fragment thereof described herein binds to an ErbB extracellular domain and inhibits ligand binding to ErbB. As used herein, the term "inhibition" in the context of an ErbB binding to an ErbB ligand refers to at least the partial inhibition of binding of the ErbB to an ErbB ligand, and in certain embodiments, the complete inhibition of ErbB binding to an ErbB ligand. In a specific embodiment, an antibody or fragment thereof that binds to an ErbB extracellular domain inhibits the binding of ErbB to an ErbB ligand by at least 5%, 10%, 15%, 20%, 25%, 30%, 35%, 40%, 45%, 50%, 55%, 60%, 65%, 70%, 75%, 80%, 85%, 90%, 95%, 98%, or by 100% as assessed by methods described herein or known to one of skill in the art, e.g., ELISA assay, flow cytometry, or competition assay. In another specific embodiment, an antibody or fragment thereof that binds to an ErbB extracellular domain inhibits the binding of ErbB to an ErbB ligand by between 5-15%, 15-25%, 25-35%, 35-45%, 45-55%, 55-65%, 65-75%, 75-85%, 85-95%, 95-98%, or by 95-100% as assessed by methods described herein or known to one of skill in the art, e.g., ELISA assay, flow cytometry, or competition assay. In another specific embodiment, an antibody or fragment thereof that binds to an ErbB extracellular domain inhibits the binding of ErbB to an ErbB ligand by at least 1.2 fold, 1.5 fold, 2 fold, 2.5 fold, 3 fold, 3.5 fold. 4 fold, 5 fold, 5.5 fold, 6 fold, 6.5 fold, 7 fold, 7.5 fold, or 8 fold, or between 1.2-1.5 fold, 1.5-2 fold, 2.0-2.5 fold, 2.5-3.0 fold, 3.5-5.0 fold, or 5.0-10-fold as assessed by methods described herein or known to one of skill in the art, e.g., ELISA assay, flow cytometry, or competition assay.

In certain embodiments, the $IC_{50}$, which reflects the concentration of an antibody or an antigen-binding fragment thereof that achieves 50% inhibition of binding of ErbB ligand to ErbB, is used to describe the activity of an antibody or fragment described herein. Thus, in specific embodiments, an antibody or antigen-binding fragment described herein inhibits binding of ErbB ligand to ErbB with an $IC_{50}$ of at most about 10,000 nM, 1,000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 5 nM, 1 nM, 0.75 nM, 0.5 nM, 0.1 nM, 0.05 nM, 0.01 nM, 0.005 nM, or 0.001 nM, as assessed by methods described herein and/or known to one of skill in the art (e.g., ELISA assay or flow cytometry). In specific embodiments, an antibody or antigen-binding fragment described herein inhibits binding of ErbB ligand to ErbB with an $IC_{50}$ of at least about 10,000 nM, 1,000 nM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 5 nM, 1 nM, 0.75 nM, 0.5 nM, 0.1 nM, 0.05 nM, 0.01 nM, 0.005 nM, or 0.001 nM, as assessed by methods described herein and/or known to one of skill in the art (e.g., ELISA assay or flow cytometry). In particular embodiments, an antibody or antigen-binding fragment described herein inhibits binding of ErbB ligand to ErbB with an $IC_{50}$ in the range of about 0.01 nM to 10,000 nM, 0.01 nM to 1,000 nM, 0.1 nM to 500 nM, 0.1 nM to 100 nM, or 0.1 nM to 50 nM, as assessed by methods described herein and/or known to one of skill in the art (e.g., ELISA assay or flow cytometry).

In certain aspects, an antibody or antigen-binding fragment described herein can inhibit (e.g., partially inhibit) dimerization, e.g., heterodimerization, of ErbB. For example, ErbB receptor dimerization can be induced when ErbB ligand binds to ErbB. Alternatively, e.g., ErbB receptor dimerization can be induced upon overexpression of ErbB receptor. High or overexpression of ErbB in a cell refers to an expression level which is at least about 10%, 20%, 30%, 40%, 50%, 60%, 70%, 80%, 90%, 100%, 150%, 200%, 250%, 300%, 400%, or 500% more than the expression level of a reference cell known to have normal ErbB expression or ErbB activity or more than the average expression level of ErbB in a population of cells or samples known to have normal ErbB expression or ErbB activity. Expression levels of ErbB can be assessed by methods described herein or known to one of skill in the art (e.g., Western blotting, ELISA, or immunohistochemistry). Thus, in specific embodiments, antibodies described herein specifically bind to ErbB and inhibit (e.g., partially inhibit) dimerization of ErbB receptors by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., immunoprecipitation assay, relative to dimerization of ErbB receptors in the presence of ErbB ligand stimulation without any antibody or with an unrelated antibody (e.g., an antibody that does not immunospecifically bind to ErbB). In a specific embodiment, antibodies described herein specifically bind to ErbB and partially inhibit dimerization of ErbB receptors by about 25% to 75%. In a specific embodiment, antibodies described herein specifically bind to ErbB and inhibit dimerization of ErbB receptors by about 25% to 75% as assessed by methods described herein or known to one of skill in the art, e.g., by an immunoprecipitation assay, relative to dimerization of ErbB receptors in the presence of ErbB ligand stimulation without any antibody or with an unrelated antibody (e.g., an antibody that does not immunospecifically bind to ErbB).

Inhibition (e.g., partial inhibition) of dimerization of ErbB receptors by antibodies described herein can be assessed in the presence of ErbB ligand stimulation. For example, cells expressing ErbB can be contacted with ErbB ligand in the presence or absence of anti-ErbB antibodies described herein, and the level of ErbB receptor dimerization can be determined. In certain embodiments, ErbB ligand induced ErbB receptor dimerization in the absence of anti-ErbB antibody is at least about 1.5 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold higher than ErbB receptor dimerization in the presence of anti-ErbB antibody provided herein as assessed by methods described herein or known to one of skill in the art (e.g., immunoprecipitation assays). Phosphorylation of one or more tyrosine residues in the cytoplasmic domain of ErbB can, for example, be an indicator of ErbB receptor dimerization. In a specific embodiment, inhibition (e.g., partial inhibition) of dimerization is assessed by methods described herein, such as, e.g., co-localization or co-immunoprecipitation assays.

In another aspect, provided herein is an antibody(ies) or fragment(s) thereof that binds to an ErbB extracellular domain, wherein the antibody(ies) or fragment(s) thereof binds to an ErbB epitope comprising at least one, two, three, four, five, six, seven, eight, nine, ten or more amino acid residues, or between 1 to 4, 2 to 4, 1 to 5, 2 to 6, 5 to 8, 5 to 10, 8 to 10, or 1 to 10 amino acid residues within domain II of the ErbB extracellular domain, e.g., human extracellular domain, and at least one, two, three, four, five, six, seven, eight, nine, ten, eleven, twelve, thirteen, fourteen or fifteen amino acid residues, or between 1 to 4, 2 to 4, 1 to 5, 2 to 6, 5 to 8, 5 to 10, 8 to 10, 1 to 10, 5 to 15, 10 to 15, 1 to 15, 5 to 15, 1 to 20, 10 to 20 or 15 to 20 amino acid residues within domain III of the ErbB extracellular domain, e.g., human ErbB extracellular domain, and inhibits ligand-dependent and ligand-independent ErbB activation. In certain embodiments, the ErbB epitope comprises one, two, three, four, five, six, seven, eight, nine, or ten amino acid residues in domain II of the ErbB extracellular domain, e.g., human ErbB extracellular domain, and one, two, three, four, five, six, seven, eight, nine, ten, eleven, twelve, thirteen, fourteen, fifteen or more amino acid residues within domain III of the ErbB extracellular domain, e.g., human ErbB extracellular domain. In a specific embodiment, the ErbB epitope is a non-linear epitope. In a specific embodiment, the antibody or fragment binds to an ErbB extracellular domain and inhibits ligand binding to ErbB. In a specific embodiment, the antibody or antigen-binding fragment thereof inhibits neuregulin (for example, human neuregulin)-dependent ErbB activation. In another specific embodiment, the antibody or antigen-binding fragment thereof inhibits neuregulin 1-dependent ErbB activation. In a particular embodiment, the neuregulin 1 is neuregulin 1β1. In another specific embodiment, the antibody or antigen-binding fragment thereof inhibits neuregulin 2-dependent ErbB activation. In certain embodiments, the antibody or antigen-binding fragment thereof is a human, humanized or chimeric antibody or antigen-binding fragment thereof. In a specific embodiment, the antibody or antigen-binding fragment thereof is a monoclonal antibody or antigen-binding fragment. In another specific embodiment, the antibody is a human, humanized or chimeric monoclonal antibody or antigen-binding fragment thereof. In certain embodiments, the antibody or antigen-binding fragment thereof is isolated.

In certain embodiments, an antibody or fragment thereof described herein binds to an ErbB extracellular domain with a dissociation rate constant ($k_{off}$) of $8.5 \times 10^{-5}$ s$^{-1}$ or less, $5 \times 10^{-5}$ s$^{-1}$ or less, $2.5 \times 10^{-5}$ s$^{-1}$ or less, $1 \times 10^{-5}$ s$^{-1}$ or less, $8.5 \times 10^{-6}$ s$^{-1}$ or less, $5 \times 10^{-6}$ s$^{-1}$ or less, $2.5 \times 10^{-6}$ s$^{-1}$ or less, $1 \times 10^{-6}$ s$^{-1}$ or less, $8.5 \times 10^{-7}$ s$^{-1}$ or less, $5 \times 10^{-7}$ s$^{-1}$ or less, $2.5 \times 10^{-7}$ s$^{-1}$ or less, $1 \times 10^{-7}$ s$^{-1}$ or less, $8.5 \times 10^{-8}$ s$^{-1}$ or less, $5 \times 10^{-8}$ s$^{-1}$ or less, $2.5 \times 10^{-8}$ s$^{-1}$ or less, $1 \times 10^{-8}$ s$^{-1}$ or less, $8.5 \times 10^{-9}$ s$^{-1}$ or less, $5 \times 10^{-9}$ s$^{-1}$ or less, $2.5 \times 10^{-9}$ s$^{-1}$ or less, or $1 \times 10^{-9}$ s$^{-1}$ or less. In some embodiments, an antibody or fragment thereof described herein binds to an ErbB extracellular domain with a $k_{off}$ of between $9.5 \times 10^{-5}$ s$^{-1}$ to $1 \times 10^{-9}$ s$^{-1}$, $8.5 \times 10^{-5}$ s$^{-1}$ to $1 \times 10^{-9}$ s$^{-1}$, $5 \times 10^{-5}$ s$^{-1}$ to $1 \times 10^{-9}$ s$^{-1}$, $9.5 \times 10^{-5}$ s$^{-1}$ to $1 \times 10^{-8}$ s$^{-1}$, $5 \times 10^{-5}$ s$^{-1}$ to $1 \times 10^{-8}$ s$^{-1}$, $9.5 \times 10^{-5}$ s$^{-1}$ to $1 \times 10^{-7}$ s$^{-1}$, $5 \times 10^{-5}$ s$^{-1}$ to $1 \times 10^{-7}$ s$^{-1}$, $9.5 \times 10^{-5}$ s$^{-1}$ to $5 \times 10^{-6}$ s$^{-1}$, or $9.5 \times 10^{-5}$ s$^{-1}$ to $1 \times 10^{-5}$ s$^{-1}$. In certain embodiments, the $k_{off}$ is determined using a monovalent antibody, such as a Fab fragment, as measured by, e.g., BIAcore™ surface plasmon resonance technology. In a particular embodiment, the $k_{off}$ is determined using an assay described in Section 6, infra.

In certain embodiments, an antibody or fragment thereof described herein binds to an ErbB extracellular domain with an association rate constant ($k_{on}$) of at least $10^5$ M$^{-1}$ s$^{-1}$, at least $5 \times 10^5$ M$^{-1}$ s$^{-1}$, at least $10^6$ M$^{-1}$ s$^{-1}$, at least $5 \times 10^6$ M$^{-1}$ s$^{-1}$, at least $10^7$ M$^{-1}$ s$^{-1}$, at least $5 \times 10^7$ M$^{-1}$ s$^{-1}$, at least $10^8$ M$^{-1}$ s$^{-1}$, at least $5\ 10^8$ M$^{-1}$ s$^{-1}$ or at least $10^9$ M$^{-1}$ s$^{-1}$. In some embodiments, an antibody or fragment thereof described herein binds to an ErbB extracellular domain with a $k_{on}$ of between $1 \times 10^5$ M$^{-1}$ s$^{-1}$ to $5 \times 10^5$ M$^{-1}$ s$^{-1}$, $1 \times 10^5$ M$^{-1}$ s$^{-1}$ to $1 \times 10^6$ M$^{-1}$ s$^{-1}$, $1 \times 10^5$ M$^{-1}$s$^{-1}$ to $5 \times 10^6$ M$^{-1}$ s$^{-1}$, $1 \times 10^5$ M$^{-1}$ s$^{-1}$ to $1 \times 10^7$ M$^{-1}$ s$^{-1}$, $1 \times 10^5$ M$^{-1}$ s$^{-1}$ to $5 \times 10^7$ M$^{-1}$ s$^{-1}$, $1 \times 10^5$ M$^{-1}$ s$^{-1}$ to $10^8$ M$^{-1}$ s$^{-1}$, $1 \times 10^5$ M$^{-1}$ s$^{-1}$ to $1 \times 10^9$ M$^{-1}$ s$^{-1}$, $1 \times 10^6$ M$^{-1}$ s$^{-1}$ to $1 \times 10^7$ M$^{-1}$ s$^{-1}$, $1 \times 10^6$ M$^{-1}$ s$^{-1}$ to $1 \times 10^8$ M$^{-1}$ s$^{-1}$, $1 \times 10^6$ M$^{-1}$ s$^{-1}$ to $1 \times 10^9$ M$^{-1}$ s$^{-1}$, $1 \times 10^7$ M$^{-1}$ s$^{-1}$ to $1 \times 10^8$ M$^{-1}$ s$^{-1}$, $1 \times 10^7$ M$^{-1}$ s$^{-1}$ to $1 \times 10^9$ M$^{-1}$ s$^{-1}$, $1 \times 10^8$ M$^{-1}$ s$^{-1}$ to $1 \times 10^9$ M$^{-1}$ s$^{-1}$. In certain embodiments, the $k_{on}$ is determined using a monovalent antibody, such as a Fab fragment, as measured by, e.g., BIAcore™ surface plasmon resonance technology. In a particular embodiment, the $k_{on}$ is determined using an assay described in Section 6, infra.

In certain embodiments, an antibody or fragment thereof described herein binds to an ErbB extracellular domain with a $K_D$ of less than 375 pM, 350 pM, 325 pM, 300 pM, 275 pM, 250 pM, 225 pM, 200 pM, 175 pM, 150 pM, 125 pM, 100 pM, 75 pM, 50 pM, 45 pM, 40 pM, or 35 pM. In some embodiments, an antibody or fragment thereof described herein binds to an ErbB extracellular domain with a $k_D$ of 375 pM, 350 pM, 325 pM, 300 pM, 275 pM, 250 pM, 225 pM, 200 pM, 175 pM, 150 pM, 125 pM, 100 pM, 75 pM, or 50 pM, or between 375 pM to 300 pM, 375 pM to 200 pM, 375 pM to 100 pM, 350 pM to 250 pM, 350 pM to 200 pM, 300 pM to 150 pM, 300 pM to 100 pM, 300 pM to 50 pM, 300 pM to 200 pM, 300 pM to 150 pM, 300 pM to 100 pM, 300 pM to 50 pM, 275 pM to 200 pM, 275 pM to 175 pM, 275 pM to 150 pM, 275 pM to 100 pM, 275 pM to 50 pM, 250 pM to 200 pM, 250 pM to 150 pM, 250 pM to 100 pM, 250 pM to 50 pM, 200 pM to 150 pM, 200 pM to 100 pM, 200 to 50 pM, 150 pM to 100 pM, 150 pM to 50 pM, 100 pM to 50 pM, 200 to 40 pM, 150 pM to 40 pM, 150 pM to 40 pM, or 100 pM to 35 pM. In certain embodiments, the $k_D$ is calculated as the quotient of $k_{off}/k_{on}$, and the $k_{on}$ and $k_{off}$ are determined using a monovalent antibody, such as a Fab fragment, as measured by, e.g., BIAcore™ surface plasmon resonance technology.

In a specific embodiment, provided herein is an antibody (ies) or fragment(s) thereof that binds to an ErbB3 extracellular domain, e.g., a human ErbB3 extracellular domain, wherein the antibody(ies) or fragment(s) thereof binds to an ErbB3 epitope comprising at least one, two, three, four, five, six, seven, eight, nine, or ten amino acid residues, or between 1 to 4, 2 to 4, 1 to 5, 2 to 6, 5 to 8, 5 to 10, 8 to 10, 1 to 10, or 5 to 15 amino acid residues within domain II of the ErbB3 extracellular domain, e.g., human ErbB3 extracellular domain, and at least one, two, three, four, five, six, seven, eight, nine, ten, eleven, twelve, thirteen, fourteen or fifteen amino acid residues, or between 1 to 4, 2 to 4, 1 to 5, 2 to 6, 5 to 8, 5 to 10, 8 to 10, 1 to 10, 5 to 15, 10 to 15, 1 to 15, 5 to 15, 1 to 20, 10 to 20 or 15 to 20 amino acid residues within domain III of the ErbB3 extracellular domain, e.g., human ErbB3 extracellular domain, and inhibits ligand-dependent and ligand-independent ErbB3 activation. In certain embodiments, the ErbB3 epitope comprises one, two, three, four, five, six, seven, eight, nine ten or more amino acid residues in domain II of the ErbB3 extracellular domain and one, two, three, four, five, six, seven, eight, nine, ten, eleven, twelve, thirteen, fourteen, fifteen or more amino acid residues within domain III of the ErbB3 extracellular domain. In some embodiments, the ErbB3 epitope comprises one, two, three, or more of amino acid residues 291, 292, 294, 299, and 309 within domain II of human ErbB3 and one, two, three, four, five, six, seven, eight, nine or more of amino acid residues 310, 311, 317, 318, 319, 337, 339, 373, 375, 400, 401, 402, 403, 404, 406, 407, 408, 429, 431, 432, 433, 456, 457, 458 and 462 within domain III of human ErbB3. In a specific embodiment, the ErbB3 epitope is a non-linear epitope. In a specific embodiment, the antibody or fragment thereof binds to an ErbB3 extracellular domain and inhibits ligand binding to ErbB3. In a specific embodiment, the antibody or antigen-binding fragment thereof inhibits neuregulin (for example, human neuregulin)-dependent ErbB3 activation. In another specific embodiment, the antibody or antigen-binding fragment thereof inhibits neuregulin 1-dependent ErbB3 activation. In a particular embodiment, the neuregulin 1 is neuregulin 1β1. In another specific embodiment, the antibody or antigen-binding fragment thereof inhibits neuregulin 2-dependent ErbB3 activation. In certain embodiments, the antibody or antigen-binding fragment thereof is a human, humanized or chimeric antibody or antigen-binding fragment thereof. In a specific embodiment, the antibody or antigen-binding fragment thereof is a monoclonal antibody or antigen-binding fragment. In another specific embodiment, the antibody is a human, humanized or chimeric monoclonal antibody or antigen-binding fragment thereof. In certain embodiments, the antibody or antigen-binding fragment thereof is isolated.

In certain embodiments, an antibody or fragment thereof described herein binds to an ErbB3 extracellular domain with a dissociation rate constant ($k_{off}$) of $8.5 \times 10^{-5}$ s$^{-1}$ or less, $5 \times 10^{-5}$ s$^{-1}$ or less, $2.5 \times 10^{-5}$ s$^{-1}$ or less, $1 \times 10^{-5}$ s$^{-1}$ or less, $8.5 \times 10^{-6}$ s$^{-1}$ or less, $5 \times 10^{-6}$ s$^{-1}$ or less, $2.5 \times 10^{-6}$ s$^{-1}$ or less, $1 \times 10^{-6}$ s$^{-1}$ or less, $8.5 \times 10^{-7}$ s$^{-1}$ or less, $5 \times 10^{-7}$ s$^{-1}$ or less, $2.5 \times 10^{-7}$ s$^{-1}$ or less, $1 \times 10^{-7}$ s$^{-1}$ or less, $8.5 \times 10^{-8}$ s$^{-1}$ or less, $5 \times 10^{-8}$ s$^{-1}$ or less, $2.5 \times 10^{-8}$ s$^{-1}$ or less, $1 \times 10^{-8}$ s$^{-1}$ or less, $8.5 \times 10^{-9}$ s$^{-1}$ or less, $5 \times 10^{-9}$ s$^{-1}$ or less, $2.5 \times 10^{-9}$ s$^{-1}$ or less, or $1 \times 10^{-9}$ s$^{-1}$ or less. In some embodiments, an antibody or fragment thereof described herein binds to an ErbB3 extracellular domain with a $k_{off}$ of between $9.5 \times 10^{-5}$ s$^{-1}$ to $1 \times 10^{-9}$ s$^{-1}$, $8.5 \times 10^{-5}$ s$^{-1}$ to $1 \times 10^{-9}$ s$^{-1}$, $5 \times 10^{-5}$ s$^{-1}$ to $1 \times 10^{-9}$ s$^{-1}$, $9.5 \times 10^{-5}$ s$^{-1}$ to $1 \times 10^{-8}$ s$^{-1}$, $5 \times 10^{-5}$ s$^{-1}$ to $1 \times 10^{-8}$ s$^{-1}$, $9.5 \times 10^{-5}$ s$^{-1}$ to $1 \times 10^{-7}$ s$^{-1}$, $5 \times 10^{-5}$ s$^{-1}$ to $1 \times 10^{-7}$ s$^{-1}$, $9.5 \times 10^{-5}$ s$^{-1}$ to $5 \times 10^{-6}$ s$^{-1}$, or $9.5 \times 10^{-5}$ s$^{-1}$ to $1 \times 10^{-5}$ s$^{-1}$. In certain embodiments, the $k_{off}$ is determined using a monovalent antibody, such as a Fab fragment, as measured by, e.g., BIAcore™ surface plasmon resonance technology. In a particular embodiment, the $k_{off}$ is determined using an assay described in Section 6, infra.

In certain embodiments, an antibody or fragment thereof described herein binds to an ErbB3 extracellular domain with an association rate constant ($k_{on}$) of at least $10^5$ M$^{-1}$ s$^{-1}$, at least $5 \times 10^5$ M$^{-1}$ s$^{-1}$, at least $10^6$ M$^{-1}$ s$^{-1}$, at least $5 \times 10^6$ M$^{-1}$ s$^{-1}$, at least $10^7$ M$^{-1}$ s$^{-1}$, at least $5 \times 10^7$ M$^{-1}$ s$^{-1}$, at least $10^8$ M$^{-1}$ s$^{-1}$, at least $5 \cdot 10^8$ M$^{-1}$ s$^{-1}$ or at least $10^9$ M$^{-1}$ s$^{-1}$. In some embodiments, an antibody or fragment thereof described herein binds to an ErbB3 extracellular domain with a $k_{off}$ between $1 \times 10^5$ M$^{-1}$ s$^{-1}$ to $5 \times 10^5$ M$^{-1}$ s$^{-1}$, $1 \times 10^5$ M$^{-1}$ s$^{-1}$ to $1 \times 10^6$ M$^{-1}$ s$^{-1}$, $1 \times 10^5$ M$^{-1}$ s$^{-1}$ to $5 \times 10^6$ M$^{-1}$ s$^{-1}$, $1 \times 10^5$ M$^{-1}$ s$^{-1}$ to $1 \times 10^7$ M$^{-1}$ s$^{-1}$, $1 \times 10^5$ M$^{-1}$ s$^{-1}$ to $5 \times 10^7$ M$^{-1}$ s$^{-1}$, $1 \times 10^5$ M$^{-1}$ s$^{-1}$ to $10^8$ M$^{-1}$ s$^{-1}$, $1 \times 10^5$ M$^{-1}$ s$^{-1}$ to $1 \times 10^9$ M$^{-1}$ s$^{-1}$, $1 \times 10^6$ M$^{-1}$ s$^{-1}$ to $1 \times 10^7$ M$^{-1}$ s$^{-1}$, $1 \times 10^6$ M$^{-1}$s$^{-1}$ to $1 \times 10^8$ M$^{-1}$ s$^{-1}$, $1 \times 10^6$ M$^{-1}$ s$^{-1}$ to $1 \times 10^9$ M$^{-1}$ s$^{-1}$, $1 \times 10^7$ M$^{-1}$ s$^{-1}$ to $1 \times 10^8$ M$^{-1}$ s$^{-1}$, $1 \times 10^7$ M$^{-1}$s$^{-1}$ to $1 \times 10^9$ M$^{-1}$ s$^{-1}$, $1 \times 10^8$ M$^{-1}$ s$^{-1}$ to $1 \times 10^9$ M$^{-1}$ s$^{-1}$. In certain embodiments, the $k_{on}$ is determined using a monovalent antibody, such as a Fab fragment, as measured by, e.g., BIAcore™ surface plasmon resonance technology. In a particular embodiment, the $k_{on}$, is determined using an assay described in Section 6, infra.

In certain embodiments, an antibody or fragment thereof described herein binds to an ErbB3 extracellular domain with a $K_D$ of less than 375 pM, 350 pM, 325 pM, 300 pM, 275 pM, 250 pM, 225 pM, 200 pM, 175 pM, 150 pM, 125 pM, 100 pM, 75 pM, 50 pM, 45 pM, 40 pM, or 35 pM. In some embodiments, an antibody or fragment thereof described herein binds to an ErbB3 extracellular domain with a $k_D$ of 375 pM, 350 pM, 325 pM, 300 pM, 275 pM, 250 pM, 225 pM, 200 pM, 175 pM, 150 pM, 125 pM, 100 pM, 75 pM, or 50 pM, or between 375 pM to 300 pM, 375 pM to 200 pM, 375 pM to 100 pM, 350 pM to 250 pM, 350 pM to 200 pM, 300 pM to 150 pM, 300 pM to 100 pM, 300 pM to 50 pM, 300 pM to 200 pM, 300 pM to 150 pM, 300 pM to 100 pM, 300 pM to 50 pM, 275 pM to 200 pM, 275 pM to 175 pM, 275 pM to 150 pM, 275 pM to 100 pM, 275 pM to 50 pM, 250 pM to 200 pM, 250 pM to 150 pM, 250 pM to 100 pM, 250 pM to 50 pM, 200 pM to 150 pM, 200 pM to 100 pM, 200 to 50 pM, 150 pM to 100 pM, 150 pM to 50 pM, 100 pM to 50 pM, 200 to 40 pM, 150 pM to 40 pM, 150 pM to 40 pM, or 100 pM to 35 pM. In certain embodiments, the $k_D$ is calculated as the quotient of $k_{off}/k_{on}$, and the $k_{on}$ and $k_{off}$ are determined using a monovalent antibody, such as a Fab fragment, as measured by, e.g., BIAcore™ surface plasmon resonance technology.

In another embodiment, provided herein is an antibody(ies) or fragment(s) thereof that binds to an ErbB1 extracellular domain, e.g., human ErbB1 extracellular domain, wherein the antibody(ies) or fragment(s) thereof binds to an ErbB1 epitope comprising at least one, two, three, four, five, six, seven, eight, nine or ten amino acid residues, or between 1 to 4, 2 to 4, 1 to 5, 2 to 6, 5 to 8, 5 to 10, 8 to 10, 1 to 10, 5 to 15, 10 to 15, 1 to 15, 5 to 15, 1 to 20, 10 to 20 or 15 to 20 amino acid residues within domain II of the ErbB1 extracellular domain, e.g., human ErbB1 extracellular domain, and at least one, two, three, four, five, six, seven, eight, nine or ten, eleven, twelve, thirteen, fourteen or fifteen amino acid residues, or between 1 to 4, 2 to 4, 1 to 5, 2 to 6, 5 to 8, 5 to 10, 8 to 10, 1 to 10, 5 to 15, 10 to 15, 1 to 15, 5 to 15, 1 to 20, 10 to 20 or 15 to 20 amino acid residues within domain III of the ErbB1 extracellular domain, e.g., human ErbB1 extracellular domain, and inhibits ligand-dependent and ligand-independent ErbB1 activation. In certain embodiments, the ErbB1 epitope comprises one, two, three, four, five, six, seven, eight, nine or ten amino acid residues in domain II of the ErbB1 extracellular domain and one, two, three, four, five, six, seven, eight, nine, ten, eleven, twelve, thirteen, fourteen, fifteen or more amino acid residues within domain III of the ErbB1 extracellular domain. In some embodiments, the ErbB1 epitope comprises one, two, three, or more of amino acid residues 274, 286, 287, 289, 291, 292, 293, 294, 295, 302, 309, 310, and 311 within domain II of human ErbB1 and one, two, three, four, five, six, seven, eight, nine or more of amino acid residues 312, 314, 318, 319, 320, 322, 340, 342, 343, 344, 378, 379, 403, 404, 405, 406, 407, 411, 431, 433, 434, 458, 459, 460, 461, and 462 within domain III of human ErbB1. In certain embodiments, the ErbB1 epitope comprises one, two, three, four or more of amino acid residues 292, 293, 295, 302, and 310 within domain II of human ErbB1 and one, two, three, four, five, six, seven, eight, nine, ten or more of amino acid residues 312, 314, 318, 319, 320, 322, 340, 342, 343, 344, 378, 379, 403, 404, 405, 406, 407, 411, 431, 433, 434, 458, 459, 460, 461, and 462 within domain III of human ErbB1. In a specific embodiment, the ErbB1 epitope is a non-linear epitope. In a specific embodiment, the antibody or fragment thereof binds to an ErbB1 extracellular domain and inhibits ligand binding to ErbB1. In a specific embodiment, the antibody or antigen-binding fragment thereof inhibits neuregulin (for example, human neuregulin)-dependent ErbB1 activation. In another specific embodiment, the antibody or antigen-binding fragment thereof inhibits neuregulin 1-dependent ErbB1 activation. In a particular embodiment, the neuregulin 1 is neuregulin 1β1. In another specific embodiment, the antibody or antigen-binding fragment thereof inhibits neuregulin 2-dependent ErbB1 activation. In certain embodiments, the antibody or antigen-binding fragment thereof is a human, humanized or chimeric antibody or antigen-binding fragment thereof. In a specific embodiment, the antibody or antigen-binding fragment thereof is a monoclonal antibody or antigen-binding fragment. In another specific embodiment, the antibody is a human, humanized or chimeric monoclonal antibody or antigen-binding fragment thereof. In certain embodiments, the antibody or antigen-binding fragment thereof is isolated.

In certain embodiments, an antibody or fragment thereof described herein binds to an ErbB1 extracellular domain with a dissociation rate constant ($k_{off}$) of $8.5 \times 10^{-5}$ s$^{-1}$ or less, $5 \times 10^{-5}$ s$^{-1}$ or less, $2.5 \times 10^{-5}$ s$^{-1}$ or less, $1 \times 10^{-5}$ s$^{-1}$ or less, $8.5 \times 10^{-6}$ s$^{-1}$ or less, $5 \times 10^{-6}$ s$^{-1}$ or less, $2.5 \times 10^{-6}$ s$^{-1}$ or less, $1 \times 10^{-6}$ s$^{-1}$ or less, $8.5 \times 10^{-7}$ s$^{-1}$ or less, $5 \times 10^{-7}$ s$^{-1}$ or less, $2.5 \times 10^{-7}$ s$^{-1}$ or less, $1 \times 10^{-7}$ s$^{-1}$ or less, $8.5 \times 10^{-8}$ s$^{-1}$ or less, $5 \times 10^{-8}$ s$^{-1}$ or less, $2.5 \times 10^{-8}$ s$^{-1}$ or less, $1 \times 10^{-8}$ s$^{-1}$ or less, $8.5 \times 10^{-9}$ s$^{-1}$ or less, $5 \times 10^{-9}$ s$^{-1}$ or less, $2.5 \times 10^{-9}$ s$^{-1}$ or less, or $1 \times 10^{-9}$ s$^{-1}$ or less. In some embodiments, an antibody or fragment thereof described herein binds to an ErbB1 extracellular domain with a $k_{off}$ of between $9.5 \times 10^{-5}$ s$^{-1}$ to $1 \times 10^{-9}$ s$^{-1}$, $8.5 \times 10^{-5}$ s$^{-1}$ to $1 \times 10^{-9}$ s$^{-1}$, $5 \times 10^{-5}$ s$^{-1}$ to $1 \times 10^{-9}$ s$^{-1}$, $9.5 \times 10^{-5}$ s$^{-1}$ to $1 \times 10^{-8}$ s$^{-1}$, $5 \times 10^{-5}$ s$^{-1}$ to $1 \times 10^{-8}$ s$^{-1}$, $9.5 \times 10^{-5}$ s$^{-1}$ to $1 \times 10^{-7}$ s$^{-1}$, $5 \times 10^{-5}$ s$^{-1}$ to $1 \times 10^{-7}$ s$^{-1}$, $9.5 \times 10^{-5}$ s$^{-1}$ to $5 \times 10^{-6}$ s$^{-1}$, or $9.5 \times 10^{-5}$ s$^{-1}$ to $1 \times 10^{-5}$ s$^{-1}$. In certain embodiments, the $k_{off}$ is determined using a monovalent antibody, such as a Fab fragment, as measured by, e.g., BIAcore™ surface plasmon resonance technology. In a particular embodiment, the $k_{off}$ is determined using an assay described in Section 6, infra.

In certain embodiments, an antibody or fragment thereof described herein binds to an ErbB1 extracellular domain with an association rate constant ($k_{on}$) of at least $10^5$ M$^{-1}$ s$^{-1}$, at least $5 \times 10^5$ M$^{-1}$ s$^{-1}$, at least $10^6$ M$^{-1}$ s$^{-1}$, at least $5 \times 10^6$ M$^{-1}$ s$^{-1}$, at least $10^7$ M$^{-1}$ s$^{-1}$, at least $5 \times 10^7$ M$^{-1}$ s$^{-1}$, at least $10^8$ M$^{-1}$ s$^{-1}$, at least $5 \; 10^8$ M$^{-1}$ s$^{-1}$ or at least $10^9$ M$^{-1}$ s$^{-1}$. In some embodiments, an antibody or fragment thereof described herein binds to an ErbB1 extracellular domain with a $k_{on}$ of between $1 \times 10^5$ M$^{-1}$ s$^{-1}$ to $5 \times 10^5$ M$^{-1}$ s$^{-1}$, $1 \times 10^5$ M$^{-1}$ s$^{-1}$ to $1 \times 10^6$ M$^{-1}$ s$^{-1}$, $1 \times 10^5$ M$^{-1}$ s$^{-1}$ to $5 \times 10^6$ M$^{-1}$ s$^{-1}$, $1 \times 10^5$ M$^{-1}$ s$^{-1}$ to $1 \times 10^7$ M$^{-1}$ s$^{-1}$, $1 \times 10^5$ M$^{-1}$ s$^{-1}$ to $5 \times 10^7$ M$^{-1}$ s$^{-1}$, $1 \times 10^5$ M$^{-1}$ s$^{-1}$ to $10^8$ M$^{-1}$ s$^{-1}$, $1 \times 10^5$ M$^{-1}$ s$^{-1}$ to $1 \times 10^9$ M$^{-1}$ s$^{-1}$, $1 \times 10^6$ M$^{-1}$ s$^{-1}$ to $1 \times 10^7$ M$^{-1}$ s$^{-1}$, $1 \times 10^6$ M$^{-1}$s$^{-1}$ to $1 \times 10^8$ M$^{-1}$ s$^{-1}$, $1 \times 10^6$ M$^{-1}$ s$^{-1}$ to $1 \times 10^9$ M$^{-1}$ s$^{-1}$, $1 \times 10^7$ M$^{-1}$ s$^{-1}$ to $1 \times 10^8$ M$^{-1}$ s$^{-1}$, $1 \times 10^7$ M$^{-1}$s$^{-1}$ to $1 \times 10^9$ M$^{-1}$ s$^{-1}$, $1 \times 10^8$ M$^{-1}$ s$^{-1}$ to $1 \times 10^9$ M$^{-1}$ s$^{-1}$. In certain embodiments, the $k_{on}$ is determined using a monovalent antibody, such as a Fab fragment, as measured by, e.g., BIAcore™ surface plasmon resonance technology. In a particular embodiment, the $k_{on}$ is determined using an assay described in Section 6, infra.

In certain embodiments, an antibody or fragment thereof described herein binds to an ErbB1 extracellular domain with a $K_D$ of less than 375 pM, 350 pM, 325 pM, 300 pM, 275 pM, 250 pM, 225 pM, 200 pM, 175 pM, 150 pM, 125 pM, 100 pM, 75 pM, 50 pM, 45 pM, 40 pM, or 35 pM. In some embodiments, an antibody or fragment thereof described herein binds to an ErbB1 extracellular domain with a $k_D$ of 375 pM, 350 pM, 325 pM, 300 pM, 275 pM, 250 pM, 225 pM, 200 pM, 175 pM, 150 pM, 125 pM, 100 pM, 75 pM, or 50 pM, or between 375 pM to 300 pM, 375 pM to 200 pM, 375 pM to 100 pM, 350 pM to 250 pM, 350 pM to 200 pM, 300 pM to 150 pM, 300 pM to 100 pM, 300 pM to 50 pM, 300 pM to 200 pM, 300 pM to 150 pM, 300 pM to 100 pM, 300 pM to 50 pM, 275 pM to 200 pM, 275 pM to 175 pM, 275 pM to 150 pM, 275 pM to 100 pM, 275 pM to 50 pM, 250 pM to 200 pM, 250 pM to 150 pM, 250 pM to 100 pM, 250 pM to 50 pM, 200 pM to 150 pM, 200 pM to 100 pM, 200 to 50 pM, 150 pM to 100 pM, 150 pM to 50 pM, 100 pM to 50 pM, 200 to 40 pM, 150 pM to 40 pM, 150 pM to 40 pM, or 100 pM to 35 pM. In certain embodiments, the $k_D$ is calculated as the quotient of $k_{off}/k_{on}$, and the $k_{on}$ and $k_{off}$ are determined using a monovalent antibody, such as a Fab fragment, as measured by, e.g., BIAcore™ surface plasmon resonance technology.

In another embodiment, provided herein is an antibody(ies) or fragment(s) thereof that binds to an ErbB4 extracellular domain, e.g., a human ErbB4 extracellular domain, wherein the antibody(ies) or fragment(s) thereof binds to an ErbB4 epitope comprising at least one, two, three, four, five, six, seven, eight, nine or ten amino acid residues, or between 1 to 4, 2 to 4, 1 to 5, 2 to 6, 5 to 8, 5 to 10, 8 to 10, or 1 to 10 amino acid residues within domain II of the ErbB4 extracellular domain, e.g., human ErbB4 extracellular domain, and at least one, two, three, four, five, six, seven, eight, nine, ten, eleven, twelve, thirteen, fourteen or fifteen amino acid residues, or between 1 to 4, 2 to 4, 1 to 5, 2 to 6, 5 to 8, 5 to 10, 8 to 10, 1 to 10, 5 to 15, 10 to 15, 1 to 15, 5 to 15, 1 to 20, 10 to 20 or 15 to 20 amino acid residues within domain III of the ErbB4 extracellular domain, e.g., human ErbB4 extracellular domain, and inhibits ligand-dependent and ligand-independent ErbB4 activation. In certain embodiments, the ErbB4 epitope comprises one, two, three, four, five, six, seven, eight, nine or ten amino acid residues in domain II of the ErbB4 extracellular domain, e.g., human ErbB4 extracellular domain, and one, two, three, four, five, six, seven, eight, nine, ten, eleven, twelve, thirteen, fourteen, fifteen or more amino acid residues within domain III of the ErbB4 extracellular domain, e.g., human ErbB4 extracellular domain. In some embodiments, the ErbB4 epitope comprises one, two, three, or more of amino acid residues 270, 271, 288, 289, 290, 291, 292, 293, 296, 301, 305, 306, and 307 within domain II of human ErbB4 and one, two, three, four, five, six, seven, eight, nine or more of amino acid residues 308, 310, 313, 314, 315, 318, 336, 338, 339, 340, 372, 374, 399, 400, 401, 402, 403, 405, 406, 429, 430, 431, 432, 454, 455, 456, 457, and 458 within domain III of human ErbB4. In certain embodiments, the ErbB4 epitope comprises one, two, three, four or more of amino acid residues 288, 289, 291, 296, and 306 within domain II of human ErbB4 and one, two, three, four, five, six, seven, eight, nine or more of amino acid residues 308, 310, 313, 314, 315, 318, 336, 338, 339, 340, 372, 374, 399, 400, 401, 402, 403, 405, 406, 429, 430, 431, 432, 454, 455, 456, 457, and 458 within domain III of human ErbB4. In a specific embodiment, the ErbB4 epitope is a non-linear epitope. In a specific embodiment, the antibody or fragment thereof binds to an ErbB4 extracellular domain and inhibits ligand binding to ErbB4. In a specific embodiment, the antibody or antigen-binding fragment thereof inhibits neuregulin (for example, human neuregulin)-dependent ErbB4 activation. In another specific embodiment, the antibody or antigen-binding fragment thereof inhibits neuregulin 1-dependent ErbB4 activation. In a particular embodiment, the neuregulin 1 is neuregulin 1β1. In another specific embodiment, the antibody or antigen-binding fragment thereof inhibits neuregulin 2-dependent ErbB4 activation. In certain embodiments, the antibody or antigen-binding fragment thereof is a human, humanized or chimeric antibody or antigen-binding fragment thereof. In a specific embodiment, the antibody or antigen-binding fragment thereof is a monoclonal antibody or antigen-binding fragment. In another specific embodiment, the antibody is a human, humanized or chimeric monoclonal antibody or antigen-binding fragment thereof. In certain embodiments, the antibody or antigen-binding fragment thereof is isolated.

In certain embodiments, an antibody or fragment thereof described herein binds to an ErbB4 extracellular domain with a dissociation rate constant ($k_{off}$) of $8.5 \times 10^{-5}$ $s^{-1}$ or less, $5 \times 10^{-5}$ $s^{-1}$ or less, $2.5 \times 10^{-5}$ $s^{-1}$ or less, $1 \times 10^{-5}$ $s^{-1}$ or less, $8.5 \times 10^{-6}$ $s^{-1}$ or less, $5 \times 10^{-6}$ $s^{-1}$ or less, $2.5 \times 10^{-6}$ $s^{-1}$ or less, $1 \times 10^{-6}$ $s^{-1}$ or less, $8.5 \times 10^{-7}$ $s^{-1}$ or less, $5 \times 10^{-7}$ $s^{-1}$ or less, $2.5 \times 10^{-7}$ $s^{-1}$ or less, $1 \times 10^{-7}$ $s^{-1}$ or less, $8.5 \times 10^{-8}$ $s^{-1}$ or less, $5 \times 10^{-8}$ $s^{-1}$ or less, $2.5 \times 10^{-8}$ $s^{-1}$ or less, $1 \times 10^{-8}$ $s^{-1}$ or less, $8.5 \times 10^{-9}$ $s^{-1}$ or less, $5 \times 10^{-9}$ $s^{-1}$ or less, $2.5 \times 10^{-9}$ $s^{-1}$ or less, or $1 \times 10^{-9}$ $s^{-1}$ or less. In some embodiments, an antibody or fragment thereof described herein binds to an ErbB4 extracellular domain with a $k_{off}$ of between $9.5 \times 10^{-5}$ $s^{-1}$ to $1 \times 10^{-9}$ $s^{-1}$, $8.5 \times 10^{-5}$ $s^{-1}$ to $1 \times 10^{-9}$ $s^{-1}$, $5 \times 10^{-5}$ $s^{-1}$ to $1 \times 10^{-9}$ $s^{-1}$, $9.5 \times 10^{-5}$ $s^{-1}$ to $1 \times 10^{-8}$ $s^{-1}$, $5 \times 10^{-5}$ $s^{-1}$ to $1 \times 10^{-8}$ $s^{-1}$, $9.5 \times 10^{-5}$ $s^{-1}$ to $1 \times 10^{-7}$ $s^{-1}$, $5 \times 10^{-5}$ $s^{-1}$ to $1 \times 10^{-7}$ $s^{-1}$, $9.5 \times 10^{-5}$ $s^{-1}$ to $5 \times 10^{-6}$ $s^{-1}$, or $9.5 \times 10^{-5}$ $s^{-1}$ to $1 \times 10^{-5}$ $s^{-1}$. In certain embodiments, the $k_{off}$ is determined using a monovalent antibody, such as a Fab fragment, as measured by, e.g., BIAcore™ surface plasmon resonance technology. In a particular embodiment, the $k_{off}$ is determined using an assay described in Section 6, infra.

In certain embodiments, an antibody or fragment thereof described herein binds to an ErbB4 extracellular domain with an association rate constant ($k_{on}$) of at least $10^5$ $M^{-1}$ $s^{-1}$, at least $5 \times 10^5$ $M^{-1}$ $s^{-1}$, at least $10^6$ $M^{-1}$ $s^{-1}$, at least $5 \times 10^6$ $M^{-1}$ $s^{-1}$, at least $10^7$ $M^{-1}$ $s^{-1}$, at least $5 \times 10^7$ $M^{-1}$ $s^{-1}$, at least $10^8$ $M^{-1}$ $s^{-1}$, at least $5 \; 10^8$ $M^{-1}$ $s^{-1}$ or at least $10^9$ $M^{-1}$ $s^{-1}$. In some embodiments, an antibody or fragment thereof described herein binds to an ErbB4 extracellular domain with a $k_{off}$ between $1 \times 10^5$ $M^{-1}$ $s^{-1}$ to $5 \times 10^5$ $M^{-1}$ $s^{-1}$, $1 \times 10^5$ $M^{-1}$ $s^{-1}$ to $1 \times 10^6$ $M^{-1}$ $s^{-1}$, $1 \times 10^5$ $M^{-1}$ $s^{-1}$ to $5 \times 10^6$ $M^{-1}$ $s^{-1}$, $1 \times 10^5$ $M^{-1}$ $s^{-1}$ to $1 \times 10^7$ $M^{-1}$ $s^{-1}$, $1 \times 10^5$ $M^{-1}$ $s^{-1}$ to $5 \times 10^7$ $M^{-1}$ $s^{-1}$, $1 \times 10^5$ $M^{-1}$ $s^{-1}$ to $10^8$ $M^{-1}$ $s^{-1}$, $1 \times 10^5$ $M^{-1}$ $s^{-1}$ to $1 \times 10^9$ $M^{-1}$ $s^{-1}$, $1 \times 10^6$ $M^{-1}$ $s^{-1}$ to $1 \times 10^7$ $M^{-1}$ $s^{-1}$, $1 \times 10^6$ $M^{-1}$ $s^{-1}$ to $1 \times 10^8$ $M^{-1}$ $s^{-1}$, $1 \times 10^6$ $M^{-1}$ $s^{-1}$ to $1 \times 10^9$ $M^{-1}$ $s^{-1}$, $1 \times 10^7$ $M^{-1}$ $s^{-1}$ to $1 \times 10^8$ $M^{-1}$ $s^{-1}$, $1 \times 10^7$ $M^{-1}$ $s^{-1}$ to $1 \times 10^9$ $M^{-1}$ $s^{-1}$, $1 \times 10^8$ $M^{-1}$ $s^{-1}$ to $1 \times 10^9$ $M^{-1}$ $s^{-1}$. In certain embodiments, the $k_{on}$ is determined using a monovalent antibody, such as a Fab fragment, as measured by, e.g., BIAcore™ surface plasmon resonance technology. In a particular embodiment, the $k_{on}$ is determined using an assay described in Section 6, infra.

In certain embodiments, an antibody or fragment thereof described herein binds to an ErbB4 extracellular domain with a $K_D$ of less than 375 pM, 350 pM, 325 pM, 300 pM, 275 pM, 250 pM, 225 pM, 200 pM, 175 pM, 150 pM, 125 pM, 100 pM, 75 pM, 50 pM, 45 pM, 40 pM, or 35 pM. In some embodiments, an antibody or fragment thereof described herein binds to an ErbB4 extracellular domain with a $k_D$ of 375 pM, 350 pM, 325 pM, 300 pM, 275 pM, 250 pM, 225 pM, 200 pM, 175 pM, 150 pM, 125 pM, 100 pM, 75 pM, or 50 pM, or between 375 pM to 300 pM, 375 pM to 200 pM, 375 pM to 100 pM, 350 pM to 250 pM, 350 pM to 200 pM, 300 pM to 150 pM, 300 pM to 100 pM, 300 pM to 50 pM, 300 pM to 200 pM, 300 pM to 150 pM, 300 pM to 100 pM, 300 pM to 50 pM, 275 pM to 200 pM, 275 pM to 175 pM, 275 pM to 150 pM, 275 pM to 100 pM, 275 pM to 50 pM, 250 pM to 200 pM, 250 pM to 150 pM, 250 pM to 100 pM, 250 pM to 50 pM, 200 pM to 150 pM, 200 pM to 100 pM, 200 to 50 pM, 150 pM to 100 pM, 150 pM to 50 pM, 100 pM to 50 pM, 200 to 40 pM, 150 pM to 40 pM, 150 pM to 40 pM, or 100 pM to 35 pM. In certain embodiments, the $k_D$ is calculated as the quotient of $k_{off}/k_{on}$, and the $k_{on}$ and $k_{off}$ are determined using a monovalent antibody, such as a Fab fragment, as measured by, e.g., BIAcore™ surface plasmon resonance technology.

In another aspect, provided herein is an antibody(ies) or fragment(s) thereof that binds to an epitope of ErbB3 comprising at least one, two, three, four or all of amino acid residues selected from human ErbB3 amino acid residues 291, 292, 294, 299, and 309, and inhibits ligand-dependent and ligand-independent ErbB3 activation. In a specific embodiment, the ErbB3 epitope is non-linear. In another specific embodiment, the antibody or fragment thereof binds an ErbB3 epitope and inhibits ligand binding to ErbB3. In a specific embodiment, the antibody or antigen-binding fragment thereof inhibits neuregulin (for example, human neuregulin)-dependent ErbB3 activation. In another specific embodiment, the antibody or antigen-binding fragment thereof inhibits neuregulin 1-dependent ErbB3 activation. In a particular embodiment, the neuregulin 1 is neuregulin 1β1. In another specific embodiment, the antibody or antigen-binding fragment thereof inhibits neuregulin 2-dependent ErbB3 activation. In certain embodiments, the antibody or antigen-binding fragment thereof is a human, humanized or chimeric antibody or antigen-binding fragment thereof. In a specific embodiment, the antibody or antigen-binding fragment thereof is a monoclonal antibody or antigen-binding fragment. In another specific embodiment, the antibody is a human, humanized or chimeric monoclonal antibody or antigen-binding fragment thereof. In certain embodiments, the antibody or antigen-binding fragment thereof is isolated.

In certain embodiments, an antibody or fragment thereof described herein binds to the ErbB3 epitope with a dissociation rate constant ($k_{off}$) of $8.5 \times 10^{-5}$ $s^{-1}$ or less, $5 \times 10^{-5}$ $s^{-1}$ or less, $2.5 \times 10^{-5}$ $s^{-1}$ or less, $1 \times 10^{-5}$ $s^{-1}$ or less, $8.5 \times 10^{-6}$ $s^{-1}$ or less, $5 \times 10^{-6}$ $s^{-1}$ or less, $2.5 \times 10^{-6}$ $s^{-1}$ or less, $1 \times 10^{-6}$ $s^{-1}$ or less, $8.5 \times 10^{-7}$ $s^{-1}$ or less, $5 \times 10^{-7}$ $s^{-1}$ or less, $2.5 \times 10^{-7}$ $s^{-1}$ or less, $1 \times 10^{-7}$ $s^{-1}$ or less, $8.5 \times 10^{-8}$ $s^{-1}$ or less, $5 \times 10^{-8}$ $s^{-1}$ or less, $2.5 \times 10^{-8}$ $s^{-1}$ or less, $1 \times 10^{-8}$ $s^{-1}$ or less, $8.5 \times 10^{-9}$ $s^{-1}$ or less, $5\times10^{-9}$ s$^{-1}$ or less, $2.5\times10^{-9}$ s$^{-1}$ or less, or $1\times10^{-9}$ s$^{-1}$ or less. In some embodiments, an antibody or fragment thereof described herein binds to the ErbB3 epitope with a $k_{off}$ of between $9.5\times10^{-5}$ s$^{-1}$ to $1\times10^{-9}$ s$^{-1}$, $8.5\times10^{-5}$ s$^{-1}$ to $1\times10^{-9}$ s$^{-1}$, $5\times10^{-5}$ s$^{-1}$ to $1\times10^{-9}$ s$^{-1}$, $9.5\times10^{-5}$ s$^{-1}$ to $1\times10^{-8}$ s$^{-1}$, $5\times10^{-5}$ s$^{-1}$ to $1\times10^{-8}$ s$^{-1}$, $9.5\times10^{-5}$ s$^{-1}$ to $1\times10^{-7}$ s$^{-1}$, $5\times10^{-5}$ s$^{-1}$ to $1\times10^{-7}$ s$^{-1}$, $9.5\times10^{-5}$ s$^{-1}$ to $5\times10^{-6}$ s$^{-1}$, or $9.5\times10^{-5}$ s$^{-1}$ to $1\times10^{-5}$ s$^{-1}$. In certain embodiments, the $k_{off}$ is determined using a monovalent antibody, such as a Fab fragment, as measured by, e.g., BIAcore™ surface plasmon resonance technology. In a particular embodiment, the $k_{off}$ is determined using an assay described in Section 6, infra.

In certain embodiments, an antibody or fragment thereof described herein binds to the ErbB3 epitope with an association rate constant ($k_{on}$) of at least $10^5$ M$^{-1}$ s$^{-1}$, at least $5\times10^5$ M$^{-1}$ s$^{-1}$, at least $10^6$ M$^{-1}$ s$^{-1}$, at least $5\times10^6$ M$^{-1}$ s$^{-1}$, at least $10^7$ M$^{-1}$ s$^{-1}$, at least $5\times10^7$ M$^{-1}$ s$^{-1}$, at least $10^8$ M$^{-1}$ s$^{-1}$, at least $5\ 10^8$ M$^{-1}$ s$^{-1}$ or at least $10^9$ M$^{-1}$ s$^{-1}$. In some embodiments, an antibody or fragment thereof described herein binds to the ErbB3 epitope with a $k_{off}$ between $1\times10^5$ M$^{-1}$ s$^{-1}$ to $5\times10^5$ M$^{-1}$ s$^{-1}$, $1\times10^5$ M$^{-1}$ s$^{-1}$ to $1\times10^6$ M$^{-1}$ s$^{-1}$, $1\times10^5$ M$^{-1}$ s$^{-1}$ to $5\times10^6$ M$^{-1}$ s$^{-1}$, $1\times10^5$ M$^{-1}$ s$^{-1}$ to $1\times10^7$ M$^{-1}$ s$^{-1}$, $1\times10^5$ M$^{-1}$ s$^{-1}$ to $5\times10^7$ M$^{-1}$ s$^{-1}$, $1\times10^5$ M$^{-1}$ s$^{-1}$ to $10^8$ M$^{-1}$ s$^{-1}$, $1\times10^5$ M$^{-1}$ s$^{-1}$ to $1\times10^9$ M$^{-1}$ s$^{-1}$, $1\times10^6$ M$^{-1}$ s$^{-1}$ to $1\times10^7$ M$^{-1}$ s$^{-1}$, $1\times10^6$ M$^{-1}$ s$^{-1}$ to $1\times10^8$ M$^{-1}$ s$^{-1}$, $1\times10^6$ M$^{-1}$ s$^{-1}$ to $1\times10^9$ M$^{-1}$ s$^{-1}$, $1\times10^7$ M$^{-1}$ s$^{-1}$ to $1\times10^8$ M$^{-1}$ s$^{-1}$, $1\times10^7$ M$^{-1}$ s$^{-1}$ to $1\times10^9$ M$^{-1}$ s$^{-1}$, $1\times10^8$ M$^{-1}$ s$^{-1}$ to $1\times10^9$ M$^{-1}$ s$^{-1}$. In certain embodiments, the $k_{on}$ is determined using a monovalent antibody, such as a Fab fragment, as measured by, e.g., BIAcore™ surface plasmon resonance technology. In a particular embodiment, the $k_{on}$, is determined using an assay described in Section 6, infra.

In certain embodiments, an antibody or fragment thereof described herein binds to the ErbB3 epitope with a $K_D$ of less than 375 pM, 350 pM, 325 pM, 300 pM, 275 pM, 250 pM, 225 pM, 200 pM, 175 pM, 150 pM, 125 pM, 100 pM, 75 pM, 50 pM, 45 pM, 40 pM, or 35 pM. In some embodiments, an antibody or fragment thereof described herein binds to the ErbB3 epitope with a $k_D$ of 375 pM, 350 pM, 325 pM, 300 pM, 275 pM, 250 pM, 225 pM, 200 pM, 175 pM, 150 pM, 125 pM, 100 pM, 75 pM, or 50 pM, or between 375 pM to 300 pM, 375 pM to 200 pM, 375 pM to 100 pM, 350 pM to 250 pM, 350 pM to 200 pM, 300 pM to 150 pM, 300 pM to 100 pM, 300 pM to 50 pM, 300 pM to 200 pM, 300 pM to 150 pM, 300 pM to 100 pM, 300 pM to 50 pM, 275 pM to 200 pM, 275 pM to 175 pM, 275 pM to 150 pM, 275 pM to 100 pM, 275 pM to 50 pM, 250 pM to 200 pM, 250 pM to 150 pM, 250 pM to 100 pM, 250 pM to 50 pM, 200 pM to 150 pM, 200 pM to 100 pM, 200 to 50 pM, 150 pM to 100 pM, 150 pM to 50 pM, 100 pM to 50 pM, 200 to 40 pM, 150 pM to 40 pM, 150 pM to 40 pM, or 100 pM to 35 pM. In certain embodiments, the $k_D$ is calculated as the quotient of $k_{off}/k_{on}$, and the $k_{on}$, and $k_{off}$ are determined using a monovalent antibody, such as a Fab fragment, as measured by, e.g., BIAcore™ surface plasmon resonance technology.

In another aspect, provided herein is an antibody(ies) or fragment(s) thereof that binds to an epitope of ErbB1 comprising at least one, two, three, four or all of amino acid residues selected from human ErbB1 amino acid residues 274, 286, 287, 289, 291, 292, 293, 294, 295, 302, 309, 310, and 311 and inhibits ligand-dependent and ligand-independent ErbB1 activation. In a specific embodiment, an antibody(ies) or fragment(s) thereof that binds to ErbB1 comprises one, two, three, four or more amino acid residues selected from human ErbB1 amino acid residues 292, 293, 295, 303, and 310, and inhibits ligand-dependent and ligand-independent ErbB1 activation. In a specific embodiment, the ErbB1 epitope is non-linear. In a specific embodiment, the antibody or fragment thereof binds an ErbB1 epitope and inhibits ligand binding to ErbB1. In a specific embodiment, the antibody or antigen-binding fragment thereof inhibits neuregulin (for example, human neuregulin)-dependent ErbB1 activation. In another specific embodiment, the antibody or antigen-binding fragment thereof inhibits neuregulin 1-dependent ErbB1 activation. In a particular embodiment, the neuregulin 1 is neuregulin 1β1. In another specific embodiment, the antibody or antigen-binding fragment thereof inhibits neuregulin 2-dependent ErbB1 activation. In certain embodiments, the antibody or antigen-binding fragment thereof is a human, humanized or chimeric antibody or antigen-binding fragment thereof. In a specific embodiment, the antibody or antigen-binding fragment thereof is a monoclonal antibody or antigen-binding fragment. In another specific embodiment, the antibody is a human, humanized or chimeric monoclonal antibody or antigen-binding fragment thereof. In certain embodiments, the antibody or antigen-binding fragment thereof is isolated.

In certain embodiments, an antibody or fragment thereof described herein binds to the ErbB1 epitope with a dissociation rate constant ($k_{off}$) of $8.5\times10^{-5}$ s$^{-1}$ or less, $5\times10^{-5}$ s$^{-1}$ or less, $2.5\times10^{-5}$ s$^{-1}$ or less, $1\times10^{-5}$ s$^{-1}$ or less, $8.5\times10^{-6}$ s$^{-1}$ or less, $5\times10^{-6}$ s$^{-1}$ or less, $2.5\times10^{-6}$ s$^{-1}$ or less, $1\times10^{-6}$ s$^{-1}$ or less, $8.5\times10^{-7}$ s$^{-1}$ or less, $5\times10^{-7}$ s$^{-1}$ or less, $2.5\times10^{-7}$ s$^{-1}$ or less, $1\times10^{-7}$ s$^{-1}$ or less, $8.5\times10^{-8}$ s$^{-1}$ or less, $5\times10^{-8}$ s$^{-1}$ or less, $2.5\times10^{-8}$ s$^{-1}$ or less, $1\times10^{-8}$ s$^{-1}$ or less, $8.5\times10^{-9}$ s$^{-1}$ or less, $5\times10^{-9}$ s$^{-1}$ or less, $2.5\times10^{-9}$ s$^{-1}$ or less, or $1\times10^{-9}$ s$^{-1}$ or less. In some embodiments, an antibody or fragment thereof described herein binds to the ErbB1 epitope with a $k_{off}$ of between $9.5\times10^{-5}$ s$^{-1}$ to $1\times10^{-9}$ s$^{-1}$, $8.5\times10^{-5}$ s$^{-1}$ to $1\times10^{-9}$ s$^{-1}$, $5\times10^{-5}$ s$^{-1}$ to $1\times10^{-9}$ s$^{-1}$, $9.5\times10^{-5}$ s$^{-1}$ to $1\times10^{-8}$ s$^{-1}$, $5\times10^{-5}$ s$^{-1}$ to $1\times10^{-8}$ s$^{-1}$, $9.5\times10^{-5}$ s$^{-1}$ to $1\times10^{-7}$ s$^{-1}$, $5\times10^{-5}$ s$^{-1}$ to $1\times10^{-7}$ s$^{-1}$, $9.5\times10^{-5}$ s$^{-1}$ to $5\times10^{-6}$ s$^{-1}$, or $9.5\times10^{-5}$ s$^{-1}$ to $1\times10^{-5}$ s$^{-1}$. In certain embodiments, the $k_{off}$ is determined using a monovalent antibody, such as a Fab fragment, as measured by, e.g., BIAcore™ surface plasmon resonance technology. In a particular embodiment, the $k_{off}$ is determined using an assay described in Section 6, infra.

In certain embodiments, an antibody or fragment thereof described herein binds to the ErbB1 epitope with an association rate constant ($k_{on}$) of at least $10^5$ M$^{-1}$ s$^{-1}$, at least $5\times10^5$ M$^{-1}$ s$^{-1}$, at least $10^6$ M$^{-1}$ s$^{-1}$, at least $5\times10^6$ M$^{-1}$ s$^{-1}$, at least $10^7$ M$^{-1}$ s$^{-1}$, at least $5\times10^7$ M$^{-1}$ s$^{-1}$, at least $10^8$ M$^{-1}$ s$^{-1}$, at least $5\ 10^8$ M$^{-1}$ s$^{-1}$ or at least $10^9$ M$^{-1}$ s$^{-1}$. In some embodiments, an antibody or fragment thereof described herein binds to the ErbB1 epitope with a $k_{off}$ between $1\times10^5$ M$^{-1}$ s$^{-1}$ to $5\times10^5$ M$^{-1}$ s$^{-1}$, $1\times10^5$ M$^{-1}$ s$^{-1}$ to $1\times10^6$ M$^{-1}$ s$^{-1}$, $1\times10^5$ M$^{-1}$ s$^{-1}$ to $5\times10^6$ M$^{-1}$ s$^{-1}$, $1\times10^5$ M$^{-1}$ s$^{-1}$ to $1\times10^7$ M$^{-1}$ s$^{-1}$, $1\times10^5$ M$^{-1}$ s$^{-1}$ to $5\times10^7$ M$^{-1}$ s$^{-1}$, $1\times10^5$ M$^{-1}$ s$^{-1}$ to $10^8$ M$^{-1}$ s$^{-1}$, $1\times10^5$ M$^{-1}$ s$^{-1}$ to $1\times10^9$ M$^{-1}$ s$^{-1}$, $1\times10^6$ M$^{-1}$ s$^{-1}$ to $1\times10^7$ M$^{-1}$ s$^{-1}$, $1\times10^6$ M$^{-1}$ s$^{-1}$ to $1\times10^8$ M$^{-1}$ s$^{-1}$, $1\times10^6$ M$^{-1}$ s$^{-1}$ to $1\times10^9$ M$^{-1}$ s$^{-1}$, $1\times10^7$ M$^{-1}$ s$^{-1}$ to $1\times10^8$ M$^{-1}$ s$^{-1}$, $1\times10^7$ M$^{-1}$ s$^{-1}$ to $1\times10^9$ M$^{-1}$ s$^{-1}$, $1\times10^8$ M$^{-1}$ s$^{-1}$ to $1\times10^9$ M$^{-1}$ s$^{-1}$. In certain embodiments, the $k_{on}$ is determined using a monovalent antibody, such as a Fab fragment, as measured by, e.g., BIAcore™ surface plasmon resonance technology. In a particular embodiment, the $k_{on}$ is determined using an assay described in Section 6, infra.

In certain embodiments, an antibody or fragment thereof described herein binds to the ErbB1 epitope with a $K_D$ of less than 375 pM, 350 pM, 325 pM, 300 pM, 275 pM, 250 pM, 225 pM, 200 pM, 175 pM, 150 pM, 125 pM, 100 pM, 75 pM, 50 pM, 45 pM, 40 pM, or 35 pM. In some embodiments, an antibody or fragment thereof described herein binds to the ErbB1 epitope with a $k_D$ of 375 pM, 350 pM, 325 pM, 300 pM, 275 pM, 250 pM, 225 pM, 200 pM, 175 pM, 150 pM, 125 pM, 100 pM, 75 pM, or 50 pM, or between 375 pM to 300 pM, 375 pM to 200 pM, 375 pM to 100 pM, 350 pM to 250 pM, 350 pM to 200 pM, 300 pM to 150 pM, 300 pM to 100 pM, 300 pM to 50 pM, 300 pM to 200 pM, 300 pM to 150 pM, 300 pM to 100 pM, 300 pM to 50 pM, 275 pM to 200 pM, 275 pM to 175 pM, 275 pM to 150 pM, 275 pM to 100 pM, 275 pM to 50 pM, 250 pM to 200 pM, 250 pM to 150 pM, 250 pM to 100 pM, 250 pM to 50 pM, 200 pM to 150 pM, 200 pM to 100 pM, 200 to 50 pM, 150 pM to 100 pM, 150 pM to 50 pM, 100 pM to 50 pM, 200 to 40 pM, 150 pM to 40 pM, 150 pM to 40 pM, or 100 pM to 35 pM. In certain embodiments, the $k_D$ is calculated as the quotient of $k_{off}/k_{on}$, and the $k_{on}$ and $k_{off}$ are determined using a monovalent antibody, such as a Fab fragment, as measured by, e.g., BIAcore™ surface plasmon resonance technology.

In another aspect, provided herein is an antibody(ies) or fragment(s) thereof that binds to an epitope of ErbB4 comprising at least one, two, three, four or more of amino acid residues selected from human ErbB4 amino acid residues 270, 271, 288, 289, 290, 291, 292, 293, 296, 301, 305, 306, and 307 and inhibits ligand-dependent and ligand-independent ErbB4 activation. In one embodiment, an antibody(ies) or fragment(s) thereof that binds to an epitope of ErbB4 comprises one, two, three, four or more of amino acid residues selected from human ErbB4 amino acid residues 288, 289, 291, 296, and 306 and inhibits ligand-dependent and ligand-independent ErbB4 activation.

In a specific embodiment, ErbB4 epitope is a non-linear. In a specific embodiment, the antibody or fragment thereof binds an ErbB4 epitope and inhibits ligand binding to ErbB4. In a specific embodiment, the antibody or antigen-binding fragment thereof inhibits neuregulin (for example, human neuregulin)-dependent ErbB4 activation. In another specific embodiment, the antibody or antigen-binding fragment thereof inhibits neuregulin 1-dependent ErbB4 activation. In a particular embodiment, the neuregulin 1 is neuregulin 1β1. In another specific embodiment, the antibody or antigen-binding fragment thereof inhibits neuregulin 2-dependent ErbB4 activation. In certain embodiments, the antibody or antigen-binding fragment thereof is a human, humanized or chimeric antibody or antigen-binding fragment thereof. In a specific embodiment, the antibody or antigen-binding fragment thereof is a monoclonal antibody or antigen-binding fragment. In another specific embodiment, the antibody is a human, humanized or chimeric monoclonal antibody or antigen-binding fragment thereof. In certain embodiments, the antibody or antigen-binding fragment thereof is isolated.

In certain embodiments, an antibody or fragment thereof described herein binds to the ErbB4 epitope with a dissociation rate constant ($k_{off}$) of $8.5 \times 10^{-5}$ s$^{-1}$ or less, $5 \times 10^{-5}$ s$^{-1}$ or less, $2.5 \times 10^{-5}$ s$^{-1}$ or less, $1 \times 10^{-5}$ s$^{-1}$ or less, $8.5 \times 10^{-6}$ s$^{-1}$ or less, $5 \times 10^{-6}$ s$^{-1}$ or less, $2.5 \times 10^{-6}$ s$^{-1}$ or less, $1 \times 10^{-6}$ s$^{-1}$ or less, $8.5 \times 10^{-7}$ s$^{-1}$ or less, $5 \times 10^{-7}$ s$^{-1}$ or less, $2.5 \times 10^{-7}$ s$^{-1}$ or less, $1 \times 10^{-7}$ s$^{-1}$ or less, $8.5 \times 10^{-8}$ s$^{-1}$ or less, $5 \times 10^{-8}$ s$^{-1}$ or less, $2.5 \times 10^{-8}$ s$^{-1}$ or less, $1 \times 10^{-8}$ s$^{-1}$ or less, $8.5 \times 10^{-9}$ s$^{-1}$ or less, $5 \times 10^{-9}$ s$^{-1}$ or less, $2.5 \times 10^{-9}$ s$^{-1}$ or less, or $1 \times 10^{-9}$ s$^{-1}$ or less. In some embodiments, an antibody or fragment thereof described herein binds to the ErbB4 epitope with a $k_{off}$ of between $9.5 \times 10^{-5}$ s$^{-1}$ to $1 \times 10^{-9}$ s$^{-1}$, $8.5 \times 10^{-5}$ s$^{-1}$ to $1 \times 10^{-9}$ s$^{-1}$, $5 \times 10^{-5}$ s$^{-1}$ to $1 \times 10^{-9}$ s$^{-1}$, $9.5 \times 10^{-5}$ s$^{-1}$ to $1 \times 10^{-8}$ s$^{-1}$, $5 \times 10^{-5}$ s$^{-1}$ to $1 \times 10^{-8}$ s$^{-1}$, $9.5 \times 10^{-5}$ s$^{-1}$ to $1 \times 10^{-7}$ s$^{-1}$, $5 \times 10^{-5}$ s$^{-1}$ to $1 \times 10^{-7}$ s$^{-1}$, $9.5 \times 10^{-5}$ s$^{-1}$ to $5 \times 10^{-6}$ s$^{-1}$, or $9.5 \times 10^{-5}$ s$^{-1}$ to $1 \times 10^{-5}$ s$^{-1}$. In certain embodiments, the $k_{off}$ is determined using a monovalent antibody, such as a Fab fragment, as measured by, e.g., BIAcore™ surface plasmon resonance technology. In a particular embodiment, the $k_{off}$ is determined using an assay described in Section 6, infra.

In certain embodiments, an antibody or fragment thereof described herein binds to the ErbB4 epitope with an association rate constant ($k_{on}$) of at least $10^5$ M$^{-1}$ s$^{-1}$, at least $5 \times 10^5$ M$^{-1}$ s$^{-1}$, at least $10^6$ M$^{-1}$ s$^{-1}$, at least $5 \times 10^6$ M$^{-1}$ s$^{-1}$, at least $10^7$ M$^{-1}$ s$^{-1}$, at least $5 \times 10^7$ M$^{-1}$ s$^{-1}$, at least $10^8$ M$^{-1}$ s$^{-1}$, at least $5 \cdot 10^8$ M$^{-1}$ s$^{-1}$ or at least $10^9$ M$^{-1}$ s$^{-1}$. In some embodiments, an antibody or fragment thereof described herein binds to the ErbB4 epitope with a $k_{on}$ of between $1 \times 10^5$ M$^{-1}$ s$^{-1}$ to $5 \times 10^5$ M$^{-1}$ s$^{-1}$, $1 \times 10^5$ M$^{-1}$ s$^{-1}$ to $1 \times 10^6$ M$^{-1}$ s$^{-1}$, $1 \times 10^5$ M$^{-1}$ s$^{-1}$ to $5 \times 10^6$ M$^{-1}$ s$^{-1}$, $1 \times 10^5$ M$^{-1}$ s$^{-1}$ to $1 \times 10^7$ M$^{-1}$ s$^{-1}$, $1 \times 10^5$ M$^{-1}$ s$^{-1}$ to $5 \times 10^7$ M$^{-1}$ s$^{-1}$, $1 \times 10^5$ M$^{-1}$ s$^{-1}$ to $10^8$ M$^{-1}$ s$^{-1}$, $1 \times 10^5$ M$^{-1}$ s$^{-1}$ to $1 \times 10^9$ M$^{-1}$ s$^{-1}$, $1 \times 10^6$ M$^{-1}$ s$^{-1}$ to $1 \times 10^7$ M$^{-1}$ s$^{-1}$, $1 \times 10^6$ M$^{-1}$ s$^{-1}$ to $1 \times 10^8$ M$^{-1}$ s$^{-1}$, $1 \times 10^6$ M$^{-1}$ s$^{-1}$ to $1 \times 10^9$ M$^{-1}$ s$^{-1}$, $1 \times 10^7$ M$^{-1}$ s$^{-1}$ to $1 \times 10^8$ M$^{-1}$ s$^{-1}$, $1 \times 10^7$ M$^{-1}$ s$^{-1}$ to $1 \times 10^9$ M$^{-1}$ s$^{-1}$, $1 \times 10^8$ M$^{-1}$ s$^{-1}$ to $1 \times 10^9$ M$^{-1}$ s$^{-1}$. In certain embodiments, the $k_{on}$ is determined using a monovalent antibody, such as a Fab fragment, as measured by, e.g., BIAcore™ surface plasmon resonance technology. In a particular embodiment, the $k_{on}$ is determined using an assay described in Section 6, infra.

In certain embodiments, an antibody or fragment thereof described herein binds to the ErbB4 epitope with a $K_D$ of less than 375 pM, 350 pM, 325 pM, 300 pM, 275 pM, 250 pM, 225 pM, 200 pM, 175 pM, 150 pM, 125 pM, 100 pM, 75 pM, 50 pM, 45 pM, 40 pM, or 35 pM. In some embodiments, an antibody or fragment thereof described herein binds to the ErbB4 epitope with a $k_D$ of 375 pM, 350 pM, 325 pM, 300 pM, 275 pM, 250 pM, 225 pM, 200 pM, 175 pM, 150 pM, 125 pM, 100 pM, 75 pM, or 50 pM, or between 375 pM to 300 pM, 375 pM to 200 pM, 375 pM to 100 pM, 350 pM to 250 pM, 350 pM to 200 pM, 300 pM to 150 pM, 300 pM to 100 pM, 300 pM to 50 pM, 300 pM to 200 pM, 300 pM to 150 pM, 300 pM to 100 pM, 300 pM to 50 pM, 275 pM to 200 pM, 275 pM to 175 pM, 275 pM to 150 pM, 275 pM to 100 pM, 275 pM to 50 pM, 250 pM to 200 pM, 250 pM to 150 pM, 250 pM to 100 pM, 250 pM to 50 pM, 200 pM to 150 pM, 200 pM to 100 pM, 200 to 50 pM, 150 pM to 100 pM, 150 pM to 50 pM, 100 pM to 50 pM, 200 to 40 pM, 150 pM to 40 pM, 150 pM to 40 pM, or 100 pM to 35 pM. In certain embodiments, the $k_D$ is calculated as the quotient of $k_{off}/k_{on}$, and the $k_{on}$ and $k_{off}$ are determined using a monovalent antibody, such as a Fab fragment, as measured by, e.g., BIAcore™ surface plasmon resonance technology.

In another aspect, provided herein is an antibody(ies) or fragment(s) thereof that specifically binds to an epitope of ErbB3 comprising (i) at least one, two, three, four or more of amino acid residues, or between 1 to 3, 2 to 4, 1 to 5, or 2 to 5 amino acid residues selected from human ErbB3 amino acid residues 291, 292, 294, 299, and 309 and (ii) at least one, two, three, four, five, six, seven, eight, nine, ten, eleven, twelve, thirteen, fourteen, or fifteen amino acid residues, or between 1 to 3, 2 to 4, 2 to 5, 5 to 10, 10 to 15, 15 to 20, 5 to 15, 10 to 20, or 20 to 25 amino acid residues selected from human ErbB3 amino acid residues 310, 311, 317-319, 337, 339, 373, 394, 402-408, 429, 431-433, 456-458, and 462, and inhibits ligand-dependent and ligand-independent ErbB3 activation. In a specific embodiment, the ErbB3 epitope is a non-linear epitope. In a specific embodiment, the antibody or fragment thereof binds an ErbB3 epitope and inhibits ligand binding to ErbB3. In a specific embodiment, the antibody or antigen-binding fragment thereof inhibits neuregulin (for example, human neuregulin)-dependent ErbB3 activation. In another specific embodiment, the antibody or antigen-binding fragment thereof inhibits neuregulin 1-dependent ErbB3 activation. In a particular embodiment, the neuregulin 1 is neuregulin 1β1. In another specific embodiment, the antibody or antigen-binding fragment thereof inhibits neuregulin 2-dependent ErbB3 activation. In certain embodiments, the antibody or antigen-binding fragment thereof is a human, humanized or chimeric antibody or antigen-binding fragment thereof. In a specific embodiment, the antibody or antigen-binding fragment thereof is a monoclonal antibody or antigen-binding fragment. In another specific embodiment, the antibody is a human, humanized or chimeric monoclonal antibody or antigen-binding fragment thereof. In certain embodiments, the antibody or antigen-binding fragment thereof is isolated.

In certain embodiments, an antibody or fragment thereof described herein binds to the ErbB3 epitope with a dissociation rate constant ($k_{off}$) of $8.5\times10^{-5}$ $s^{-1}$ or less, $5\times10^{-5}$ $s^{-1}$ or less, $2.5\times10^{-5}$ $s^{-1}$ or less, $1\times10^{-5}$ $s^{-1}$ or less, $8.5\times10^{-6}$ $s^{-1}$ or less, $5\times10^{-6}$ $s^{-1}$ or less, $2.5\times10^{-6}$ $s^{-1}$ or less, $1\times10^{-6}$ $s^{-1}$ or less, $8.5\times10^{-7}$ $s^{-1}$ or less, $5\times10^{-7}$ $s^{-1}$ or less, $2.5\times10^{-7}$ $s^{-1}$ or less, $1\times10^{-7}$ $s^{-1}$ or less, $8.5\times10^{-8}$ $s^{-1}$ or less, $5\times10^{-8}$ $s^{-1}$ or less, $2.5\times10^{-8}$ $s^{-1}$ or less, $1\times10^{-8}$ $s^{-1}$ or less, $8.5\times10^{-9}$ $s^{-1}$ or less, $5\times10^{-9}$ $s^{-1}$ or less, $2.5\times10^{-9}$ $s^{-1}$ or less, or $1\times10^{-9}$ $s^{-1}$ or less. In some embodiments, an antibody or fragment thereof described herein binds to the ErbB3 epitope with a $k_{off}$ of between $9.5\times10^{-5}$ $s^{-1}$ to $1\times10^{-9}$ $s^{-1}$, $8.5\times10^{-5}$ $s^{-1}$ to $1\times10^{-9}$ $s^{-1}$, $5\times10^{-5}$ $s^{-1}$ to $1\times10^{-9}$ $s^{-1}$, $9.5\times10^{-5}$ $s^{-1}$ to $1\times10^{-8}$ $s^{-1}$, $5\times10^{-5}$ $s^{-1}$ to $1\times10^{-8}$ $s^{-1}$, $9.5\times10^{-5}$ $s^{-1}$ to $1\times10^{-7}$ $s^{-1}$, $5\times10^{-5}$ $s^{-1}$ to $1\times10^{-7}$ $s^{-1}$, $9.5\times10^{-5}$ $s^{-1}$ to $5\times10^{-6}$ $s^{-1}$, or $9.5\times10^{-5}$ $s^{-1}$ to $1\times10^{-5}$ $s^{-1}$. In certain embodiments, the $k_{off}$ is determined using a monovalent antibody, such as a Fab fragment, as measured by, e.g., BIAcore™ surface plasmon resonance technology. In a particular embodiment, the $k_{off}$ is determined using an assay described in Section 6, infra.

In certain embodiments, an antibody or fragment thereof described herein binds to the ErbB3 epitope with an association rate constant ($k_{on}$) of at least $10^5$ $M^{-1}$ $s^{-1}$, at least $5\times10^5$ $M^{-1}$ $s^{-1}$, at least $10^6$ $M^{-1}$ $s^{-1}$, at least $5\times10^6$ $M^{-1}$ $s^{-1}$, at least $10^7$ $M^{-1}$ $s^{-1}$, at least $5\times10^7$ $M^{-1}$ $s^{-1}$, at least $10^8$ $M^{-1}$ $s^{-1}$, at least $5\ 10^8$ $M^{-1}$ $s^{-1}$ or at least $10^9$ $M^{-1}$ $s^{-1}$. In some embodiments, an antibody or fragment thereof described herein binds to the ErbB3 epitope with a $k_{on}$ of between $1\times10^5$ $M^{-1}$ $s^{-1}$ to $5\times10^5$ $M^{-1}$ $s^{-1}$, $1\times10^5$ $M^{-1}$ $s^{-1}$ to $1\times10^6$ $M^{-1}$ $s^{-1}$, $1\times10^5$ $M^{-1}$ $s^{-1}$ to $5\times10^6$ $M^{-1}$ $s^{-1}$, $1\times10^5$ $M^{-1}$ $s^{-1}$ to $1\times10^7$ $M^{-1}$ $s^{-1}$, $1\times10^5$ $M^{-1}$ $s^{-1}$ to $5\times10^7$ $M^{-1}$ $s^{-1}$, $1\times10^5$ $M^{-1}$ $s^{-1}$ to $10^8$ $M^{-1}$ $s^{-1}$, $1\times10^5$ $M^{-1}$ $s^{-1}$ to $1\times10^9$ $M^{-1}$ $s^{-1}$, $1\times10^6$ $M^{-1}$ $s^{-1}$ to $1\times10^7$ $M^{-1}$ $s^{-1}$, $1\times10^6$ $M^{-1}$ $s^{-1}$ to $1\times10^8$ $M^{-1}$ $s^{-1}$, $1\times10^6$ $M^{-1}$ $s^{-1}$ to $1\times10^9$ $M^{-1}$ $s^{-1}$, $1\times10^7$ $M^{-1}$ $s^{-1}$ to $1\times10^8$ $M^{-1}$ $s^{-1}$, $1\times10^7$ $M^{-1}$ $s^{-1}$ to $1\times10^9$ $M^{-1}$ $s^{-1}$, $1\times10^8$ $M^{-1}$ $s^{-1}$ to $1\times10^9$ $M^{-1}$ $s^{-1}$. In certain embodiments, the $k_{on}$ is determined using a monovalent antibody, such as a Fab fragment, as measured by, e.g., BIAcore™ surface plasmon resonance technology. In a particular embodiment, the $k_{on}$ is determined using an assay described in Section 6, infra.

In certain embodiments, an antibody or fragment thereof described herein binds to the ErbB3 epitope with a $K_D$ of less than 375 pM, 350 pM, 325 pM, 300 pM, 275 pM, 250 pM, 225 pM, 200 pM, 175 pM, 150 pM, 125 pM, 100 pM, 75 pM, 50 pM, 45 pM, 40 pM, or 35 pM. In some embodiments, an antibody or fragment thereof described herein binds to the ErbB3 epitope with a $k_D$ of 375 pM, 350 pM, 325 pM, 300 pM, 275 pM, 250 pM, 225 pM, 200 pM, 175 pM, 150 pM, 125 pM, 100 pM, 75 pM, or 50 pM, between 375 pM to 300 pM, 375 pM to 200 pM, 375 pM to 100 pM, 350 pM to 250 pM, 350 pM to 200 pM, 300 pM to 150 pM, 300 pM to 100 pM, 300 pM to 50 pM, 300 pM to 200 pM, 300 pM to 150 pM, 300 pM to 100 pM, 300 pM to 50 pM, 275 pM to 200 pM, 275 pM to 175 pM, 275 pM to 150 pM, 275 pM to 100 pM, 275 pM to 50 pM, 250 pM to 200 pM, 250 pM to 150 pM, 250 pM to 100 pM, 250 pM to 50 pM, 200 pM to 150 pM, 200 pM to 100 pM, 200 to 50 pM, 150 pM to 100 pM, 150 pM to 50 pM, 100 pM to 50 pM, 200 to 40 pM, 150 pM to 40 pM, 150 pM to 40 pM, or 100 pM to 35 pM. In certain embodiments, the $k_D$ is calculated as the quotient of $k_{off}/k_{on}$, and the $k_{on}$ and $k_{off}$ are determined using a monovalent antibody, such as a Fab fragment, as measured by, e.g., BIAcore™ surface plasmon resonance technology.

In another aspect, provided herein is an antibody(ies) or fragment(s) thereof that specifically binds to an epitope of ErbB1 comprising (i) at least one, two, three, four or more of amino acid residues, or between 1 to 3, 2 to 4, 1 to 5, or 2 to 5 amino acid residues selected from human ErbB1 amino acid residues 274, 286, 287, 289, 291, 292, 293, 294, 295, 302, 309, 310, and 311 and (ii) at least one, two, three, four, five, six, seven, eight, nine, ten, eleven, twelve, thirteen, fourteen, or fifteen amino acid residues, or between 1 to 3, 2 to 4, 2 to 5, 5 to 10, 10 to 15, 15 to 20, 5 to 15, 10 to 20, or 20 to 25 amino acid residues selected from human ErbB1 amino acid residues 312, 314, 318, 319, 320, 322, 340, 342, 343, 344, 378, 379, 403, 404, 405, 406, 407, 411, 431, 433, 434, 458, 459, 460, 461, and 462, and inhibits ligand-dependent and ligand-independent ErbB1 activation. In one embodiment, an antibody(ies) or fragment(s) thereof specifically bind to an epitope comprising: (i) at least one, two, three, four, or more of amino acid residues selected from human ErbB1 amino acid residues 292, 293, 295, 302, and 310, and (ii) at least one, two, three, four, five, six, seven, eight, nine, ten, eleven, twelve, thirteen, fourteen, or fifteen amino acid residues, or between 1 to 3, 2 to 4, 2 to 5, 5 to 10, 10 to 15, 15 to 20, 5 to 15, 10 to 20, or 20 to 25 amino acid residues selected from human ErbB1 amino acid residues 312, 314, 318, 319, 320, 322, 340, 342, 343, 344, 378, 379, 403, 404, 405, 406, 407, 411, 431, 433, 434, 458, 459, 460, 461, and 462, and inhibits ligand-dependent and ligand-independent ErbB1 activation. In a specific embodiment, the ErbB1 epitope is a non-linear epitope. In a specific embodiment, the antibody or fragment thereof binds an ErbB1 epitope and inhibits ligand binding to ErbB1. In a specific embodiment, the antibody or antigen-binding fragment thereof inhibits neuregulin (for example, human neuregulin)-dependent ErbB1 activation. In another specific embodiment, the antibody or antigen-binding fragment thereof inhibits neuregulin 1-dependent ErbB1 activation. In a particular embodiment, the neuregulin 1 is neuregulin 1β1. In another specific embodiment, the antibody or antigen-binding fragment thereof inhibits neuregulin 2-dependent ErbB1 activation. In certain embodiments, the antibody or antigen-binding fragment thereof is a human, humanized or chimeric antibody or antigen-binding fragment thereof. In a specific embodiment, the antibody or antigen-binding fragment thereof is a monoclonal antibody or antigen-binding fragment. In another specific embodiment, the antibody is a human, humanized or chimeric monoclonal antibody or antigen-binding fragment thereof. In certain embodiments, the antibody or antigen-binding fragment thereof is isolated.

In certain embodiments, an antibody or fragment thereof described herein binds to the ErbB1 epitope with a dissociation rate constant ($k_{off}$) of $8.5\times10^{-5}$ $s^{-1}$ or less, $5\times10^{-5}$ $s^{-1}$ or less, $2.5\times10^{-5}$ $s^{-1}$ or less, $1\times10^{-5}$ $s^{-1}$ or less, $8.5\times10^{-6}$ $s^{-1}$ or less, $5\times10^{-6}$ $s^{-1}$ or less, $2.5\times10^{-6}$ $s^{-1}$ or less, $1\times10^{-6}$ $s^{-1}$ or less, $8.5\times10^{-7}$ $s^{-1}$ or less, $5\times10^{-7}$ $s^{-1}$ or less, $2.5\times10^{-7}$ $s^{-1}$ or less, $1\times10^{-7}$ $s^{-1}$ or less, $8.5\times10^{-8}$ $s^{-1}$ or less, $5\times10^{-8}$ $s^{-1}$ or less, $2.5 \times 10^{-8}$ s$^{-1}$ or less, $1 \times 10^{-8}$ s$^{-1}$ or less, $8.5 \times 10^{-9}$ s$^{-1}$ or less, $5 \times 10^{-9}$ s$^{-1}$ or less, $2.5 \times 10^{-9}$ s$^{-1}$ or less, or $1 \times 10^{-9}$ s$^{-1}$ or less. In some embodiments, an antibody or fragment thereof described herein binds to the ErbB1 epitope with a $k_{off}$ of between $9.5 \times 10^{-5}$ s$^{-1}$ to $1 \times 10^{-9}$ s$^{-1}$, $8.5 \times 10^{-5}$ s$^{-1}$ to $1 \times 10^{-9}$ s$^{-1}$, $5 \times 10^{-5}$ s$^{-1}$ to $1 \times 10^{-9}$ s$^{-1}$, $9.5 \times 10^{-5}$ s$^{-1}$ to $1 \times 10^{-8}$ s$^{-1}$, $5 \times 10^{-5}$ s$^{-1}$ to $1 \times 10^{-8}$ s$^{-1}$, $9.5 \times 10^{-5}$ s$^{-1}$ to $1 \times 10^{-7}$ s$^{-1}$, $5 \times 10^{-5}$ s$^{-1}$ to $1 \times 10^{-7}$ s$^{-1}$, $9.5 \times 10^{-5}$ s$^{-1}$ to $5 \times 10^{-6}$ s$^{-1}$, or $9.5 \times 10^{-5}$ s$^{-1}$ to $1 \times 10^{-5}$ s$^{-1}$. In certain embodiments, the $k_{off}$ is determined using a monovalent antibody, such as a Fab fragment, as measured by, e.g., BIAcore™ surface plasmon resonance technology. In a particular embodiment, the $k_{off}$ is determined using an assay described in Section 6, infra.

In certain embodiments, an antibody or fragment thereof described herein binds to the ErbB1 epitope with an association rate constant ($k_{on}$) of at least $10^5$ M$^{-1}$ s$^{-1}$, at least $5 \times 10^5$ M$^{-1}$ s$^{-1}$, at least $10^6$ M$^{-1}$ s$^{-1}$, at least $5 \times 10^6$ M$^{-1}$ s$^{-1}$, at least $10^7$ M$^{-1}$ s$^{-1}$, at least $5 \times 10^7$ M$^{-1}$ s$^{-1}$, at least $10^8$ M$^{-1}$ s$^{-1}$, at least $5\ 10^8$ M$^{-1}$ s$^{-1}$ or at least $10^9$ M$^{-1}$ s$^{-1}$. In some embodiments, an antibody or fragment thereof described herein binds to the ErbB1 epitope with a $k_{off}$ between $1 \times 10^5$ M$^{-1}$ s$^{-1}$ to $5 \times 10^5$ M$^{-1}$ s$^{-1}$, $1 \times 10^5$ M$^{-1}$ s$^{-1}$ to $1 \times 10^6$ M$^{-1}$ s$^{-1}$, $1 \times 10^5$ M$^{-1}$ s$^{-1}$ to $5 \times 10^6$ M$^{-1}$ s$^{-1}$, $1 \times 10^5$ M$^{-1}$ s$^{-1}$ to $1 \times 10^7$ M$^{-1}$ s$^{-1}$, $1 \times 10^5$ M$^{-1}$ s$^{-1}$ to $5 \times 10^7$ M$^{-1}$ s$^{-1}$, $1 \times 10^5$ M$^{-1}$ s$^{-1}$ to $10^8$ M$^{-1}$ s$^{-1}$, $1 \times 10^5$ M$^{-1}$ s$^{-1}$ to $1 \times 10^9$ M$^{-1}$ s$^{-1}$, $1 \times 10^6$ M$^{-1}$ s$^{-1}$ to $1 \times 10^7$ M$^{-1}$ s$^{-1}$, $1 \times 10^6$ M$^{-1}$ s$^{-1}$ to $1 \times 10^8$ M$^{-1}$ s$^{-1}$, $1 \times 10^6$ M$^{-1}$ s$^{-1}$ to $1 \times 10^9$ M$^{-1}$ s$^{-1}$, $1 \times 10^7$ M$^{-1}$ s$^{-1}$ to $1 \times 10^8$ M$^{-1}$ s$^{-1}$, $1 \times 10^7$ M$^{-1}$ s$^{-1}$ to $1 \times 10^9$ M$^{-1}$ s$^{-1}$, $1 \times 10^8$ M$^{-1}$ s$^{-1}$ to $1 \times 10^9$ M$^{-1}$ s$^{-1}$. In certain embodiments, the $k_{on}$ is determined using a monovalent antibody, such as a Fab fragment, as measured by, e.g., BIAcore™ surface plasmon resonance technology. In a particular embodiment, the $k_{on}$ is determined using an assay described in Section 6, infra.

In certain embodiments, an antibody or fragment thereof described herein binds to the ErbB1 epitope with a $K_D$ of less than 375 pM, 350 pM, 325 pM, 300 pM, 275 pM, 250 pM, 225 pM, 200 pM, 175 pM, 150 pM, 125 pM, 100 pM, 75 pM, 50 pM, 45 pM, 40 pM, or 35 pM. In some embodiments, an antibody or fragment thereof described herein binds to the ErbB1 epitope with a $k_D$ of 375 pM, 350 pM, 325 pM, 300 pM, 275 pM, 250 pM, 225 pM, 200 pM, 175 pM, 150 pM, 125 pM, 100 pM, 75 pM, or 50 pM, or between 375 pM to 300 pM, 375 pM to 200 pM, 375 pM to 100 pM, 350 pM to 250 pM, 350 pM to 200 pM, 300 pM to 150 pM, 300 pM to 100 pM, 300 pM to 50 pM, 300 pM to 200 pM, 300 pM to 150 pM, 300 pM to 100 pM, 300 pM to 50 pM, 275 pM to 200 pM, 275 pM to 175 pM, 275 pM to 150 pM, 275 pM to 100 pM, 275 pM to 50 pM, 250 pM to 200 pM, 250 pM to 150 pM, 250 pM to 100 pM, 250 pM to 50 pM, 200 pM to 150 pM, 200 pM to 100 pM, 200 to 50 pM, 150 pM to 100 pM, 150 pM to 50 pM, 100 pM to 50 pM, 200 to 40 pM, 150 pM to 40 pM, 150 pM to 40 pM, or 100 pM to 35 pM. In certain embodiments, the $k_D$ is calculated as the quotient of $k_{off}/k_{on}$, and the $k_{on}$ and $k_{off}$ are determined using a monovalent antibody, such as a Fab fragment, as measured by, e.g., BIAcore™ surface plasmon resonance technology.

In another aspect, provided herein is an antibody(ies) or fragment(s) thereof that specifically binds to an epitope of ErbB4 comprising (i) at least one, two, three, four or more of amino acid residues, or between 1 to 3, 2 to 4, 1 to 5, or 2 to 5 amino acid residues selected from human ErbB4 amino acid residues 270, 271, 288, 289, 290, 291, 292, 293, 296, 301, 305, 306, and 307, and (ii) at least one, two, three, four, five, six, seven, eight, nine, ten, eleven, twelve, thirteen, fourteen, or fifteen amino acid residues, or between 1 to 3, 2 to 4, 2 to 5, 5 to 10, 10 to 15, 15 to 20, 5 to 15, 10 to 20, or 20 to 25 amino acid residues selected from human ErbB4 amino acid residues 308, 310, 313, 314, 315, 318, 336, 338, 339, 340, 372, 374, 399, 400, 401, 402, 403, 405, 406, 429, 430, 431, 432, 454, 455, 456, 457, and 458, and inhibits ligand-dependent and ligand-independent ErbB4 activation. In one embodiment, an antibody(ies) or fragment(s) thereof that specifically binds to an epitope of ErbB4 comprises (i) at least one, two, three, four or more of amino acid residues selected from human ErbB4 amino acid residues 288, 289, 291, 296, and 306, and (ii) at least one, two, three, four, five, six, seven, eight, nine, ten, eleven, twelve, thirteen, fourteen, or fifteen amino acid residues, or between 1 to 3, 2 to 4, 2 to 5, 5 to 10, 10 to 15, 15 to 20, 5 to 15, 10 to 20, or 20 to 25 amino acid residues selected from human ErbB4 amino acid residues 308, 310, 313, 314, 315, 318, 336, 338, 339, 340, 372, 374, 399, 400, 401, 402, 403, 405, 406, 429, 430, 431, 432, 454, 455, 456, 457, and 458, and inhibits ligand-dependent and ligand-independent ErbB4 activation. In a specific embodiment, the ErbB4 epitope is a non-linear epitope. In a specific embodiment, the antibody or fragment thereof binds an ErbB4 epitope and inhibits ligand binding to ErbB4. In a specific embodiment, the antibody or antigen-binding fragment thereof inhibits neuregulin (for example, human neuregulin)-dependent ErbB4 activation. In another specific embodiment, the antibody or antigen-binding fragment thereof inhibits neuregulin 1-dependent ErbB4 activation. In a particular embodiment, the neuregulin 1 is neuregulin 1β1. In another specific embodiment, the antibody or antigen-binding fragment thereof inhibits neuregulin 2-dependent ErbB4 activation. In certain embodiments, the antibody or antigen-binding fragment thereof is a human, humanized or chimeric antibody or antigen-binding fragment thereof. In a specific embodiment, the antibody or antigen-binding fragment thereof is a monoclonal antibody or antigen-binding fragment. In another specific embodiment, the antibody is a human, humanized or chimeric monoclonal antibody or antigen-binding fragment thereof. In certain embodiments, the antibody or antigen-binding fragment thereof is isolated.

In certain embodiments, an antibody or fragment thereof described herein binds to the ErbB4 epitope with a dissociation rate constant ($k_{off}$) of $8.5 \times 10^{-5}$ s$^{-1}$ or less, $5 \times 10^{-5}$ s$^{-1}$ or less, $2.5 \times 10^{-5}$ s$^{-1}$ or less, $1 \times 10^{-5}$ s$^{-1}$ or less, $8.5 \times 10^{-6}$ s$^{-1}$ or less, $5 \times 10^{-6}$ s$^{-1}$ or less, $2.5 \times 10^{-6}$ s$^{-1}$ or less, $1 \times 10^{-6}$ s$^{-1}$ or less, $8.5 \times 10^{-7}$ s$^{-1}$ or less, $5 \times 10^{-7}$ s$^{-1}$ or less, $2.5 \times 10^{-7}$ s$^{-1}$ or less, $1 \times 10^{-7}$ s$^{-1}$ or less, $8.5 \times 10^{-8}$ s$^{-1}$ or less, $5 \times 10^{-8}$ s$^{-1}$ or less, $2.5 \times 10^{-8}$ s$^{-1}$ or less, $1 \times 10^{-8}$ s$^{-1}$ or less, $8.5 \times 10^{-9}$ s$^{-1}$ or less, $5 \times 10^{-9}$ s$^{-1}$ or less, $2.5 \times 10^{-9}$ s$^{-1}$ or less, or $1 \times 10^{-9}$ s$^{-1}$ or less. In some embodiments, an antibody or fragment thereof described herein binds to the ErbB4 epitope with a $k_{off}$ of between $9.5 \times 10^{-5}$ s$^{-1}$ to $1 \times 10^{-9}$ s$^{-1}$, $8.5 \times 10^{-5}$ s$^{-1}$ to $1 \times 10^{-9}$ s$^{-1}$, $5 \times 10^{-5}$ s$^{-1}$ to $1 \times 10^{-9}$ s$^{-1}$, $9.5 \times 10^{-5}$ s$^{-1}$ to $1 \times 10^{-8}$ s$^{-1}$, $5 \times 10^{-5}$ s$^{-1}$ to $1 \times 10^{-8}$ s$^{-1}$, $9.5 \times 10^{-5}$ s$^{-1}$ to $1 \times 10^{-7}$ s$^{-1}$, $5 \times 10^{-5}$ s$^{-1}$ to $1 \times 10^{-7}$ s$^{-1}$, $9.5 \times 10^{-5}$ s$^{-1}$ to $5 \times 10^{-6}$ s$^{-1}$, or $9.5 \times 10^{-5}$ s$^{-1}$ to $1 \times 10^{-5}$ s$^{-1}$. In certain embodiments, the $k_{off}$ is determined using a monovalent antibody, such as a Fab fragment, as measured by, e.g., BIAcore™ surface plasmon resonance technology. In a particular embodiment, the $k_{off}$ is determined using an assay described in Section 6, infra.

In certain embodiments, an antibody or fragment thereof described herein binds to the ErbB4 epitope with an association rate constant ($k_{on}$) of at least $10^5$ M$^{-1}$ s$^{-1}$, at least $5 \times 10^5$ M$^{-1}$ s$^{-1}$, at least $10^6$ M$^{-1}$ s$^{-1}$, at least $5 \times 10^6$ M$^{-1}$ s$^{-1}$, at least $10^7$ M$^{-1}$ s$^{-1}$, at least $5 \times 10^7$ M$^{-1}$ s$^{-1}$, at least $10^8$ M$^{-1}$ s$^{-1}$, at least $5\ 10^8$ M$^{-1}$ s$^{-1}$ or at least $10^9$ M$^{-1}$ s$^{-1}$. In some embodiments, an antibody or fragment thereof described herein binds to the ErbB4 epitope with a $k_{on}$ of between $1 \times 10^5$ $M^{-1}$ $s^{-1}$ to $5 \times 10^5$ $M^{-1}$ $s^{-1}$, $1 \times 10^5$ $M^{-1}$ $s^{-1}$ to $1 \times 10^6$ $M^{-1}$ $s^{-1}$, $1 \times 10^5$ $M^{-1}$ $s^{-1}$ to $5 \times 10^6$ $M^{-1}$ $s^{-1}$, $1 \times 10^5$ $M^{-1}$ $s^{-1}$ to $1 \times 10^7$ $M^{-1}$ $s^{-1}$, $1 \times 10^5$ $M^{-1}$ $s^{-1}$ to $5 \times 10^7$ $M^{-1}$ $s^{-1}$, $1 \times 10^5$ $M^{-1}$ $s^{-1}$ to $10^8$ $M^{-1}$ $s^{-1}$, $1 \times 10^5$ $M^{-1}$ $s^{-1}$ to $1 \times 10^9$ $M^{-1}$ $s^{-1}$, $1 \times 10^6$ $M^{-1}$ $s^{-1}$ to $1 \times 10^7$ $M^{-1}$ $s^{-1}$, $1 \times 10^6$ $M^{-1}$ $s^{-1}$ to $1 \times 10^8$ $M^{-1}$ $s^{-1}$, $1 \times 10^6$ $M^{-1}$ $s^{-1}$ to $1 \times 10^9$ $M^{-1}$ $s^{-1}$, $1 \times 10^7$ $M^{-1}$ $s^{-1}$ to $1 \times 10^8$ $M^{-1}$ $s^{-1}$, $1 \times 10^7$ $M^{-1}$ $s^{-1}$ to $1 \times 10^9$ $M^{-1}$ $s^{-1}$, $1 \times 10^8$ $M^{-1}$ $s^{-1}$ to $1 \times 10^9$ $M^{-1}$ $s^{-1}$. In certain embodiments, the $k_{on}$ is determined using a monovalent antibody, such as a Fab fragment, as measured by, e.g., BIAcore™ surface plasmon resonance technology. In a particular embodiment, the $k_{on}$ is determined using an assay described in Section 6, infra.

In certain embodiments, an antibody or fragment thereof described herein binds to the ErbB4 epitope with a $K_D$ of less than 375 pM, 350 pM, 325 pM, 300 pM, 275 pM, 250 pM, 225 pM, 200 pM, 175 pM, 150 pM, 125 pM, 100 pM, 75 pM, 50 pM, 45 pM, 40 pM, or 35 pM. In some embodiments, an antibody or fragment thereof described herein binds to the ErbB4 epitope with a $k_D$ of 375 pM, 350 pM, 325 pM, 300 pM, 275 pM, 250 pM, 225 pM, 200 pM, 175 pM, 150 pM, 125 pM, 100 pM, 75 pM, or 50 pM, or between 375 pM to 300 pM, 375 pM to 200 pM, 375 pM to 100 pM, 350 pM to 250 pM, 350 pM to 200 pM, 300 pM to 150 pM, 300 pM to 100 pM, 300 pM to 50 pM, 300 pM to 200 pM, 300 pM to 150 pM, 300 pM to 100 pM, 300 pM to 50 pM, 275 pM to 200 pM, 275 pM to 175 pM, 275 pM to 150 pM, 275 pM to 100 pM, 275 pM to 50 pM, 250 pM to 200 pM, 250 pM to 150 pM, 250 pM to 100 pM, 250 pM to 50 pM, 200 pM to 150 pM, 200 pM to 100 pM, 200 to 50 pM, 150 pM to 100 pM, 150 pM to 50 pM, 100 pM to 50 pM, 200 to 40 pM, 150 pM to 40 pM, 150 pM to 40 pM, or 100 pM to 35 pM. In certain embodiments, the $k_D$ is calculated as the quotient of $k_{off}/k_{on}$, and the $k_{on}$ and $k_{off}$ are determined using a monovalent antibody, such as a Fab fragment, as measured by, e.g., BIAcore™ surface plasmon resonance technology.

In another aspect, provided herein is an antibody(ies) or fragment(s) thereof that binds to an ErbB extracellular domain, wherein the antibody(ies) or fragment(s) thereof binds to an ErbB epitope comprising (i) at least one, two, three, four, five or more amino acid residues within the domain II/domain III hinge region of the ErbB, e.g., human ErbB, and (ii) at least one, two, three, four, five, six, seven, eight, nine, ten or more additional amino acid residues, or between 1 to 4, 2 to 4, 1 to 5, 2 to 6, 5 to 8, 5 to 10, 8 to 10, or 1 to 10 additional amino acid residues within domain II of the ErbB extracellular domain, e.g., human extracellular domain, and inhibits ligand-dependent and ligand-independent ErbB activation.

In another aspect, provided herein is an antibody(ies) or fragment(s) thereof that binds to an ErbB extracellular domain, wherein the antibody(ies) or fragment(s) thereof binds to an ErbB epitope comprising (i) at least one, two, three, four, five or more amino acid residues within the domain II/domain III hinge region of the ErbB, e.g., human ErbB, and (ii) at least one, two, three, four, five, six, seven, eight, nine, ten, eleven, twelve, thirteen, fourteen or fifteen additional amino acid residues, or between 1 to 4, 2 to 4, 1 to 5, 2 to 6, 5 to 8, 5 to 10, 8 to 10, 1 to 10, 5 to 15, 10 to 15, 1 to 15, 5 to 15, 1 to 20, 10 to 20 or 15 to 20 additional amino acid residues within domain III of the ErbB extracellular domain, e.g., human ErbB extracellular domain, and inhibits ligand-dependent and ligand-independent ErbB activation.

In another aspect, provided herein is an antibody(ies) or fragment(s) thereof that binds to an ErbB extracellular domain, wherein the antibody(ies) or fragment(s) thereof binds to an ErbB epitope comprising (i) at least one, two, three, four, five or more amino acid residues within the domain II/domain III hinge region of the ErbB, e.g., human ErbB, (ii) at least one, two, three, four, five, six, seven, eight, nine, ten or more additional amino acid residues, or between 1 to 4, 2 to 4, 1 to 5, 2 to 6, 5 to 8, 5 to 10, 8 to 10, or 1 to 10 additional amino acid residues within domain II of the ErbB extracellular domain, e.g., human extracellular domain, and (iii) at least one, two, three, four, five, six, seven, eight, nine, ten, eleven, twelve, thirteen, fourteen or fifteen additional amino acid residues, or between 1 to 4, 2 to 4, 1 to 5, 2 to 6, 5 to 8, 5 to 10, 8 to 10, 1 to 10, 5 to 15, 10 to 15, 1 to 15, 5 to 15, 1 to 20, 10 to 20 or 15 to 20 additional amino acid residues within domain III of the ErbB extracellular domain, e.g., human ErbB extracellular domain, and inhibits ligand-dependent and ligand-independent ErbB activation.

In certain embodiments, an antibody or fragment thereof described herein binds to an ErbB extracellular domain with a dissociation rate constant ($k_{off}$) of $8.5 \times 10^{-5}$ $s^{-1}$ or less, $5 \times 10^{-5}$ $s^{-1}$ or less, $2.5 \times 10^{-5}$ $s^{-1}$ or less, $1 \times 10^{-5}$ $s^{-1}$ or less, $8.5 \times 10^{-6}$ $s^{-1}$ or less, $5 \times 10^{-6}$ $s^{-1}$ or less, $2.5 \times 10^{-6}$ $s^{-1}$ or less, $1 \times 10^{-6}$ $s^{-1}$ or less, $8.5 \times 10^{-7}$ $s^{-1}$ or less, $5 \times 10^{-7}$ $s^{-1}$ or less, $2.5 \times 10^{-7}$ $s^{-1}$ or less, $1 \times 10^{-7}$ $s^{-1}$ or less, $8.5 \times 10^{-8}$ $s^{-1}$ or less, $5 \times 10^{-8}$ $s^{-1}$ or less, $2.5 \times 10^{-8}$ $s^{-1}$ or less, $1 \times 10^{-8}$ $s^{-1}$ or less, $8.5 \times 10^{-9}$ $s^{-1}$ or less, $5 \times 10^{-9}$ $s^{-1}$ or less, $2.5 \times 10^{-9}$ $s^{-1}$ or less, or $1 \times 10^{-9}$ $s^{-1}$ or less. In some embodiments, an antibody or fragment thereof described herein binds to an ErbB extracellular domain with a $k_{off}$ of between $9.5 \times 10^{-5}$ $s^{-1}$ to $1 \times 10^{-9}$ $s^{-1}$, $8.5 \times 10^{-5}$ $s^{-1}$ to $1 \times 10^{-9}$ $s^{-1}$, $5 \times 10^{-5}$ $s^{-1}$ to $1 \times 10^{-9}$ $s^{-1}$, $9.5 \times 10^{-5}$ $s^{-1}$ to $1 \times 10^{-8}$ $s^{-1}$, $5 \times 10^{-5}$ $s^{-1}$ to $1 \times 10^{-8}$ $s^{-1}$, $9.5 \times 10^{-5}$ $s^{-1}$ to $1 \times 10^{-7}$ $s^{-1}$, $5 \times 10^{-5}$ $s^{-1}$ to $1 \times 10^{-7}$ $s^{-1}$, $9.5 \times 10^{-5}$ $s^{-1}$ to $5 \times 10^{-6}$ $s^{-1}$, or $9.5 \times 10^{-5}$ $s^{-1}$ to $1 \times 10^{-5}$ $s^{-1}$. In certain embodiments, the $k_{off}$ is determined using a monovalent antibody, such as a Fab fragment, as measured by, e.g., BIAcore™ surface plasmon resonance technology. In a particular embodiment, the $k_{off}$ is determined using an assay described in Section 6, infra.

In certain embodiments, an antibody or fragment thereof described herein binds to an ErbB extracellular domain with an association rate constant ($k_{on}$) of at least $10^5$ $M^{-1}$ $s^{-1}$, at least $5 \times 10^5$ $M^{-1}$ $s^{-1}$, at least $10^6$ $M^{-1}$ $s^{-1}$, at least $5 \times 10^6$ $M^{-1}$ $s^{-1}$, at least $10^7$ $M^{-1}$ $s^{-1}$, at least $5 \times 10^7$ $M^{-1}$ $s^{-1}$, at least $10^8$ $M^{-1}$ $s^{-1}$, at least $5 \cdot 10^8$ $M^{-1}$ $s^{-1}$ or at least $10^9$ $M^{-1}$ $s^{-1}$. In some embodiments, an antibody or fragment thereof described herein binds to an ErbB extracellular domain with a $k_{on}$ of between $1 \times 10^5$ $M^{-1}$ $s^{-1}$ to $5 \times 10^5$ $M^{-1}$ $s^{-1}$, $1 \times 10^5$ $M^{-1}$ $s^{-1}$ to $1 \times 10^6$ $M^{-1}$ $s^{-1}$, $1 \times 10^5$ $M^{-1}$ $s^{-1}$ to $5 \times 10^6$ $M^{-1}$ $s^{-1}$, $1 \times 10^5$ $M^{-1}$ $s^{-1}$ to $1 \times 10^7$ $M^{-1}$ $s^{-1}$, $1 \times 10^5$ $M^{-1}$ $s^{-1}$ to $5 \times 10^7$ $M^{-1}$ $s^{-1}$, $1 \times 10^5$ $M^{-1}$ $s^{-1}$ to $10^8$ $M^{-1}$ $s^{-1}$, $1 \times 10^5$ $M^{-1}$ $s^{-1}$ to $1 \times 10^9$ $M^{-1}$ $s^{-1}$, $1 \times 10^6$ $M^{-1}$ $s^{-1}$ to $1 \times 10^7$ $M^{-1}$ $s^{-1}$, $1 \times 10^6$ $M^{-1}$ $s^{-1}$ to $1 \times 10^8$ $M^{-1}$ $s^{-1}$, $1 \times 10^6$ $M^{-1}$ $s^{-1}$ to $1 \times 10^9$ $M^{-1}$ $s^{-1}$, $1 \times 10^7$ $M^{-1}$ $s^{-1}$ to $1 \times 10^8$ $M^{-1}$ $s^{-1}$, $1 \times 10^7$ $M^{-1}$ $s^{-1}$ to $1 \times 10^9$ $M^{-1}$ $s^{-1}$, $1 \times 10^8$ $M^{-1}$ $s^{-1}$ to $1 \times 10^9$ $M^{-1}$ $s^{-1}$. In certain embodiments, the $k_{on}$ is determined using a monovalent antibody, such as a Fab fragment, as measured by, e.g., BIAcore™ surface plasmon resonance technology. In a particular embodiment, the $k_{on}$ is determined using an assay described in Section 6, infra.

In certain embodiments, an antibody or fragment thereof described herein binds to an ErbB extracellular domain with a $K_D$ of less than 375 pM, 350 pM, 325 pM, 300 pM, 275 pM, 250 pM, 225 pM, 200 pM, 175 pM, 150 pM, 125 pM, 100 pM, 75 pM, 50 pM, 45 pM, 40 pM, or 35 pM. In some embodiments, an antibody or fragment thereof described herein binds to an ErbB extracellular domain with a $k_D$ of 375 pM, 350 pM, 325 pM, 300 pM, 275 pM, 250 pM, 225 pM, 200 pM, 175 pM, 150 pM, 125 pM, 100 pM, 75 pM, or 50 pM, or between 375 pM to 300 pM, 375 pM to 200 pM, 375 pM to 100 pM, 350 pM to 250 pM, 350 pM to 200 pM, 300 pM to 150 pM, 300 pM to 100 pM, 300 pM to 50 pM, 300 pM to 200 pM, 300 pM to 150 pM, 300 pM to 100 pM, 300 pM to 50 pM, 275 pM to 200 pM, 275 pM to 175 pM, 275 pM to 150 pM, 275 pM to 100 pM, 275 pM to 50 pM, 250 pM to 200 pM, 250 pM to 150 pM, 250 pM to 100 pM, 250 pM to 50 pM, 200 pM to 150 pM, 200 pM to 100 pM, 200 to 50 pM, 150 pM to 100 pM, 150 pM to 50 pM, 100 pM to 50 pM, 200 to 40 pM, 150 pM to 40 pM, 150 pM to 40 pM, or 100 pM to 35 pM. In certain embodiments, the $k_D$ is calculated as the quotient of $k_{off}/k_{on}$, and the $k_{on}$ and $k_{off}$ are determined using a monovalent antibody, such as a Fab fragment, as measured by, e.g., BIAcore™ surface plasmon resonance technology.

In a specific embodiment, the ErbB epitope is a non-linear epitope. In a specific embodiment, the antibody or fragment binds to an ErbB extracellular domain and inhibits ligand binding to ErbB. In a specific embodiment, the antibody or antigen-binding fragment thereof inhibits neuregulin (for example, human neuregulin)-dependent ErbB activation. In another specific embodiment, the antibody or antigen-binding fragment thereof inhibits neuregulin 1-dependent ErbB activation. In a particular embodiment, the neuregulin 1 is neuregulin 1β1. In another specific embodiment, the antibody or antigen-binding fragment thereof inhibits neuregulin 2-dependent ErbB activation. In certain embodiments, the antibody or antigen-binding fragment thereof is a human, humanized or chimeric antibody or antigen-binding fragment thereof. In a specific embodiment, the antibody or antigen-binding fragment thereof is a monoclonal antibody or antigen-binding fragment. In another specific embodiment, the antibody is a human, humanized or chimeric monoclonal antibody or antigen-binding fragment thereof. In certain embodiments, the antibody or antigen-binding fragment thereof is isolated.

In certain aspects the ErbB is ErbB3, e.g., human ErbB3, and in a specific embodiment, provided herein is an antibody(ies) or fragment(s) thereof that binds to an ErbB3 extracellular domain, e.g., a human ErbB3 extracellular domain, wherein the antibody(ies) or fragment(s) thereof binds to an ErbB3 epitope comprising (i) at least one, two, three, four, five or more amino acid residues within the domain II/domain III hinge region of human ErbB3, e.g., amino acid residues 309, 310, or 311 of the human ErbB3 domain II/domain III hinge region, and (ii) at least one, two, three, four, five, six, seven, eight, nine, ten or more additional amino acid residues, or between 1 to 4, 2 to 4, 1 to 5, 2 to 6, 5 to 8, 5 to 10, 8 to 10, or 1 to 10 additional amino acid residues within domain II of the ErbB3 extracellular domain, e.g., human ErbB3 extracellular domain, for example, one or more of amino acid residues 291, 292, 294, or 299 within domain II of human ErbB3, and inhibits ligand-dependent and ligand-independent ErbB activation.

In certain aspects the ErbB is ErbB3, e.g., human ErbB3, and in a specific embodiment, provided herein is an antibody(ies) or fragment(s) thereof that binds to an ErbB3 extracellular domain, e.g., a human ErbB3 extracellular domain, wherein the antibody(ies) or fragment(s) thereof binds to an ErbB3 epitope comprising (i) at least one, two, three, four, five or more amino acid residues within the domain II/domain III hinge region of ErbB3, e.g., amino acid residues 309, 310, or 311 of the human ErbB3 domain II/domain III hinge region, and (ii) at least one, two, three, four, five, six, seven, eight, nine, ten, eleven, twelve, thirteen, fourteen or fifteen additional amino acid residues, or between 1 to 4, 2 to 4, 1 to 5, 2 to 6, 5 to 8, 5 to 10, 8 to 10, 1 to 10, 5 to 15, 10 to 15, 1 to 15, 5 to 15, 1 to 20, 10 to 20 or 15 to 20 additional amino acid residues within domain III of the ErbB3 extracellular domain, e.g., human ErbB3 extracellular domain, for example, one or more of amino acid residues 310, 311, 317, 318, 319, 337, 339, 373, 375, 400, 401, 402, 403, 404, 406, 407, 408, 429, 431, 432, 433, 456, 457, 458 and 462 within domain III of human ErbB3, and inhibits ligand-dependent and ligand-independent ErbB activation.

In certain aspects the ErbB is ErbB3, e.g., human ErbB3, and in a specific embodiment, provided herein is an antibody(ies) or fragment(s) thereof that binds to an ErbB3 extracellular domain, e.g., a human ErbB3 extracellular domain, wherein the antibody(ies) or fragment(s) thereof binds to an ErbB3 epitope comprising (i) at least one, two, three, four, five or more amino acid residues within the domain II/domain III hinge region of human ErbB3, e.g., amino acid residues 309, 310, or 311 of the human ErbB3 domain II/domain III hinge region, (ii) at least one, two, three, four, five, six, seven, eight, nine, ten or more additional amino acid residues, or between 1 to 4, 2 to 4, 1 to 5, 2 to 6, 5 to 8, 5 to 10, 8 to 10, or 1 to 10 additional amino acid residues within domain II of the ErbB3 extracellular domain, e.g., human ErbB3 extracellular domain, for example, one or more of amino acid residues 291, 292, 294, or 299 within domain II of human ErbB3, and (iii) at least one, two, three, four, five, six, seven, eight, nine, ten, eleven, twelve, thirteen, fourteen or fifteen additional amino acid residues, or between 1 to 4, 2 to 4, 1 to 5, 2 to 6, 5 to 8, 5 to 10, 8 to 10, 1 to 10, 5 to 15, 10 to 15, 1 to 15, 5 to 15, 1 to 20, 10 to 20 or 15 to 20 additional amino acid residues within domain III of the ErbB3 extracellular domain, e.g., human ErbB3 extracellular domain, for example, one or more of amino acid residues 310, 311, 317, 318, 319, 337, 339, 373, 375, 400, 401, 402, 403, 404, 406, 407, 408, 429, 431, 432, 433, 456, 457, 458 and 462 within domain III of human ErbB3, and inhibits ligand-dependent and ligand-independent ErbB activation.

In a specific embodiment, the ErbB3 epitope is a non-linear epitope. In a specific embodiment, the antibody or fragment binds to an ErbB3 extracellular domain and inhibits its ligand binding to ErbB3. In a specific embodiment, the antibody or antigen-binding fragment thereof inhibits neuregulin (for example, human neuregulin)-dependent ErbB3 activation. In another specific embodiment, the antibody or antigen-binding fragment thereof inhibits neuregulin 1-dependent ErbB3 activation. In a particular embodiment, the neuregulin 1 is neuregulin 1β1. In another specific embodiment, the antibody or antigen-binding fragment thereof inhibits neuregulin 2-dependent ErbB3 activation. In certain embodiments, the antibody or antigen-binding fragment thereof is a human, humanized or chimeric antibody or antigen-binding fragment thereof. In a specific embodiment, the antibody or antigen-binding fragment thereof is a monoclonal antibody or antigen-binding fragment. In another specific embodiment, the antibody is a human, humanized or chimeric monoclonal antibody or antigen-binding fragment thereof. In certain embodiments, the antibody or antigen-binding fragment thereof is isolated.

In certain embodiments, the ErbB3 epitope comprises (i) at least one, two, three, four, five or more amino acid residues within the domain II/domain III hinge region of the ErbB3, e.g., human ErbB3, and (ii) one, two, three, four, five, six, seven, eight, nine, or ten additional amino acid residues in domain II of the ErbB3 extracellular domain, e.g., human ErbB3 extracellular domain, and one, two, three, four, five, six, seven, eight, nine, ten, eleven, twelve, thirteen, fourteen or fifteen additional amino acid residues within domain III of the ErbB3 extracellular domain, e.g., human ErbB3 extracellular domain.

In certain embodiments, an antibody or fragment thereof described herein binds to an ErbB3 extracellular domain with a dissociation rate constant ($k_{off}$) of $8.5 \times 10^{-5}$ s$^{-1}$ or less, $5 \times 10^{-5}$ s$^{-1}$ or less, $2.5 \times 10^{-5}$ s$^{-1}$ or less, $1 \times 10^{-5}$ s$^{-1}$ or less, $8.5 \times 10^{-6}$ s$^{-1}$ or less, $5 \times 10^{-6}$ s$^{-1}$ or less, $2.5 \times 10^{-6}$ s$^{-1}$ or less, $1 \times 10^{-6}$ s$^{-1}$ or less, $8.5 \times 10^{-7}$ s$^{-1}$ or less, $5 \times 10^{-7}$ s$^{-1}$ or less, $2.5 \times 10^{-7}$ s$^{-1}$ or less, $1 \times 10^{-7}$ s$^{-1}$ or less, $8.5 \times 10^{-8}$ s$^{-1}$ or less, $5 \times 10^{-8}$ s$^{-1}$ or less, $2.5 \times 10^{-8}$ s$^{-1}$ or less, $1 \times 10^{-8}$ s$^{-1}$ or less, $8.5 \times 10^{-9}$ s$^{-1}$ or less, $5 \times 10^{-9}$ s$^{-1}$ or less, $2.5 \times 10^{-9}$ s$^{-1}$ or less, or $1 \times 10^{-9}$ s$^{-1}$ or less. In some embodiments, an antibody or fragment thereof described herein binds to an ErbB3 extracellular domain with a $k_{off}$ of between $9.5 \times 10^{-5}$ s$^{-1}$ to $1 \times 10^{-9}$ s$^{-1}$, $8.5 \times 10^{-5}$ s$^{-1}$ to $1 \times 10^{-9}$ s$^{-1}$, $5 \times 10^{-5}$ s$^{-1}$ to $1 \times 10^{-9}$ s$^{-1}$, $9.5 \times 10^{-5}$ s$^{-1}$ to $1 \times 10^{-8}$ s$^{-1}$, $5 \times 10^{-5}$ s$^{-1}$ to $1 \times 10^{-8}$ s$^{-1}$, $9.5 \times 10^{-5}$ s$^{-1}$ to $1 \times 10^{-7}$ s$^{-1}$, $5 \times 10^{-5}$ s$^{-1}$ to $1 \times 10^{-7}$ s$^{-1}$, $9.5 \times 10^{-5}$ s$^{-1}$ to $5 \times 10^{-6}$ s$^{-1}$, or $9.5 \times 10^{-5}$ s$^{-1}$ to $1 \times 10^{-5}$ s$^{-1}$. In certain embodiments, the $k_{off}$ is determined using a monovalent antibody, such as a Fab fragment, as measured by, e.g., BIAcore™ surface plasmon resonance technology. In a particular embodiment, the $k_{off}$ is determined using an assay described in Section 6, infra.

In certain embodiments, an antibody or fragment thereof described herein binds to an ErbB3 extracellular domain with an association rate constant ($k_{on}$) of at least $10^5$ M$^{-1}$ s$^{-1}$, at least $5 \times 10^5$ M$^{-1}$ s$^{-1}$, at least $10^6$ M$^{-1}$ s$^{-1}$, at least $5 \times 10^6$ M$^{-1}$ s$^{-1}$, at least $10^7$ M$^{-1}$ s$^{-1}$, at least $5 \times 10^7$ M$^{-1}$ s$^{-1}$, at least $10^8$ M$^{-1}$ s$^{-1}$, at least $5 \times 10^8$ M$^{-1}$ s$^{-1}$ or at least $10^9$ M$^{-1}$ s$^{-1}$. In some embodiments, an antibody or fragment thereof described herein binds to an ErbB3 extracellular domain with a $k_{on}$ of between $1 \times 10^5$ M$^{-1}$ s$^{-1}$ to $5 \times 10^5$ M$^{-1}$ s$^{-1}$, $1 \times 10^5$ M$^{-1}$ s$^{-1}$ to $1 \times 10^6$ M$^{-1}$ s$^{-1}$, $1 \times 10^5$ M$^{-1}$ s$^{-1}$ to $5 \times 10^6$ M$^{-1}$ s$^{-1}$, $1 \times 10^5$ M$^{-1}$ s$^{-1}$ to $1 \times 10^7$ M$^{-1}$ s$^{-1}$, $1 \times 10^5$ M$^{-1}$ s$^{-1}$ to $5 \times 10^7$ M$^{-1}$ s$^{-1}$, $1 \times 10^5$ M$^{-1}$ s$^{-1}$ to $10^8$ M$^{-1}$ s$^{-1}$, $1 \times 10^5$ M$^{-1}$ s$^{-1}$ to $1 \times 10^9$ M$^{-1}$ s$^{-1}$, $1 \times 10^6$ M$^{-1}$ s$^{-1}$ to $1 \times 10^7$ M$^{-1}$ s$^{-1}$, $1 \times 10^6$ M$^{-1}$s$^{-1}$ to $1 \times 10^8$ M$^{-1}$ s$^{-1}$, $1 \times 10^6$ M$^{-1}$ s$^{-1}$ to $1 \times 10^9$ M$^{-1}$ s$^{-1}$, $1 \times 10^7$ M$^{-1}$ s$^{-1}$ to $1 \times 10^8$ M$^{-1}$ s$^{-1}$, $1 \times 10^7$ M$^{-1}$s$^{-1}$ to $1 \times 10^9$ M$^{-1}$ s$^{-1}$, $1 \times 10^8$ M$^{-1}$ s$^{-1}$ to $1 \times 10^9$ M$^{-1}$ s$^{-1}$. In certain embodiments, the $k_{on}$ is determined using a monovalent antibody, such as a Fab fragment, as measured by, e.g., BIAcore™ surface plasmon resonance technology. In a particular embodiment, the $k_{on}$ is determined using an assay described in Section 6, infra.

In certain embodiments, an antibody or fragment thereof described herein binds to an ErbB3 extracellular domain with a $K_D$ of less than 375 pM, 350 pM, 325 pM, 300 pM, 275 pM, 250 pM, 225 pM, 200 pM, 175 pM, 150 pM, 125 pM, 100 pM, 75 pM, 50 pM, 45 pM, 40 pM, or 35 pM. In some embodiments, an antibody or fragment thereof described herein binds to an ErbB3 extracellular domain with a $k_D$ of 375 pM, 350 pM, 325 pM, 300 pM, 275 pM, 250 pM, 225 pM, 200 pM, 175 pM, 150 pM, 125 pM, 100 pM, 75 pM, or 50 pM, or between 375 pM to 300 pM, 375 pM to 200 pM, 375 pM to 100 pM, 350 pM to 250 pM, 350 pM to 200 pM, 300 pM to 150 pM, 300 pM to 100 pM, 300 pM to 50 pM, 300 pM to 200 pM, 300 pM to 150 pM, 300 pM to 100 pM, 300 pM to 50 pM, 275 pM to 200 pM, 275 pM to 175 pM, 275 pM to 150 pM, 275 pM to 100 pM, 275 pM to 50 pM, 250 pM to 200 pM, 250 pM to 150 pM, 250 pM to 100 pM, 250 pM to 50 pM, 200 pM to 150 pM, 200 pM to 100 pM, 200 to 50 pM, 150 pM to 100 pM, 150 pM to 50 pM, 100 pM to 50 pM, 200 pM to 40 pM, 150 pM to 40 pM, 150 pM to 40 pM, or 100 pM to 35 pM. In certain embodiments, the $k_D$ is calculated as the quotient of $k_{off}/k_{on}$, and the $k_{on}$ and $k_{off}$ are determined using a monovalent antibody, such as a Fab fragment, as measured by, e.g., BIAcore™ surface plasmon resonance technology.

In certain aspects the ErbB is ErbB1, e.g., human ErbB1, and in a specific embodiment, provided herein is an antibody(ies) or fragment(s) thereof that binds to an ErbB3 extracellular domain, e.g., a human ErbB1 extracellular domain, wherein the antibody(ies) or fragment(s) thereof binds to an ErbB1 epitope comprising (i) at least one, two, three, four, five or more amino acid residues within the domain II/domain III hinge region of human ErbB1, e.g., amino acid residues 310, 311, or 312 of the human ErbB1 domain II/domain III hinge region, and (ii) at least one, two, three, four, five, six, seven, eight, nine, ten or more additional amino acid residues, or between 1 to 4, 2 to 4, 1 to 5, 2 to 6, 5 to 8, 5 to 10, 8 to 10, or 1 to 10 additional amino acid residues within domain II of the ErbB1 extracellular domain, e.g., human ErbB1 extracellular domain, for example, one or more of amino acid residues 274, 286, 287, 289, 291, 292, 293, 294, 295, 302, 309, 310, or 311 within domain II of human ErbB1, and inhibits ligand-dependent and ligand-independent ErbB1 activation. In one embodiment, an antibody or fragment thereof binds to an ErbB1 extracellular domain, e.g., a human ErbB2 extracellular domain, wherein the antibody or fragment thereof binds to an ErbB1 epitope comprising (i) one, two, or more of amino acid residues 292, 293, 295, 302, and 310 within domain II of human ErbB2, and (ii) one or more of amino acid residues 274, 286, 287, 289, 291, 292, 293, 294, 295, 302, 309, 310, or 311 within domain II of human ErbB1, and inhibits ligand-dependent and ligand-independent ErbB1 activation.

In certain aspects the ErbB is ErbB1, e.g., human ErbB1, and in a specific embodiment, provided herein is an antibody(ies) or fragment(s) thereof that binds to an ErbB1 extracellular domain, e.g., a human ErbB1 extracellular domain, wherein the antibody(ies) or fragment(s) thereof binds to an ErbB1 epitope comprising (i) at least one, two, three, four, five or more amino acid residues within the domain II/domain III hinge region of ErbB1, e.g., amino acid residues 310, 311, or 312 of the human ErbB1 domain II/domain III hinge region, and (ii) at least one, two, three, four, five, six, seven, eight, nine, ten, eleven, twelve, thirteen, fourteen or fifteen additional amino acid residues, or between 1 to 4, 2 to 4, 1 to 5, 2 to 6, 5 to 8, 5 to 10, 8 to 10, 1 to 10, 5 to 15, 10 to 15, 1 to 15, 5 to 15, 1 to 20, 10 to 20 or 15 to 20 additional amino acid residues within domain III of the ErbB1 extracellular domain, e.g., human ErbB1 extracellular domain, for example, one or more of amino acid residues 312, 314, 318, 319, 320, 322, 340, 342, 343, 344, 378, 379, 403, 404, 405, 406, 407, 411, 431, 433, 434, 458, 459, 460, 461, or 462 within domain III of human ErbB1, and inhibits ligand-dependent and ligand-independent ErbB1 activation.

In certain aspects the ErbB is ErbB1, e.g., human ErbB1, and in a specific embodiment, provided herein is an antibody(ies) or fragment(s) thereof that binds to an ErbB3 extracellular domain, e.g., a human ErbB1 extracellular domain, wherein the antibody(ies) or fragment(s) thereof binds to an ErbB1 epitope comprising (i) at least one, two, three, four, five or more amino acid residues within the domain II/domain III hinge region of human ErbB1, e.g., amino acid residues 310, 311, or 312 of the human ErbB1 domain II/domain III hinge region, (ii) at least one, two, three, four, five, six, seven, eight, nine, ten or more additional amino acid residues, or between 1 to 4, 2 to 4, 1 to 5, 2 to 6, 5 to 8, 5 to 10, 8 to 10, or 1 to 10 additional amino acid residues within domain II of the ErbB1 extracellular domain, e.g., human ErbB1 extracellular domain, for example, one or more of amino acid residues 274, 286, 287, 289, 291, 292, 293, 294, 295, 302, 209, 210, or 311 within domain II of human ErbB1, and (iii) at least one, two, three, four, five, six, seven, eight, nine, ten, eleven, twelve, thirteen, fourteen or fifteen additional amino acid residues, or between 1 to 4, 2 to 4, 1 to 5, 2 to 6, 5 to 8, 5 to 10, 8 to 10, 1 to 10, 5 to 15, 10 to 15, 1 to 15, 5 to 15, 1 to 20, 10 to 20 or 15 to 20 additional amino acid residues within domain III of the ErbB1 extracellular domain, e.g., human ErbB1 extracellular domain, for example, one or more of amino acid residues 312, 314, 318, 319, 320, 322, 340, 342, 343, 344, 378, 379, 403, 404, 405, 406, 407, 411, 431, 433, 434, 458, 459, 460, 461, or 462 within domain III of human ErbB1, and inhibits ligand-dependent and ligand-independent ErbB1 activation.

In a specific embodiment, the ErbB1 epitope is a non-linear epitope. In a specific embodiment, the antibody or fragment binds to an ErbB1 extracellular domain and inhibits ligand binding to ErbB1. In a specific embodiment, the antibody or antigen-binding fragment thereof inhibits neuregulin (for example, human neuregulin)-dependent ErbB1 activation. In another specific embodiment, the antibody or antigen-binding fragment thereof inhibits neuregulin 1-dependent ErbB1 activation. In a particular embodiment, the neuregulin 1 is neuregulin 1β1. In another specific embodiment, the antibody or antigen-binding fragment thereof inhibits neuregulin 2-dependent ErbB1 activation. In certain embodiments, the antibody or antigen-binding fragment thereof is a human, humanized or chimeric antibody or antigen-binding fragment thereof. In a specific embodiment, the antibody or antigen-binding fragment thereof is a monoclonal antibody or antigen-binding fragment. In another specific embodiment, the antibody is a human, humanized or chimeric monoclonal antibody or antigen-binding fragment thereof. In certain embodiments, the antibody or antigen-binding fragment thereof is isolated.

In certain embodiments, the ErbB1 epitope comprises (i) at least one, two, three, four, five or more amino acid residues within the domain II/domain III hinge region of the ErbB1, e.g., human ErbB, and (ii) one, two, three, four, five, six, seven, eight, nine, or ten additional amino acid residues in domain II of the ErbB1 extracellular domain, e.g., human ErbB1 extracellular domain, and one, two, three, four, five, six, seven, eight, nine, ten, eleven, twelve, thirteen, fourteen or fifteen additional amino acid residues within domain III of the ErbB1 extracellular domain, e.g., human ErbB1 extracellular domain.

In certain embodiments, an antibody or fragment thereof described herein binds to an ErbB1 extracellular domain with a dissociation rate constant ($k_{off}$) of $8.5 \times 10^{-5}$ $s^{-1}$ or less, $5 \times 10^{-5}$ $s^{-1}$ or less, $2.5 \times 10^{-5}$ $s^{-1}$ or less, $1 \times 10^{-5}$ $s^{-1}$ or less, $8.5 \times 10^{-6}$ $s^{-1}$ or less, $5 \times 10^{-6}$ $s^{-1}$ or less, $2.5 \times 10^{-6}$ $s^{-1}$ or less, $1 \times 10^{-6}$ $s^{-1}$ or less, $8.5 \times 10^{-7}$ $s^{-1}$ or less, $5 \times 10^{-7}$ $s^{-1}$ or less, $2.5 \times 10^{-7}$ $s^{-1}$ or less, $1 \times 10^{-7}$ $s^{-1}$ or less, $8.5 \times 10^{-8}$ $s^{-1}$ or less, $5 \times 10^{-8}$ $s^{-1}$ or less, $2.5 \times 10^{-8}$ $s^{-1}$ or less, $1 \times 10^{-8}$ $s^{-1}$ or less, $8.5 \times 10^{-9}$ $s^{-1}$ or less, $5 \times 10^{-9}$ $s^{-1}$ or less, $2.5 \times 10^{-9}$ $s^{-1}$ or less, or $1 \times 10^{-9}$ $s^{-1}$ or less. In some embodiments, an antibody or fragment thereof described herein binds to an ErbB1 extracellular domain with a $k_{off}$ of between $9.5 \times 10^{-5}$ $s^{-1}$ to $1 \times 10^{-9}$ $s^{-1}$, $8.5 \times 10^{-5}$ $s^{-1}$ to $1 \times 10^{-9}$ $s^{-1}$, $5 \times 10^{-5}$ $s^{-1}$ to $1 \times 10^{-9}$ $s^{-1}$, $9.5 \times 10^{-5}$ $s^{-1}$ to $1 \times 10^{-8}$ $s^{-1}$, $5 \times 10^{-5}$ $s^{-1}$ to $1 \times 10^{-8}$ $s^{-1}$, $9.5 \times 10^{-5}$ $s^{-1}$ to $1 \times 10^{-7}$ $s^{-1}$, $5 \times 10^{-5}$ $s^{-1}$ to $1 \times 10^{-7}$ $s^{-1}$, $9.5 \times 10^{-5}$ $s^{-1}$ to $5 \times 10^{-6}$ $s^{-1}$, or $9.5 \times 10^{-5}$ $s^{-1}$ to $1 \times 10^{-5}$ $s^{-1}$. In certain embodiments, the $k_{off}$ is determined using a monovalent antibody, such as a Fab fragment, as measured by, e.g., BIAcore™ surface plasmon resonance technology. In a particular embodiment, the $k_{off}$ is determined using an assay described in Section 6, infra.

In certain embodiments, an antibody or fragment thereof described herein binds to an ErbB1 extracellular domain with an association rate constant ($k_{on}$) of at least $10^5$ $M^{-1}$ $s^{-1}$, at least $5 \times 10^5$ $M^{-1}$ $s^{-1}$, at least $10^6$ $M^{-1}$ $s^{-1}$, at least $5 \times 10^6$ $M^{-1}$ $s^{-1}$, at least $10^7$ $M^{-1}$ $s^{-1}$, at least $5 \times 10^7$ $M^{-1}$ $s^{-1}$, at least $10^8$ $M^{-1}$ $s^{-1}$, at least $5$ $10^8$ $M^{-1}$ $s^{-1}$ or at least $10^9$ $M^{-1}$ $s^{-1}$. In some embodiments, an antibody or fragment thereof described herein binds to an ErbB1 extracellular domain with a $k_{on}$ of between $1 \times 10^5$ $M^{-1}$ $s^{-1}$ to $5 \times 10^5$ $M^{-1}$ $s^{-1}$, $1 \times 10^5$ $M^{-1}$ $s^{-1}$ to $1 \times 10^6$ $M^{-1}$ $s^{-1}$, $1 \times 10^5$ $M^{-1}$ $s^{-1}$ to $5 \times 10^6$ $M^{-1}$ $s^{-1}$, $1 \times 10^5$ $M^{-1}$ $s^{-1}$ to $1 \times 10^7$ $M^{-1}$ $s^{-1}$, $1 \times 10^5$ $M^{-1}$ $s^{-1}$ to $5 \times 10^7$ $M^{-1}$ $s^{-1}$, $1 \times 10^5$ $M^{-1}$ $s^{-1}$ to $10^8$ $M^{-1}$ $s^{-1}$, $1 \times 10^5$ $M^{-1}$ $s^{-1}$ to $1 \times 10^9$ $M^{-1}$ $s^{-1}$, $1 \times 10^6$ $M^{-1}$ $s^{-1}$ to $1 \times 10^7$ $M^{-1}$ $s^{-1}$, $1 \times 10^6$ $M^{-1}$$s^{-1}$ to $1 \times 10^8$ $M^{-1}$ $s^{-1}$, $1 \times 10^6$ $M^{-1}$ $s^{-1}$ to $1 \times 10^9$ $M^{-1}$ $s^{-1}$, $1 \times 10^7$ $M^{-1}$ $s^{-1}$ to $1 \times 10^8$ $M^{-1}$ $s^{-1}$, $1 \times 10^7$ $M^{-1}$$s^{-1}$ to $1 \times 10^9$ $M^{-1}$ $s^{-1}$, $1 \times 10^8$ $M^{-1}$ $s^{-1}$ to $1 \times 10^9$ $M^{-1}$ $s^{-1}$. In certain embodiments, the $k_{on}$ is determined using a monovalent antibody, such as a Fab fragment, as measured by, e.g., BIAcore™ surface plasmon resonance technology. In a particular embodiment, the $k_{on}$ is determined using an assay described in Section 6, infra.

In certain embodiments, an antibody or fragment thereof described herein binds to an ErbB1 extracellular domain with a $K_D$ of less than 375 pM, 350 pM, 325 pM, 300 pM, 275 pM, 250 pM, 225 pM, 200 pM, 175 pM, 150 pM, 125 pM, 100 pM, 75 pM, 50 pM, 45 pM, 40 pM, or 35 pM. In some embodiments, an antibody or fragment thereof described herein binds to an ErbB1 extracellular domain with a $k_D$ of 375 pM, 350 pM, 325 pM, 300 pM, 275 pM, 250 pM, 225 pM, 200 pM, 175 pM, 150 pM, 125 pM, 100 pM, 75 pM, or 50 pM, or between 375 pM to 300 pM, 375 pM to 200 pM, 375 pM to 100 pM, 350 pM to 250 pM, 350 pM to 200 pM, 300 pM to 150 pM, 300 pM to 100 pM, 300 pM to 50 pM, 300 pM to 200 pM, 300 pM to 150 pM, 300 pM to 100 pM, 300 pM to 50 pM, 275 pM to 200 pM, 275 pM to 175 pM, 275 pM to 150 pM, 275 pM to 100 pM, 275 pM to 50 pM, 250 pM to 200 pM, 250 pM to 150 pM, 250 pM to 100 pM, 250 pM to 50 pM, 200 pM to 150 pM, 200 pM to 100 pM, 200 to 50 pM, 150 pM to 100 pM, 150 pM to 50 pM, 100 pM to 50 pM, 200 to 40 pM, 150 pM to 40 pM, 150 pM to 40 pM, or 100 pM to 35 pM. In certain embodiments, the $k_D$ is calculated as the quotient of $k_{off}/k_{on}$, and the $k_{on}$ and $k_{off}$ are determined using a monovalent antibody, such as a Fab fragment, as measured by, e.g., BIAcore™ surface plasmon resonance technology.

In certain aspects the ErbB is ErbB4, e.g., human ErbB4, and in a specific embodiment, provided herein is an antibody(ies) or fragment(s) thereof that binds to an ErbB4 extracellular domain, e.g., a human ErbB4 extracellular domain, wherein the antibody(ies) or fragment(s) thereof binds to an ErbB4 epitope comprising (i) at least one, two, three, four, five or more amino acid residues within the domain II/domain III hinge region of human ErbB4, e.g., amino acid residues 306, 307, or 308 of the human ErbB4 domain II/domain III hinge region, and (ii) at least one, two, three, four, five, six, seven, eight, nine, ten or more additional amino acid residues, or between 1 to 4, 2 to 4, 1 to 5, 2 to 6, 5 to 8, 5 to 10, 8 to 10, or 1 to 10 additional amino acid residues within domain II of the ErbB4 extracellular domain, e.g., human ErbB4 extracellular domain, for example, one or more of amino acid residues 270, 271, 288, 289, 290, 291, 292, 293, 296, 301, 305, 306, or 307 within domain II of human ErbB4, and inhibits ligand-dependent and ligand-independent ErbB4 activation.

In certain aspects the ErbB is ErbB4, e.g., human ErbB4, and in a specific embodiment, provided herein is an antibody(ies) or fragment(s) thereof that binds to an ErbB4 extracellular domain, e.g., a human ErbB4 extracellular domain, wherein the antibody(ies) or fragment(s) thereof binds to an ErbB4 epitope comprising (i) at least one, two, three, four, five or more amino acid residues within the domain II/domain III hinge region of ErbB4, e.g., amino acid residues 306, 307, or 308 of the human ErbB4 domain II/domain III hinge region, and (ii) at least one, two, three, four, five, six, seven, eight, nine, ten, eleven, twelve, thirteen, fourteen or fifteen additional amino acid residues, or between 1 to 4, 2 to 4, 1 to 5, 2 to 6, 5 to 8, 5 to 10, 8 to 10, 1 to 10, 5 to 15, 10 to 15, 1 to 15, 5 to 15, 1 to 20, 10 to 20 or 15 to 20 additional amino acid residues within domain III of the ErbB4 extracellular domain, e.g., human ErbB4 extracellular domain, for example, one or more of amino acid residues 308, 310, 313, 314, 315, 318, 336, 338, 339, 340, 372, 374, 399, 400, 401, 402, 403, 405, 406, 429, 430, 431, 432, 454, 455, 456, 457, or 458 within domain III of human ErbB4, and inhibits ligand-dependent and ligand-independent ErbB4 activation.

In certain aspects the ErbB is ErbB4, e.g., human ErbB4, and in a specific embodiment, provided herein is an antibody(ies) or fragment(s) thereof that binds to an ErbB4 extracellular domain, e.g., a human ErbB4 extracellular domain, wherein the antibody(ies) or fragment(s) thereof binds to an ErbB4 epitope comprising (i) at least one, two, three, four, five or more amino acid residues within the domain II/domain III hinge region of human ErbB4, e.g., amino acid residues 306, 307, or 308 of the human ErbB4 domain II/domain III hinge region, (ii) at least one, two, three, four, five, six, seven, eight, nine, ten or more additional amino acid residues, or between 1 to 4, 2 to 4, 1 to 5, 2 to 6, 5 to 8, 5 to 10, 8 to 10, or 1 to 10 additional amino acid residues within domain II of the ErbB4 extracellular domain, e.g., human ErbB4 extracellular domain, for example, one or more of amino acid residues 270, 271, 288, 289, 290, 291, 292, 293, 296, 301, 305, 306, or 307 within domain II of human ErbB4, and (iii) at least one, two, three, four, five, six, seven, eight, nine, ten, eleven, twelve, thirteen, fourteen or fifteen additional amino acid residues, or between 1 to 4, 2 to 4, 1 to 5, 2 to 6, 5 to 8, 5 to 10, 8 to 10, 1 to 10, 5 to 15, 10 to 15, 1 to 15, 5 to 15, 1 to 20, 10 to 20 or 15 to 20 additional amino acid residues within domain III of the ErbB4 extracellular domain, e.g., human ErbB4 extracellular domain, for example, one or more of amino acid residues 308, 310, 313, 314, 315, 318, 336, 338, 339, 340, 372, 374, 399, 400, 401, 402, 403, 405, 406, 429, 430, 431, 432, 454, 455, 456, 457, or 458 within domain III of human ErbB4, and inhibits ligand-dependent and ligand-independent ErbB4 activation.

In a specific embodiment, the ErbB4 epitope is a non-linear epitope. In a specific embodiment, the antibody or fragment binds to an ErbB4 extracellular domain and inhibits ligand binding to ErbB4. In a specific embodiment, the antibody or antigen-binding fragment thereof inhibits neuregulin (for example, human neuregulin)-dependent ErbB4 activation. In another specific embodiment, the antibody or antigen-binding fragment thereof inhibits neuregulin 1-dependent ErbB4 activation. In a particular embodiment, the neuregulin 1 is neuregulin 1β1. In another specific embodiment, the antibody or antigen-binding fragment thereof inhibits neuregulin 2-dependent ErbB4 activation. In certain embodiments, the antibody or antigen-binding fragment thereof is a human, humanized or chimeric antibody or antigen-binding fragment thereof. In a specific embodiment, the antibody or antigen-binding fragment thereof is a monoclonal antibody or antigen-binding fragment. In another specific embodiment, the antibody is a human, humanized or chimeric monoclonal antibody or antigen-binding fragment thereof. In certain embodiments, the antibody or antigen-binding fragment thereof is isolated.

In certain embodiments, the ErbB4 epitope comprises (i) at least one, two, three, four, five or more amino acid residues within the domain II/domain III hinge region of the ErbB4, e.g., human ErbB4, and (ii) one, two, three, four, five, six, seven, eight, nine, or ten additional amino acid residues in domain II of the ErbB4 extracellular domain, e.g., human ErbB4 extracellular domain, and one, two, three, four, five, six, seven, eight, nine, ten, eleven, twelve, thirteen, fourteen or fifteen additional amino acid residues within domain III of the ErbB4 extracellular domain, e.g., human ErbB4 extracellular domain.

In certain embodiments, an antibody or fragment thereof described herein binds to an ErbB4 extracellular domain with a dissociation rate constant ($k_{off}$) of $8.5 \times 10^{-5}$ s$^{-1}$ or less, $5 \times 10^{-5}$ s$^{-1}$ or less, $2.5 \times 10^{-5}$ s$^{-1}$ or less, $1 \times 10^{-5}$ s$^{-1}$ or less, $8.5 \times 10^{-6}$ s$^{-1}$ or less, $5 \times 10^{-6}$ s$^{-1}$ or less, $2.5 \times 10^{-6}$ s$^{-1}$ or less, $1 \times 10^{-6}$ s$^{-1}$ or less, $8.5 \times 10^{-7}$ s$^{-1}$ or less, $5 \times 10^{-7}$ s$^{-1}$ or less, $2.5 \times 10^{-7}$ s$^{-1}$ or less, $1 \times 10^{-7}$ s$^{-1}$ or less, $8.5 \times 10^{-8}$ s$^{-1}$ or less, $5 \times 10^{-8}$ s$^{-1}$ or less, $2.5 \times 10^{-8}$ s$^{-1}$ or less, $1 \times 10^{-8}$ s$^{-1}$ or less, $8.5 \times 10^{-9}$ s$^{-1}$ or less, $5 \times 10^{-9}$ s$^{-1}$ or less, $2.5 \times 10^{-9}$ s$^{-1}$ or less, or $1 \times 10^{-9}$ s$^{-1}$ or less. In some embodiments, an antibody or fragment thereof described herein binds to an ErbB4 extracellular domain with a $k_{off}$ of between $9.5 \times 10^{-5}$ s$^{-1}$ to $1 \times 10^{-9}$ s$^{-1}$, $8.5 \times 10^{-5}$ s$^{-1}$ to $1 \times 10^{-9}$ s$^{-1}$, $5 \times 10^{-5}$ s$^{-1}$ to $1 \times 10^{-9}$ s$^{-1}$, $9.5 \times 10^{-5}$ s$^{-1}$ to $1 \times 10^{-8}$ s$^{-1}$, $5 \times 10^{-5}$ s$^{-1}$ to $1 \times 10^{-8}$ s$^{-1}$, $9.5 \times 10^{-5}$ s$^{-1}$ to $1 \times 10^{-7}$ s$^{-1}$, $5 \times 10^{-5}$ s$^{-1}$ to $1 \times 10^{-7}$ s$^{-1}$, $9.5 \times 10^{-5}$ s$^{-1}$ to $5 \times 10^{-6}$ s$^{-1}$, or $9.5 \times 10^{-5}$ s$^{-1}$ to $1 \times 10^{-5}$ s$^{-1}$. In certain embodiments, the $k_{off}$ is determined using a monovalent antibody, such as a Fab fragment, as measured by, e.g., BIAcore™ surface plasmon resonance technology. In a particular embodiment, the $k_{off}$ is determined using an assay described in Section 6, infra.

In certain embodiments, an antibody or fragment thereof described herein binds to an ErbB4 extracellular domain with an association rate constant ($k_{on}$) of at least $10^5$ M$^{-1}$ s$^{-1}$, at least $5 \times 10^5$ M$^{-1}$ s$^{-1}$, at least $10^6$ M$^{-1}$ s$^{-1}$, at least $5 \times 10^6$ M$^{-1}$ s$^{-1}$, at least $10^7$ M$^{-1}$ s$^{-1}$, at least $5 \times 10^7$ M$^{-1}$ s$^{-1}$, at least $10^8$ M$^{-1}$ s$^{-1}$, at least $5 \times 10^8$ M$^{-1}$ s$^{-1}$ or at least $10^9$ M$^{-1}$ s$^{-1}$. In some embodiments, an antibody or fragment thereof described herein binds to an ErbB4 extracellular domain with a $k_{on}$ of between $1 \times 10^5$ M$^{-1}$ s$^{-1}$ to $5 \times 10^5$ M$^{-1}$ s$^{-1}$, $1 \times 10^5$ M$^{-1}$ s$^{-1}$ to $1 \times 10^6$ M$^{-1}$ s$^{-1}$, $1 \times 10^5$ M$^{-1}$ s$^{-1}$ to $5 \times 10^6$ M$^{-1}$ s$^{-1}$, $1 \times 10^5$ M$^{-1}$ s$^{-1}$ to $1 \times 10^7$ M$^{-1}$ s$^{-1}$, $1 \times 10^5$ M$^{-1}$ s$^{-1}$ to $5 \times 10^7$ M$^{-1}$ s$^{-1}$, $1 \times 10^5$ M$^{-1}$ s$^{-1}$ to $10^8$ M$^{-1}$ s$^{-1}$, $1 \times 10^5$ M$^{-1}$ s$^{-1}$ to $1 \times 10^9$ M$^{-1}$ s$^{-1}$, $1 \times 10^6$ M$^{-1}$ s$^{-1}$ to $1 \times 10^7$ M$^{-1}$ s$^{-1}$, $1 \times 10^6$ M$^{-1}$ s$^{-1}$ to $1 \times 10^8$ M$^{-1}$ s$^{-1}$, $1 \times 10^6$ M$^{-1}$ s$^{-1}$ to $1 \times 10^9$ M$^{-1}$ s$^{-1}$, $1 \times 10^7$ M$^{-1}$ s$^{-1}$ to $1 \times 10^8$ M$^{-1}$ s$^{-1}$, $1 \times 10^7$ M$^{-1}$ s$^{-1}$ to $1 \times 10^9$ M$^{-1}$ s$^{-1}$, $1 \times 10^8$ M$^{-1}$ s$^{-1}$ to $1 \times 10^9$ M$^{-1}$ s$^{-1}$. In certain embodiments, the $k_{on}$ is determined using a monovalent antibody, such as a Fab fragment, as measured by, e.g., BIAcore™ surface plasmon resonance technology. In a particular embodiment, the $k_{on}$ is determined using an assay described in Section 6, infra.

In certain embodiments, an antibody or fragment thereof described herein binds to an ErbB4 extracellular domain with a $K_D$ of less than 375 pM, 350 pM, 325 pM, 300 pM, 275 pM, 250 pM, 225 pM, 200 pM, 175 pM, 150 pM, 125 pM, 100 pM, 75 pM, 50 pM, 45 pM, 40 pM, or 35 pM. In some embodiments, an antibody or fragment thereof described herein binds to an ErbB4 extracellular domain with a $k_D$ of 375 pM, 350 pM, 325 pM, 300 pM, 275 pM, 250 pM, 225 pM, 200 pM, 175 pM, 150 pM, 125 pM, 100 pM, 75 pM, or 50 pM, or between 375 pM to 300 pM, 375 pM to 200 pM, 375 pM to 100 pM, 350 pM to 250 pM, 350 pM to 200 pM, 300 pM to 150 pM, 300 pM to 100 pM, 300 pM to 50 pM, 300 pM to 200 pM, 300 pM to 150 pM, 300 pM to 100 pM, 300 pM to 50 pM, 275 pM to 200 pM, 275 pM to 175 pM, 275 pM to 150 pM, 275 pM to 100 pM, 275 pM to 50 pM, 250 pM to 200 pM, 250 pM to 150 pM, 250 pM to 100 pM, 250 pM to 50 pM, 200 pM to 150 pM, 200 pM to 100 pM, 200 to 50 pM, 150 pM to 100 pM, 150 pM to 50 pM, 100 pM to 50 pM, 200 to 40 pM, 150 pM to 40 pM, 150 pM to 40 pM, or 100 pM to 35 pM. In certain embodiments, the $k_D$ is calculated as the quotient of $k_{off}/k_{on}$, and the $k_{on}$ and $k_{off}$ are determined using a monovalent antibody, such as a Fab fragment, as measured by, e.g., BIAcore™ surface plasmon resonance technology.

In another aspect, provided herein are antibodies or fragments thereof that bind to an epitope comprising (i) one, two or more amino acid residues in domain II of the ErbB3 extracellular domain and one, two or more amino acid residues in domain III of the ErbB3 extracellular domain, or (ii) one, two or more amino acid residues in the domainII/domain III hinge region, wherein the antibodies or fragments thereof inhibit ligand-dependent and ligand-independent ErbB3 activation and comprises one, two, three, four, five, six or more amino acid mutations (e.g., amino acid substitutions), or between 1 to 3, 1 to 5, 2 to 4, 2 to 5, 2 to 6, or 5 to 10 amino acid mutations (e.g., amino acid substitutions) in 1, 2, 3, 4, 5 or 6 of the CDRs and/or 1, 2, 3, 4, 5, 6, 7, or 8 of the framework regions of the VH domain having the amino acid sequence of SEQ ID NO: 4 and/or VL domain having the amino acid sequence of SEQ ID NO: 5 that improve one, two, three or more of the properties of the antibody or antigen-binding fragment thereof, such as the affinity, avidity, inhibition of ligand-dependent ErbB3 activation and/or ligand-independent ErbB3 activation. In a specific embodiment, the amino acid mutations (e.g., amino acid substitutions) increase the number of contacts between ErbB3 and the antibody or antigen-binding fragment thereof. In another specific embodiment, the amino acid mutations, (e.g., amino acid substitutions) decrease the $K_D$ and/or $k_{off}$ of the antibody or antigen-binding fragment thereof. In certain embodiments, the amino acid mutations, (e.g., amino acid substitutions) decrease the $K_D$ and/or $k_{off}$ of the antibody or antigen-binding fragment thereof by 1.5 fold or more, 2 fold or more, 2.5 fold or more, 3 fold or more, 3.5 fold or more, 4 fold or more, 4.5 fold or more, 5 fold or more, 5.5 fold or more, or between 1.5 to 3 fold, 2 to 4 fold, 3 to 5 fold, 2 to 5 fold, 4 to 6 fold or 5 to 10 fold. In another specific embodiment, the amino acid mutations, (e.g., amino acid substitutions) increase the $K_a$ and/or $k_{on}$ of the antibody or antigen-binding fragment thereof. In certain embodiments, the amino acid mutations, (e.g., amino acid substitutions) increase the $K_a$ and/or $k_{on}$ of the antibody or antigen-binding fragment thereof by 1.5 fold or more, 2 fold or more, 2.5 fold or more, 3 fold or more, 3.5 fold or more, 4 fold or more, 4.5 fold or more, 5 fold or more, 5.5 fold or more, or between 1.5 to 3 fold, 2 to 4 fold, 3 to 5 fold, 2 to 5 fold, 4 to 6 fold or 5 to 10 fold. In one embodiment, the amino acid mutations are amino acid substitutions. In a specific embodiment, the amino acid substitutions are conservative amino acid substitutions.

As used herein, a "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In a specific embodiment, provided herein is an antibody(ies) or fragment(s) thereof that binds to ErbB3 or a fragment thereof (e.g., the extracellular domain of ErbB3), wherein the antibody or fragment thereof comprises one, two, three, four, five or all six of the following CDRs:
(a) a VH CDR1 comprising the following amino acid sequence: YYYMQ (SEQ ID NO: 6); and/or
(b) a VH CDR2 comprising the following amino acid sequence: YIGX$_1$SGGX$_2$TNYADSVKG (SEQ ID NO: 24); and/or
(c) a VH CDR3 comprising the following amino acid sequence: VGX$_3$GDAFDI (SEQ ID NO: 27); and/or
(d) a VL CDR1 comprising the following amino acid sequence: X$_4$GX$_5$X$_6$SNIGX$_7$NYVS (SEQ ID NO: 30); and/or
(e) a VL CDR2 comprising the following amino acid sequence: RNNQRPS (SEQ ID NO: 10); and/or
(f) a VL CDR3 comprising the following amino acid sequence: AAWDX$_8$SPPGEA (SEQ ID NO: 33);
wherein X$_1$ represents amino acid residues S or T; X$_2$ represents amino acid residues V, Q, T, S, or N; X$_3$ represents amino acid residues R, Q, L, M, I, W, or Y; X$_4$ represents amino acid residues S, N, D, E, Q, H, R or K; X$_5$ represents amino acid residues S, N, T, D, R, K, H, F, or Y; X$_6$ represents amino acid residues L, F, Y, M, or I; X$_7$ represents amino acid residues L or M; X$_8$ represents amino acid residues D, N, or H. In certain embodiments, X$_4$ is not R.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

In certain embodiments, the antibody or antigen-binding fragment thereof comprises the framework regions of VL domain having the amino acid sequence of SEQ ID NO: 5 and/or the framework regions of the VH domain having the amino acid sequence of SEQ ID NO: 4. In other embodiments, the antibody or antigen-binding fragment thereof comprises the framework regions of the VL domain having the amino acid sequence of SEQ ID NO: 5 with 1, 2, 3, 4, 5, 6, 7, 8, 9 or more amino acid mutations (e.g., amino acid substitutions, such as conservative amino acid substitutions) and/or the framework regions of the VH domain having the amino acid sequence of SEQ ID NO: 4. In some embodiments, the antibody or antigen-binding thereof comprises the frameworks of VL domain having the amino acid sequence of SEQ ID NO: 5 with amino acid substitutions at amino acid position 71 and/or amino acid position 70. In specific embodiments, the amino acid substitution at amino acid position 70 substitutes S for N, H, Y, K, or R and/or the amino acid substitution at amino acid position 71 substitutes T for N or Y. In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In certain embodiments, the antibody or antigen-binding fragment thereof is a human, chimeric, or humanized antibody or an antigen-binding fragment thereof. In a specific embodiment, the antibody or antigen-binding fragment thereof is a monoclonal antibody. In specific embodiments, the antibody or antigen-binding fragment thereof inhibits ligand-dependent and ligand-independent ErbB3 activation.

In a specific embodiment, provided herein is an antibody(ies) or fragment(s) thereof that binds to ErbB3 or a fragment thereof (e.g., the extracellular domain of ErbB3), wherein the antibody or fragment thereof comprises one, two, three, four, five or all six of the following CDRs:
(a) a VH CDR1 comprising the following amino acid sequence: GFTFSYYYM (SEQ ID NO: 12); and/or
(b) a VH CDR2 comprising the following amino acid sequence: GX$_1$SGG (SEQ ID NO: 25); and/or
(c) a VH CDR3 comprising the following amino acid sequence: VGX$_2$GDAFDI (SEQ ID NO: 28); and/or
(d) a VL CDR1 comprising the following amino acid sequence: X$_3$GX$_4$X$_5$SNIGX$_6$NYVS (SEQ ID NO: 31); and/or
(e) a VL CDR2 comprising the following amino acid sequence: RNNQRPS (SEQ ID NO: 16); and/or
(f) a VL CDR3 comprising the following amino acid sequence: AAWDX$_7$SPPGEA (SEQ ID NO: 34);
wherein X$_1$ represents amino acid residues S or T; X$_2$ represents amino acid residues R, Q, L, M, I, W, or Y; X$_3$ represents amino acid residues S, N, D, E, Q, H, R or K; X$_4$ represents amino acid residues S, N, T, D, R, K, H, F, or Y; X$_5$ represents amino acid residues L, F, Y, M, or I; X$_6$ represents amino acid residues L or M; X$_7$ represents amino acid residues D, N, or H. In certain embodiments, X$_4$ is not R.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

In certain embodiments, the antibody or antigen-binding fragment thereof comprises the framework regions of VL domain having the amino acid sequence of SEQ ID NO: 5 and/or the framework regions of the VH domain having the amino acid sequence of SEQ ID NO: 4. In other embodiments, the antibody or antigen-binding fragment thereof comprises the framework regions of the VL domain having the amino acid sequence of SEQ ID NO: 5 with 1, 2, 3, 4, 5, 6, 7, 8, 9 or more amino acid mutations (e.g., amino acid substitutions, such as conservative amino acid substitutions) and/or the framework regions of the VH domain having the amino acid sequence of SEQ ID NO: 4. In some embodiments, the antibody or antigen-binding thereof comprises the frameworks of VL domain having the amino acid sequence of SEQ ID NO: 5 with amino acid substitutions at amino acid position 71 and/or amino acid position 70. In specific embodiments, the amino acid substitution at amino acid position 70 substitutes S for N, H, Y, K, or R and/or the amino acid substitution at amino acid position 71 substitutes T for N or Y. In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In certain embodiments, the antibody or antigen-binding fragment thereof is a human, chimeric, or humanized antibody or an antigen-binding fragment thereof. In a specific embodiment, the antibody or antigen-binding fragment thereof is a monoclonal antibody. In specific embodiments, the antibody or antigen-binding fragment thereof inhibits ligand-dependent and ligand-independent ErbB3 activation.

In a specific embodiment, provided herein is an antibody(ies) or fragment(s) thereof that binds to ErbB3 or a fragment thereof (e.g., the extracellular domain of ErbB3), wherein the antibody or fragment thereof comprises one, two, three, four, five or all six of the following CDRs:
(a) a VH CDR1 comprising the following amino acid sequence: GFTFSYYY (SEQ ID NO: 18); and/or
(b) a VH CDR2 comprising the following amino acid sequence: IGX$_1$SGGX$_2$T (SEQ ID NO: 26); and/or
(c) a VH CDR3 comprising the following amino acid sequence: ARVGX$_3$GDAFDI (SEQ ID NO: 29); and/or
(d) a VL CDR1 comprising the following amino acid sequence: X$_4$SNIGX$_5$NY (SEQ ID NO: 32); and/or
(e) a VL CDR2 comprising the following amino acid sequence: RNN (SEQ ID NO: 22); and/or
(f) a VL CDR3 comprising the following amino acid sequence: AAWDX$_6$SPPGEA (SEQ ID NO: 35);
wherein X$_1$ represents amino acid residues S or T; X$_2$ represents amino acid residues V, Q, T, S, or N; X$_3$ represents amino acid residues R, Q, L, M, I, W, or Y; X$_4$ represents amino acid residues L, F, Y, M, or I; X$_5$ represents amino acid residues L or M; X$_6$ represents amino acid residues D, N, or H. In certain embodiments, X$_4$ is not R.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

In certain embodiments, the antibody or antigen-binding fragment thereof comprises the framework regions of VL domain having the amino acid sequence of SEQ ID NO: 5 and/or the framework regions of the VH domain having the amino acid sequence of SEQ ID NO: 4. In other embodiments, the antibody or antigen-binding fragment thereof comprises the framework regions of the VL domain having the amino acid sequence of SEQ ID NO: 5 with 1, 2, 3, 4, 5, 6, 7, 8, 9 or more amino acid mutations (e.g., amino acid substitutions, such as conservative amino acid substitutions) and/or the framework regions of the VH domain having the amino acid sequence of SEQ ID NO: 4. In some embodiments, the antibody or antigen-binding thereof comprises the frameworks of VL domain having the amino acid sequence of SEQ ID NO: 5 with amino acid substitutions at amino acid position 71 and/or amino acid position 70. In specific embodiments, the amino acid substitution at amino acid position 70 substitutes S for N, H, Y, K, or R and/or the amino acid substitution at amino acid position 71 substitutes T for N or Y. In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In certain embodiments, the antibody or antigen-binding fragment thereof is a human, chimeric, or humanized antibody or an antigen-binding fragment thereof. In a specific embodiment, the antibody or antigen-binding fragment thereof is a monoclonal antibody. In specific embodiments, the antibody or antigen-binding fragment thereof inhibits ligand-dependent and ligand-independent ErbB3 activation.

In a specific embodiment, provided herein is an antibody or fragment thereof that binds to ErbB3 or a fragment thereof (e.g., the extracellular domain of ErbB3), wherein the antibody or fragment thereof comprises VH CDRs and VL CDRs having the amino acid sequences in Table 2, infra, numbered according to the Kabat numbering system or Chothia numbering system, wherein $X_1$ is R, N, D, E, Q, or H. In a specific embodiment, $X_1$ is R. In other embodiments, $X_1$ is not R.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

TABLE 2

| | Kabat | Chothia |
|---|---|---|
| VH CDR1 | YYYMQ (SEQ ID NO: 6) | GFTFSYYYM (SEQ ID NO: 12) |
| VH CDR2 | YIGSSGGVTNYADSVKG (SEQ ID NO: 7) | GSSGG (SEQ ID NO: 13) |
| VH CDR3 | VGLGDAFDI (SEQ ID NO: 8) | VGLGDAFDI (SEQ ID NO: 14) |
| VL CDR1 | $X_1$GSLSNIGLNYVS (SEQ ID NO: 36) | $X_1$GSLSNIGLNYVS (SEQ ID NO: 37) |
| VL CDR2 | RNNQRPS (SEQ ID NO: 10) | RNNQRPS (SEQ ID NO: 16) |
| VL CDR3 | AAWDDSPPGEA (SEQ ID NO: 11) | AAWDDSPPGEA (SEQ ID NO: 17) |

In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In one embodiment, provided herein is an antibody or fragment thereof that binds to ErbB3 or a fragment thereof (e.g., the extracellular domain of ErbB3, for example, human ErbB3), wherein the antibody or antigen-binding fragment thereof comprises a VL domain having the amino acid sequence of SEQ ID NO: 101. In another embodiment, provided herein is an antibody or fragment thereof that binds to ErbB3 or a fragment thereof (e.g., the extracellular domain of ErbB3, for example, human ErbB3), wherein the antibody or antigen-binding fragment thereof comprises a VL domain having the amino acid sequence of SEQ ID NO: 101 and a VH domain having the amino acid sequence of SEQ ID NO: 4. In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In a specific embodiment, provided herein is an antibody or fragment thereof that binds to ErbB3 or a fragment thereof (e.g., the extracellular domain of ErbB3), wherein the antibody or fragment thereof comprises VH CDRs and VL CDRs having the amino acid sequences reported in Table 3, infra, wherein X is H, N, T, D, R, L, F, or Y. In a specific embodiment X is H.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

TABLE 3

| | Kabat | Chothia |
|---|---|---|
| VH CDR1 | YYYMQ (SEQ ID NO: 6) | GFTFSYYYM (SEQ ID NO: 12) |
| VH CDR2 | YIGSSGGVTNYADSV KG (SEQ ID NO: 7) | GSSGG (SEQ ID NO: 13) |
| VH CDR3 | VGLGDAFDI (SEQ ID NO: 8) | VGLGDAFDI (SEQ ID NO: 14) |
| VL CDR1 | SGXLSNIGLNYVS (SEQ ID NO: 38) | SGXLSNIGLNYVS (SEQ ID NO: 39) |
| VL CDR2 | RNNQRPS (SEQ ID NO: 10) | RNNQRPS (SEQ ID NO: 16) |
| VL CDR3 | AAWDDSPPGEA (SEQ ID NO: 11) | AAWDDSPPGEA (SEQ ID NO: 17) |

In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In one embodiment, provided herein is an antibody or fragment thereof that binds to ErbB3 or a fragment thereof (e.g., the extracellular domain of ErbB3), wherein the antibody or antigen-binding fragment thereof comprises a VL domain having the amino acid sequence of SEQ ID NO: 102. In another embodiment, provided herein is an antibody or fragment thereof that binds to ErbB3 or a fragment thereof (e.g., the extracellular domain of ErbB3), wherein the antibody or antigen-binding fragment thereof comprises a VL domain having the amino acid sequence of SEQ ID NO: 102 and a VH domain having the amino acid sequence of SEQ ID NO: 4. In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In a specific embodiment, provided herein is an antibody or fragment thereof that binds to ErbB3 or a fragment thereof (e.g., the extracellular domain of ErbB3), wherein the antibody or fragment thereof comprises: VH CDRs and VL CDRs having the amino acid sequences reported in Table 4, infra, wherein X is Q, T, S or N.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

TABLE 4

| | Kabat |
|---|---|
| VH CDR1 | YYYMQ (SEQ ID NO: 6) |
| VH CDR2 | YIGSSGGVTNYADSXKG (SEQ ID NO: 45) |
| VH CDR3 | VGLGDAFDI (SEQ ID NO: 8) |
| VL CDR1 | SGSLSNIGLNYVS (SEQ ID NO: 9) |
| VL CDR2 | RNNQRPS (SEQ ID NO: 10) |
| VL CDR3 | AAWDDSPPGEA (SEQ ID NO: 11) |

In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In one embodiment, provided herein is an antibody or fragment thereof that binds to ErbB3 or a fragment thereof (e.g., the extracellular domain of ErbB3), wherein the antibody or antigen-binding fragment thereof comprises a VH domain having the amino acid sequence of SEQ ID NO: 103. In another embodiment, provided herein is an antibody or fragment thereof that binds to ErbB3 or a fragment thereof (e.g., the extracellular domain of ErbB3), wherein the antibody or antigen-binding fragment thereof comprises a VH domain having the amino acid sequence of SEQ ID NO: 103 and a VL domain having the amino acid sequence of SEQ ID NO: 5. In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In a specific embodiment, provided herein is an antibody or fragment thereof that binds to ErbB3 or a fragment thereof (e.g., the extracellular domain of ErbB3), wherein the antibody or fragment thereof comprises VH CDRs and VL CDRs having the amino acid sequences reported in Table 5, infra, numbered according to the Kabat numbering system, Chothia numbering system, or IMGT numbering system, wherein X is I, M, F, or Y.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

domain the amino acid sequence of SEQ ID NO: 104. In another embodiment, provided herein is an antibody or fragment thereof that binds to ErbB3 or a fragment thereof (e.g., the extracellular domain of ErbB3), wherein the antibody or antigen-binding fragment thereof comprises a VL domain having the amino acid sequence of SEQ ID NO: 104 and a VH domain having the amino acid sequence of SEQ ID NO: 4. In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In a specific embodiment, provided herein is an antibody or fragment thereof that binds to ErbB3 or a fragment thereof (e.g., the extracellular domain of ErbB3), wherein the antibody or fragment thereof comprises VH CDRs and VL CDRs having the amino acid sequences reported in Table 6, infra, numbered according to the Kabat numbering system, Chothia numbering system, or IMGT numbering system, wherein $X_1$ is R, N, E, Q, H, or K and $X_2$ is H, N, T, D, R, L, F or Y.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by

TABLE 5

|         | Kabat                          | Chothia                        | IMGT                           |
|---------|--------------------------------|--------------------------------|--------------------------------|
| VH CDR1 | YYYMQ (SEQ ID NO: 6)           | GFTFSYYYM (SEQ ID NO: 12)      | GFTFSYYY (SEQ ID NO: 18)       |
| VH CDR2 | YIGSSGGVTNYADSVKG (SEQ ID NO: 7) | GSSGG (SEQ ID NO: 13)        | IGSSGGVT (SEQ ID NO: 19)       |
| VH CDR3 | VGLGDAFDI (SEQ ID NO: 8)       | VGLGDAFDI (SEQ ID NO: 14)      | ARVGLGDAFDI (SEQ ID NO: 20)    |
| VL CDR1 | SGSXSNIGLNYVS (SEQ ID NO: 40)  | SGSXSNIGLNYVS (SEQ ID NO: 41)  | XSNIGLNY (SEQ ID NO: 42)       |
| VL CDR2 | RNNQRPS (SEQ ID NO: 10)        | RNNQRPS (SEQ ID NO: 16)        | RNN (SEQ ID NO: 22)            |
| VL CDR3 | AAWDDSPPGEA (SEQ ID NO: 11)    | AAWDDSPPGEA (SEQ ID NO: 17)    | AAWDDSPPGEA (SEQ ID NO: 23)    |

In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In one embodiment, provided herein is an antibody or fragment thereof that binds to ErbB3 or a fragment thereof (e.g., the extracellular domain of ErbB3), wherein the antibody or antigen-binding fragment thereof comprises a VL the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

TABLE 6

| | Kabat | Chothia |
|---|---|---|
| VH CDR1 | YYYMQ (SEQ ID NO: 6) | GFTFSYYYM (SEQ ID NO: 12) |
| VH CDR2 | YIGSSGGVTNYADSVKG (SEQ ID NO: 7) | GSSGG (SEQ ID NO: 13) |
| VH CDR3 | VGLGDAFDI (SEQ ID NO: 8) | VGLGDAFDI (SEQ ID NO: 14) |
| VL CDR1 | $X_1GX_2$LSNIGLNYVS (SEQ ID NO: 43) | $X_1GX_2$LSNIGLNYVS (SEQ ID NO: 44) |
| VL CDR2 | RNNQRPS (SEQ ID NO: 10) | RNNQRPS (SEQ ID NO: 16) |
| VL CDR3 | AAWDDSPPGEA (SEQ ID NO: 11) | AAWDDSPPGEA (SEQ ID NO: 17) |

In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In one embodiment, provided herein is an antibody or fragment thereof that binds to ErbB3 or a fragment thereof (e.g., the extracellular domain of ErbB3), wherein the antibody or antigen-binding fragment thereof comprises a VL domain the amino acid sequence of SEQ ID NO: 105. In another embodiment, provided herein is an antibody or fragment thereof that binds to ErbB3 or a fragment thereof (e.g., the extracellular domain of ErbB3), wherein the antibody or antigen-binding fragment thereof comprises a VL domain having the amino acid sequence of SEQ ID NO: 105 and a VH domain having the amino acid sequence of SEQ ID NO: 4. In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In a specific embodiment, provided herein is an antibody or fragment thereof that binds to ErbB3 or a fragment thereof (e.g., the extracellular domain of ErbB3), wherein the antibody or fragment thereof comprises VH CDRs and VL CDRs having the amino acid sequences reported in Table 7, infra, numbered according to the Kabat numbering system or Chothia numbering system, wherein $X_1$ is R, N, E, Q, H, or K and $X_2$ is Q, T, S or N.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

TABLE 7

| | Kabat | Chothia |
|---|---|---|
| VH CDR1 | YYYMQ (SEQ ID NO: 6) | GFTFSYYYM (SEQ ID NO: 12) |
| VH CDR2 | YIGSSGGVTNYADSX$_2$KG (SEQ ID NO: 45) | GSSGG (SEQ ID NO: 13) |
| VH CDR3 | VGLGDAFDI (SEQ ID NO: 8) | VGLGDAFDI (SEQ ID NO: 14) |
| VL CDR1 | $X_1$GSLSNIGLNYVS (SEQ ID NO: 46) | $X_1$GSLSNIGLNYVS (SEQ ID NO: 47) |
| VL CDR2 | RNNQRPS (SEQ ID NO: 10) | RNNQRPS (SEQ ID NO: 16) |
| VL CDR3 | AAWDDSPPGEA (SEQ ID NO: 11) | AAWDDSPPGEA (SEQ ID NO: 17) |

In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In one embodiment, provided herein is an antibody or fragment thereof that binds to ErbB3 or a fragment thereof (e.g., the extracellular domain of ErbB3), wherein the antibody or antigen-binding fragment thereof comprises a VL domain having the amino acid sequence of SEQ ID NO: 106. In one embodiment, provided herein is an antibody or fragment thereof that binds to ErbB3 or a fragment thereof (e.g., the extracellular domain of ErbB3), wherein the antibody or antigen-binding fragment thereof comprises a VH domain having the amino acid sequence of SEQ ID NO: 103. In another embodiment, provided herein is an antibody or fragment thereof that binds to ErbB3 or a fragment thereof (e.g., the extracellular domain of ErbB3), wherein the antibody or antigen-binding fragment thereof comprises a VL domain having the amino acid sequence of SEQ ID NO: 106 and a VH domain having the amino acid sequence of SEQ ID NO: 103. In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In a specific embodiment, provided herein is an antibody or fragment thereof that binds to ErbB3 or a fragment thereof (e.g., the extracellular domain of ErbB3), wherein the antibody or fragment thereof comprises VH CDRs and VL CDRs having the amino acid sequences reported in Table 8, infra, numbered according to the Kabat numbering system, Chothia numbering system, or IMGT numbering system, wherein $X_1$ is R, N, E, Q, H, or K and $X_2$ is I, M, F or Y.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

(e.g., the extracellular domain of ErbB3), wherein the antibody or antigen-binding fragment thereof comprises a VL domain having the amino acid sequence of SEQ ID NO: 107 and a VH domain having the amino acid sequence of SEQ ID NO: 4. In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In a specific embodiment, provided herein is an antibody or fragment thereof that binds to ErbB3 or a fragment thereof (e.g., the extracellular domain of ErbB3), wherein the antibody or fragment thereof comprises VH CDRs and VL CDRs having the amino acid sequences reported in Table 9, infra, numbered according to the Kabat numbering system, Chothia numbering system, or IMGT numbering system, wherein $X_1$ is H, N, T, D, R, L, F or Y and $X_2$ is Q, T, S or N.

In certain embodiments, an antibody or antigen-binding fragment thereof comprises one, two, three, or more of the

TABLE 8

|  | Kabat | Chothia | IMGT |
|---|---|---|---|
| VH CDR1 | YYYMQ (SEQ ID NO: 6) | GFTFSYYYM (SEQ ID NO: 12) | GFTFSYYY (SEQ ID NO: 18) |
| VH CDR2 | YIGSSGGVTNYADSVKG (SEQ ID NO: 7) | GSSGG (SEQ ID NO: 13) | IGSSGGVT (SEQ ID NO: 19) |
| VH CDR3 | VGLGDAFDI (SEQ ID NO: 8) | VGLGDAFDI (SEQ ID NO: 14) | ARVGLGDAFDI (SEQ ID NO: 20) |
| VL CDR1 | $X_1$GSX$_2$SNIGLNYVS (SEQ ID NO: 48) | $X_1$GSX$_2$SNIGLNYVS (SEQ ID NO: 49) | X$_2$SNIGLNY (SEQ ID NO: 42) |
| VL CDR2 | RNNQRPS (SEQ ID NO: 10) | RNNQRPS (SEQ ID NO: 16) | RNN (SEQ ID NO: 22) |
| VL CDR3 | AAWDDSPPGEA (SEQ ID NO: 11) | AAWDDSPPGEA (SEQ ID NO: 17) | AAWDDSPPGEA (SEQ ID NO: 23) |

In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In one embodiment, provided herein is an antibody or fragment thereof that binds to ErbB3 or a fragment thereof (e.g., the extracellular domain of ErbB3), wherein the antibody or antigen-binding fragment thereof comprises a VL domain the amino acid sequence of SEQ ID NO: 107. In another embodiment, provided herein is an antibody or fragment thereof that binds to ErbB3 or a fragment thereof CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

TABLE 9

| | Kabat | Chothia |
|---|---|---|
| VH CDR1 | YYYMQ (SEQ ID NO: 6) | GFTFSYYYM (SEQ ID NO: 12) |
| VH CDR2 | YIGSSGGVTNYADSX$_2$KG (SEQ ID NO: 45) | GSSGG (SEQ ID NO: 13) |
| VH CDR3 | VGLGDAFDI (SEQ ID NO: 8) | VGLGDAFDI (SEQ ID NO: 14) |
| VL CDR1 | SGX$_1$LSNIGLNYVS (SEQ ID NO: 38) | SGX$_1$LSNIGLNYVS (SEQ ID NO: 39) |
| VL CDR2 | RNNQRPS (SEQ ID NO: 10) | RNNQRPS (SEQ ID NO: 16) |
| VL CDR3 | AAWDDSPPGEA (SEQ ID NO: 11) | AAWDDSPPGEA (SEQ ID NO: 17) |

In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In one embodiment, provided herein is an antibody or fragment thereof that binds to ErbB3 or a fragment thereof (e.g., the extracellular domain of ErbB3), wherein the antibody or antigen-binding fragment thereof comprises a VL domain having the amino acid sequence of SEQ ID NO: 102. In one embodiment, provided herein is an antibody or fragment thereof that binds to ErbB3 or a fragment thereof (e.g., the extracellular domain of ErbB3), wherein the antibody or antigen-binding fragment thereof comprises a VH domain having the amino acid sequence of SEQ ID NO: 103. In another embodiment, provided herein is an antibody or fragment thereof that binds to ErbB3 or a fragment thereof (e.g., the extracellular domain of ErbB3), wherein the antibody or antigen-binding fragment thereof comprises a VL domain having the amino acid sequence of SEQ ID NO: 102 and a VH domain having the amino acid sequence of SEQ ID NO: 103. In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In a specific embodiment, provided herein is an antibody or fragment thereof that binds to ErbB3 or a fragment thereof (e.g., the extracellular domain of ErbB3), wherein the antibody or fragment thereof comprises VH CDRs and VL CDRs having the amino acid sequences reported in Table 10, infra, numbered according to the Kabat numbering system, Chothia numbering system, or IMGT numbering system, wherein X$_1$ is H, N, T, D, R, L, F or Y and X$_2$ is I, M, F or Y.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

TABLE 10

| | Kabat | Chothia | IMGT |
|---|---|---|---|
| VH CDR1 | YYYMQ (SEQ ID NO: 6) | GFTFSYYYM (SEQ ID NO: 12) | GFTFSYYY (SEQ ID NO: 18) |
| VH CDR2 | YIGSSGGVTNYADSVKG (SEQ ID NO: 7) | GSSGG (SEQ ID NO: 13) | IGSSGGVT (SEQ ID NO: 19) |
| VH CDR3 | VGLGDAFDI (SEQ ID NO: 8) | VGLGDAFDI (SEQ ID NO: 14) | ARVGLGDAFDI (SEQ ID NO: 20) |
| VL CDR1 | SGX$_1$X$_2$SNIGLNYVS (SEQ ID NO: 50) | SGX$_1$X$_2$SNIGLNYVS (SEQ ID NO: 51) | X$_2$SNIGLNY (SEQ ID NO: 42) |
| VL CDR2 | RNNQRPS (SEQ ID NO: 10) | RNNQRPS (SEQ ID NO: 16) | RNN (SEQ ID NO: 22) |
| VL CDR3 | AAWDDSPPGEA (SEQ ID NO: 11) | AAWDDSPPGEA (SEQ ID NO: 17) | AAWDDSPPGEA (SEQ ID NO: 23) |

In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In one embodiment, provided herein is an antibody or fragment thereof that binds to ErbB3 or a fragment thereof (e.g., the extracellular domain of ErbB3), wherein the antibody or antigen-binding fragment thereof comprises a VL domain the amino acid sequence of SEQ ID NO: 108. In another embodiment, provided herein is an antibody or fragment thereof that binds to ErbB3 or a fragment thereof (e.g., the extracellular domain of ErbB3), wherein the antibody or antigen-binding fragment thereof comprises a VL domain having the amino acid sequence of SEQ ID NO: 108 and a VH domain having the amino acid sequence of SEQ ID NO: 4. In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In a specific embodiment, provided herein is an antibody or fragment thereof that binds to ErbB3 or a fragment thereof (e.g., the extracellular domain of ErbB3), wherein the antibody or fragment thereof comprises VH CDRs and VL CDRs having the amino acid sequences reported in Table 11, infra, numbered according to the Kabat numbering system, Chothia numbering system, or IMGT numbering system, wherein X1 is R, N, D, E, Q, H, or K, $X_2$ is H, N, T, D, R, L, F or Y and $X_3$ is Q, T, S or N.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

TABLE 11

|  | Kabat | Chothia |
| --- | --- | --- |
| VH CDR1 | YYYMQ (SEQ ID NO: 6) | GFTFSYYYM (SEQ ID NO: 12) |
| VH CDR2 | YIGSSGGVTNYADSX$_3$KG (SEQ ID NO: 45) | GSSGG (SEQ ID NO: 13) |
| VH CDR3 | VGLGDAFDI (SEQ ID NO: 8) | VGLGDAFDI (SEQ ID NO: 14) |
| VL CDR1 | X$_1$GX$_2$LSNIGLNYVS (SEQ ID NO: 52) | X$_1$GX$_2$LSNIGLNYVS (SEQ ID NO: 53) |

TABLE 11-continued

|  | Kabat | Chothia |
| --- | --- | --- |
| VL CDR2 | RNNQRPS (SEQ ID NO: 10) | RNNQRPS (SEQ ID NO: 16) |
| VL CDR3 | AAWDDSPPGEA (SEQ ID NO: 11) | AAWDDSPPGEA (SEQ ID NO: 17) |

In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In one embodiment, provided herein is an antibody or fragment thereof that binds to ErbB3 or a fragment thereof (e.g., the extracellular domain of ErbB3), wherein the antibody or antigen-binding fragment thereof comprises a VL domain having the amino acid sequence of SEQ ID NO: 109. In one embodiment, provided herein is an antibody or fragment thereof that binds to ErbB3 or a fragment thereof (e.g., the extracellular domain of ErbB3), wherein the antibody or antigen-binding fragment thereof comprises a VH domain having the amino acid sequence of SEQ ID NO: 103. In another embodiment, provided herein is an antibody or fragment thereof that binds to ErbB3 or a fragment thereof (e.g., the extracellular domain of ErbB3), wherein the antibody or antigen-binding fragment thereof comprises a VL domain having the amino acid sequence of SEQ ID NO: 109 and a VH domain having the amino acid sequence of SEQ ID NO: 103. In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In a specific embodiment, provided herein is an antibody or fragment thereof that binds to ErbB3 or a fragment thereof (e.g., the extracellular domain of ErbB3), wherein the antibody or fragment thereof comprises VH CDRs and VL CDRs having the amino acid sequences reported in Table 12, infra, numbered according to the Kabat numbering system, Chothia numbering system, or IMGT numbering system, wherein $X_1$ is R, N, D, E, Q, H or K, $X_2$ is H, N, T, D, R, L, F or Y and $X_3$ is I, M, F or Y.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

TABLE 12

|  | Kabat | Chothia | IMGT |
| --- | --- | --- | --- |
| VH CDR1 | YYYMQ (SEQ ID NO: 6) | GFTFSYYYM (SEQ ID NO: 12) | GFTFSYYY (SEQ ID NO: 18) |
| VH CDR2 | YIGSSGGVTNYADSVKG (SEQ ID NO: 7) | GSSGG (SEQ ID NO: 13) | IGSSGGVT (SEQ ID NO: 19) |
| VH CDR3 | VGLGDAFDI (SEQ ID NO: 8) | VGLGDAFDI (SEQ ID NO: 14) | ARVGLGDAFDI (SEQ ID NO: 20) |
| VL CDR1 | $X_1GX_2X_3$SNIGLNYVS (SEQ ID NO: 54) | $X_1GX_2X_3$SNIGLNYVS (SEQ ID NO: 55) | $X_3$SNIGLNY (SEQ ID NO: 42) |
| VL CDR2 | RNNQRPS (SEQ ID NO: 10) | RNNQRPS (SEQ ID NO: 16) | RNN (SEQ ID NO: 22) |
| VL CDR3 | AAWDDSPPGEA (SEQ ID NO: 11) | AAWDDSPPGEA (SEQ ID NO: 17) | AAWDDSPPGEA (SEQ ID NO: 23) |

In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In one embodiment, provided herein is an antibody or fragment thereof that binds to ErbB3 or a fragment thereof (e.g., the extracellular domain of ErbB3), wherein the antibody or antigen-binding fragment thereof comprises a VL domain the amino acid sequence of SEQ ID NO: 110. In another embodiment, provided herein is an antibody or fragment thereof that binds to ErbB3 or a fragment thereof (e.g., the extracellular domain of ErbB3), wherein the antibody or antigen-binding fragment thereof comprises a VL domain having the amino acid sequence of SEQ ID NO: 110 and a VH domain having the amino acid sequence of SEQ ID NO: 4. In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In a specific embodiment, provided herein is an antibody or fragment thereof that binds to ErbB3 or a fragment thereof (e.g., the extracellular domain of ErbB3), wherein the antibody or fragment thereof comprises VH CDRs and VL CDRs having the amino acid sequences reported in Table 13, infra, numbered according to the Kabat numbering system, Chothia numbering system, or IMGT numbering system, wherein $X_1$ is H, N, T, D, R, L, F or Y, $X_2$ is I, M, F or Y and $X_3$ is Q, T, S or N.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

TABLE 13

|  | Kabat | Chothia | IMGT |
| --- | --- | --- | --- |
| VH CDR1 | YYYMQ (SEQ ID NO: 6) | GFTFSYYYM (SEQ ID NO: 12) | GFTFSYYY (SEQ ID NO: 18) |
| VH CDR2 | YIGSSGGVTNYADSX$_3$KG (SEQ ID NO: 45) | GSSGG (SEQ ID NO: 13) | IGSSGGVT (SEQ ID NO: 19) |
| VH CDR3 | VGLGDAFDI (SEQ ID NO: 8) | VGLGDAFDI (SEQ ID NO: 14) | ARVGLGDAFDI (SEQ ID NO: 20) |

TABLE 13-continued

| | Kabat | Chothia | IMGT |
|---|---|---|---|
| VL CDR1 | SGX$_1$X$_2$SNIGLNYVS (SEQ ID NO: 50) | SGX$_1$X$_2$SNIGLNYVS (SEQ ID NO: 51) | X$_2$SNIGLNY (SEQ ID NO: 42) |
| VL CDR2 | RNNQRPS (SEQ ID NO: 10) | RNNQRPS (SEQ ID NO: 16) | RNN (SEQ ID NO: 22) |
| VL CDR3 | AAWDDSPPGEA (SEQ ID NO: 11) | AAWDDSPPGEA (SEQ ID NO: 17) | AAWDDSPPGEA (SEQ ID NO: 23) |

In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In one embodiment, provided herein is an antibody or fragment thereof that binds to ErbB3 or a fragment thereof (e.g., the extracellular domain of ErbB3), wherein the antibody or antigen-binding fragment thereof comprises a VL domain having the amino acid sequence of SEQ ID NO: 108. In one embodiment, provided herein is an antibody or fragment thereof that binds to ErbB3 or a fragment thereof (e.g., the extracellular domain of ErbB3), wherein the antibody or antigen-binding fragment thereof comprises a VH domain having the amino acid sequence of SEQ ID NO: 103. In another embodiment, provided herein is an antibody or fragment thereof that binds to ErbB3 or a fragment thereof (e.g., the extracellular domain of ErbB3), wherein the antibody or antigen-binding fragment thereof comprises a VL domain having the amino acid sequence of SEQ ID NO: 108 and a VH domain having the amino acid sequence of SEQ ID NO: 103. In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In a specific embodiment, provided herein is an antibody or fragment thereof that binds to ErbB3 or a fragment thereof (e.g., the extracellular domain of ErbB3), wherein the antibody or fragment thereof comprises VH CDRs and VL CDRs having the amino acid sequences reported in Table 14, infra, numbered according to the Kabat numbering system, Chothia numbering system, or IMGT numbering system, wherein X$_1$ is R, N, D, E, Q, H or K, X$_2$ is H, N, T, D, R, L, F or Y, X$_3$ is I, M, F or Y and X$_4$ is Q, T, S or N.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

TABLE 14

| | Kabat | Chothia | IMGT |
|---|---|---|---|
| VH CDR1 | YYYMQ (SEQ ID NO: 6) | GFTFSYYYM (SEQ ID NO: 12) | GFTFSYYY (SEQ ID NO: 18) |
| VH CDR2 | YIGSSGGVTNYADSX$_4$KG (SEQ ID NO: 45) | GSSGG (SEQ ID NO: 13) | IGSSGGVT (SEQ ID NO: 19) |
| VH CDR3 | VGLGDAFDI (SEQ ID NO: 8) | VGLGDAFDI (SEQ ID NO: 14) | ARVGLGDAFDI (SEQ ID NO: 20) |
| VL CDR1 | X$_1$GX$_2$X$_3$SNIGLNYVS (SEQ ID NO: 54) | X$_1$GX$_2$X$_3$SNIGLNYVS (SEQ ID NO: 55) | X$_3$SNIGLNY (SEQ ID NO: 42) |
| VL CDR2 | RNNQRPS (SEQ ID NO: 10) | RNNQRPS (SEQ ID NO: 16) | RNN (SEQ ID NO: 22) |
| VL CDR3 | AAWDDSPPGEA (SEQ ID NO: 11) | AAWDDSPPGEA (SEQ ID NO: 17) | AAWDDSPPGEA (SEQ ID NO: 23) | two or more amino acid residues within the ErbB3 domain II/domain III hinge region. In another specific embodiment, the epitope is a non-linear epitope.

In one embodiment, provided herein is an antibody or fragment thereof that binds to ErbB3 or a fragment thereof (e.g., the extracellular domain of ErbB3), wherein the antibody or antigen-binding fragment thereof comprises a VL domain having the amino acid sequence of SEQ ID NO: 110. In one embodiment, provided herein is an antibody or fragment thereof that binds to ErbB3 or a fragment thereof (e.g., the extracellular domain of ErbB3), wherein the antibody or antigen-binding fragment thereof comprises a VH domain having the amino acid sequence of SEQ ID NO: 103. In another embodiment, provided herein is an antibody or fragment thereof that binds to ErbB3 or a fragment thereof (e.g., the extracellular domain of ErbB3), wherein the antibody or antigen-binding fragment thereof comprises a VL domain having the amino acid sequence of SEQ ID NO: 110 and a VH domain having the amino acid sequence of SEQ ID NO: 103. In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope.

In certain embodiments, provided herein is an antibody or fragment thereof that binds to ErbB3 or a fragment thereof (e.g., the extracellular domain of ErbB3), wherein the antibody or fragment thereof comprises a VL domain having the amino acid sequence of SEQ ID NO: 112. In some embodiments, the antibody or antigen-binding fragment thereof comprises a variable VH domain described herein. In specific embodiments, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB3 activation.

In certain embodiments, the antibody or fragment thereof binds to ErbB3 or a fragment thereof (e.g., the extracellular domain of ErbB3) with a dissociation rate constant ($k_{off}$) of $8.5 \times 10^{-5}$ $s^{-1}$ or less, $5 \times 10^{-5}$ $s^{-1}$ or less, $2.5 \times 10^{-5}$ $s^{-1}$ or less, $1 \times 10^{-5}$ $s^{-1}$ or less, $8.5 \times 10^{-6}$ $s^{-1}$ or less, $5 \times 10^{-6}$ $s^{-1}$ or less, $2.5 \times 10^{-6}$ $s^{-1}$ or less, $1 \times 10^{-6}$ $s^{-1}$ or less, $8.5 \times 10^{-7}$ $s^{-1}$ or less, $5 \times 10^{-7}$ $s^{-1}$ or less, $2.5 \times 10^{-7}$ $s^{-1}$ or less, $1 \times 10^{-7}$ $s^{-1}$ or less, $8.5 \times 10^{-8}$ $s^{-1}$ or less, $5 \times 10^{-8}$ $s^{-1}$ or less, $2.5 \times 10^{-8}$ $s^{-1}$ or less, $1 \times 10^{-8}$ $s^{-1}$ or less, $8.5 \times 10^{-9}$ $s^{-1}$ or less, $5 \times 10^{-9}$ $s^{-1}$ or less, $2.5 \times 10^{-9}$ $s^{-1}$ or less, or $1 \times 10^{-9}$ $s^{-1}$ or less. In some embodiments, the antibody or fragment thereof binds to ErbB3 or a fragment thereof (e.g., the extracellular domain of ErbB3) with a $k_{off}$ of between $9.5 \times 10^{-5}$ $s^{-1}$ to $1 \times 10^{-9}$ $s^{-1}$, $8.5 \times 10^{-5}$ $s^{-1}$ to $1 \times 10^{-9}$ $s^{-1}$, $5 \times 10^{-5}$ $s^{-1}$ to $1 \times 10^{-9}$ $s^{-1}$, $9.5 \times 10^{-5}$ $s^{-1}$ to $1 \times 10^{-8}$ $s^{-1}$, $5 \times 10^{-5}$ $s^{-1}$ to $1 \times 10^{-8}$ $s^{-1}$, $9.5 \times 10^{-5}$ $s^{-1}$ to $1 \times 10^{-7}$ $s^{-1}$, $5 \times 10^{-5}$ $s^{-1}$ to $1 \times 10^{-7}$ $s^{-1}$, $9.5 \times 10^{-5}$ $s^{-1}$ to $5 \times 10^{-6}$ $s^{-1}$, or $9.5 \times 10^{-5}$ $s^{-1}$ to $1 \times 10^{-5}$ $s^{-1}$. In certain embodiments, the $k_{off}$ is determined using a monovalent antibody, such as a Fab fragment, as measured by, e.g., BIAcore™ surface plasmon resonance technology. In a particular embodiment, the $k_{off}$ is determined using an assay described in Section 6, infra.

In certain embodiments, the antibody or fragment thereof binds to ErbB3 or a fragment thereof (e.g., the extracellular domain of ErbB3) with an association rate constant ($k_{on}$) of at least $10^5$ $M^{-1}$ $s^{-1}$, at least $5 \times 10^5$ $M^{-1}$ $s^{-1}$, at least $10^6$ $M^{-1}$ $s^{-1}$, at least $5 \times 10^6$ $M's^{-1}$, at least $10^7$ $M^{-1}$ $s^{-1}$, at least $5 \times 10^7$ $M^{-1}$ $s^{-1}$, at least $10^8$ $M^{-1}$ $s^{-1}$, at least $5\ 10^8$ $M^{-1}$ $s^{-1}$ or at least $10^9$ $M^{-1}$ $s^{-1}$. In some embodiments, the antibody or fragment thereof binds to ErbB3 or a fragment thereof (e.g., the extracellular domain of ErbB3) with a $k_{on}$ of between $1 \times 10^5$ $M^{-1}$ $s^{-1}$ to $5 \times 10^5$ $M^{-1}$ $s^{-1}$, $1 \times 10^5$ $M^{-1}$ $s^{-1}$ to $1 \times 10^6$ $M^{-1}$ $s^{-1}$, $1 \times 10^5$ $M^{-1}$ $s^{-1}$ to $5 \times 10^6$ $M^{-1}$ $s^{-1}$, $1 \times 10^5$ $M^{-1}$ $s^{-1}$ to $1 \times 10^7$ $M^{-1}$ $s^{-1}$, $1 \times 10^5$ $M^{-1}$ $s^{-1}$ to $5 \times 10^7$ $M^{-1}$ $s^{-1}$, $1 \times 10^5$ $M^{-1}$ $s^{-1}$ to $10^8$ $M^{-1}$ $s^{-1}$, $1 \times 10^5$ $M^{-1}$ $s^{-1}$ to $1 \times 10^9$ $M^{-1}$ $s^{-1}$, $1 \times 10^6$ $M^{-1}$ $s^{-1}$ to $1 \times 10^7$ $M^{-1}$ $s^{-1}$, $1 \times 10^6$ $M^{-1}$ $s^{-1}$ to $1 \times 10^8$ $M^{-1}$ $s^{-1}$, $1 \times 10^6$ $M^{-1}$ $s^{-1}$ to $1 \times 10^9$ $M^{-1}$ $s^{-1}$, $1 \times 10^7$ $M^{-1}$ $s^{-1}$ to $1 \times 10^8$ $M^{-1}$ $s^{-1}$, $1 \times 10^7$ $M^{-1}$ $s^{-1}$ to $1 \times 10^9$ $M^{-1}$ $s^{-1}$, $1 \times 10^8$ $M^{-1}$ $s^{-1}$ to $1 \times 10^9$ $M^{-1}s^{-1}$. In certain embodiments, the $k_{on}$ is determined using a monovalent antibody, such as a Fab fragment, as measured by, e.g., BIAcore™ surface plasmon resonance technology. In a particular embodiment, the $k_{on}$ is determined using an assay described in Section 6, infra.

In certain embodiments the antibody or fragment thereof binds to ErbB3 or a fragment thereof (e.g., the extracellular domain of ErbB3) with a $K_D$ of less than 375 pM, 350 pM, 325 pM, 300 pM, 275 pM, 250 pM, 225 pM, 200 pM, 175 pM, 150 pM, 125 pM, 100 pM, 75 pM, 50 pM, 45 pM, 40 pM, or 35 pM. In some embodiments the antibody or fragment thereof binds to ErbB3 or a fragment thereof (e.g., the extracellular domain of ErbB3) with a $k_D$ of 375 pM, 350 pM, 325 pM, 300 pM, 275 pM, 250 pM, 225 pM, 200 pM, 175 pM, 150 pM, 125 pM, 100 pM, 75 pM, or 50 pM, or between 375 pM to 300 pM, 375 pM to 200 pM, 375 pM to 100 pM, 350 pM to 250 pM, 350 pM to 200 pM, 300 pM to 150 pM, 300 pM to 100 pM, 300 pM to 50 pM, 300 pM to 200 pM, 300 pM to 150 pM, 300 pM to 100 pM, 300 pM to 50 pM, 275 pM to 200 pM, 275 pM to 175 pM, 275 pM to 150 pM, 275 pM to 100 pM, 275 pM to 50 pM, 250 pM to 200 pM, 250 pM to 150 pM, 250 pM to 100 pM, 250 pM to 50 pM, 200 pM to 150 pM, 200 pM to 100 pM, 200 to 50 pM, 150 pM to 100 pM, 150 pM to 50 pM, 100 pM to 50 pM, 200 to 40 pM, 150 pM to 40 pM, 150 pM to 40 pM, or 100 pM to 35 pM. In certain embodiments, the $k_D$ is calculated as the quotient of $k_{off}/k_{on}$, and the $k_{on}$ and $k_{off}$ are determined using a monovalent antibody, such as a Fab fragment, as measured by, e.g., BIAcore™ surface plasmon resonance technology.

In another aspect, provided herein is an antibody(ies) or fragments thereof that binds to ErbB1 or a fragment thereof, wherein the antibody or antigen-binding fragment thereof inhibits ligand-dependent and ligand-independent ErbB1 activation. In one embodiment, provided herein is an antibody(ies) or fragments thereof that binds to ErbB1 or a fragment thereof (e.g., the extracellular domain of ErbB1), wherein the antibody or fragment thereof comprises a VH CDR1 comprising the following amino acid sequence: $X_1$YYMQ, wherein $X_1$ represents amino acid residues Y, S, A, or G, and wherein the antibody or antigen-binding fragment thereof inhibits ligand-dependent and ligand-independent ErbB1 activation. In another embodiment, provided herein is an antibody(ies) or fragments thereof that binds to ErbB1 or a fragment thereof (e.g., the extracellular domain of ErbB1), wherein the antibody or fragment thereof comprises a VL CDR1 comprising the following amino acid sequence: SGSLSNIGX$_2$NYVS, wherein $X_2$ represents amino acid residues L, S, A, G or V, and wherein the antibody or antigen-binding fragment thereof inhibits ligand-dependent and ligand-independent ErbB1 activation. In another embodiment, provided herein is an antibody(ies) or fragments thereof that binds to ErbB1 or a fragment thereof (e.g., the extracellular domain of ErbB1), wherein the antibody or fragment thereof comprises a VL CDR2 comprising the following amino acid sequence: X$_3$NNQRPS, wherein X3 represents amino acid residues R, F, Y, H, A, L, I or V, and wherein the antibody or antigen-binding fragment thereof inhibits ligand-dependent and ligand-independent ErbB1 activation.

In a specific embodiment, the antibody or fragment thereof binds to an epitope comprising: (i) one, two or more amino acid residues within domain II of the extracellular domain of ErbB1 and one, two or more amino acid residues with domain III of the extracellular domain of ErbB1, or (ii) one, two or more amino acid residues within the ErbB1 domain II/domain III hinge region. In another specific embodiment, the epitope is a non-linear epitope.

In a specific embodiment, provided herein is an antibody(ies) or fragment(s) thereof that binds to ErbB1 or a fragment thereof (e.g., the extracellular domain of ErbB1), wherein the antibody or fragment thereof comprises one, two, three, four, five, or six of the following CDRs:
(a) a VH CDR1 comprising the following amino acid sequence: X$_1$YYMQ (SEQ ID NO: 56); and/or
(b) a VH CDR2 comprising the following amino acid sequence: YIGSSGGVTNYADSVKG (SEQ ID NO: 7); and/or
(c) a VH CDR3 comprising the following amino acid sequence: VGLGDAFDI (SEQ ID NO: 8); and/or
(d) a VL CDR1 comprising the following amino acid sequence: SGSLSNIGX$_2$NYVS (SEQ ID NO: 59); and/or
(e) a VL CDR2 comprising the following amino acid sequence: X$_3$NNQRPS (SEQ ID NO: 62); and/or
(f) a VL CDR3 comprising the following amino acid sequence: AAWDDSPPGEA (SEQ ID NO: 11);
wherein X$_1$ represents amino acid residues Y, S, A, or G, X$_2$ represents amino acid residues L, S, A, G or V, and X$_3$ represents amino acid residues R, F, Y, H, A, L, I or V.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system. In certain embodiments, the antibody or antigen-binding fragment thereof comprises the framework regions of VL domain having the amino acid sequence of SEQ ID NO: 5 and/or the framework regions of the VH domain having the amino acid sequence of SEQ ID NO: 4. In other embodiments, the antibody or antigen-binding fragment thereof comprises the framework regions of the VL domain having the amino acid sequence of SEQ ID NO: 5 with 1, 2, 3, 4, 5, 6, 7, 8, 9 or more amino acid mutations (e.g., amino acid substitutions, such as conservative amino acid substitutions) and/or the framework regions of the VH domain having the amino acid sequence of SEQ ID NO: 4. In a specific embodiment, the antibody or fragment thereof binds to an epitope comprising: (i) one, two or more amino acid residues within domain II of the extracellular domain of ErbB1 and one, two or more amino acid residues with domain III of the extracellular domain of ErbB1, or (ii) one, two or more amino acid residues within the ErbB1 domain II/domain III hinge region. In another specific embodiment, the epitope is a non-linear epitope. In certain embodiments, the antibody or antigen-binding fragment thereof is a human, chimeric, or humanized antibody or an antigen-binding fragment thereof. In a specific embodiment, the antibody or antigen-binding fragment thereof is a monoclonal antibody. In specific embodiments, the antibody or antigen-binding fragment thereof inhibits ligand-dependent and ligand-independent ErbB1 activation.

In a specific embodiment, provided herein is an antibody(ies) or fragment(s) thereof that binds to ErbB1 or a fragment thereof (e.g., the extracellular domain of ErbB1), wherein the antibody or fragment thereof comprises one, two, three, four, five, or six of the following CDRs:
(a) a VH CDR1 comprising the following amino acid sequence: GFTFX$_1$YYMQ (SEQ ID NO: 57); and/or
(b) a VH CDR2 comprising the following amino acid sequence: GSSGG (SEQ ID NO: 13); and/or
(c) a VH CDR3 comprising the following amino acid sequence: VGLGDAFDI (SEQ ID NO: 14); and/or
(d) a VL CDR1 comprising the following amino acid sequence: SGSLSNIGX$_2$NYVS (SEQ ID NO: 60); and/or
(e) a VL CDR2 comprising the following amino acid sequence: X$_3$NNQRPS (SEQ ID NO: 63); and/or
(f) a VL CDR3 comprising the following amino acid sequence: AAWDDSPPGEA (SEQ ID NO: 17);
wherein X$_1$ represents amino acid residues Y, S, A, or G, X$_2$ represents amino acid residues L, S, A, G or V, and X$_3$ represents amino acid residues R, F, Y, H, A, L, I or V.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system. In certain embodiments, the antibody or antigen-binding fragment thereof comprises the framework regions of VL domain having the amino acid sequence of SEQ ID NO: 5 and/or the framework regions of the VH domain having the amino acid sequence of SEQ ID NO: 4. In other embodiments, the antibody or antigen-binding fragment thereof comprises the framework regions of the VL domain having the amino acid sequence of SEQ ID NO: 5 with 1, 2, 3, 4, 5, 6, 7, 8, 9 or more amino acid mutations (e.g., amino acid substitutions, such as conservative amino acid substitutions) and/or the framework regions of the VH domain having the amino acid sequence of SEQ ID NO: 4. In a specific embodiment, the antibody or fragment thereof binds to an epitope comprising: (i) one, two or more amino acid residues within domain II of the extracellular domain of ErbB1 and one, two or more amino acid residues with domain III of the extracellular domain of ErbB1, or (ii) one, two or more amino acid residues within the ErbB1 domain II/domain III hinge region. In another specific embodiment, the epitope is a non-linear epitope. In certain embodiments, the antibody or antigen-binding fragment thereof is a human, chimeric, or humanized antibody or an antigen-binding fragment thereof. In a specific embodiment, the antibody or antigen-binding fragment thereof is a monoclonal antibody. In specific embodiments, the antibody or antigen-binding fragment thereof inhibits ligand-dependent and ligand-independent ErbB1 activation.

In a specific embodiment, provided herein is an antibody(ies) or fragment(s) thereof that binds to ErbB1 or a fragment thereof (e.g., the extracellular domain of ErbB1), wherein the antibody or fragment thereof comprises one, two, three, four, five, or six of the following CDRs:
  (a) a VH CDR1 comprising the following amino acid sequence: GFTFSX$_1$YY (SEQ ID NO: 58); and/or
  (b) a VH CDR2 comprising the following amino acid sequence: IGSSGGVT (SEQ ID NO: 19); and/or
  (c) a VH CDR3 comprising the following amino acid sequence: ARVGLGDAFDI (SEQ ID NO: 20); and/or
  (d) a VL CDR1 comprising the following amino acid sequence: LSNIGX$_2$NY (SEQ ID NO: 61); and/or
  (e) a VL CDR2 comprising the following amino acid sequence: X$_3$NN (SEQ ID NO: 64); and/or
  (f) a VL CDR3 comprising the following amino acid sequence: AAWDDSPPGEA (SEQ ID NO: 23);
wherein X$_1$ represents amino acid residues Y, S, A, or G, X$_2$ represents amino acid residues L, S, A, G or V, and X$_3$ represents amino acid residues R, F, Y, H, A, L, I or V.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system. In certain embodiments, the antibody or antigen-binding fragment thereof comprises the framework regions of VL domain having the amino acid sequence of SEQ ID NO: 5 and/or the framework regions of the VH domain having the amino acid sequence of SEQ ID NO: 4. In other embodiments, the antibody or antigen-binding fragment thereof comprises the framework regions of the VL domain having the amino acid sequence of SEQ ID NO: 5 with 1, 2, 3, 4, 5, 6, 7, 8, 9 or more amino acid mutations (e.g., amino acid substitutions, such as conservative amino acid substitutions) and/or the framework regions of the VH domain having the amino acid sequence of SEQ ID NO: 4. In a specific embodiment, the antibody or fragment thereof binds to an epitope comprising: (i) one, two or more amino acid residues within domain II of the extracellular domain of ErbB1 and one, two or more amino acid residues with domain III of the extracellular domain of ErbB1, or (ii) one, two or more amino acid residues within the ErbB1 domain II/domain III hinge region. In another specific embodiment, the epitope is a non-linear epitope. In certain embodiments, the antibody or antigen-binding fragment thereof is a human, chimeric, or humanized antibody or an antigen-binding fragment thereof. In a specific embodiment, the antibody or antigen-binding fragment thereof is a monoclonal antibody. In specific embodiments, the antibody or antigen-binding fragment thereof inhibits ligand-dependent and ligand-independent ErbB1 activation.

In a specific embodiment, provided herein is an antibody or fragment thereof that binds to ErbB1 or a fragment thereof (e.g., the extracellular domain of ErbB1), wherein the antibody or fragment thereof comprises VH CDRs and VL CDRs having the amino acid sequences reported in Table 15, infra, numbered according to the Kabat numbering system or Chothia numbering system, wherein X$_1$ is S, A, or G.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

TABLE 15

|  | Kabat | Chothia | IMGT |
| --- | --- | --- | --- |
| VH CDR1 | X$_1$YYMQ (SEQ ID NO: 65) | GFTFSX$_1$YYM (SEQ ID NO: 66) | GFTFSX$_1$YY (SEQ ID NO: 67) |
| VH CDR2 | YIGSSGGVTNYADSVKG (SEQ ID NO: 7) | GSSGG (SEQ ID NO: 13) | IGSSGGVT (SEQ ID NO: 19) |
| VH CDR3 | VGLGDAFDI (SEQ ID NO: 8) | VGLGDAFDI (SEQ ID NO: 14) | ARVGLGDAFDI (SEQ ID NO: 20) |
| VL CDR1 | SGSLSNIGLNYVS (SEQ ID NO: 9) | SGSLSNIGLNYVS (SEQ ID NO: 15) | LSNIGLNY (SEQ ID NO: 21) |

TABLE 15-continued

| | Kabat | Chothia | IMGT |
|---|---|---|---|
| VL CDR2 | RNNQRPS (SEQ ID NO: 10) | RNNQRPS (SEQ ID NO: 16) | RNN (SEQ ID NO: 22) |
| VL CDR3 | AAWDDSPPGEA (SEQ ID NO: 11) | AAWDDSPPGEA (SEQ ID NO: 17) | AAWDDSPPGEA (SEQ ID NO: 23) |

In a specific embodiment, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. In another specific embodiment, the epitope is a non-linear epitope. In specific embodiments, the antibody or antigen-binding fragment thereof inhibits ligand-dependent and ligand-independent ErbB1 activation.

In one embodiment, provided herein is an antibody or fragment thereof that binds to ErbB1 or a fragment thereof (e.g., the extracellular domain of ErbB1), wherein the antibody or antigen-binding fragment thereof comprises a VH domain the amino acid sequence of SEQ ID NO: 111. In another embodiment, provided herein is an antibody or fragment thereof that binds to ErbB1 or a fragment thereof (e.g., the extracellular domain of ErbB1), wherein the antibody or antigen-binding fragment thereof comprises a VH domain having the amino acid sequence of SEQ ID NO: 111 and a VL domain having the amino acid sequence of SEQ ID NO: 5. In a specific embodiment, the antibody or fragment thereof binds to an epitope comprising: (i) one, two or more amino acid residues within domain II of the extracellular domain of ErbB1 and one, two or more amino acid residues with domain III of the extracellular domain of ErbB1, or (ii) one, two or more amino acid residues within the ErbB1 domain II/domain III hinge region. In another specific embodiment, the epitope is a non-linear epitope. In specific embodiments, the antibody or antigen-binding fragment thereof inhibits ligand-dependent and ligand-independent ErbB1 activation.

In a specific embodiment, provided herein is an antibody or fragment thereof that binds to ErbB1 or a fragment thereof (e.g., the extracellular domain of ErbB1), wherein the antibody or fragment thereof comprises VH CDRs and VL CDRs having the amino acid sequences reported in Table 16, infra, numbered according to the Kabat numbering system, Chothia numbering system, or IMGT numbering system, wherein $X_1$ is S, A, G, or V.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

TABLE 16

| | Kabat | Chothia | IMGT |
|---|---|---|---|
| VH CDR1 | YYYMQ (SEQ ID NO: 6) | GFTFSYYYM (SEQ ID NO: 12) | GFTFSYYY (SEQ ID NO: 18) |
| VH CDR2 | YIGSSGGVTNYADSVKG (SEQ ID NO: 7) | GSSGG (SEQ ID NO: 13) | IGSSGGVT (SEQ ID NO: 19) |
| VH CDR3 | VGLGDAFDI (SEQ ID NO: 8) | VGLGDAFDI (SEQ ID NO: 14) | ARVGLGDAFDI (SEQ ID NO: 20) |
| VL CDR1 | SGSLSNIGX$_1$NYVS (SEQ ID NO: 68) | SGSLSNIGX$_1$NYVS (SEQ ID NO: 69) | LSNIGX$_1$NY (SEQ ID NO: 70) |
| VL CDR2 | RNNQRPS (SEQ ID NO: 10) | RNNQRPS (SEQ ID NO: 16) | RNN (SEQ ID NO: 21) |
| VL CDR3 | AAWDDSPPGEA (SEQ ID NO: 11) | AAWDDSPPGEA (SEQ ID NO: 17) | AAWDDSPPGEA (SEQ ID NO: 22) |

In a specific embodiment, the antibody or fragment thereof binds to an epitope comprising: (i) one, two or more amino acid residues within domain II of the extracellular domain of ErbB1 and one, two or more amino acid residues with domain III of the extracellular domain of ErbB1, or (ii) one, two or more amino acid residues within the ErbB1 domain II/domain III hinge region. In another specific embodiment, the epitope is a non-linear epitope. In specific embodiments, the antibody or antigen-binding fragment thereof inhibits ligand-dependent and ligand-independent ErbB1 activation.

In one embodiment, provided herein is an antibody or fragment thereof that binds to ErbB1 or a fragment thereof (e.g., the extracellular domain of ErbB1), wherein the antibody or antigen-binding fragment thereof comprises a VL domain the amino acid sequence of SEQ ID NO: 115. In another embodiment, provided herein is an antibody or fragment thereof that binds to ErbB1 or a fragment thereof (e.g., the extracellular domain of ErbB1), wherein the antibody or antigen-binding fragment thereof comprises a VL domain having the amino acid sequence of SEQ ID NO: 115 and a VH domain having the amino acid sequence of SEQ ID NO: 4. In a specific embodiment, the antibody or fragment thereof binds to an epitope comprising: (i) one, two or more amino acid residues within domain II of the extracellular domain of ErbB1 and one, two or more amino acid residues with domain III of the extracellular domain of ErbB1, or (ii) one, two or more amino acid residues within the ErbB1 domain II/domain III hinge region. In another specific embodiment, the epitope is a non-linear epitope. In specific embodiments, the antibody or antigen-binding fragment thereof inhibits ligand-dependent and ligand-independent ErbB1 activation.

In a specific embodiment, provided herein is an antibody or fragment thereof that binds to ErbB1 or a fragment thereof (e.g., the extracellular domain of ErbB1), wherein the antibody or fragment thereof comprises VH CDRs and VL CDRs having the amino acid sequences reported in Table 17, infra, numbered according to the Kabat numbering system, Chothia numbering system, or IMGT numbering system, wherein $X_1$ is F, Y, H, A, L, I, or V.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

In a specific embodiment, the antibody or fragment thereof binds to an epitope comprising: (i) one, two or more amino acid residues within domain II of the extracellular domain of ErbB1 and one, two or more amino acid residues with domain III of the extracellular domain of ErbB1, or (ii) one, two or more amino acid residues within the ErbB1 domain II/domain III hinge region. In another specific embodiment, the epitope is a non-linear epitope. In specific embodiments, the antibody or antigen-binding fragment thereof inhibits ligand-dependent and ligand-independent ErbB1 activation.

In one embodiment, provided herein is an antibody or fragment thereof that binds to ErbB1 or a fragment thereof (e.g., the extracellular domain of ErbB1), wherein the antibody or antigen-binding fragment thereof comprises a VL domain the amino acid sequence of SEQ ID NO: 113. In another embodiment, provided herein is an antibody or fragment thereof that binds to ErbB1 or a fragment thereof (e.g., the extracellular domain of ErbB1), wherein the antibody or antigen-binding fragment thereof comprises a VL domain having the amino acid sequence of SEQ ID NO: 113 and a VH domain having the amino acid sequence of SEQ ID NO: 4. In a specific embodiment, the antibody or fragment thereof binds to an epitope comprising: (i) one, two or more amino acid residues within domain II of the extracellular domain of ErbB1 and one, two or more amino acid residues with domain III of the extracellular domain of ErbB1, or (ii) one, two or more amino acid residues within the ErbB1 domain II/domain III hinge region. In another specific embodiment, the epitope is a non-linear epitope. In specific embodiments, the antibody or antigen-binding fragment thereof inhibits ligand-dependent and ligand-independent ErbB1 activation.

In a specific embodiment, provided herein is an antibody or fragment thereof that binds to ErbB1 or a fragment thereof (e.g., the extracellular domain of ErbB1), wherein the antibody or fragment thereof comprises VH CDRs and VL CDRs having the amino acid sequences reported in Table 18, infra, numbered according to the Kabat numbering system, Chothia numbering system, or IMGT numbering system, wherein $X_1$ is S, A, G, or V and $X_2$ is F, Y, H, A, L, I, or V.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by

TABLE 17

| | Kabat | Chothia | IMGT |
|---|---|---|---|
| VH CDR1 | YYYMQ (SEQ ID NO: 6) | GFTFSYYYM (SEQ ID NO: 12) | GFTFSYYY (SEQ ID NO: 18) |
| VH CDR2 | YIGSSGGVTNYADSVKG (SEQ ID NO: 7) | GSSGG (SEQ ID NO: 13) | IGSSGGVT (SEQ ID NO: 19) |
| VH CDR3 | VGLGDAFDI (SEQ ID NO: 8) | VGLGDAFDI (SEQ ID NO: 14) | ARVGLGDAFDI (SEQ ID NO: 20) |
| VL CDR1 | SGSLSNIGLNYVS (SEQ ID NO: 9) | SGSLSNIGLNYVS (SEQ ID NO: 15) | LSNIGLNY (SEQ ID NO: 21) |
| VL CDR2 | $X_1$NNQRPS (SEQ ID NO: 71) | $X_1$NNQRPS (SEQ ID NO: 72) | $X_1$NN (SEQ ID NO: 73) |
| VL CDR3 | AAWDDSPPGEA (SEQ ID NO: 11) | AAWDDSPPGEA (SEQ ID NO: 17) | AAWDDSPPGEA (SEQ ID NO: 23) | the Kabat numbering system and one, two, or three CDRs as defined by the Chothia numbering system. In TABLE 19-continued

| | Kabat | Chothia | IMGT |
|---|---|---|---|
| VH CDR3 | VGLGDAFDI (SEQ ID NO: 8) | VGLGDAFDI (SEQ ID NO: 14) | ARVGLGDAFDI (SEQ ID NO: 20) |
| VL CDR1 | SGSLSNIGX$_2$NYVS (SEQ ID NO: 68) | SGSLSNIGX$_2$NYVS (SEQ ID NO: 69) | LSNIGX$_2$NY (SEQ ID NO: 70) |
| VL CDR2 | RNNQRPS (SEQ ID NO: 10) | RNNQRPS (SEQ ID NO: 16) | RNN (SEQ ID NO: 22) |
| VL CDR3 | AAWDDSPPGEA (SEQ ID NO: 11) | AAWDDSPPGEA (SEQ ID NO: 17) | AAWDDSPPGEA (SEQ ID NO: 23) |

In a specific embodiment, the antibody or fragment thereof binds to an epitope comprising: (i) one, two or more amino acid residues within domain II of the extracellular domain of ErbB1 and one, two or more amino acid residues with domain III of the extracellular domain of ErbB1, or (ii) one, two or more amino acid residues within the ErbB1 domain II/domain III hinge region. In another specific embodiment, the epitope is a non-linear epitope. In specific embodiments, the antibody or antigen-binding fragment thereof inhibits ligand-dependent and ligand-independent ErbB1 activation.

In one embodiment, provided herein is an antibody or fragment thereof that binds to ErbB1 or a fragment thereof (e.g., the extracellular domain of ErbB1), wherein the antibody or antigen-binding fragment thereof comprises a VL domain the amino acid sequence of SEQ ID NO: 115. In one embodiment, provided herein is an antibody or fragment thereof that binds to ErbB1 or a fragment thereof (e.g., the extracellular domain of ErbB1), wherein the antibody or antigen-binding fragment thereof comprises a VH domain the amino acid sequence of SEQ ID NO: 116. In another embodiment, provided herein is an antibody or fragment thereof that binds to ErbB1 or a fragment thereof (e.g., the extracellular domain of ErbB1), wherein the antibody or antigen-binding fragment thereof comprises a VL domain having the amino acid sequence of SEQ ID NO: 115 and a VH domain having the amino acid sequence of SEQ ID NO: 116. In a specific embodiment, the antibody or fragment thereof binds to an epitope comprising: (i) one, two or more amino acid residues within domain II of the extracellular domain of ErbB1 and one, two or more amino acid residues with domain III of the extracellular domain of ErbB1, or (ii) one, two or more amino acid residues within the ErbB1 domain II/domain III hinge region. In another specific embodiment, the epitope is a non-linear epitope. In specific embodiments, the antibody or antigen-binding fragment thereof inhibits ligand-dependent and ligand-independent ErbB1 activation.

In a specific embodiment, provided herein is an antibody or fragment thereof that binds to ErbB1 or a fragment thereof (e.g., the extracellular domain of ErbB1), wherein the antibody or fragment thereof comprises VH CDRs and VL CDRs having the amino acid sequences reported in Table 20, infra, numbered according to the Kabat numbering system, Chothia numbering system, or IMGT numbering system, wherein X$_1$ is S, A or G and X$_2$ is F, Y, H, A, L, I, or V.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

TABLE 20

| | Kabat | Chothia | IMGT |
|---|---|---|---|
| VH CDR1 | X$_1$YYMQ (SEQ ID NO: 65) | GFTFSX$_1$YYM (SEQ ID NO: 66) | GFTFSX$_1$YY (SEQ ID NO: 67) |
| VH CDR2 | YIGSSGGVTNYADSVKG (SEQ ID NO: 7) | GSSGG (SEQ ID NO: 13) | IGSSGGVT (SEQ ID NO: 19) |
| VH CDR3 | VGLGDAFDI (SEQ ID NO: 8) | VGLGDAFDI (SEQ ID NO: 14) | ARVGLGDAFDI (SEQ ID NO: 20) |
| VL CDR1 | SGSLSNIGLNYVS (SEQ ID NO: 9) | SGSLSNIGLNYVS (SEQ ID NO: 15) | LSNIGLNY (SEQ ID NO: 21) |
| VL CDR2 | X$_2$NNQRPS (SEQ ID NO: 71) | X$_2$NNQRPS (SEQ ID NO: 72) | X$_2$NN (SEQ ID NO: 73) |

TABLE 20-continued

| Kabat | Chothia | IMGT |
|---|---|---|
| VL CDR3 AAWDDSPPGEA (SEQ ID NO: 11) | AAWDDSPPGEA (SEQ ID NO: 17) | AAWDDSPPGEA (SEQ ID NO: 23) |

In a specific embodiment, the antibody or fragment thereof binds to an epitope comprising: (i) one, two or more amino acid residues within domain II of the extracellular domain of ErbB1 and one, two or more amino acid residues with domain III of the extracellular domain of ErbB1, or (ii) one, two or more amino acid residues within the ErbB1 domain II/domain III hinge region. In another specific embodiment, the epitope is a non-linear epitope. In specific embodiments, the antibody or antigen-binding fragment thereof inhibits ligand-dependent and ligand-independent ErbB1 activation.

In one embodiment, provided herein is an antibody or fragment thereof that binds to ErbB1 or a fragment thereof (e.g., the extracellular domain of ErbB1), wherein the antibody or antigen-binding fragment thereof comprises a VL domain the amino acid sequence of SEQ ID NO: 113. In one embodiment, provided herein is an antibody or fragment thereof that binds to ErbB1 or a fragment thereof (e.g., the extracellular domain of ErbB1), wherein the antibody or antigen-binding fragment thereof comprises a VH domain the amino acid sequence of SEQ ID NO: 116. In another embodiment, provided herein is an antibody or fragment thereof that binds to ErbB1 or a fragment thereof (e.g., the extracellular domain of ErbB1), wherein the antibody or antigen-binding fragment thereof comprises a VL domain having the amino acid sequence of SEQ ID NO: 113 and a VH domain having the amino acid sequence of SEQ ID NO: 116. In a specific embodiment, the antibody or fragment thereof binds to an epitope comprising: (i) one, two or more amino acid residues within domain II of the extracellular domain of ErbB1 and one, two or more amino acid residues with domain III of the extracellular domain of ErbB1, or (ii) one, two or more amino acid residues within the ErbB1 domain II/domain III hinge region. In another specific embodiment, the epitope is a non-linear epitope. In specific embodiments, the antibody or antigen-binding fragment thereof inhibits ligand-dependent and ligand-independent ErbB1 activation.

In another aspect, provided herein is an antibody(ies) or fragments thereof that binds to ErbB4 or a fragment thereof (e.g., the extracellular domain of ErbB4), wherein the antibody or antigen-binding fragment thereof inhibits ligand-dependent and ligand-independent ErbB4 activation. In one embodiment, provided herein is an antibody(ies) or fragments thereof that binds to ErbB4 or a fragment thereof (e.g., the extracellular domain of ErbB4), wherein the antibody or fragment thereof comprises SGSLSNIGLNX$_1$VS, wherein X$_1$ is Y, F, I, V, L or A, and wherein the antibody or antigen-binding fragment thereof inhibits ligand-dependent and ligand-independent ErbB4 activation. In a specific embodiment, the antibody or fragment thereof binds to an epitope comprising: (i) one, two or more amino acid residues within domain II of the extracellular domain of ErbB4 and one, two or more amino acid residues with domain III of the extracellular domain of ErbB4, or (ii) one, two or more amino acid residues within the ErbB4 domain II/domain III hinge region. In another specific embodiment, the epitope is a non-linear epitope.

In a specific embodiment, provided herein is an antibody or fragment thereof that binds to ErbB4 or a fragment thereof (e.g., the extracellular domain of ErbB4), wherein the antibody or fragment thereof comprises VH CDRs and VL CDRs having the amino acid sequences reported in Table 21, infra, numbered according to the Kabat numbering system, Chothia numbering system, or IMGT numbering system, wherein X$_1$ is Y, F, I, V, L or A.

In certain embodiments, an antibody or antigen-binding fragment thereof comprises one, two, three, or more of the CDRs that are defined by two or more different numbering systems. For example, an antibody or antigen-binding fragment may comprise one, two, or three CDRs as defined by the Kabat numbering system and one, two, or three CDRs as defined by the Chothia numbering system. In another example, an antibody or antigen-binding fragment may comprise one, two, or three CDRs as defined by the Kabat numbering system and one, two, or three CDRs as defined by the IMGT numbering system. In another example, an antibody or antigen-binding fragment may comprise one, two, or three CDRs as defined by the IMGT numbering system and one, two, or three CDRs as defined by the Chothia numbering system. In a specific embodiment, an antibody or antigen-binding fragment comprises the CDRs as defined by a single numbering system, e.g., the Kabat numbering system, the Chothia numbering system, or the IMGT numbering system.

TABLE 21

| | Kabat | Chothia | IMGT |
|---|---|---|---|
| VH CDR1 | YYYMQ (SEQ ID NO: 6) | GFTFSYYYM (SEQ ID NO: 12) | GFTFSYYY (SEQ ID NO: 18) |
| VH CDR2 | YIGSSGGVTNYADSVKG (SEQ ID NO: 7) | GSSGG (SEQ ID NO: 13) | IGSSGGVT (SEQ ID NO: 19) |
| VH CDR3 | VGLGDAFDI (SEQ ID NO: 8) | VGLGDAFDI (SEQ ID NO: 14) | ARVGLGDAFDI (SEQ ID NO: 20) |
| VL CDR1 | SGSLSNIGLNX$_1$VS (SEQ ID NO: 74) | SGSLSNIGLNX$_1$VS (SEQ ID NO: 75) | LSNIGLNX$_1$ (SEQ ID NO: 76) |
| VL CDR2 | RNNQRPS (SEQ ID NO: 10) | RNNQRPS (SEQ ID NO: 16) | RNN (SEQ ID NO: 22) |

TABLE 21-continued

| Kabat | Chothia | IMGT |
| --- | --- | --- |
| VL CDR3 AAWDDSPPGEA (SEQ ID NO: 11) | AAWDDSPPGEA (SEQ ID NO: 17) | AAWDDSPPGEA (SEQ ID NO: 23) |

In a specific embodiment, the antibody or fragment thereof binds to an epitope comprising: (i) one, two or more amino acid residues within domain II of the extracellular domain of ErbB4 and one, two or more amino acid residues with domain III of the extracellular domain of ErbB4, or (ii) one, two or more amino acid residues within the ErbB4 domain II/domain III hinge region. In another specific embodiment, the epitope is a non-linear epitope. In specific embodiments, the antibody or antigen-binding fragment thereof inhibits ligand-dependent and ligand-independent ErbB4 activation In one embodiment, provided herein is an antibody or fragment thereof that binds to ErbB4 or a fragment thereof (e.g., the extracellular domain of ErbB4), wherein the antibody or antigen-binding fragment thereof comprises a VL domain the amino acid sequence of SEQ ID NO: 117. In another embodiment, provided herein is an antibody or fragment thereof that binds to ErbB4 or a fragment thereof (e.g., the extracellular domain of ErbB4), wherein the antibody or antigen-binding fragment thereof comprises a VL domain having the amino acid sequence of SEQ ID NO: 117 and a VH domain having the amino acid sequence of SEQ ID NO: 4. In a specific embodiment, the antibody or fragment thereof binds to an epitope comprising: (i) one, two or more amino acid residues within domain II of the extracellular domain of ErbB4 and one, two or more amino acid residues with domain III of the extracellular domain of ErbB4, or (ii) one, two or more amino acid residues within the ErbB4 domain II/domain III hinge region. In another specific embodiment, the epitope is a non-linear epitope. In specific embodiments, the antibody or antigen-binding fragment thereof inhibits ligand-dependent and ligand-independent ErbB4 activation.

In a specific embodiment, the position of one or more CDRs along the VH (e.g., CDR1, CDR2, or CDR3) and/or VL (e.g., CDR1, CDR2, or CDR3) region of an antibody or antigen-binding fragment described herein may vary by one, two, three, four, five, or six amino acid positions so long as binding to ErbB (e.g., ErbB3) is maintained (e.g., substantially maintained, for example, at least 50%, at least 60%, at least 70%, at least 80%, at least 90%, at least 95%). For example, in one embodiment, the position defining a CDR of any of antibody or antigen-binding fragment may vary by shifting the N-terminal and/or C-terminal boundary of the CDR by one, two, three, four, five, or six amino acids, relative to the CDR position depicted in disclosed herein and Tables 2-21, so long as binding to ErbB (e.g., ErbB3) is maintained (e.g., substantially maintained, for example, at least 50%, at least 60%, at least 70%, at least 80%, at least 90%, at least 95%). In another embodiment, the length of one or more CDRs along the VH (e.g., CDR1, CDR2, or CDR3) and/or VL (e.g., CDR1, CDR2, or CDR3) region of an antibody or antigen-binding fragment described herein may vary (e.g., be shorter or longer) by one, two, three, four, five, or more amino acids, so long as binding to ErbB (e.g., ErbB3) is maintained (e.g., substantially maintained, for example, at least 50%, at least 60%, at least 70%, at least 80%, at least 90%, at least 95%). For example, in one embodiment, a VH CDR1, VH CDR2, and/or VH CDR3, and/or VL CDR1, CDR2, and/or CDR3 described herein may be one, two, three, four, five or more amino acids shorter than one or more of the CDRs described by SEQ ID NO:6-23 so long as binding to ErbB (e.g., ErbB3) is maintained (e.g., substantially maintained, for example, at least 50%, at least 60%, at least 70%, at least 80%, at least 90%, at least 95%). In another embodiment, a VH CDR1, VH CDR2, and/or VH CDR3, and/or VL CDR1, CDR2, and/or CDR3 described herein may be one, two, three, four, five or more amino acids longer than one or more of the CDRs described by SEQ ID NO: 6-23 so long as binding to ErbB (e.g., ErbB3) is maintained (e.g., substantially maintained, for example, at least 50%, at least 60%, at least 70%, at least 80%, at least 90%, at least 95%). In another embodiment, the amino terminus of a VH CDR1, VH CDR2, and/or VH CDR3, and/or VL CDR1, CDR2, and/or CDR3 described herein may be extended by one, two, three, four, five or more amino acids compared to one or more of the CDRs described by SEQ ID NO: 6-23 so long as binding to ErbB (e.g., ErbB3) is maintained (e.g., substantially maintained, for example, at least 50%, at least 60%, at least 70%, at least 80%, at least 90%, at least 95%). In another embodiment, the carboxy terminus of a VH CDR1, VH CDR2, and/or VH CDR3, and/or VL CDR1, CDR2, and/or CDR3 described herein may be extended by one, two, three, four, five or more amino acids compared to one or more of the CDRs described by SEQ ID NO: 6-23 so long as binding to ErbB (e.g., ErbB3) is maintained (e.g., substantially maintained, for example, at least 50%, at least 60%, at least 70%, at least 80%, at least 90%, at least 95%). In another embodiment, the amino terminus of a VH CDR1, VH CDR2, and/or VH CDR3, and/or VL CDR1, CDR2, and/or CDR3 described herein may be shortened by one, two, three, four, five or more amino acids compared to one or more of the CDRs described by SEQ ID NO: 6-23 so long as binding to ErbB (e.g., ErbB3) is maintained (e.g., substantially maintained, for example, at least 50%, at least 60%, at least 70%, at least 80%, at least 90%, at least 95%). In one embodiment, the carboxy terminus of a VH CDR1, VH CDR2, and/or VH CDR3, and/or VL CDR1, CDR2, and/or CDR3 described herein may be shortened by one, two, three, four, five or more amino acids compared to one or more of the CDRs described by SEQ ID NO: 6-23 so long as binding to ErbB (e.g., ErbB3) is maintained (e.g., substantially maintained, for example, at least 50%, at least 60%, at least 70%, at least 80%, at least 90%, at least 95%). Any method known in the art can be used to ascertain whether binding to ErbB (e.g., ErbB3) is maintained, for example, the binding assays and conditions described in the "Examples" section (Section 6) provided herein, e.g., an ELISA or flow cytometry assay described in Section 6, infra.

In specific embodiments, an antibody or fragment thereof described herein, which binds to ErbB (e.g., ErbB3) or a fragment thereof (e.g., the extracellular domain of ErbB3), comprises framework regions (e.g., framework regions of the VL domain and/or VH domain) that are human framework regions or derived from human framework regions. Non-limiting examples of human framework regions are described in the art, e.g., see Kabat et al. (1991) *Sequences of Proteins of Immunological Interest*, Fifth Edition, U.S. Department of Health and Human Services, NIH Publication No. 91-3242). In certain embodiment, an antibody described herein comprises framework regions (e.g., framework regions of the VL domain and/or VH domain) that are primate (e.g., non-human primate) framework regions or derived from primate (e.g., non-human primate) framework regions.

For example, CDRs from antigen-specific non-human antibodies, typically of rodent origin (e.g., mouse or rat), can be grafted onto homologous human or non-human primate acceptor frameworks. In one embodiment, the non-human primate acceptor frameworks are from Old World apes. In a specific embodiment, the Old World ape acceptor framework is from Pan troglodytes, Pan paniscus or Gorilla gorilla. In a particular embodiment, the non-human primate acceptor frameworks are from the chimpanzee Pan troglodytes. In a particular embodiment, the non-human primate acceptor frameworks are Old World monkey acceptor frameworks. In a specific embodiment, the Old World monkey acceptor frameworks are from the genus *Macaca*. In a certain embodiment, the non-human primate acceptor frameworks are is derived from the cynomolgus monkey *Macaca cynomolgus*. Non-human primate framework sequences are described, for example, in U.S. Patent Application Publication No. US 2005/0208625.

In some embodiments, the antibody or antigen-binding fragment thereof comprises the framework regions of VL domain having the amino acid sequence of SEQ ID NO: 5 and/or the framework regions of the VH domain having the amino acid sequence of SEQ ID NO: 4. In other embodiments, the antibody or antigen-binding fragment thereof comprises one, two, three or four framework regions of the VL domain having the amino acid sequence of SEQ ID NO: 5. In certain other embodiments, the antibody or antigen-binding fragment thereof comprises one, two, three, or four framework regions of the VL domain having the amino acid sequence of SEQ ID NO: 5 with 1, 2, 3, 4, 5, 6, 7, 8, 9 or more amino acid mutations (e.g., amino acid substitutions, such as conservative amino acid substitutions). In other embodiments, the antibody or antigen-binding fragment thereof comprises one, two, three or four framework regions of the VH domain having the amino acid sequence of SEQ ID NO: 4. In certain other embodiments, the antibody or antigen-binding fragment thereof comprises one, two, three, or four framework regions of the VH domain having the amino acid sequence of SEQ ID NO: 4 with 1, 2, 3, 4, 5, 6, 7, 8, 9 or more amino acid mutations (e.g., amino acid substitutions, such as conservative amino acid substitutions). In certain other embodiments, the antibody or antigen-binding fragment thereof comprises one, two, three, or four framework regions of the VH domain having the amino acid sequence of SEQ ID NO: 4 with 1, 2, 3, 4, 5, 6, 7, 8, 9 or more amino acid mutations (e.g., amino acid substitutions, such as conservative amino acid substitutions) and/or comprises one, two, three, or four framework regions of the VL domain having the amino acid sequence of SEQ ID NO: 5 with 1, 2, 3, 4, 5, 6, 7, 8, 9 or more amino acid mutations (e.g., amino acid substitutions, such as conservative amino acid substitutions). In some embodiments, the antibody or antigen-binding thereof comprises the frameworks of VL domain having the amino acid sequence of SEQ ID NO: 5 with amino acid substitutions at amino acid position 71 and/or amino acid position 70. In specific embodiments, the amino acid substitution at amino acid position 70 substitutes S for N, H, Y, K, or R and/or the amino acid substitution at amino acid position 71 substitutes T for N or Y. In certain embodiments, an antibody or fragment thereof described herein comprises VL framework regions (FRs) having at least 80%, at least 85%, at least 90%, at least 95%, or at least 98% sequence identity to the VL framework regions described herein in Table 22, wherein the antibody binds to ErbB (e.g., ErbB3) or a fragment thereof (e.g., the extracellular domain of ErbB). In certain embodiments, an antibody or fragment thereof described herein comprises VH framework regions (FRs) having at least 80%, at least 85%, at least 90%, at least 95%, or at least 98% sequence identity to the VH framework regions described herein Table 22, wherein the antibody binds to ErbB (e.g., ErbB3) or a fragment thereof (e.g., the extracellular domain of ErbB).

In certain embodiments, an antibody or fragment thereof described herein comprises one, two, three or all four of the VH framework regions (FRs) having the amino acid sequence described herein Table 22, wherein the antibody binds to ErbB (e.g., ErbB) or a fragment thereof (e.g., the extracellular domain of ErbB). In specific embodiments, an antibody or fragment thereof described herein comprises a VH region comprising FR1, CDR1, FR2, CDR2, FR3, CDR3, and FR4.

In certain embodiments, an antibody or fragment thereof described herein comprises one, two, three or all four of the VL framework regions (FRs) having the amino acid sequence described herein Table 22, wherein the antibody binds to ErbB (e.g., ErbB) or a fragment thereof (e.g., the extracellular domain of ErbB). In specific embodiments, an antibody or fragment thereof described herein comprises a VL region comprising FR1, CDR1, FR2, CDR2, FR3, CDR3, and FR4.

In certain embodiments, an antibody or fragment thereof described herein comprises one, two, three or all four of the VL framework regions (FRs) having the amino acid sequence described herein Table 22 and one, two, three, or all four of the VH framework regions (FRs) having the amino acid sequence described in Table 22, wherein the antibody binds to ErbB (e.g., ErbB) or a fragment thereof (e.g., the extracellular domain of ErbB). In specific embodiments, an antibody or fragment thereof described herein comprises a VL region comprising FR1, CDR1, FR2, CDR2, FR3, CDR3, and FR4, and a VH region comprising FR1, CDR1, FR2, CDR2, FR3, CDR3, and FR4.

Framework regions described herein are determined based upon the boundaries of the CDR numbering system. In other words, if the CDRs are determined by, e.g., Kabat, then the framework regions are the amino acid residues surrounding the CDRs in the variable region in the format FR1, CDR1, FR2, CDR2, FR3, CDR3, FR4. For example, FR1 is defined as the amino acid residues N-terminal to the CDR1 amino acid residues as defined by, e.g., the Kabat numbering system, FR2 is defined as the amino acid residues between CDR1 and CDR2 amino acid residues as defined by, e.g., the Kabat numbering system, FR3 is defined as the amino acid residues between CDR2 and CDR3 amino acid residues as defined by, e.g., the Kabat numbering system, and FR4 is defined as the amino acid residues C-terminal to the CDR3 amino acid residues as defined by, e.g., the Kabat numbering system.

TABLE 22

| | Framework Region | SEQUENCE |
|---|---|---|
| Kabat | VL FR1 | QSVLTQPPSASGTPGQRVTISC (SEQ ID NO: 77) |
| | VL FR2 | WYQQLPGTAPKLLIS (SEQ ID NO: 78) |
| | VL FR3 | GVPDRFSGSKSGX$_1$X$_2$ASLAISGLRSEDEADYYC, wherein X$_1$ is T, N or Y and X$_2$ is S, N, H, Y, K or R (SEQ ID NO: 79) |
| | VL FR4 | FGGGTKLTVLGQPKAAPSVTL (SEQ ID NO: 80) |
| | VH FR1 | EVQLLESGGGLVQPGGSLRLSCAASGFTFS (SEQ ID NO: 81) |
| | VH FR2 | WVRQAPGKGLEWVS (SEQ ID NO: 82) |
| | VH FR3 | RFTISRDNSKNTLYLQMNSLRAEDTAVYYCAR (SEQ ID NO: 83) |
| | VH FR4 | WGQGTMVTVSS (SEQ ID NO: 84) |
| Chothia | VL FR1 | QSVLTQPPSASGTPGQRVTISC (SEQ ID NO: 85) |
| | VL FR2 | WYQQLPGTAPKLLIS (SEQ ID NO: 86) |
| | VL FR3 | GVPDRFSGSKSGX$_1$X$_2$ASLAISGLRSEDEADYYC, wherein X$_1$ is T, N or Y and X$_2$ is S, N, H, Y, K or R (SEQ ID NO: 87) |
| | VL FR4 | FGGGTKLTV (SEQ ID NO: 88) |
| | VH FR1 | EVQLLESGGGLVQPGGSLRLSCAAS (SEQ ID NO: 89) |
| | VH FR2 | QWVRQAPGKGLEWVSYI (SEQ ID NO: 90) |
| | VH FR3 | VTNYADSX$_1$KGRFTISRDNSKNTLYLQMNSLRAEDTAVYYCAR, wherein X$_1$ is V, Q, T, S, or N (SEQ ID NO: 91) |
| | VH FR4 | WGQGTMVTVSS (SEQ ID NO: 92) |
| IMGT | VL FR1 | QSVLTQPPSASGTPGQRVTISCX$_1$GX$_2$, wherein X$_1$ is S, R, N, D, E, Q, or H, and X$_2$ is S, H, N, T, D, R, L, F, or Y (SEQ ID NO: 93) |
| | VL FR2 | VSWYQQLPGTAPKLLIS (SEQ ID NO: 94) |
| | VL FR3 | QRPSGVPDRFSGSKSGX$_1$X$_2$ASLAISGLRSEDEADYYC, wherein X$_1$ is T, N or Y and X$_2$ is S, N, H, Y, K or R (SEQ ID NO: 95) |
| | VL FR4 | FGGGTKLTVL (SEQ ID NO: 96) |
| | VH FR1 | EVQLLESGGGLVQPGGSLRLSCAAS (SEQ ID NO: 97) |
| | VH FR2 | MQWVRQAPGKGLEWVSY (SEQ ID NO: 98) |
| | VH FR3 | NYADSX$_1$KGRFTISRDNSKNTLYLQMNSLRAEDTAVYYC wherein X$_1$ is V, Q, T, S, or N (SEQ ID NO: 99) |
| | VH FR4 | WGQGTMVTVSS (SEQ ID NO: 100) |

In certain aspects, an antibody or antigen-binding fragment thereof described herein may be described by its VL region alone, or its VH region alone, or by its 3 VL CDRs alone, or its 3 VH CDRs alone. See, for example, Rader et al., 1998, Proc. Natl. Acad. Sci. USA, 95: 8910-8915, which is incorporated herein by reference in its entirety, describing the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also, Clackson et al., 1991, Nature 352:624-628, which is incorporated herein by reference in its entirety, describing methods of producing antibodies that bind a specific antigen by using a specific VL domain (or VH domain) and screening a library for the complementary variable domains. The screen produced 14 new partners for a specific VH domain and 13 new partners for a specific VL domain, which were strong binders, as determined by ELISA. See also, Kim & Hong, 2007, J. Microbiol. 45:572-577, which is incorporated herein by reference in its entirety, describing methods of producing antibodies that bind a specific antigen by using a specific VH domain and screening a library (e.g., human VL library) for complementary VL domains; the selected VL domains in turn could be used to guide selection of additional complementary (e.g., human) VH domains.

In certain embodiments, an antibody or fragment thereof described herein that binds to an ErbB polypeptide and/or fragment thereof (e.g., the extracellular domain an ErbB polypeptide) comprises a VL domain having at least 80%, at least 85%, at least 90%, at least 95%, or at least 98% sequence identity to the amino acid sequence of SEQ ID NO: 5. In certain aspects, in accordance with these embodiments, the antibody or fragment thereof binds to an epitope comprising: (i) one, two or more amino acid residues within domain II of the extracellular domain of ErbB3 and one, two or more amino acid residues with domain III of the extracellular domain of ErbB, or (ii) one, two or more amino acid residues within the ErbB3 domain II/domain III hinge region. In specific embodiments, the antibody or antigen-binding fragment thereof inhibits ligand-dependent and ligand-independent ErbB (e.g., ErbB3) activation. In one embodiment, the ErbB is ErbB1 or ErbB4. In a specific embodiment, the ErbB is ErbB3. In certain embodiments, the antibody or fragment thereof binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region.

In certain embodiments, an antibody or fragment thereof described herein that binds to an ErbB polypeptide and/or fragment thereof (e.g., the extracellular domain an ErbB polypeptide) comprises a VH domain having at least 80%, at least 85%, at least 90%, at least 95%, or at least 98% sequence identity to the amino acid sequence of SEQ ID NO: 4. In certain aspects, in accordance with these embodiments, the antibody or fragment thereof binds to an epitope comprising: (i) one, two or more amino acid residues within domain II of the extracellular domain of ErbB and one, two or more amino acid residues with domain III of the extracellular domain of ErbB, or (ii) one, two or more amino acid residues within the ErbB domain II/domain III hinge region. In specific embodiments, the antibody or antigen-binding fragment thereof inhibits ligand-dependent and ligand-independent ErbB (e.g., ErbB3) activation. In one embodiment, the ErbB is ErbB1 or ErbB4. In a specific embodiment, the ErbB is ErbB3. In certain embodiments, the antibody or antigen-binding fragment binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region.

In certain embodiments, an antibody or fragment thereof that binds to an ErbB polypeptide and/or a fragment thereof (e.g., the extracellular domain of an ErbB polypeptide) comprises (i) a VL domain having at least 80%, at least 85%, at least 90%, at least 95%, or at least 98% sequence identity to the amino acid sequence of SEQ ID NO: 5, and (ii) a VH domain having at least 80%, at least 85%, at least 90%, at least 95%, or at least 98% sequence identity to the amino acid sequence of SEQ ID NO: 4. In certain embodiments, an antibody or fragment thereof that binds to ErbB and/or a fragment thereof comprises (i) a VL domain comprising VL framework regions having at least 80%, at least 85%, at least 90%, at least 95%, or at least 98% sequence identity to the amino acid sequence of the framework regions of SEQ ID NO: 5, and (ii) a VH domain comprising VH framework regions having at least 80%, at least 85%, at least 90%, at least 95%, or at least 98% sequence identity to the amino acid sequence of the framework regions of SEQ ID NO: 4. In certain aspects, in accordance with these embodiments, the antibody or fragment thereof binds to an epitope comprising: (i) one, two or more amino acid residues within domain II of the extracellular domain of ErbB and one, two or more amino acid residues with domain III of the extracellular domain of ErbB, or (ii) one, two or more amino acid residues within the ErbB domain II/domain III hinge region. In one embodiment, the ErbB is ErbB1 or ErbB4. In a specific embodiment, the ErbB is ErbB3. In certain embodiments, the antibody or antigen-binding fragment binds to an epitope comprising: (i) one, two or more amino acid residues within domain II of the extracellular domain of ErbB3 and one, two or more amino acid residues with domain III of the extracellular domain of ErbB3, or (ii) one, two or more amino acid residues within the ErbB3 domain II/domain III hinge region. The determination of percent identity between two sequences (e.g., amino acid sequences or nucleic acid sequences) can be accomplished using a mathematical algorithm. A non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

In certain embodiments, an antibody or fragment thereof described herein which binds to ErbB (e.g., ErbB3) or a fragment thereof (e.g., the extracellular domain of ErbB3) comprises a VH region comprising SEQ ID NO: 4.

In certain embodiments, an antibody or fragment thereof described herein which binds to ErbB (e.g., ErbB3) or a fragment thereof (e.g., the extracellular domain of ErbB3) comprises a VL region comprising: QSVLTQPPSASGT-PGQRVTISCSGSLSNIGLNYVSWYQQLPGT APKLLISRNNQRPSGVPD RFSGSKSGX$_1$X$_2$ASLAISGLRSEDEADYYCAA WDDSPPGEAFGGGTKLTVL, wherein X$_1$ is T, N or Y and X$_2$ is S, N, H, Y, K or R (SEQ ID NO: 118).

In certain embodiments, an antibody or fragment thereof described herein which binds to ErbB (e.g., ErbB3) or a fragment thereof (e.g., the extracellular domain of ErbB3) comprises a VL region comprising SEQ ID NO: 118 and a VH region comprising SEQ ID NO: 4.

In specific aspects, provided herein is an antibody(ies) or antigen-binding fragment thereof comprising an antibody light chain and heavy chain, e.g., a separate light chain and heavy chain. Non-limiting examples of human constant region sequences have been described in the art, e.g., see U.S. Pat. No. 5,693,780 and Kabat et al. (1991) *Sequences of Proteins of Immunological Interest*, Fifth Edition, U.S. Department of Health and Human Services, NIH Publication No. 91-3242. With respect to the light chain, in a specific embodiment, the light chain of an antibody described herein is a kappa light chain. In another specific embodiment, the light chain of an antibody described herein is a lambda light chain. In yet another specific embodiment, the light chain of an antibody described herein is a human kappa light chain or a human lambda light chain.

With respect to the heavy chain, in a specific embodiment, the heavy chain of an antibody described herein can be an alpha ($\alpha$), delta ($\delta$), epsilon ($\epsilon$), gamma ($\gamma$) or mu ($\mu$) heavy chain. In another specific embodiment, the heavy chain of an antibody described can comprise a human alpha ($\alpha$), delta ($\delta$), epsilon ($\epsilon$), gamma ($\gamma$) or mu ($\mu$) heavy chain.

In a specific embodiment, an antibody or fragment thereof described herein, which binds to an ErbB polypeptide (e.g., ErbB3) or a fragment thereof (e.g., the extracellular domain of ErbB) comprises a VL chain region and a VH chain region comprising any amino acid sequences described herein, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In another specific embodiment, an antibody or fragment thereof described herein, which binds to an ErbB polypeptide (e.g., ErbB3) or a fragment thereof (e.g., the extracellular domain of ErbB) comprises a VL chain region and a VH chain region comprising any amino acid sequences described herein, and wherein the constant regions comprise the amino acid sequences of the constant regions of an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. In a particular embodiment, the constant regions comprise the amino acid sequences of the constant regions of a human IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule.

In yet another specific embodiment, an antibody or fragment thereof described herein, which binds to an ErbB polypeptide (e.g., ErbB3) or a fragment thereof (e.g., the extracellular domain of ErbB) comprises a VL chain region and a VH chain region comprising any amino acid sequences described herein, and wherein the constant regions comprise the amino acid sequences of the constant regions of a human IgG1 (e.g., isotype a, z, or f) or human IgG4. In a particular embodiment, an antibody or fragment thereof described herein, which binds to an ErbB polypeptide (e.g., ErbB3) or a fragment thereof (e.g., the extracellular domain of ErbB) comprises a VL chain region and a VH chain region comprising any amino acid sequences described herein, and wherein the constant regions comprise the amino acid sequences of the constant region of a human IgG1 (isotype f). Non-limiting examples of human constant regions are described in the art, e.g., see Kabat et al. (1991) *Sequences of Proteins of Immunological Interest*, Fifth Edition, U.S. Department of Health and Human Services, NIH Publication No. 91-3242.

In another particular embodiment, an antibody or fragment thereof described herein, which binds to an ErbB polypeptide (e.g., ErbB3) or a fragment thereof (e.g., the extracellular domain of ErbB) comprises a light chain and a heavy chain, wherein (i) the light chain comprises a VL chain region comprising a VL CDR1, VL CDR2, and VL CDR3 having the amino acid sequences of those described herein (e.g., those listed in Tables 2-21); (ii) the heavy chain comprises a VH chain region comprising a VH CDR1, VH CDR2, and VH CDR3 having the amino acid sequences of those described herein (e.g., those listed in Tables 2-21); (iii) the light chain further comprises a constant light chain domain comprising the amino acid sequence of the constant domain of a human kappa light chain; and (iv) the heavy chain further comprises a constant heavy chain domain comprising the amino acid sequence of the constant domain of a human IgG1 (optionally IgG1 (isotype f)) heavy chain.

In certain embodiments, one, two or more mutations (e.g., amino acid substitutions) are introduced into the Fc region of an antibody described herein or a fragment thereof (e.g., CH2 domain (residues 231-340 of human IgG1) and/or CH3 domain (residues 341-447 of human IgG1) and/or the hinge region, with numbering according to the Kabat numbering system (e.g., the EU index in Kabat)) to increase the affinity of the antibody for an Fc receptor (e.g., an activated Fc receptor) on the surface of an effector cell. Mutations in the Fc region of an antibody or fragment thereof that increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith, P., et al. (2012) PNAS. 109:6181-6186, U.S. Pat. No. 6,737,056, and International Publication Nos. WO 02/060919; WO 98/23289; and WO 97/34631, which is incorporated herein by reference. In a specific embodiment, one, two or more amino acid modifications (i.e., substitutions, insertions or deletions) are introduced into an IgG constant domain, or FcRn-binding fragment thereof (preferably a Fc or hinge-Fc domain fragment) to increase half-life of the antibody in vivo. See, e.g., International Publication Nos. WO 02/060919; WO 98/23289; and WO 97/34631; and U.S. Pat. No. 6,277,375 for examples of mutations that will increase the half-life of an antibody in vivo. In a specific embodiment, the modified antibodies may have one or more amino acid mutations (e.g., substitutions) in the second constant CH2 domain (residues 231-340 of human IgG1) and/or the third constant CH3 domain (residues 341-447 of human IgG1), with numbering according to the EU index in Kabat (Kabat et al., 1991, Sequences of Proteins of Immunological Interest, U.S. Public Health Service, National Institutes of Health, Washington, D.C.). In a specific embodiment, the constant region of the IgG1 of an antibody or antigen-binding fragment thereof described herein comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display four-times increased half-life as compared to wild-type versions of the same antibody (see Dall'Acqua et al, 2006, J. Biol. Chem. 281: 23514-24). In certain embodiments, an antibody or antigen-binding fragment thereof comprises an IgG constant domain comprising one, two, three or more amino acid substitutions of amino acid residues at positions 251-257, 285-290, 308-314, 385-389, and 428-436, numbered according to the EU index as in Kabat.

In another aspect, an antibody described herein is a bispecific antibody. The term "bispecific antibody" is a term of art and refers to an antibody having specificities for at least two different, typically non-overlapping, epitopes. Such epitopes may be on the same or different targets. If the epitopes are on different targets, such targets may be on the same cell or different cells or cell types. In certain embodiments, an antibody described herein is a bispecific antibody, wherein one arm of the bispecific antibody comprises a first antibody or antigen-binding fragment described herein and the other arm of the bispecific antibody comprises a second antibody or fragment thereof that binds to a receptor tyrosine kinase (e.g., insulin receptor, platelet derived growth factor, fibroblast growth factor, vascular endothelial growth factor, hepatocyte growth factor receptor, tropomyosin receptor kinase, ephrin receptor, AXL, leukocyte receptor tyrosine kinase, angiopoietin receptor, receptor tyrosine kinase-like orphan receptor, discoidin domain receptor, RET proto-oncogene, tyrosine-protein kinase-like 7, related to receptor tyrosine kinase, and muscle-specific kinase) other than ErbB, a T-cell epitope, or a dendritic cell-engaging epitope. In a specific embodiment, an antibody described herein is a bispecific antibody, wherein one arm (the "first arm") of the bispecific antibody comprises first antibody or antigen-binding fragment described herein and the other arm (the "second arm") of the bispecific antibody comprises a second antibody or fragment thereof that binds to an ErbB receptor family member (e.g., ErbB1, ErbB2, or ErbB4), wherein the second arm comprises a different antibody or antigen-binding fragment thereof than the first arm of the bispecific antibody. In another specific embodiment, an antibody described herein is a bispecific antibody, wherein one arm of the bispecific antibody comprises an antibody or antigen-binding fragment described herein and the other arm of the bispecific antibody comprises an antibody or fragment thereof that binds to c-Met. In another specific embodiment, an antibody described herein is a bispecific antibody, wherein one arm of the bispecific antibody comprises a first antibody or antigen-binding fragment described herein and the other arm of the bispecific antibody comprises a second antibody or fragment thereof that binds to insulin growth factor 1 receptor (referred to as "IGFR" or "IGF1R").

Antibodies with reduced fucose content have been reported to have an increased affinity for Fc receptors, such as, e.g., FcγRIIIa. Accordingly, in certain embodiments, the antibodies or antigen-binding fragments thereof described herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

In certain aspects, an antibody or antigen-binding fragment thereof described herein inhibits (e.g., partially inhibit) dimerization of ErbB. Generally, ErbB receptor dimerization is induced when an ErbB ligand binds to ErbB. Thus, in specific embodiments, antibodies or antigen-binding fragments described herein inhibit (e.g., partially inhibit) dimerization of ErbB by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., immunoprecipitation assay, relative to dimerization of ErbB in the presence of ErbB ligand stimulation without any antibody or with an unrelated antibody (e.g., an antibody that does not bind to ErbB). In a specific embodiment, antibodies or antigen-binding fragments thereof described herein partially inhibit dimerization of ErbB by about 25% to 75%. Inhibition (e.g., partial inhibition) of dimerization of ErbB by antibodies or antigen-binding fragments thereof described herein can be assessed in the presences of ErbB ligand stimulation. For example, cells expressing ErbB are contacted with ErbB ligand in the presence or absence of an antibody or antigen-binding fragment described herein, and the level of ErbB dimerization is determined. In certain embodiments, ErbB ligand induced ErbB dimerization in the absence of an antibody or antigen-binding fragment thereof described herein is at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold higher than ErbB dimerization in the presence of an antibody or antigen-binding fragment thereof provided herein as assessed by methods described herein or known to one of skill in the art (e.g., immunoprecipitation assays). Tyrosine phosphorylation of one or more residues in the cytoplasmic domain of ErbB can be an indicator of ErbB dimerization.

In specific embodiments, an antibody or an antigen-binding fragment thereof described herein inhibits or reduces tyrosine phosphorylation in the cytoplasmic domain of ErbB by at least about 5%, 10%, 15%, 20%, 25%, 30%, 35%, 40%, 45%, 50%, 55%, 60%, 65%, 70%, 75%, 80%, 85%, 90%, 95%, 98%, 99%, or 100% as assessed by methods described herein or known to one of skill in the art, e.g., ELISA assay or immunoblotting assay, relative to phosphorylation in the presence of ErbB ligand stimulation without any antibody or with an unrelated antibody (e.g., an antibody that does not bind to ErbB). In particular embodiments, antibodies or antigen-binding fragments described herein inhibit tyrosine phosphorylation in the cytoplasmic domain of ErbB by at least about 25%, optionally to about 65% or 75%, as assessed by methods described herein or known to one of skill in the art, e.g., ELISA assay or immunoblotting assay. In certain embodiments, antibodies or antigen-binding fragments described herein inhibit tyrosine phosphorylation of the cytoplasmic domain of ErbB by at least about 25% to about 80% as assessed by methods described herein or known to one of skill in the art, e.g., ELISA assay or immunoblotting assay. In certain embodiments, antibodies or antigen-binding fragments described herein inhibit tyrosine phosphorylation of the cytoplasmic domain of ErbB by at least about 50% to about 100% as assessed by methods described herein or known to one of skill in the art, e.g., ELISA assay or immunoblotting assay. In specific embodiments, antibodies or antigen-binding fragments described herein inhibit tyrosine phosphorylation of the cytoplasmic domain of ErbB with an $IC_{50}$ of less than about 400 pM or less than about 500 pM as assessed by methods described herein or known to one of skill in the art. In specific embodiments, antibodies or antigen-binding fragments described herein inhibit tyrosine phosphorylation of the cytoplasmic domain of ErbB with an $IC_{50}$ of less than about 200 pM. In specific embodiments, antibodies or antigen-binding fragments described herein inhibit tyrosine phosphorylation of the cytoplasmic domain of ErbB with an $IC_{50}$ of less than about 150 pM. In specific embodiments, antibodies or antigen-binding fragments described herein inhibit tyrosine phosphorylation of the cytoplasmic domain of ErbB with an $IC_{50}$ of less than about 50 pM. In specific embodiments, antibodies or antigen-binding fragments described herein inhibit tyrosine phosphorylation of the cytoplasmic domain of ErbB with an $IC_{50}$ in the range of about 100 pM to about 500 pM, about 25 pM to about 200 pM, or about 40 pM to about 160 pM, about 50 pM to about 125 pM, or about 5 pM to about 100 pM. For example, an $IC_{50}$ for inhibition of tyrosine phosphorylation can be determined by assaying lysates from cells, e.g., cells expressing ErbB, in ELISA which detects tyrosine phosphorylation.

In specific embodiments, antibodies or antigen-binding fragments described herein inhibit phosphorylation of one or more tyrosine residues in the cytoplasmic domain of ErbB by at least about 5%, 10%, 15%, 20%, 25%, 30%, 35%, 40%, 45%, 50%, 55%, 60%, 65%, 70%, 75%, 80%, 85%, 90%, 95%, 98%, 99%, or 100% as assessed by methods described herein or known to one of skill in the art, e.g., immunoblotting assay, relative to phosphorylation in the presence of ErbB ligand stimulation without any antibody or with an unrelated antibody (e.g., an antibody that does not bind to ErbB). In specific embodiments, inhibition (e.g., partial inhibition) of phosphorylation of one or more tyrosine residues of the cytoplasmic domain of ErbB by antibodies or antigen-binding fragments described herein can be assessed upon ErbB ligand stimulation. For example, cells expressing ErbB are contacted with ErbB ligand in the presence or absence of an antibody or antigen-binding fragment described herein, and the level of phosphorylation of one or more tyrosine residues in the cytoplasmic domain of ErbB can be determined. In certain embodiments, ErbB ligand induced phosphorylation of one or more tyrosine residues of the cytoplasmic domain of ErbB in the absence of an antibody or antigen-binding fragment described herein is at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold higher than ErbB ligand induced phosphorylation of one or more tyrosine residues of the cytoplasmic domain of ErbB in the presence of an antibody or antigen-binding fragment described herein, as assessed by methods described herein or known to one of skill in the art (e.g., immunoblotting assays), relative to phosphorylation in the presence of ErbB ligand stimulation without any antibody or with an unrelated antibody (e.g., an antibody that does not bind to ErbB).

In specific embodiments, an antibody described herein (e.g., in Section 5.1) or an antigen-binding fragment thereof induces or enhances ErbB receptor internalization by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, relative to internalization in the presence of an unrelated antibody (e.g., an antibody that does not bind to ErbB). In specific embodiments, an antibody described herein (e.g., in Section 5.1) or an antigen-binding fragment thereof induces or enhances ErbB receptor internalization by at least about 25% or 35%, optionally to about 75%, as assessed by methods described herein or known to one of skill in the art, relative to internalization in the presence of an unrelated antibody (e.g., an antibody that does not bind to ErbB). In specific embodiments, an antibody described herein (e.g., in Section 5.1) or an antigen-binding fragment thereof induces or enhances ErbB receptor internalization by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art, relative to internalization in the presence of an unrelated antibody (e.g., an antibody that does not bind to ErbB). Techniques for the quantitation or visualization of cell surface receptors are well known in the art and include a variety of fluorescent and radioactive techniques. For example, one method involves incubating the cells with a radiolabeled anti-receptor antibody. Alternatively, the natural ligand of the receptor can be conjugated to a fluorescent molecule or radioactive-label and incubated with the cells. Additional receptor internalization assays are well known in the art and are described in, for example, Jimenez et al., Biochemical Pharmacology, 1999, 57:1125-1131; Bernhagen et al., Nature Medicine, 2007, 13:587-596; and Conway et al., J. Cell Physiol., 2001, 189:341-55.

In specific embodiments, an antibody described herein (e.g., in Section 5.1) or an antigen-binding fragment thereof inhibits or reduces ErbB receptor internalization by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, relative to internalization in the presence of an unrelated antibody (e.g., an antibody that does not bind to ErbB). In specific embodiments, an antibody described herein (e.g., in Section 5.1) or an antigen-binding fragment thereof inhibits or reduces ErbB receptor internalization by at least about 25% or 35%, optionally to about 75%, as assessed by methods described herein or known to one of skill in the art, relative to internalization in the presence of an unrelated antibody (e.g., an antibody that does not bind to ErbB). In specific embodiments, an antibody described herein (e.g., in Section 5.1) or an antigen-binding fragment thereof inhibits or reduces ErbB receptor internalization by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art, relative to internalization in the presence of an unrelated antibody (e.g., an antibody that does not bind to ErbB).

In specific embodiments an antibody described herein (e.g., in Section 5.1) or an antigen-binding fragment thereof induces or enhances ErbB receptor turnover by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., pulse-chase assay), relative to turnover in the presence of an unrelated antibody (e.g., an antibody that does not bind to ErbB). In specific embodiments, an antibody described herein (e.g., in Section 5.1) or an antigen-binding fragment thereof induces or enhances ErbB receptor turnover by at least about 25% or 35%, optionally to about 75%, as assessed by methods described herein or known to one of skill in the art (e.g., pulse-chase assay), relative to turnover in the presence of an unrelated antibody (e.g., an antibody that does not bind to ErbB). In specific embodiments, an antibody described herein (e.g., in Section 5.1) or an antigen-binding fragment thereof induces or enhances ErbB receptor turnover by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., pulse-chase assay), relative to turnover in the presence of an unrelated antibody (e.g., an antibody that does not bind to ErbB). Methods for the determining receptor turnover are well known in the art. For example, cells expressing ErbB can be pulse-labeled using $^{35}$S-EXPRESS Protein Labeling mix (NEG772, NEN Life Science Products), washed and chased with unlabeled medium for a period of time before protein lysates from the labeled cells are immunoprecipitated using an anti-ErbB antibody and resolved by SDS-PAGE and visualized (e.g., exposed to a PhosphoImager screen (Molecular Dynamics), scanned using the Typhoon8600 scanner (Amersham), and analyzed using ImageQuant software (Molecular Dynamics)) (see, e.g., Chan et al., Development, 2004, 131:5551-5560).

In specific embodiments, an antibody described herein (e.g., in Section 5.1) or an antigen-binding fragment thereof induces or enhances ErbB receptor degradation by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., pulse-chase assays), relative to degradation in the presence of an unrelated antibody (e.g., an antibody that does not bind to ErbB). In specific embodiments, an antibody described herein (e.g., in Section 5.1) or an antigen-binding fragment thereof induces or enhances ErbB receptor degradation by at least about 25% or 35%, optionally to about 75%, as assessed by methods described herein or known to one of skill in the art (e.g., pulse-chase assays), relative to degradation in the presence of an unrelated antibody (e.g., an antibody that does not bind to ErbB). In specific embodiments, an antibody described herein (e.g., in Section 5.1) or an antigen-binding fragment thereof induces or enhances ErbB receptor degradation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., pulse-chase assays), relative to degradation in the presence of an unrelated antibody (e.g., an antibody that does not bind to ErbB). Techniques for quantitating or monitoring ubiquitination and/or degradation (e.g., kinetics or rate of degradation) of cell surface receptors are well known in the art and involve a variety of fluorescent and radioactive techniques (see, e.g., International Patent Application Publication No. WO 2008/153926 A2). For example, pulse chase experiments or experiments using radiolabeled ligands such as $^{125}$I-neuregulin can be carried out to quantitatively measure degradation of ErbB.

Signaling events downstream of ErbB phosphorylation can serve as indicators of ErbB activity. For example, ErbB ligand (e.g., neuregulin) binding to its ErbB receptor stimulates several distinct signaling pathways, including for example members of phosphatidylinositol (PI) 3-kinases, and mitogen-activated protein kinase (MAPK). In certain aspects, a an antibody or antigen-binding fragment thereof described herein can inhibit signaling of a member of the PI 3-kinases or MAPK. In particular embodiments, an antibody or antigen-binding fragment thereof described herein can inhibit binding (or inhibit interaction), to the cytoplasmic domain of ErbB, of one or more of PI3K, PLC, and Grb2. In certain embodiments, an antibody or antigen-binding fragment thereof described herein can inhibit activation by ErbB of one or more of PI3K, PLC, and Grb2.

In particular embodiments, an antibody or antigen-binding fragment thereof described herein can inhibit downstream signaling such as phosphorylation of MAPK, phosphorylatin of P13K, or phosphorylation of AKT. Thus, in certain embodiments, an antibody or antigen-binding fragment thereof described herein can inhibit or reduce phosphorylation of MAPK (e.g., ErbB ligand (e.g., neuregulin) induced phosphorylation of MAPK) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay or phospho-specific immunoprecipitation or immunoblotting assay, relative to phosphorylation in the presence of ErbB ligand stimulation without any antibody or with an unrelated antibody (e.g., an antibody that does not bind to ErbB). In certain embodiments, an antibody or antigen-binding fragment thereof described herein can inhibit or reduce phosphorylation of PI3K (e.g., ErbB ligand (e.g., neuregulin) induced phosphorylation of PI3K) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay or phospho-specific immunoprecipitation or immunoblotting assay, relative to phosphorylation in the presence of ErbB ligand stimulation without any antibody or with an unrelated antibody (e.g., an antibody that does not bind to ErbB). In certain embodiments, an antibody or antigen-binding fragment thereof described herein can inhibit or reduce phosphorylation of AKT (e.g., ErbB ligand (e.g., neuregulin) induced phosphorylation of AKT) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay or phospho-specific immunoprecipitation or immunoblotting assay, relative to phosphorylation in the presence of ErbB ligand stimulation without any antibody or with an unrelated antibody (e.g., an antibody that does not bind to ErbB).

In particular embodiments, an antibody or antigen-binding fragment thereof described herein can inhibit downstream signaling such as interaction between Grb2 and the ErbB receptor. Thus, in certain embodiments, an antibody or antigen-binding fragment thereof described herein can inhibit or reduce the binding of Grb2 to ErbB (e.g., ErbB ligand (e.g., neuregulin) induced interaction binding of Grb2 to ErbB) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., co-immunoprecipitation assay and immunoblotting assay, or immunofluorescent microscopy, relative to interaction in the presence of ErbB ligand stimulation without any antibody or with an unrelated antibody (e.g., an antibody that does not bind to ErbB).

In particular embodiments, an antibody or antigen-binding fragment thereof described herein can inhibit downstream signaling such as nuclear import of STAT, nuclear import of AKT, or nuclear import of MAPK. Thus, in certain embodiments, an antibody or antigen-binding fragment thereof described herein can inhibit or reduce nuclear import of STAT (e.g., ErbB ligand (e.g., neuregulin) induced nuclear import of STAT) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., subcellular fractionation and immunoblotting assay, or immunofluorescent microscopy, relative to nuclear import in the presence of ErbB ligand stimulation without any antibody or with an unrelated antibody (e.g., an antibody that does not bind to ErbB). In certain embodiments, an antibody or antigen-binding fragment thereof described herein can inhibit or reduce nuclear import of AKT (e.g., ErbB ligand (e.g., neuregulin) induced nuclear import of AKT) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., subcellular fractionation and immunoblotting assay, or immunofluorescent microscopy, relative to nuclear import in the presence of ErbB ligand stimulation without any antibody or with an unrelated antibody (e.g., an antibody that does not bind to ErbB). In certain embodiments, an antibody or antigen-binding fragment thereof described herein can inhibit or reduce nuclear import of MAPK (e.g., ErbB ligand (e.g., neuregulin) induced nuclear import of MAPK) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., subcellular fractionation and immunoblotting assay, or immunofluorescent microscopy, relative to nuclear import in the presence of ErbB ligand stimulation without any antibody or with an unrelated antibody (e.g., an antibody that does not bind to ErbB).

In certain aspects, an antibody or antigen-binding fragment thereof described herein can inhibit cellular proliferation of cells (e.g., cancer cells), for example, cells that express ErbB and that respond to ErbB signaling (e.g., cells that proliferate in response to ErbB ligand stimulation and ErbB signaling). Cell proliferation assays are described in the art and can be readily carried out by one of skill in the art. For example, cell proliferation can be assayed by measuring Bromodeoxyuridine (BrdU) incorporation (see, e.g., Hoshino et al., 1986, Int. J. Cancer 38, 369; Campana et al., 1988, J. Immunol. Meth. 107:79) or ($^3$H) thymidine incorporation (see, e.g., Blechman et al., Cell, 1995, 80:103-113; Chen, J., 1996, Oncogene 13:1395-403; Jeoung, J., 1995, J. Biol. Chem. 270:18367 73), by direct cell count at various time intervals (e.g., 12-hour or 24-hour intervals), or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription.

In specific embodiments, an antibody or antigen-binding fragment thereof described herein inhibit cell proliferation by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., BrdU incorporation assay).

In certain aspects, an antibody or antigen-binding fragment thereof described herein can reduce or inhibit survival of cells (e.g., cancer cells), for example, cells that express ErbB and that respond to ErbB signaling (e.g., cells that proliferate in response to ErbB ligand stimulation and ErbB signaling). Cell survival assays are described in the art and can be readily carried out by one of skill in the art. For example, cell viability can be assessed by using trypan-blue staining or other cell death or viability markers known in the art. In a specific embodiment, the level of cellular ATP is measured to determined cell viability. In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes can include enlargement, granularity, cells with ragged edges, a filmy appearance, rounding, detachment from the surface of the well, or other changes. These changes can be given a designation of T (100% toxic), PVH (partially toxic-very heavy-80%), PH (partially toxic-heavy-60%), P (partially toxic-40%), Ps (partially toxic-slight-20%), or 0 (no toxicity-0%), conforming to the degree of cytotoxicity seen. A 50% cell inhibitory (cytotoxic) concentration (IC50) is determined by regression analysis of these data.

In specific embodiments, an antibody or antigen-binding fragment thereof described herein inhibits (e.g., partially inhibit) cell survival by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., trypan blue exclusion assay).

In certain aspects, an antibody or antigen-binding fragment thereof described herein is capable of inducing apoptosis (i.e., programmed cell death) of cells (e.g., cancer cells or immune cells), for example, cells that express ErbB and that respond to ErbB signaling (e.g., cells that grow or proliferate in response to ErbB ligand stimulation and ErbB signaling). Apoptosis are described in the art and can be readily carried out by one of skill in the art. For example, flow cytometry can be used to detect activated caspase 3, an apoptosis-mediating enzyme, in cells undergoing apoptosis, or Western blotting can be used to detect cleavage of poly(ADP-ribose) polymerase (PARP) (see, e.g., Smolich et al., Blood, 2001, 97:1413-1421). Cleavage of PARP is an indicator of apoptosis. In specific embodiments, an antibody or antigen-binding fragment thereof described herein induces or enhances apoptosis by at least about 5%, 10%, 15%, 20%, 25%, 30%, 35%, 40%, 45%, 50%, 55%, 60%, 65%, 70%, 75%, 80%, 85%, 90%, 95%, 98%, 99%, or 100% as assessed by methods described herein or known to one of skill in the art (e.g., flow cytometry to detect activated caspase 3). In specific embodiments, an antibody or antigen-binding fragment thereof described herein induces or enhances apoptosis by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., flow cytometry to detect activated caspase 3).

Cells and cell lines which are appropriate for use in the assays described herein relating to ErbB activity are readily available (e.g., ATCC) or can be readily identified using methods known in the art. For example, cells and/or cell lines that express ErbB endogenously or that possess ErbB signaling or activity are known to one of skill in the art. In certain embodiments, cells or cell lines that are appropriate for use in the assays described herein can express ErbB, either endogenously or recombinantly. In particular embodiments, cells or cell lines for use in cell proliferation assays can express ErbB, endogenously or recombinantly, and proliferate or increase proliferation in response to ErbB ligand (e.g., neuregulin) stimulation. Cells or cell lines for use in cell viability assays can express ErbB, endogenously or recombinantly, and exert changes in cell viability in response to ErbB ligand (e.g., neuregulin) stimulation. Cells or cell lines for use in apoptosis assays can express ErbB, endogenously or recombinantly, and exert changes in apoptosis in response to ErbB ligand (e.g., neuregulin) stimulation. Cells or cell lines for use in cell proliferation, cell viability, or other assays can express ErbB, endogenously or recombinantly, and exert changes in proliferation or activation of other cell types response to ErbB ligand (e.g., neuregulin) stimulation.

Non-limiting examples of cells that can be used in the methods and assays described herein include primary cells, transformed cells, stem cells, mast cells, primordial germ cells, oocytes, spermatocytes, embryonic stem cells, hematopoietic cells, erythroleukemia cells (e.g., F36P and TF-1 cell lines), human myeloid leukemia cell lines, such as MOTE cells; gastrointestinal stromal tumor cell lines such as ST-882, GIST430, and GIST882; neuroblastoma cell lines such as SK-N-SH, SK-SY5Y, SK-N-BE(2), SK-N-BE (ZkM17), SK-N-BE(2)C, LA-N-1, or LA-N-1-5s; small cell lung carcinoma cell lines such as H526, DMS153, and DMS79; head and neck cancer cell lines such as A-253, SCC-15, SCC-25, SCC-9, FaDu, and Detroit 562; colorectal cancer cell lines such as SNU-C1, SW48, RKO, COLO 205, SW1417, LS411N, NCI-H508, HT-29, SK-CO-1, SW1116, SW948, T84, LS123, LoVo, and SW837; breast cancer cell lines such as 184B5, AU-565, BT-20, BT-474, BT-483, BT-549, CAMA-1, DU4475, HCC38, HCC70, HCC202, HCC1143, HCC1187, HCC1395, HCC 1419, HCC1428, HCC1500, HCC1569, HCC1599, HCC1806, HCC1937, HCC1954, HCC2157, HCC2218; Hs 578 Bst, Hs 578T, MCF7, MCF 10A, MCF 10F, MFC-12A, MDA-kb2, MDA-MB-134-VI, MDA-MB-157, MDA-MB-175, MDA-MB- 231, MDA-MB-361, MDA-MB-415, MDA-MB-436, MDA-MB-453, MDA-MB-468, SK-BR-3, T47D, UACC-812, UACC-893, UACC-3199, UACC-3133, UACC-1179, UACC-732, UACC-2087, ZR-75-1, and ZR-75-30; thyroid cancer cell lines such as KAT-4, KAT-10, KAK-1, FTC-133, TPC-1, 8505C, WRO, and B-CPAP; melanoma cell lines such as HMCB, SK-MEL-1, SK-MEL-3, SK-MEL-24, SH-4, RPMI-7951, SKA375, G-361, and WM-115; gastric cancer cell lines such as HGC27, GCIY, MKN7, TMK1, ECC12, AGS, CLS-145, 23132/87, MKN-45, SK-GT-2, HGC-27, and KATO-III; lung cancer cell lines such as NCI-H2126, NCI-H1299, NCI-H1437, NCI-H1563, NCI-H1573, NCI-H1975, HCl-H661, and HCC827; prostate cancer cell lines such as PC-93, PC-3, DU-145, TSU-Pr1, LNCaP, LNCaP-FGC, LNCaP-LN-3, LNCaP-C4, LNCaP-C4B, MDA PCa 2a, alva-101, ALVA-31, ALVA-41, 22Rv1, ARCaP, PPC-1, LAPC3, LAPC4, P69SV40T, RQPE-2, CA-HPV-10, and PZ-HPV-7; neurofibromatosis cell lines such as Hs 53.T; bladder cancer cell lines such as 5637, HT-1197, HT-1376, RT4, SW780, T-24, TCCSUP, and UM-UC-3; ovarian cancer cell lines such as PA-1, Caov-3, SW 626, and SK-OV-3; pancreatic cancer cell lines such as Capan-2, Panc 10.05, CFPAC-1, HPAF-II, SW 1990, BxPC-3, AsPC-1, SU.86.86, MIA-PaCa-2, and PANC-1; and renal cancer cell lines such as 769-P, 786-O, A-498, CaKi-1, CaKi-2, RCC-ER, RCC-FG1, RCC-FG2, FCC-GH, RCC-GS, RCC-HB, RCC-JF, RCC-JW, RCC-KL, RCC-KP, RCC-LR, RCC-MF, RCC-MH, RCC-OF1, RCC-PR, RCC-WK, SK-NEP-1, and WT-CLS1. Alternatively, cells and cell lines that express ErbB can routinely be generated recombinantly.

In certain aspects, an antibody or antigen-binding fragment thereof described herein is capable of inhibiting or reducing metastasis, inhibiting tumor growth or inducing tumor regression in mouse model studies. For example, tumor cell lines can be introduced into nude mice, and the mice can be administered with an antibody or antigen-binding fragment thereof described herein one or more times, and tumor progression of the injected tumor cells can be monitored over a period of weeks and/or months. In some cases, administration of an antibody or antigen-binding fragment thereof described herein to the nude mice can occur prior to introduction of the tumor cell lines. Any appropriate tumor cell line (e.g., tumor cell line expressing ErbB) can be used in the mouse xenograft models described herein. Non-limiting examples of tumor cell lines for use in these xenograft mouse models include non-small cell lung carcinoma cell line H1299, megakaryoblastic leukemia cell lines such as MO7e; gastrointestinal stromal tumor cell lines such as ST-882, GIST430, GIST48, GIST48B and GIST882; human erythroleukemic cell lines such as HEL and TF-1; human promyelocytic leukemia cell line, HL60; neuroblastoma cell lines such as SK-N-SH, SK-SY5Y, SK-N-BE(2), SK-N-BE(ZkM17), SK-N-BE(2)C, LA-N-1, or LA-N-1-5s; small cell lung carcinoma cell lines such as H526, DMS153, and DMS79; head and neck cancer cell lines such as A-253, SCC-15, SCC-25, SCC-9, FaDu, and Detroit 562; colorectal cancer cell lines such as SNU-C1, SW48, RKO, COLO 205, SW1417, LS411N, NCI-H508, HT-29, SK-CO-1, SW1116, SW948, T84, LS123, LoVo, and SW837; breast cancer cell lines such as 184B5, AU-565, BT-20, BT-474, BT-483, BT-549, CAMA-1, DU4475, HCC38, HCC70, HCC202, HCC1143, HCC1187, HCC1395, HCC 1419, HCC1428, HCC1500, HCC1569, HCC1599, HCC1806, HCC1937, HCC1954, HCC2157, HCC2218; Hs 578 Bst, Hs 578T, MCF7, MCF 10A, MCF 10F, MFC-12A, MDA-kb2, MDA-MB-134-VI, MDA-MB-157, MDA-MB-175, MDA-MB-231, MDA-MB-361, MDA-MB-415, MDA-MB-436, MDA-MB-453, MDA-MB-468, SK-BR-3, T47D, UACC-812, UACC-893, UACC-3199, UACC-3133, UACC-1179, UACC-732, UACC-2087, ZR-75-1, and ZR-75-30; thyroid cancer cell lines such as KAT-4, KAT-10, KAK-1, FTC-133, TPC-1, 8505C, WRO, and B-CPAP; melanoma cell lines such as HMCB, SK-MEL-1, SK-MEL-3, SK-MEL-24, SH-4, RPMI-7951, SKA375, G-361, and WM-115; gastric cancer cell lines such as HGC27, GCIY, MKN7, TMK1, ECC12, AGS, CLS-145, 23132/87, MKN-45, SK-GT-2, HGC-27, and KATO-III; lung cancer cell lines such as NCI-H2126, NCI-H1299, NCI-H1437, NCI-H1563, NCI-H1573, NCI-H1975, HCl-H661, and HCC827; prostate cancer cell lines such as PC-93, PC-3, DU-145, TSU-Pr1, LNCaP, LNCaP-FGC, LNCaP-LN-3, LNCaP-C4, LNCaP-C4B, MDA PCa 2a, alva-101, ALVA-31, ALVA-41, 22Rv1, ARCaP, PPC-1, LAPC3, LAPC4, P69SV40T, RQPE-2, CA-HPV-10, and PZ-HPV-7; neurofibromatosis cell lines such as Hs 53.T; bladder cancer cell lines such as 5637, HT-1197, HT-1376, RT4, SW780, T-24, TCCSUP, and UM-UC-3; ovarian cancer cell lines such as PA-1, Caov-3, SW 626, and SK-OV-3; pancreatic cancer cell lines such as Capan-2, Panc 10.05, CFPAC-1, HPAF-II, SW 1990, BxPC-3, AsPC-1, SU.86.86, MIA-PaCa-2, and PANC-1; and renal cancer cell lines such as 769-P, 786-O, A-498, CaKi-1, CaKi-2, RCC-ER, RCC-FG1, RCC-FG2, FCC-GH, RCC-GS, RCC-HB, RCC-JF, RCC-JW, RCC-KL, RCC-KP, RCC-LR, RCC-MF, RCC-MH, RCC-OF1, RCC-PR, RCC-WK, SK-NEP-1, and WT-CLS1. In a specific embodiments, a tumor cell line for use in a xenograft mouse model is the GIST882, GIST430, GIST48, GIST48B, HEL, HL60, H526, DMS153, or DMS79 cell line. In certain embodiments, suitable cell lines for use in xenograft tumor models can be generated by recombinantly expressing ErbB in cell. In specific embodiments, an antibody or antigen-binding fragment thereof described herein inhibits tumor grow or induce tumor regression in a mouse model by at least about 5%, 10%, 15%, 20%, 25%, 30%, 35%, 40%, 45%, 50%, 55%, 60%, 65%, 70%, 75%, 80%, 85%, 90%, 95%, 98%, 99%, or 100% as assessed by methods described herein or known to one of skill in the art.

In specific embodiments, an antibody or antigen-binding fragment thereof described herein inhibits tumor grow or induce tumor regression in a mouse model by at least about 25% or 35%, optionally to about 75%, as assessed by methods described herein or known to one of skill in the art. In specific embodiments, an antibody or antigen-binding fragment thereof described herein inhibits tumor grow or induce tumor regression in a mouse model by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art. Determining tumor growth inhibition or tumor regression can be assessed by monitoring tumor size over a period of time, such as by physical measurement of palpable tumors, or other visual detection methods. For example, tumor cell lines can be generated to recombinantly express a visualization agent, such as green fluorescent protein (GFP) or luciferase, then in vivo visualization of GFP can be carried out by microscopy, and in vivo visualization of luciferase can be carried out by administering luciferase substrate to the xenograft mice and detecting luminescent due to the luciferase enzyme processing the luciferase substrate. The degree or level of detection of GFP or luciferase correlates to the size of the tumor in the xenograft mice.

In certain aspects, an antibody or antigen-binding fragment thereof described herein can increases survival of animals in tumor xenograft models. In specific embodiments, an antibody or antigen-binding fragment thereof described herein increase survival of mice in tumor xenograft models by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art. In specific embodiments, an antibody or antigen-binding fragment thereof described herein increases survival of mice in tumor xenograft models by at least about 25% or 35%, optionally to about 75%, as assessed by methods described herein or known to one of skill in the art. In specific embodiments, an antibody or antigen-binding fragment thereof described herein increases survival of mice in tumor xenograft models by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art. Survival can be determined by plotting a survival curve of number of surviving mice against time (e.g., days or weeks) after tumor cell line injection.

In some aspects, an antibody or antigen-binding fragment thereof described herein can suppress ErbB phosphorylation. In a specific embodiment, an antibody or antigen-binding fragment thereof described herein can suppress AKT phosphorylation. In another aspect, an antibody or antigen-binding fragment thereof described herein can suppress ErbB2-ErbB3 dimer formation. In some aspects, an antibody or antigen-binding fragment thereof described herein can suppress cell growth. In some aspects, an antibody or antigen-binding fragment thereof described herein lacks an antibody-dependent cell-mediated cytotoxicity (ADCC) effect. In specific aspects, an antibody or antigen-binding fragment thereof described herein can suppress ErbB (e.g., ErbB3) phosphorylation, AKT phosphorylation, and/or tumor colony formation.

In some aspects, an antibody or antigen-binding fragment thereof described herein can suppress ErbB3 phosphorylation in HRG-driven breast cancer MCF-7 cells as measured by, e.g., ELISA, with an $IC_{50}$ lower than about 30 ng/mL, lower than about 25 ng/mL, lower than about 20 ng/mL, lower than about 15 ng/mL, or lower than about 10 ng/mL. In a specific aspect, an antibody or antigen-binding fragment thereof described herein can suppress ErbB3 phosphorylation in HRG-driven breast cancer MCF-7 cells as measured by, e.g., ELISA, with an $IC_{50}$ lower than about 20 ng/mL. In a specific aspect, an antibody or antigen-binding fragment thereof described herein can suppress ErbB3 phosphorylation in HRG-driven breast cancer MCF-7 cells as measured by, e.g., ELISA, with an $IC_{50}$ lower than about 15 ng/mL. In another specific aspect, an antibody or antigen-binding fragment thereof described herein can suppress ErbB3 phosphorylation in HRG-driven breast cancer MCF-7 cells as measured by, e.g., ELISA, with an $IC_{50}$ lower than about 10 ng/mL.

In some aspects, an antibody or antigen-binding fragment thereof described herein can suppress cell growth in MDA-MB-175 breast cancer cells with an $IC_{50}$ lower than about 0.90 μg/mL, lower than about 0.80 μg/mL, lower than about 0.70 μg/mL, lower than about 0.60 μg/mL, lower than about 0.50 μg/mL, lower than about 0.40 μg/mL, lower than about 0.30 μg/mL, or lower than about 0.20 μg/mL. In a specific aspect, an antibody or antigen-binding fragment thereof described herein can suppress cell growth in MDA-MB-175 breast cancer cells, with an $IC_{50}$ lower than about 0.50 μg/mL. In a specific aspect, an antibody or antigen-binding fragment thereof described herein can suppress cell growth in MDA-MB-175 breast cancer cells, with an $IC_{50}$ lower than about 0.40 μg/mL. In another specific aspect, an antibody or antigen-binding fragment thereof described herein can suppress cell growth in MDA-MB-175 breast cancer cells, with an $IC_{50}$ lower than about 0.30 μg/mL. In another specific aspect, an antibody or antigen-binding fragment thereof described herein can suppress cell growth in MDA-MB-175 breast cancer cells, with an $IC5_0$ lower than about 0.20 μg/mL.

In some aspects, an antibody or antigen-binding fragment thereof described herein can suppress cell growth in HMCB melanoma cells with an $IC_{50}$ lower than about 0.20 μg/mL, lower than about 0.15 μg/mL, lower than about 0.10 μg/mL, lower than about 0.05 μg/mL, lower than about 0.04 μg/mL, or lower than about 0.03 μg/mL. In a specific aspect, an antibody or antigen-binding fragment thereof described herein can suppress cell growth in HMCB melanoma cells, with an $IC_{50}$ lower than about 0.10 μg/mL. In another specific aspect, an antibody or antigen-binding fragment thereof described herein can suppress cell growth in HMCB melanoma cells, with an $IC_{50}$ lower than about 0.05 μg/mL. In a specific aspect, an antibody or antigen-binding fragment thereof described herein can suppress cell growth in HMCB melanoma cells, with an $IC_{50}$ lower than about 0.04 μg/mL. In another specific aspect, an antibody or antigen-binding fragment thereof described herein can suppress cell growth in HMCB melanoma cells, with an IC50 lower than about 0.03 μg/mL.

In some aspects, an antibody or antigen-binding fragment thereof described herein can suppress ErbB3 phosphorylation in EGFR-driven HCC827 lung cancer cells with an $IC_{50}$ lower than about 20 ng/mL, lower than about 15 ng/mL, lower than about 10 ng/mL, lower than about 8 ng/mL, lower than about 6 ng/mL, lower than about 4 ng/mL, or lower than about 2 ng/mL. In a specific aspect, an antibody or antigen-binding fragment thereof described herein can suppress ErbB3 phosphorylation in EGFR-driven HCC827 lung cancer cells, with an $IC_{50}$ lower than about 10 ng/mL. In another specific aspect, an antibody or antigen-binding fragment thereof described herein can suppress ErbB3 phosphorylation in EGFR-driven HCC827 lung cancer cells, with an $IC_{50}$ lower than about 8 ng/mL. In another specific aspect, an antibody or antigen-binding fragment thereof described herein can suppress ErbB3 phosphorylation in EGFR-driven HCC827 lung cancer cells, with an $IC_{50}$ lower than about 6 ng/mL. In another specific aspect, an antibody or antigen-binding fragment thereof described herein can suppress ErbB3 phosphorylation in EGFR-driven HCC827 lung cancer cells, with an $IC_{50}$ lower than about 4 ng/mL. In another specific aspect, an antibody or antigen-binding fragment thereof described herein can suppress ErbB3 phosphorylation in EGFR-driven HCC827 lung cancer cells, with an $IC5_0$ lower than about 2 ng/mL.

In some aspects, an antibody or antigen-binding fragment thereof described herein can suppress ErbB3 phosphorylation in EGFR-driven HCC827 lung cancer cells resistant to TKI with an $IC_{50}$ lower than about 30 ng/mL, lower than about 25 ng/mL, lower than about 20 ng/mL, lower than about 15 ng/mL, lower than about 10 ng/mL, or lower than about 5 ng/mL. In a specific aspect, an antibody or antigen-binding fragment thereof described herein can suppress ErbB3 phosphorylation in EGFR-driven HCC827 lung cancer cells resistant to TKI, with an $IC_{50}$ lower than about 20 ng/mL. In another specific aspect, an antibody or antigen-binding fragment thereof described herein can suppress ErbB3 phosphorylation in EGFR-driven HCC827 lung cancer cells resistant to TKI, with an $IC_{50}$ lower than about 15 ng/mL. In another specific aspect, an antibody or antigen-binding fragment thereof described herein can suppress ErbB3 phosphorylation in EGFR-driven HCC827 lung cancer cells resistant to TKI, with an $IC_{50}$ lower than about 10 ng/mL. In another specific aspect, an antibody or antigen-binding fragment thereof described herein can suppress ErbB3 phosphorylation in EGFR-driven HCC827 lung cancer cells resistant to TKI, with an $IC_{50}$ lower than about 5 ng/mL.

In some aspects, an antibody or antigen-binding fragment thereof described herein can suppress ErbB3 phosphorylation in cMET-driven MKN45 human gastric adenocarcinoma cells with an $IC_{50}$ is lower than about 15 ng/mL, lower than about 10 ng/mL, lower than about 9 ng/mL, lower than about 8 ng/mL, lower than about 7 ng/mL, lower than about 6 ng/mL, lower than about 5 ng/mL, or lower than about 4 ng/mL. In a specific aspect, an antibody or antigen-binding fragment thereof described herein can suppress ErbB3 phosphorylation in cMET-driven MKN45 human gastric adenocarcinoma cells with an $IC_{50}$ lower than about 10 ng/mL. In another specific aspect, an antibody or antigen-binding fragment thereof described herein can suppress ErbB3 phosphorylation in cMET-driven MKN45 human gastric adenocarcinoma cells with an $IC_{50}$ lower than about 8 ng/mL. In another specific aspect, an antibody or antigen-binding fragment thereof described herein can suppress ErbB3 phosphorylation in cMET-driven MKN45 human gastric adenocarcinoma cells with an IC50 lower than about 6 ng/mL. In another specific aspect, an antibody or antigen-binding fragment thereof described herein can suppress ErbB3 phosphorylation in cMET-driven MKN45 human gastric adenocarcinoma cells with an $IC_{50}$ lower than about 4 ng/mL.

In some aspects, an antibody or antigen-binding fragment thereof described herein can suppress pAKT in cMET-driven MKN45 cells with an $IC_{50}$ lower than about 15 ng/mL, lower than about 10 ng/mL, lower than about 9 ng/mL, lower than about 8 ng/mL, lower than about 7 ng/mL, lower than about 6 ng/mL, lower than about 5 ng/mL, lower than about 4 ng/mL, or lower than about 3 ng/mL. In a specific aspect, an antibody or antigen-binding fragment thereof described herein can suppress can suppress pAKT in cMET-driven MKN45 cells with an $IC_{50}$ lower than about 8 ng/mL. In another specific aspect, an antibody or antigen-binding fragment thereof described herein can suppress can suppress pAKT in cMET-driven MKN45 cells with an $IC_{50}$ lower than about 6 ng/mL. In another specific aspect, an antibody or antigen-binding fragment thereof described herein can suppress can suppress pAKT in cMET-driven MKN45 cells with an $IC_{50}$ lower than about 4 ng/mL. In another specific aspect, an antibody or antigen-binding fragment thereof described herein can suppress can suppress pAKT in cMET-driven MKN45 cells with an $IC_{50}$ lower than about 3 ng/mL.

In some aspects, an antibody or antigen-binding fragment thereof described herein can suppress can suppress pHER in FGFR2-driven Kato III human gastric signet ring carcinoma cells with an $IC_{50}$ lower than about 9 ng/mL, lower than about 8 ng/mL, lower than about 7 ng/mL, lower than about 6 ng/mL, lower than about 5 ng/mL, lower than about 4 ng/mL, lower than about 3 ng/mL, lower than about 2 ng/mL, or lower than about 1 ng/mL. In a specific aspect, an antibody or antigen-binding fragment thereof described herein can suppress can suppress pHER in FGFR2-driven Kato III human gastric signet ring carcinoma cells with an $IC_{50}$ lower than about 5 ng/mL. In another specific aspect, an antibody or antigen-binding fragment thereof described herein can suppress can suppress pHER in FGFR2-driven Kato III human gastric signet ring carcinoma cells with an $IC_{50}$ lower than about 4 ng/mL. In another specific aspect, an antibody or antigen-binding fragment thereof described herein can suppress can suppress pHER in FGFR2-driven Kato III human gastric signet ring carcinoma cells with an $IC_{50}$ lower than about 3 ng/mL. In a specific aspect, an antibody or antigen-binding fragment thereof described herein can suppress pHER in FGFR2-driven Kato III human gastric signet ring carcinoma cells with an $IC_{50}$ lower than about 2 ng/mL. In another specific aspect, an antibody or antigen-binding fragment thereof described herein can suppress can suppress pHER in FGFR2-driven Kato III human gastric signet ring carcinoma cells with an $IC_{50}$ lower than about 1 ng/mL.

In some aspects, an antibody or antigen-binding fragment thereof described herein can suppress can suppress pAKT in FGFR-2 driven Kato III cells with an $IC_{50}$ lower than about 6 ng/mL, lower than about 5 ng/mL, lower than about 4 ng/mL, lower than about 3 ng/mL, lower than about 2 ng/mL, or lower than about 1 ng/mL. In a specific aspect, an antibody or antigen-binding fragment thereof described herein can suppress can suppress pAKT in FGFR-2 driven Kato III cells with an $IC_{50}$ lower than about 4 ng/mL. In another specific aspect, an antibody or antigen-binding fragment thereof described herein can suppress can suppress pAKT in FGFR-2 driven Kato III cells with an $IC_{50}$ lower than about 3 ng/mL. In another specific aspect, an antibody or antigen-binding fragment thereof described herein can suppress can suppress pAKT in FGFR-2 driven Kato III cells with an $IC_{50}$ lower than about 2 ng/mL. In another specific aspect, an antibody or antigen-binding fragment thereof described herein can suppress can suppress pAKT in FGFR-2 driven Kato III cells with an $IC_{50}$ lower than about 1 ng/mL.

In some aspects, an antibody or antigen-binding fragment thereof described herein can suppress can suppress pHER in ligand independent BT-474 breast cancer cells with an $IC_{50}$ lower than about 10 ng/mL, lower than about 9 ng/mL, lower than about 8 ng/mL, lower than about 7 ng/mL, lower than about 6 ng/mL, lower than about 5 ng/mL, lower than about 4 ng/mL. In a specific aspect, an antibody or antigen-binding fragment thereof described herein can suppress can suppress pHER in ligand independent BT-474 breast cancer cells with an $IC_{50}$ lower than about 8 ng/mL. In another specific aspect, an antibody or antigen-binding fragment thereof described herein can suppress pHER in ligand independent BT-474 breast cancer cells with an $IC_{50}$ lower than about 6 ng/mL. In another specific aspect, an antibody or antigen-binding fragment thereof described herein can suppress can suppress pHER in ligand independent BT-474 breast cancer cells with an $IC_{50}$ lower than about 4 ng/mL.

In some aspects, an antibody or antigen-binding fragment thereof described herein can suppress can suppress pAKT in ligand independent BT-474 breast cancer cells with an $IC_{50}$ lower than about 10 ng/mL, lower than about 9 ng/mL, lower than about 8 ng/mL, lower than about 7 ng/mL, lower than about 6 ng/mL, lower than about 5 ng/mL, lower than about 4 ng/mL. In a specific aspect, an antibody or antigen-binding fragment thereof described herein can suppress can suppress pAKT in ligand independent BT-474 breast cancer cells with an $IC_{50}$ lower than about 8 ng/mL. In another specific aspect, an antibody or antigen-binding fragment thereof described herein can suppress can suppress pAKT in ligand independent BT-474 breast cancer cells with an $IC_{50}$ lower than about 6 ng/mL. In another specific aspect, an antibody or antigen-binding fragment thereof described herein can suppress can suppress pAKT in ligand independent BT-474 breast cancer cells with an $IC_{50}$ lower than about 4 ng/mL. In some aspects, can suppress pHER3, pAKT, and tumor colony formation in BT-474 cells, a ligand independent breast cancer model.

In some aspects, an antibody or antigen-binding fragment thereof described herein can suppress can suppress HRG induced VEGF secretion. In a specific aspect, an antibody or antigen-binding fragment thereof described herein can suppress can suppress HRG induced VEGF secretion in ligand-independent BT-474 breast cancer cells and/or HRG-driven breast cancer MCF-7 cells.

In some aspects, an antibody or antigen-binding fragment thereof described herein can suppress can cause cell cycle arrest. In a specific aspect, an antibody or antigen-binding fragment thereof described herein can suppress can cause cell cycle arrest in breast cancer cells, including but not limited to SKBR3 or BT474 cells.

5.2 Antibody Conjugates

In some embodiments, provided herein are antibodies (e.g., monoclonal antibodies such as chimeric or humanized antibodies), or antigen-binding fragments thereof, conjugated or recombinantly fused to a diagnostic, detectable or therapeutic agent or any other molecule. The conjugated or recombinantly fused antibodies or antigen-binding fragments thereof can be useful, e.g., for monitoring or prognosing the onset, development, progression and/or severity of a condition or disease, for example, as part of a clinical testing procedure, such as determining the efficacy of a particular therapy. The conjugated or recombinantly fused antibodies or antigen-binding fragments thereof can be useful, e.g., for treating a condition or disorder described herein.

Antibodies or antigen-binding fragments thereof described herein can also be conjugated to a molecule (e.g., polyethylene glycol) which can affect one or more biological and/or molecular properties of the antibodies, for example, stability (e.g., in serum), half-life, solubility, and antigenicity.

In a particular aspect, provided herein is a conjugate comprising an agent (e.g., therapeutic agent) linked to an antibody described herein (or an antigen-binding fragment thereof).

Diagnosis and detection can be accomplished, for example, by coupling an antibody or antigen-binding fragment thereof described herein to detectable molecules or substances including, but not limited to, various enzymes, prosthetic groups (such as, but not limited to, streptavidin/biotin and avidin/biotin), fluorescent molecules, bioluminescent molecules, radioactive molecules, and positron emitting metals using various positron emission tomographies, and non-radioactive paramagnetic metal ions.

In specific aspects, provided are antibodies described herein, or antigen-binding fragments thereof, conjugated (e.g., chemical conjugation) or recombinantly fused to a agent or toxin (e.g., or one or more therapeutic agents or toxins) and uses of such antibodies or antigen-binding fragments thereof. The antibody can be conjugated or recombinantly fused to a therapeutic agent or toxin. Examples of therapeutic agents and toxins include, but are not limited to cetuximab (Erbitux®), panitumumab (Vectibix®), lapatinib (Tykerb®/Tyverb®), and paclitaxel (Taxol®, Abraxane®) and derivatives (e.g., docetaxel).

In some aspects, an antibody or fragment thereof that binds to ErbB3 can be conjugated to antibodies or antibody fragments targeting epidermal growth factor receptor (EGFR). In other aspects, an antibody or fragment thereof that binds to ErbB3 can be conjugated to tyrosine kinase inhibitors. In some specific aspects, an antibody or fragment thereof that binds to ErbB3 can be conjugated to inhibitors of the tyrosine kinase activity associated with EGFR and/or ErbB2. In some aspects, an antibody or fragment thereof that binds to ErbB3 can be conjugated to antimitotic agents. In some specific aspects, an antibody or an fragment thereof that binds to ErbB3 be conjugated to agents that stabilize the mitotic spindle microtubule assembly.

Methods for fusing or conjugating therapeutic agents and toxins (including polypeptides) to antibodies are well known.

Fusion proteins can be generated, for example, through the techniques of gene-shuffling, motif-shuffling, exon-shuffling, and/or codon-shuffling (collectively referred to as "DNA shuffling"). DNA shuffling can be employed to alter the activities of antibodies described herein (e.g., antibodies with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-313 (each of these patents and publications is hereby incorporated by reference).

Antibodies described herein can also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

5.3 Antibody Production

Antibodies described herein (or an antigen-binding fragment thereof) that bind to ErbB or a fragment thereof (e.g., the extracellular domain of ErbB) can be produced by any method known in the art for the synthesis of antibodies, for example, by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual, Second Edition*, Cold Spring Harbor Laboratory Press; Sambrook et al. (2001) *Molecular Cloning: A Laboratory Manual*, Cold Spring Harbor Laboratory Press, Cold Spring Harbor, N.Y.; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press.

In a specific embodiment, an antibody described herein is an antibody (e.g., recombinant antibody) prepared, expressed, created or isolated by any means that involves creation, e.g., via synthesis, genetic engineering of DNA sequences. In certain embodiments, such antibody comprise sequences (e.g., DNA sequences or amino acid sequences) that do not naturally exist within the antibody germline repertoire of an animal or mammal (e.g., human) in vivo.

In a certain aspect, provided herein is a method of making an antibody or an antigen-binding fragment thereof which binds to ErbB comprising culturing a cell or host cell described herein. In a certain aspect, provided herein is a method of making an antibody or an antigen-binding fragment thereof which binds to ErbB comprising expressing (e.g., recombinantly expressing) the antibody or antigen-binding fragment thereof using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody or antigen-binding fragment thereof obtained from the cell or host cell.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563 681 (Elsevier, N.Y., 1981). The term "monoclonal antibody" as used herein is not limited to antibodies produced through hybridoma technology. For example, monoclonal antibodies can be produced recombinantly from host cells exogenously expressing an antibody described herein or a fragment thereof, for example, light chain and/or heavy chain of such antibody.

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will bind to the protein (e.g., ErbB) used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)). Additionally, a RIMMS (repetitive immunization multiple sites) technique can be used to immunize an animal (Kilptrack et al., 1997 Hybridoma 16:381-9, incorporated by reference in its entirety).

In some embodiments, mice (or other animals, such as rats, monkeys, donkeys, pigs, sheep, hamster, or dogs) can be immunized with an antigen (e.g., ErbB or fragment thereof, such as the extracellular domain of ErbB) and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the American Type Culture Collection (ATCC®) (Manassas, Va.), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as NS0 cell line or those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against an antigen (e.g., ErbB or a fragment thereof, such as the extracellular domain of ErbB). The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein include antibody fragments which recognize specific ErbB antigens (e.g., extracellular domain of ErbB) and can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region.

Further, the antibodies described herein or antigen-binding fragments thereof can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antigen-binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

As described in the above references, after phage selection, the antibody coding regions from the phage can be isolated and used to generate whole antibodies, including human antibodies, or any other desired antigen-binding fragment, and expressed in any desired host, including mammalian cells, insect cells, plant cells, yeast, and bacteria, e.g., as described below. Techniques to recombinantly produce antibody fragments such as Fab, Fab' and F(ab')$_2$ fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043.

In one aspect, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816, 567, 4,816,397, and 6,331,415.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including IgG$_1$, IgG$_2$, IgG$_3$ and IgG$_4$. Humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), which is incorporated by reference herein in its entirety.

Methods for making multispecific (e.g., bispecific antibodies) have been described, see, for example, U.S. Pat. Nos. 7,951,917, 7,183,076, 8,227,577, 5,837,242, 5,989, 830, 5,869,620, 6,132,992, and 8,586,713.

Single domain antibodies, for example, antibodies lacking the light chains, can be produced by methods well-known in the art. See Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301.

Further, antibodies that bind to an ErbB antigen can, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8):2429-2438).

In particular embodiments, an antibody described herein, which binds to the same epitope of ErbB as an antibody described herein, the 2C2 antibody, 2C2-YTE antibody, 5H6 antibody, 8A3 antibody, 4H6 antibody, 6E3 antibody, 2B11 antibody, 2D1 antibody, 3A6 antibody, 4C4 antibody, 15D12.1 antibody, 15D12.2 antibody, 1A4 antibody, 3E1 antibody, 2F10 antibody, Clone 16 germlined antibody or Clone 16 antibody, is a human antibody or an antigen-binding fragment thereof. In particular embodiments, an antibody described herein, which competitively inhibits (e.g., in a dose-dependent manner) an antibody described herein, the 2C2 antibody, 2C2-YTE antibody, 5H6 antibody, 8A3 antibody, 4H6 antibody, 6E3 antibody, 2B11 antibody, 2D1 antibody, 3A6 antibody, 4C4 antibody, 15D12.1 antibody, 15D12.2 antibody, 1A4 antibody, 3E1 antibody, 2F10 antibody, Clone 16 germlined antibody or Clone 16 antibody from binding to ErbB, is a human antibody or an antigen-binding fragment thereof. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., ErbB). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, Int. Rev. Immunol. 13:65-93. For a detailed discussion of this technology for producing human antibodies and human monoclonal antibodies and protocols for producing such antibodies, see, e.g., PCT publication Nos. WO 98/24893, WO 96/34096, and WO 96/33735; and U.S. Pat. Nos. 5,413,923, 5,625,126, 5,633, 425, 5,569,825, 5,661,016, 5,545,806, 5,814,318, and 5,939, 598.

Human antibodies which bind to ErbB or a fragment thereof (e.g., the extracellular domain of ErbB) can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen (e.g., ErbB). Such methods are known and are described in the art, see, e.g., Shinmoto et al., Cytotechnology, 2004, 46:19-23; Naganawa et al., Human Antibodies, 2005, 14:27-31.

5.3.1 Polynucleotides

In certain aspects, provided herein are polynucleotides comprising a nucleotide sequence encoding an antibody described herein or a fragment thereof (e.g., a variable light chain region and/or variable heavy chain region) that binds to an ErbB antigen, and vectors, e.g., vectors comprising such polynucleotides for recombinant expression in host cells (e.g., E. coli and mammalian cells). Provided herein are polynucleotides comprising nucleotide sequences encoding any of the antibodies provided herein or antigen-binding fragments thereof (see, e.g., Section 5.1), as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

In particular aspects, provided herein are polynucleotides comprising nucleotide sequences encoding antibodies or antigen-binding fragments thereof, which bind to an ErbB polypeptide or a fragment thereof (e.g., the extracellular domain of ErbB) and comprises an amino acid sequence as described herein.

In certain aspects, provided herein are polynucleotides comprising a nucleotide sequence encoding the light chain or heavy chain of an antibody described herein. The polynucleotides can comprise nucleotide sequences encoding a light chain comprising the VL FRs and CDRs of antibodies described herein (see, e.g., Tables 2-22). The polynucleotides can comprise nucleotide sequences encoding a heavy chain comprising the VH FRs and CDRs of antibodies described herein (see, e.g., Tables 2-22). In specific embodiments, a polynucleotide described herein encodes a VH chain comprising the amino acid sequence of SEQ ID NO: 4. In specific embodiments, a polynucleotide described herein encodes a VH chain comprising the amino acid sequence of any one of SEQ ID NOs: 6-8, 12-14, 18-20, 24-29, 36-37, 45, 56-57, 65-67, 81-83, 89-92, 97-99, 103, 111, 116, or 121.

In certain aspects, provided herein are polynucleotides comprising a nucleotide sequence encoding the VL domain or VH domain of an antibody described herein. The polynucleotides can comprise nucleotide sequences encoding a VL domain comprising the VL FRs and CDRs of antibodies described herein (see, e.g., Tables 2-22). The polynucleotides can comprise nucleotide sequences encoding a VH domain comprising the VH FRs and CDRs of antibodies described herein (see, e.g., Tables 2-22). In specific embodiments, a polynucleotide described herein encodes a VL domain comprising the amino acid sequence of SEQ ID NO: 5. In specific embodiments, a polynucleotide described herein encodes a VL domain comprising the amino acid sequence of any one of SEQ ID NOs: 9-11, 15-17, 21-23, 30-35, 38-51, 52-55, 59-64, 68-79, 85-88, 93-96, 101-102, 104-110, 112-115, or 117-120.

In particular embodiments, provided herein are polynucleotides comprising a nucleotide sequence encoding an antibody comprising three VH chain CDRs, e.g., containing VH CDR1, VH CDR2, and VH CDR3 of antibody described herein (e.g., see Tables 2-21). In specific embodiments, provided herein are polynucleotides comprising three VL chain CDRs, e.g., containing VL CDR1, VLCDR2, and VL CDR3 of antibody described herein (e.g., see Tables 2-21). In specific embodiments, provided herein are polynucleotides comprising a nucleotide sequence encoding an antibody comprising three VL chain CDRs, e.g., containing VL CDR1, VL CDR2, and VL CDR3 of antibody described herein (e.g., see Tables 2-21) and three VH chain CDRs, e.g., containing VH CDR1, VH CDR2, and VH CDR3 of antibody described herein (e.g., see Tables 2-21).

In particular embodiments, provided herein are polynucleotides comprising a nucleotide sequence encoding an antibody comprising a VL domain, e.g., containing FR1-CDR1-FR2-CDR2-FR3-CDR3-FR4, comprising an amino acid sequences described herein (e.g., see Tables 2-22). In specific embodiments, provided herein are polynucleotides comprising a nucleotide sequence encoding an antibody comprising a VH domain, e.g., containing FR1-CDR1-FR2-CDR2-FR3-CDR3-FR4, comprising an amino acid sequence described herein (e.g., see Tables 2-22).

In certain embodiments, a polynucleotide described herein comprises a nucleotide sequence encoding an antibody provided herein comprising a variable light (VL) chain region comprising an amino acid described herein. In some embodiments, a polynucleotide described herein comprises a nucleotide sequence encoding an antibody provided herein comprising a variable light (VH) chain region comprising an amino acid described herein.

In certain aspects, a polynucleotide comprises a nucleotide sequence encoding an antibody described herein comprising a VL chain region comprising one or more VL FRs having the amino acid sequence described herein (e.g., see Table 22). In certain aspects, a polynucleotide comprises a nucleotide sequence encoding an antibody described herein comprising a VH chain region comprising one or more VH FRs having the amino acid sequence described herein (e.g., see Table 22).

In specific embodiments, a polynucleotide provided herein comprises a nucleotide sequence encoding an antibody described herein comprising: framework regions (e.g., framework regions of the VL domain and VH domain) that are human framework regions.

In specific aspects, provided herein is a polynucleotide comprising a nucleotide sequence encoding an antibody comprising a light chain and a heavy chain, e.g., a separate light chain and heavy chain. With respect to the light chain, in a specific embodiment, a polynucleotide provided herein comprises a nucleotide sequence encoding a kappa light chain. In another specific embodiment, a polynucleotide provided herein comprises a nucleotide sequence encoding a lambda light chain. In yet another specific embodiment, a polynucleotide provided herein comprises a nucleotide sequence encoding an antibody described herein comprising a human kappa light chain or a human lambda light chain. In a particular embodiment, a polynucleotide provided herein comprises a nucleotide sequence encoding an antibody described herein, which binds to an ErbB polypeptide, wherein the antibody comprises a light chain, and wherein the amino acid sequence of the VL chain region can comprise any amino acid sequence described herein (e.g., SEQ ID NOs: 9-11, 15-17, 21-23, 30-35, 38-51, 52-55, 59-64, 68-79, 85-88, 93-96, 101-102, 104-110, 112-115, or 117-120), and wherein the constant region of the light chain comprises the amino acid sequence of a human kappa light chain constant region. In another particular embodiment, a polynucleotide provided herein comprises a nucleotide sequence encoding an antibody described herein, which immunospecifically binds to an ErbB polypeptide and comprises a light chain, wherein the amino acid sequence of the VL chain region can comprises any amino acid sequence described herein (e.g., SEQ ID NOs: 9-11, 15-17, 21-23, 30-35, 38-51, 52-55, 59-64, 68-79, 85-88, 93-96, 101-102, 104-110, 112-115, or 117-120), and wherein the constant region of the light chain comprises the amino acid sequence of a human lambda light chain constant region. For example, human constant region sequences can be those described in U.S. Pat. No. 5,693,780.

In a particular embodiment, a polynucleotide provided herein comprises a nucleotide sequence encoding an antibody described herein, which immunospecifically binds to an ErbB polypeptide, wherein the antibody comprises a heavy chain, wherein the amino acid sequence of the VH chain region can comprise any amino acid sequence described herein (e.g., SEQ ID NOs: 6-8, 12-14, 18-20, 24-29, 36-37, 45, 56-57, 65-67, 81-83, 89-92, 97-99, 103, 111, 116, or 121), and wherein the constant region of the heavy chain comprises the amino acid sequence of a human gamma (γ) heavy chain constant region.

In a certain embodiment, a polynucleotide provided herein comprises a nucleotide sequence below encoding a VH domain or a VL domain of an antibody described herein, which binds to an ErbB polypeptide.

In yet another specific embodiment, a polynucleotide provided herein comprises a nucleotide sequence encoding an antibody described herein (or an antigen-binding fragment thereof), which binds an ErbB polypeptide, wherein the antibody comprises a VL chain region and a VH chain region comprising any amino acid sequences described herein, and wherein the constant regions comprise the amino acid sequences of the constant regions of a human IgG1 (e.g., isotype a, z, or f) or human IgG4.

Also provided herein are polynucleotides encoding an antibody or a fragment thereof that are optimized, e.g., by codon/RNA optimization, replacement with heterologous signal sequences, and elimination of mRNA instability elements. Methods to generate optimized nucleic acids encoding an antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of an antibody or fragment thereof by at least 1.5 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an antibody encoded by polynucleotides that have not been optimized.

In certain embodiments, an optimized polynucleotide sequence encoding an antibody described herein or a fragment thereof (e.g., VL domain and/or VH domain) can hybridize to an antisense (e.g., complementary) polynucleotide of an unoptimized polynucleotide sequence encoding an antibody described herein or a fragment thereof (e.g., VL domain and/or VH domain). In specific embodiments, an optimized nucleotide sequence encoding an antibody described herein or a fragment hybridizes under high stringency conditions to antisense polynucleotide of an unoptimized polynucleotide sequence encoding an antibody described herein or a fragment thereof. In a specific embodiment, an optimized nucleotide sequence encoding an antibody described herein or a fragment thereof hybridizes under high stringency, intermediate or lower stringency hybridization conditions to an antisense polynucleotide of an unoptimized nucleotide sequence encoding an antibody described herein or a fragment thereof. Information regarding hybridization conditions have been described, see, e.g., U.S. Patent Application Publication No. US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding antibodies described herein, e.g., antibodies described in Tables 2-22, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding antibodies described herein can be readily isolated and sequenced using conventional procedures (e.g., by using oligonucleotide probes that are capable of binding specifically to genes encoding the heavy and light chains of the antibodies). Hybridoma cells can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of antibodies in the recombinant host cells.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable domain, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH region (e.g., SEQ ID NO: 4) and/or VL region (e.g., SEQ ID NO: 5) provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3.

5.3.2 Cells and Vectors

In certain aspects, provided herein are cells (e.g., host cells) expressing (e.g., recombinantly) antibodies described herein (or an antigen-binding fragment thereof) which bind to ErbB. Also provided herein are vectors (e.g., expression vectors) comprising polynucleotides comprising nucleotide sequences encoding antibodies or a fragment thereof for recombinant expression in host cells, preferably in mammalian cells. Also provided herein are host cells comprising such vectors for recombinantly expressing antibodies described herein (e.g., human or humanized antibody) or antigen-binding fragments thereof. Also provided herein are methods for preparing a protein by expressing a polynucleotide containing an antibody or antibody fragment (e.g., light chain or heavy chain) encoding nucleotide sequence are described herein. In a particular aspect, provided herein are methods for producing an antibody described herein or antigen-binding fragment thereof, comprising expressing such antibody or antigen-binding fragment from a host cell.

As used herein, the term "host cell" refers to any type of cell, e.g., a primary cell, a cell in culture, or a cell from a cell line. In specific embodiments, the term "host cell" refers a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome.

Recombinant expression of an antibody described herein (e.g., a full-length antibody, heavy and/or light chain of an antibody, or a single chain antibody described herein) can, for example, involve construction of an expression vector containing a polynucleotide that encodes the antibody. Once a polynucleotide encoding an antibody molecule, heavy and/or light chain of an antibody, or a fragment thereof (e.g., heavy and/or light chain variable domains) described herein has been obtained, a vector for the production of the antibody molecule can be produced by recombinant DNA technology using techniques well-known in the art.

Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable domain of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464) and variable domains of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein or a fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain or a heavy chain variable region of an antibody described herein or a fragment thereof, and a second vector comprising a polynucleotide encoding a light chain or a light chain variable region of an antibody described herein or a fragment thereof. In other embodiments, a first host cell comprises a first vector comprising a polynucleotide encoding a heavy chain or a heavy chain variable region of an antibody described herein or a fragment thereof, and a second host cell comprises a second vector comprising a polynucleotide encoding a light chain or a light chain variable region of an antibody described herein. In specific embodiments, a heavy chain/ heavy chain variable region expressed by a first cell associated with a light chain/light chain variable region of a second cell to form an antibody described herein or an antigen-binding fragment thereof. In certain embodiments, provided herein is a population of host cells comprising such first host cell and such second host cell.

In a particular embodiment, provided herein is a population of vectors comprising a first vector comprising a polynucleotide encoding a light chain/light chain variable region of an antibody described herein, and a second vector comprising a polynucleotide encoding a heavy chain/heavy chain variable region of an antibody described herein.

A variety of host-expression vector systems can be utilized to express antibody molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, MDCK, HEK 293, NS0, PER.C6, VERO, CRL7O3O, HsS78Bst, HeLa, and NIH 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein or an antigen-binding fragment thereof are CHO cells, for example CHO cells from the CHO GS System™ (Lonza). In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In certain embodiments, antibodies described herein are produced by CHO cells or NS0 cells. In a specific embodiment, the expression of nucleotide sequences encoding antibodies described herein is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the E. coli expression vector pUR278 (Ruther et al., 1983, EMBO 12:1791), in which the antibody coding sequence can be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, Methods in Enzymol. 153:51-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, COS, MDCK, HEK 293, NIH 3T3, W138, BT483, Hs578T, HTB2, BT2O and T47D, NS0 (a murine myeloma cell line that does not endogenously produce any immunoglobulin chains), CRL7O3O and HsS78Bst cells. In certain embodiments, antibodies described herein are produced in mammalian cells, such as CHO cells.

In a specific embodiment, the antibodies described herein or antigen-binding fragments thereof have reduced fucose content or no fucose content, wherein antibody is further defined as encompassing 2C2, 2C2-YTE, 5H6 antibody, 8A3 antibody, 4H6 antibody, 6E3 antibody, 2B11 antibody, 2D1 antibody, 3A6 antibody, 4C4 antibody, 15D12.1 antibody, 15D12.2 antibody, 1A4 antibody, 3E1 antibody, 2F10 antibody, Clone 16 germlined antibody and Clone 16 antibody. Such antibodies can be produced using techniques known one skilled in the art. For example, the antibodies can be expressed in cells deficient or lacking the ability of to fucosylate. In a specific example, cell lines with a knockout of both alleles of $\alpha$1,6-fucosyltransferase can be used to produce antibodies or antigen-binding fragments thereof with reduced fucose content. The Potelligent® system (Lonza) is an example of such a system that can be used to produce antibodies or antigen-binding fragments thereof with reduced fucose content.

For long-term, high-yield production of recombinant proteins, stable expression cells can be generated. For example, cell lines which stably express an antibody described herein or an antigen-binding fragment thereof can be engineered. In specific embodiments, a cell provided herein stably expresses a light chain/light chain variable domain and a heavy chain/heavy chain variable domain which associate to form an antibody described herein or an antigen-binding fragment thereof.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an antibody described herein or a fragment thereof. Such engineered cell lines can be particularly useful in screening and evaluation of compositions that interact directly or indirectly with the antibody molecule.

A number of selection systems can be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-2 15); and hygro, which confers resistance to hygromycin (Santerre et al., 1984, Gene 30:147). Methods commonly known in the art of recombinant DNA technology can be routinely applied to select the desired recombinant clone, and such methods are described, for example, in Ausubel et al. (eds.), *Current Protocols in Molecular Biology*, John Wiley & Sons, N Y (1993); Kriegler, *Gene Transfer and Expression*, A Laboratory Manual, Stockton Press, N Y (1990); and in Chapters 12 and 13, Dracopoli et al. (eds.), *Current Protocols in Human Genetics*, John Wiley & Sons, N Y (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

5.4 Pharmaceutical Compositions

Provided herein are compositions, pharmaceutical compositions comprising one or more antibodies described herein, or antigen-binding fragments thereof, or conjugates thereof. In particular aspects, compositions (e.g., pharmaceutical compositions) described herein can be for in vitro, in vivo, or ex vivo uses. Non-limiting examples of uses include uses to inhibit ErbB activity and uses to treat a disorder, for example, cancer. In specific embodiments, provided herein is a pharmaceutical composition comprising an antibody (e.g., a humanized antibody) described herein (or an antigen-binding fragment thereof) and a pharmaceutically acceptable carrier or excipient.

As used herein, the term "pharmaceutically acceptable" means being approved by a regulatory agency of the Federal or a state government, or listed in the U.S. Pharmacopeia, European Pharmacopeia or other generally recognized Pharmacopeia for use in animals, and more particularly in humans.

Therapeutic formulations containing one or more antibodies provided herein or an antigen-binding fragment thereof can be prepared for storage by mixing the antibody having the desired degree of purity with optional physiologically acceptable carriers, excipients or stabilizers (*Remington's Pharmaceutical Sciences* (1990) Mack Publishing Co., Easton, Pa.; *Remington: The Science and Practice of Pharmacy,* 21st ed. (2006) Lippincott Williams & Wilkins, Baltimore, Md.), in the form of lyophilized formulations or aqueous solutions. Acceptable carriers, excipients, or stabilizers are nontoxic to recipients at the dosages and concentrations employed, and include buffers such as phosphate, citrate, and other organic acids; and/or non-ionic surfactants such as TWEEN™, PLURONICS™ or polyethylene glycol (PEG).

Formulations, such as those described herein, can also contain more than one active compounds (for example, molecules, e.g., antibody or antibodies described herein) as necessary for the particular indication being treated. In certain embodiments, formulations comprise an antibody provided herein and one or more active compounds with complementary activities that do not adversely affect each other. Such molecules are suitably present in combination in amounts that are effective for the purpose intended. For example, an antibody described herein can be combined with one or more other therapeutic agents (e.g., a tyrosine kinase inhibitor such as imatinib mesylated or sunitinib, or a histone deacetylase inhibitor such as vorinostat). Such combination therapy can be administered to the patient serially or simultaneously or in sequence.

The formulations to be used for in vivo administration can be sterile. This is readily accomplished by filtration through, e.g., sterile filtration membranes.

In specific aspects, the pharmaceutical compositions provided herein contain therapeutically effective amounts of one or more of the antibodies provided herein, and optionally one or more additional prophylactic of therapeutic agents, in a pharmaceutically acceptable carrier. Such pharmaceutical compositions are useful in the prevention, treatment, management or amelioration of a condition or disorder described herein or one or more symptoms thereof.

Pharmaceutical carriers suitable for administration of the antibodies provided herein include any such carriers known to those skilled in the art to be suitable for the particular mode of administration.

In addition, the antibodies described herein can be formulated as the sole pharmaceutically active ingredient in the composition or can be combined with other active ingredients (such as one or more other prophylactic or therapeutic agents).

Compositions provided herein can contain one or more antibodies provided herein or an antigen-binding fragment thereof. In one embodiment, the antibodies are formulated into suitable pharmaceutical preparations, such as solutions, suspensions, powders, sustained release formulations or elixirs in sterile solutions or suspensions for parenteral administration, or as transdermal patch preparation and dry powder inhalers.

In compositions provided herein, one or more antibodies described herein is (are) mixed with a suitable pharmaceutical carrier. The concentrations of the antibody or antibodies in the compositions can, for example, be effective for delivery of an amount, upon administration, that treats, prevents, or ameliorates a condition or disorder described herein or a symptom thereof.

In one embodiment, compositions provided herein are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

In certain aspects, an antibody provided herein is included in the pharmaceutically acceptable carrier in an effective amount sufficient to exert a therapeutically useful effect in the absence of, or with minimal or negligible, undesirable side effects on the patient treated.

As used herein, the term "side effects" encompasses unwanted and adverse effects of a therapy (e.g., a prophylactic or therapeutic agent). Unwanted effects are not necessarily adverse. An adverse effect from a therapy (e.g., a prophylactic or therapeutic agent) can be harmful or uncomfortable or risky. Examples of side effects include, diarrhea, cough, gastroenteritis, wheezing, nausea, vomiting, anorexia, abdominal cramping, fever, pain, loss of body weight, dehydration, alopecia, dyspenea, insomnia, dizziness, mucositis, nerve and muscle effects, fatigue, dry mouth, and loss of appetite, rashes or swellings at the site of administration, flu-like symptoms such as fever, chills and fatigue, digestive tract problems and allergic reactions. Additional undesired effects experienced by patients are numerous and known in the art. Many are described in the *Physician's Desk Reference* ($63^{rd}$ ed., 2009).

Concentrations of an antibody in a pharmaceutical composition provided herein will depend on, e.g., the physicochemical characteristics of the antibody, the dosage schedule, and amount administered as well as other factors known to those of skill in the art.

The pharmaceutical compositions, in another embodiment, provide a dosage of about 50 mg of antibody per kilogram of body weight for administration over a period of time, e.g., every day or few days, every week, every 2 weeks, or every 3 weeks. Pharmaceutical dosage unit forms can be prepared to provide from about 500 mg.

Pharmaceutical compositions described herein are provided for administration to humans or animals (e.g., mammals) in unit dosage forms, such as sterile parenteral (e.g., intravenous) solutions or suspensions containing suitable quantities of the compounds or pharmaceutically acceptable derivatives thereof. Pharmaceutical compositions are also provided for administration to humans and animals in unit dosage form, such as tablets, capsules, pills, powders, granules, and oral or nasal solutions or suspensions, and oil-water emulsions containing suitable quantities of an antibody or pharmaceutically acceptable derivatives thereof. The antibody is, in one embodiment, formulated and administered in unit-dosage forms or multiple-dosage forms. Unit-dose forms as used herein refers to physically discrete units suitable for human or animal (e.g., mammal) subjects and packaged individually as is known in the art. Each unit-dose contains a predetermined quantity of an antibody sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles. Hence, in specific aspects, multiple dose form is a multiple of unit-doses which are not segregated in packaging.

In certain embodiments, one or more antibodies described herein or an antigen-binding fragment thereof are in a liquid pharmaceutical formulation. Liquid pharmaceutically administrable compositions can, for example, be prepared by dissolving, dispersing, or otherwise mixing an antibody and optional pharmaceutical adjuvants in a carrier, such as, for example, water, saline, aqueous dextrose, glycerol, glycols, and the like, to thereby form a solution or suspension. In certain embodiments, a pharmaceutical composition provided herein to be administered can also contain minor amounts of nontoxic auxiliary substances such as wetting agents, emulsifying agents, solubilizing agents, and pH buffering agents and the like.

Actual methods of preparing such dosage forms are known, or will be apparent, to those skilled in this art; for example, see, e.g., *Remington's Pharmaceutical Sciences* (1990) Mack Publishing Co., Easton, Pa.; *Remington: The Science and Practice of Pharmacy,* 21st ed. (2006) Lippincott Williams & Wilkins, Baltimore, Md. Dosage forms or compositions containing antibody in the range of 0.005% to 100% with the balance made up from non-toxic carrier can be prepared.

Parenteral administration, in one embodiment, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. Other routes of administration may include, enteric administration, intracerebral administration, nasal administration, intraarterial administration, intracardiac administration, intraosseous infusion, intrathecal administration, and intraperitoneal administration.

Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Pharmaceutical carriers also include ethyl alcohol, polyethylene glycol and propylene glycol for water miscible vehicles; and sodium hydroxide, hydrochloric acid, citric acid or lactic acid for pH adjustment.

In certain embodiments, intravenous or intraarterial infusion of a sterile aqueous solution containing an antibody described herein is an effective mode of administration. Another embodiment is a sterile aqueous or oily solution or suspension containing an antibody described herein injected as necessary to produce the desired pharmacological effect.

In specific embodiments, an antibody described herein can be suspended in micronized or other suitable form. The form of the resulting mixture depends upon a number of factors, including the intended mode of administration and the solubility of the compound in the selected carrier or vehicle.

In other embodiments, the pharmaceutical formulations are lyophilized powders, which can be reconstituted for administration as solutions, emulsions and other mixtures. They can also be reconstituted and formulated as solids or gels.

The lyophilized powder is prepared by dissolving an antibody provided herein, in a suitable solvent. In some embodiments, the lyophilized powder is sterile. Suitable solvents can contain an excipient which improves the stability or other pharmacological component of the powder or reconstituted solution, prepared from the powder. Excipients that can be used include, but are not limited to, dextrose, sorbital, fructose, corn syrup, xylitol, glycerin, glucose, sucrose or other suitable agent. A suitable solvent can also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides an example of a formulation. In one embodiment, the resulting solution will be apportioned into vials for lyophilization. Lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier.

In certain aspects, antibodies provided herein can be formulated for local administration or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

Antibodies and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In some embodiments, antibodies described herein are targeted (or otherwise administered) to the visual organs, bone marrow, gastrointestinal tract, lungs, brain, or joints. In specific embodiments, an antibody described herein or an antigen-binding fragment thereof is capable of crossing the blood-brain barrier.

5.5 Uses and Methods

In particular aspects, provided herein are methods of inhibiting (e.g., partially inhibiting) ErbB activity with an antibody described herein (e.g., in Section 5.1) or an antigen-binding fragment thereof, or an antibody conjugate described herein (e.g., in Section 5.2). In specific embodiments, provided herein are methods of inhibiting an ErbB activity by at least 10%, 15%, 20%, 25%, 30%, 35%, 40%, 45%, 50%, 55%, 60%, 65%, 70%, 75%, 80%, 85%, 90%, 95% or more. Activities of ErbB which can be inhibited by antibodies described herein are known in the art. Non-limiting examples of ErbB activities which can be inhibited by an antibody described herein include phosphorylation (e.g., autophosphorylation) of ErbB receptor (e.g., cytoplasmic domain of ErbB), ErbB ligand (e.g., neuregulin) binding to ErbB receptor, and ErbB receptor dimerization. Methods for measuring these activities are known in the art. In specific embodiments, an antibody described herein or an antigen-binding fragment thereof inhibits one, two or more of ErbB activities.

In some embodiments, provided herein is a method for inhibiting the proliferation of a ErbB-expressing cell(s) (e.g., a cell characterized by uncontrolled growth, such as cancer or another hyperproliferative disorder), comprising contacting the cell(s) with an antibody described herein (e.g., in Section 5.1) or an antigen-binding fragment thereof, or an antibody conjugate described herein (e.g., in Section 5.2). In a specific embodiment, the antibody or antigen-binding fragment thereof, or an antibody conjugate described herein (e.g., in Section 5.2) is contacted with the ErbB-expressing cell in a subject. In another specific embodiment, the antibody or antigen-binding fragment thereof is contacted with the ErbB-expressing cell in cell culture. In certain embodiments, the ErbB-expressing cells are characterized by uncontrolled growth.

In another aspect, provided herein are methods for treating a disease, disorder or condition associated with ErbB expression or ErbB-expressing cells in a patient, comprising administering to a patient in need thereof an antibody described herein (e.g., in Section 5.1) or an antigen-binding fragment thereof, or an antibody conjugate described herein (e.g., in Section 5.2). In a specific embodiment, provided herein is a method for treating a disease, disorder or condition associated with ErbB expression or ErbB-expressing cells in a patient, comprising administering to a patient in need thereof an effective amount of an antibody described herein (e.g., in Section 5.1) or an antigen-binding fragment thereof, or an antibody conjugate described herein (e.g., in Section 5.2). In certain embodiments, the method further comprises administering another therapy to the patient. In certain embodiments, the ErbB-expressing cells are characterized by uncontrolled growth.

In certain embodiments, the ErbB-expressing cell overexpress ErbB. In some embodiment, the ErbB-expressing cell expresses at least 10%, 15%, 20%, 25%, 30%, 35%, 40%, 45%, 50%, 55%, 60%, 65%, 70%, 75%, 80%, 85%, 90%, 95% or 98%, or 10% to 25%, 25% to 50%, 50% to 75%, 75% to 98% or 25% to 75% more ErbB than normal healthy cells of the same cell type. In certain embodiment, the ErbB-expressing cell expresses at least 10%, 15%, 20%, 25%, 30%, 35%, 40%, 45%, 50%, 55%, 60%, 65%, 70%, 75%, 80%, 85%, 90%, 95% or 98%, or 10% to 25%, 25% to 50%, 50% to 75%, 75% to 98% or 25% to 75% more ErbB than cells of the same cell type that are not characterized by uncontrolled growth. In certain embodiments, the ErbB-expressing cell expresses an ErbB associated with cancer or considered to be an oncogenic mutation. In certain embodiments, the ErbB-expressing cell expresses an ErbB3 associated with cancer or considered to be an oncogenic mutation, such as those described in Jaiswal et al., Oncogenic ERBB3 mutations in human cancers. Cancer Cell, 2013, 23: 603-617. Methods for detecting ErbB expression by cells are well known in the art and include, but are not limited to, PCR techniques, immunohistochemistry, flow cytometry, Western blot, ELISA, and the like.

In another aspect, provided herein are methods for treating a disease, disorder or condition characterized by uncontrolled growth of ErbB-expressing cells in a patient, comprising administering to patients in need thereof an antibody described herein (e.g., in Section 5.1) or an antigen-binding fragment thereof, or an antibody conjugate described herein (e.g., in Section 5.2). In a specific embodiment, provided herein is a method for treating a disease, disorder or condition characterized by uncontrolled growth of ErbB expression or ErbB-expressing cells in a patient, comprising administering to patients in need thereof an effective amount of an antibody described herein (e.g., in Section 5.1) or an antigen-binding fragment thereof, or an antibody conjugate described herein (e.g., in Section 5.2). In a specific embodiment, provided herein is a method of treating a disease, disorder or condition characterized by uncontrolled growth of ErbB-expressing cells in a subject, comprising administering (e.g., administering concurrently or sequentially) to a subject in need thereof (i) an antibody described herein (e.g., in Section 5.1) or an antigen-binding fragment thereof, or an antibody conjugate described herein (e.g., in Section 5.2), and (ii) another therapy, e.g., an anti-cancer agent.

In another aspect, provided herein are methods for treating a hyperproliferative disorder, comprising administering to a patient in need thereof an antibody described herein (e.g., in Section 5.1) or an antigen-binding fragment thereof, or an antibody conjugate described herein (e.g., in Section 5.2). In a specific embodiment, provided herein is a method for treating a hyperproliferative disorder, comprising administering to a patient in need thereof an effective amount of an antibody described herein (e.g., in Section 5.1) or an antigen-binding fragment thereof. In another specific embodiment, provided herein is a method of treating hyperproliferative disorder in a subject, comprising administering (e.g., administering concurrently or sequentially) to a subject in need thereof (i) an antibody described herein (e.g., in Section 5.1) or an antigen-binding fragment thereof, or an antibody conjugate described herein (e.g., in Section 5.2), and (ii) another therapy, e.g., an anti-cancer agent.

In another aspect, provided herein are methods for treating cancer, comprising administering to a patient in need thereof an antibody described herein (e.g., in Section 5.1) or an antigen-binding fragment thereof, or an antibody conjugate described herein (e.g., in Section 5.2). In a specific embodiment, provided herein is a method for treating cancer, comprising administering to a patient in need thereof an effective amount of an antibody described herein (e.g., in Section 5.1) or an antigen-binding fragment thereof, or an antibody conjugate described herein (e.g., in Section 5.2). In a specific embodiment, provided herein is a method of treating cancer in a subject, comprising administering to a subject in need thereof an antibody described herein (e.g., in Section 5.1) or an antigen-binding fragment thereof, or an antibody conjugate described herein (e.g., in Section 5.2) in an effective amount to enhancing an immune response to the cancer. In another specific embodiment, provided herein is a method of treating cancer in a subject, comprising administering (e.g., administering concurrently or sequentially) to a subject in need thereof (i) an antibody described herein (e.g., in Section 5.1) or an antigen-binding fragment thereof, or an antibody conjugate described herein (e.g., in Section 5.2), and (ii) another therapy, e.g., an anti-cancer agent.

In certain embodiments, provided herein is a method for treating cancer comprising: (a) obtaining a biological sample suspected of containing ErbB3 from a subject and determining whether the amino acid sequence of the ErbB3 comprises a T336I amino acid substitution; and (b) administering to the subject an antibody described herein (e.g., in Section 5.1), the 2C2 antibody, 2C2-YTE antibody, 5H6 antibody, 8A3 antibody, 4H6 antibody, 6E3 antibody, 2B11 antibody, 2D1 antibody, 3A6 antibody, 4C4 antibody, 15D12.1 antibody, 15D12.2 antibody, 1A4 antibody, 3E1 antibody, 2F10 antibody, Clone 16 germlined antibody or Clone 16 antibody, or an antigen-binding fragment thereof or an antibody conjugate described herein (e.g., in Section 5.2), if the amino acid sequence of the ErbB3 in the biological sample does not comprise a T336I amino acid substitution. In another embodiment, provided herein is a method for treating cancer comprising: (a) obtaining a biological sample suspected of containing ErbB3 from a subject and determining whether the amino acid sequence of the ErbB3 comprises a V85M, A213V, P243H, G265R, V714M, Q809R, S8461, E928G, R667H, R667L, R669H, R675S, M677I, R678K, K695N, L712R, V723A, H724Y, K742E, R750W, L783V, L792V, K820N, G898D, T889A, Q934H, I938V, L976L, E1018Q, A1023T, S1046G, S1049G, S1065F, S1074N, G1103D, M1114V, R1120G, or R1127H amino acid substitution or the amino acid deletion of D1013-L1015; and (b) administering to the subject an antibody described herein (e.g., in Section 5.1), the 2C2 antibody, 2C2-YTE antibody, 5H6 antibody, 8A3 antibody, 4H6 antibody, 6E3 antibody, 2B11 antibody, 2D1 antibody, 3A6 antibody, 4C4 antibody, 15D12.1 antibody, 15D12.2 antibody, 1A4 antibody, 3E1 antibody, 2F10 antibody, Clone 16 germlined antibody or Clone 16 antibody, or an antigen-binding fragment thereof or an antibody conjugate described herein (e.g., in Section 5.2), if the amino acid sequence of the ErbB3 in the biological sample comprises at least one such amino acid substitution or deletion.

Examples of cancers to be treated in accordance with the methods provided herein include, but are not limited to, carcinoma including adenocarcinomas, lymphomas, blastomas, melanomas, sarcomas, and leukemias. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer (including hormonally mediated breast cancer, see, e.g., Innes et al. (2006) Br. J. Cancer 94:1057-1065), colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, various types of head and neck cancer and cancers of mucinous origins, such as, mucinous ovarian cancer, cholangiocarcinoma (liver) and renal papillary carcinoma. In a specific embodiment, cancers to be treated in accordance with the methods provided herein include head and neck cancer, colorectal cancer, breast cancer, thyroid cancer, melanoma, gastric cancer, lung cancer, prostate cancer, neurofibromatosis, bladder cancer, ovarian cancer, pancreatic cancer or renal cancer. In some embodiment, the cancer to be treated in accordance with the methods provided herein is a carcinoma of the skin, lung, colon, stomach, breast, prostate and thyroid gland. In a specific embodiment, the cancer treated in accordance with the methods provided herein is metastatic or malignant. In another specific embodiment, the cancer treated in accordance with the methods provided herein is associated with a cell expressing an oncogenic form of ErbB3, such as those described in Jaiswal et al., Oncogenic ERBB3 mutations in human cancers. Cancer Cell, 2013, 23: 603-617.

In one aspect, the cancer comprises the KRAS mutation. In specific aspects, the KRAS mutation is located at codon 12 of a human KRAS gene. As demonstrated in the Examples section, anti-ErbB3 antibodies disclosed herein as capable on inhibiting the growth of tumor cells that comprise a KRAS mutation, either when used as a single agent (monotherapy) or in combination with another therapeutic agent. The term "KRAS mutation," as used herein, refers to mutations found in certain cancers in a human homolog of the v-Ki-ras2 Kirsten rat sarcoma viral oncogene. Non-limiting examples of human KRAS gene mRNA sequences include Genbank Accession Nos. NM004985 and NM033360.

In another specific embodiment, provided herein is a method of inhibiting or treating metastasis in a subject, comprising administering to a subject in need thereof an effective amount of an antibody described herein (e.g., in Section 5.1) or an antigen-binding fragment thereof, or an antibody conjugate described herein (e.g., in Section 5.2). In a particular embodiment, provided herein is a method of inhibiting or reducing tumor growth or cancer cell proliferation in a subject, comprising administering to a subject in need thereof an effective amount of an antibody described herein (e.g., in Section 5.1) or an antigen-binding fragment, or an antibody conjugate described herein (e.g., in Section 5.2).

As used herein, the terms "treat," "treating" and "treatment" in the context of the administration of a therapy to a subject refer to the beneficial effects that a subject derives from a therapy. Non-limiting examples of such benefits include the reduction or inhibition of the progression, spread and/or duration of a condition, disease or disorder, the reduction or amelioration of the severity of a condition, disease or disorder, amelioration of one or more symptoms of a condition, disease or disorder, and/or the reduction in the duration of one or more symptom of a condition, disease or disorder resulting from the administration of one or more therapies. In certain embodiments, a subject is administered one or more therapies (e.g., prophylactic or therapeutic agents, such as an antibody described herein) to "treat" a condition, disease or disorder described herein, one or more symptoms thereof, so as to inhibit the progression or worsening of the condition, disease or disorder.

In specific embodiments, the administration of an antibody described herein (e.g., in Section 5.1) or an antigen-binding fragment thereof, or an antibody conjugate described herein (e.g., in Section 5.2) to a subject in accordance with the methods described herein achieves one, two, or three or more results: (1) a reduction in the growth of a tumor or neoplasm; (2) a reduction in the formation of a tumor; (3) an eradication, removal, or control of primary, regional and/or metastatic cancer; (4) a reduction in metastatic spread; (5) a reduction in mortality; (6) an increase in survival rate; (7) an increase in length of survival; (8) an increase in the number of patients in remission; (9) a decrease in hospitalization rate; (10) a decrease in hospitalization lengths; and (11) the maintenance in the size of the tumor so that it does not increase by more than 10%, or by more than 8%, or by more than 6%, or by more than 4%; preferably the size of the tumor does not increase by more than 2%.

In accordance with the methods provided herein, an antibody described herein (e.g., in Section 5.1) or an antigen-binding fragment thereof, or an antibody conjugate described herein (e.g., in Section 5.2) is used to promote a positive therapeutic response with respect to cancer. In accordance with the methods provided herein, an antibody described herein (e.g., in Section 5.1) or an antigen-binding fragment thereof is used to promote a positive therapeutic response with respect to cancer. The term "positive therapeutic response" with respect to cancer treatment refers to an improvement in the disease and/or an improvement in the symptoms associated with the disease. Thus, for example, an improvement in the disease can be characterized as a complete response. By "complete response" is intended an absence of clinically detectable disease with normalization of any previously test results. Alternatively, an improvement in the disease can be categorized as being a partial response. A "positive therapeutic response" encompasses a reduction or inhibition of the progression and/or duration of cancer, the reduction or amelioration of the severity of cancer, and/or the amelioration of one or more symptoms thereof resulting from the administration of an antibody described herein (e.g., in Section 5.1) or an antigen-binding fragment thereof. Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like.

In a specific embodiment, the administration of an antibody described herein (e.g., in Section 5.1) or an antigen-binding fragment thereof, or an antibody conjugate described herein (e.g., in Section 5.2) in accordance with the methods described herein inhibits or reduces the growth of a tumor by at least 2 fold, preferably at least 2.5 fold, at least 3 fold, at least 4 fold, at least 5 fold, at least 7 fold, or at least 10 fold relative to the growth of a tumor in a subject with cancer administered a negative control as measured using assays well known in the art. In another embodiment, the administration of an antibody described herein (e.g., in Section 5.1) or antigen-binding fragment thereof, or an antibody conjugate described herein (e.g., in Section 5.2) in accordance with the methods described herein inhibits or reduces the growth of a tumor by at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% relative to the growth of a tumor in a subject with cancer administered a negative control as measured using assays well known in the art.

In a specific embodiment, the administration of an antibody described herein (e.g., in Section 5.1) or antigen-binding fragment thereof, or an antibody conjugate described herein (e.g., in Section 5.2) in accordance with the methods described herein reduces the size of a tumor by at least 2 fold, preferably at least 2.5 fold, at least 3 fold, at least 4 fold, at least 5 fold, at least 7 fold, or at least 10 fold relative to the growth of a tumor in a subject with cancer in accordance with the methods described herein administered a negative control as measured using assays well known in the art. In another embodiment, the administration of an antibody described herein (e.g., in Section 5.1) or antigen-binding fragment thereof, or an antibody conjugate described herein (e.g., in Section 5.2) reduces the size of a tumor by at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% relative to the growth of a tumor in a subject with cancer administered a negative control (e.g., saline or PBS) as measured using assays well known in the art.

As used herein, the terms "subject" and "patient" are used interchangeably. As used herein, a subject is a mammal such as a non-primate (e.g., cows, pigs, horses, cats, dogs, goats, rabbits, rats, mice, etc.) or a primate (e.g., monkey and human), for example a human. In one embodiment, the subject is a mammal, e.g., a human, diagnosed with a condition or disorder provided herein. In another embodiment, the subject is a mammal, e.g., a human, at risk of developing a condition or disorder provided herein. In another embodiment, the subject is human.

As used herein, "administer" or "administration" refers to the act of injecting or otherwise physically delivering a substance (e.g., an antibody provided herein (e.g., in Section 5.1) or an antigen-binding fragment thereof, or an antibody conjugate described herein (e.g., in Section 5.2)) to a subject or a patient (e.g., human), such as by mucosal, topical, intradermal, parenteral, intravenous, intramuscular delivery and/or any other method of physical delivery described herein or known in the art.

As used herein, the terms "effective amount" or "therapeutically effective amount" refer to an amount of a therapy (e.g., an antibody or pharmaceutical composition provided herein) which is sufficient to have a beneficial effect. In specific embodiment, the effective amount is an amount sufficient to reduce and/or ameliorate the severity and/or duration of a given condition, disorder or disease and/or a symptom related thereto. These terms also encompass an amount necessary for the reduction, slowing, or amelioration of the advancement or progression of a given disease, reduction, slowing, or amelioration of the recurrence, development or onset of a given disease, and/or to improve or enhance the prophylactic or therapeutic effect(s) of another therapy (e.g., a therapy other than an antibody provided herein). In some embodiments, "effective amount" as used herein also refers to the amount of an antibody described herein to achieve a specified result.

As used herein, the terms "impede" or "impeding" in the context of a condition or disorder provided herein refer to the total or partial inhibition (e.g., less than 100%, 95%, 90%, 80%, 70%, 60%, 50%, 40%, 30%, 20%, 10%, or 5%) of the development, recurrence, onset or spread of a condition or disorder provided herein and/or symptom related thereto, resulting from the administration of a therapy or combination of therapies provided herein (e.g., a combination of prophylactic or therapeutic agents, such as an antibody described herein).

As used herein, the terms "therapies" and "therapy" can refer to any protocol(s), method(s), compositions, formulations, and/or agent(s) that can be used in the prevention, treatment, management, or amelioration of a condition or disorder or symptom thereof (e.g., a condition or disorder provided herein or one or more symptoms or condition associated therewith). In certain embodiments, the terms "therapies" and "therapy" refer to drug therapy, adjuvant therapy, radiation, surgery, biological therapy, supportive therapy, and/or other therapies useful in treatment of a condition or disorder or one or more symptoms thereof. In certain embodiments, the term "therapy" refers to a therapy other than an antibody described herein or pharmaceutical composition thereof. In specific embodiments, an "additional therapy" and "additional therapies" refer to a therapy other than a treatment using an antibody described herein or pharmaceutical composition thereof. In a specific embodiment, a therapy includes the use of an antibody described herein as an adjuvant therapy. For example, using an antibody described herein in conjunction with a drug therapy, biological therapy, surgery, and/or supportive therapy.

As used herein, the term "therapeutic agent" refers to any agent that can be used in the treatment of a condition or disorder or symptom thereof. In certain embodiments, the term "therapeutic agent" refers to an antibody described herein or an antigen-binding fragment thereof. In certain other embodiments, the term "therapeutic agent" refers to an agent other than an antibody described herein or antigen-binding fragment thereof. In specific embodiments, a therapeutic agent is an agent which is known to be useful for, or has been or is currently being used for the treatment of a condition or disorder provided herein or one or more symptoms or condition associated therewith or one or more symptoms related thereto.

As used herein, the term "prophylactic agent" refers to any agent that can totally or partially inhibit the development, recurrence, onset or spread of a condition or disorder provided herein and/or symptom related thereto in a subject. In certain embodiments, the term "prophylactic agent" refers to an antibody described herein. In certain other embodiments, the term "prophylactic agent" refers to an agent other than an antibody described herein or an antigen-binding fragment thereof. Generally, a prophylactic agent is an agent which is known to be useful to or has been or is currently being used to prevent a condition or disorder provided herein and/or a symptom related thereto or impede the onset, development, progression and/or severity of a condition or disorder provided herein and/or a symptom related thereto. In specific embodiments, the prophylactic agent is an antibody or antigen-binding fragment thereof described in Section 5.1, supra, or an antibody conjugate thereof described in Section 5.2, supra.

5.5.1 Patient Populations

In a particular embodiment, a patient treated in accordance with the methods described herein has or has been diagnosed with cancer. In specific embodiments, the cancer is a head and neck cancer, colorectal cancer, breast cancer, thyroid cancer, melanoma, gastric cancer, lung cancer, prostate cancer, neurofibromatosis, bladder cancer, ovarian cancer, pancreatic cancer or renal cancer. In some embodiments, the cancer is a tyrosine kinase inhibitor-resistant cancer. In certain embodiments, the cancer is associated with VEGF signaling.

In a particular embodiment, provided herein is a method for treating cancer in a subject, comprising administering to the subject an antibody described herein, or an antibody conjugate thereof (e.g., an antibody conjugate described in Section 5.2), or a combination therapy, wherein the subject expresses an oncogenic form of ErbB3, such as described in Jaiswal et al., Oncogenic ERBB3 mutations in human cancers. Cancer Cell, 2013, 23: 603-617. In a particular embodiment, provided herein is a method for treating cancer in a subject, comprising administering to the subject an antibody described herein (e.g., in Section 5.1), the 2C2 antibody, the 2C2-YTE antibody, the 5H6 antibody, the 8A3 antibody, the 4H6 antibody, the 6E3 antibody, the 2B11 antibody, the 2D1 antibody, the 3A6 antibody, the 4C4 antibody, the 15D12.1 antibody, the 15D12.2 antibody, the 1A4 antibody, the 3E1 antibody, the 2F10 antibody, the Clone 16 germlined antibody, the Clone 16 antibody, or an antigen-binding fragment thereof, or an antibody conjugate thereof (e.g., an antibody conjugate described in Section 5.2), or a combination therapy, wherein the subject expresses ErbB3 comprising one or more of the amino acid substitutions of V85M, A213V, P243H, or G265R. In a particular embodiment, provided herein is a method for treating cancer in a subject, comprising administering to the subject an antibody described herein (e.g., in Section 5.1), the 2C2 antibody, the 2C2-YTE antibody, the 5H6 antibody, the 8A3 antibody, the 4H6 antibody, the 6E3 antibody, the 2B11 antibody, the 2D1 antibody, the 3A6 antibody, the 4C4 antibody, the 15D12.1 antibody, the 15D12.2 antibody, the 1A4 antibody, the 3E1 antibody, the 2F10 antibody, the Clone 16 germlined antibody, the Clone 16 antibody, or an antigen-binding fragment thereof, or an antibody conjugate thereof (e.g., an antibody conjugate described in Section 5.2), or a combination therapy, wherein the subject expresses ErbB3 comprising one or more of the amino acid substitutions of V714M, Q809R, S846I, E928G, R667H, R667L, R669H, R675S, M677I, R678K, K695N, L712R, V723A, H724Y, K742E, R750W, L783V, L792V, K820N, G898D, T889A, Q934H, I938V, L976L, E1018Q, A1023T, 51046G, 51049G, S1065F, S1074N, G1103D, M1114V, R1120G, or R1127H, or an amino acid deletion of D1014-L1015.

In a particular embodiment, provided herein is a method for treating cancer in a subject, comprising administering to the subject an antibody described herein (e.g., in Section 5.1), the 2C2 antibody, the 2C2-YTE antibody, the 5H6 antibody, the 8A3 antibody, the 4H6 antibody, the 6E3 antibody, the 2B11 antibody, the 2D1 antibody, the 3A6 antibody, the 4C4 antibody, the 15D12.1 antibody, the 15D12.2 antibody, the 1A4 antibody, the 3E1 antibody, the 2F10 antibody, the Clone 16 germlined antibody, the Clone 16 antibody, or an antigen-binding fragment thereof, or an antibody conjugate thereof (e.g., an antibody conjugate described in Section 5.2), or a combination therapy, wherein the subject expresses ErbB3 which does not comprise the amino acid substitution T336I.

In another embodiment, a subject treated in accordance with the methods described herein overexpresses an ErbB protein. In a specific embodiment, the subject overexpresses ErbB1. In another specific embodiment, the subject overexpresses ErbB3. In another specific embodiment, the subject overexpresses ErbB4. In another embodiment, a subject treated in accordance with the methods described herein overexpresses an ErbB2 protein. Overexpression of ErbB can be determined by assays described herein, such as, for example, western blot.

In another embodiment, a subject treated in accordance with the methods described herein overexpresses neuregulin protein. In a specific embodiment, the subject overexpresses neuregulin 1. In another specific embodiment, the subject overexpresses neuregulin 2. In another specific embodiment, the subject overexpresses neuregulin 1-beta. Overexpression of neuregulin can be determined by assays described herein, such as, e.g., western blot.

In a specific embodiment, provided herein is a method to assess if the patient will be responsive to treatment with an antibody described herein (e.g., in Section 5.1) or an antigen-binding fragment thereof, wherein an ex vivo assay for the bioactivity of an antibody described herein (e.g., in Section 5.1) or an antigen-binding fragment thereof, or an antibody conjugate thereof (e.g., an antibody conjugate described in Section 5.2), or a combination therapy is assessed. In a specific embodiment, the ex vivo assay comprises a skin biopsy. In a specific embodiment, the level of phosphorylated ErbB is determined in the presence and absence of the antibody or antibody fragment described herein by methods known to one of ordinary skill in the art, such as, for e.g., western blot. In a specific embodiment, a subject is determined to be responsive to treatment with the antibody or fragment thereof if the level of phosphorylated ErbB is at least 1.2-, 1.4-1.5-, 2.0-, 2.5-, 5.0-, or at least 10 fold decreased upon treatment with an antibody or an antigen-binding fragment thereof described herein as compared with treatment with an unrelated antibody.

In another embodiment, provided herein is a method to assess if the patient will be responsive to treatment with an antibody described herein (e.g., in Section 5.1), the 2C2 antibody, the 2C2-YTE antibody, the 5H6 antibody, the 8A3 antibody, the 4H6 antibody, the 6E3 antibody, the 2B11 antibody, the 2D1 antibody, the 3A6 antibody, the 4C4 antibody, the 15D12.1 antibody, the 15D12.2 antibody, the 1A4 antibody, the 3E1 antibody, the 2F10 antibody, the Clone 16 germlined antibody, the Clone 16 antibody, or an antigen-binding fragment thereof, comprising (a) obtaining a biological sample suspected of containing ErbB3 from a subject and determining whether the amino acid sequence of the ErbB3 comprises a V85M, A213V, P243H, or G265R amino acid substitution; and (b) concluding the subject will be responsive to treatment with the antibody described herein, the 2C2 antibody, the 2C2-YTE antibody, the 5H6 antibody, the 8A3 antibody, the 4H6 antibody, the 6E3 antibody, the 2B11 antibody, the 2D1 antibody, the 3A6 antibody, the 4C4 antibody, the 15D12.1 antibody, the 15D12.2 antibody, the 1A4 antibody, the 3E1 antibody, the 2F10 antibody, the Clone 16 germlined antibody, the Clone 16 antibody, or an antigen-binding fragment thereof if the amino acid sequence of the ErbB3 in the biological sample comprises at least one such amino acid substitution. In another embodiment, provided herein is a method to assess if the patient will be responsive to treatment with an antibody described herein (e.g., in Section 5.1), the 2C2 antibody, the 2C2-YTE antibody, the 5H6 antibody, the 8A3 antibody, the 4H6 antibody, the 6E3 antibody, the 2B11 antibody, the 2D1 antibody, the 3A6 antibody, the 4C4 antibody, the 15D12.1 antibody, the 15D12.2 antibody, the 1A4 antibody, the 3E1 antibody, the 2F10 antibody, the Clone 16 germlined antibody, the Clone 16 antibody, or an antigen-binding fragment thereof, comprising (a) obtaining a biological sample suspected of containing ErbB3 from a subject and determining whether the amino acid sequence of the ErbB3 comprises a V714M, Q809R, S846I, E928G, R667H, R667L, R669H, R675S, M677I, R678K, K695N, L712R, V723A, H724Y, K742E, R750W, L783V, L792V, K820N, G898D, T889A, Q934H, I938V, L976L, E1018Q, A1023T, 51046G, 51049G, S1065F, S1074N, G1103D, M1114V, R1120G, or R1127H, V85M, A213V, P243H, G265R amino acid substitution or a D1014-L1015 amino acid deletion; and (b) concluding the subject will be responsive to treatment with the antibody described herein, the 2C2 antibody, the 2C2-YTE antibody, the 5H6 antibody, the 8A3 antibody, the 4H6 antibody, the 6E3 antibody, the 2B11 antibody, the 2D1 antibody, the 3A6 antibody, the 4C4 antibody, the 15D12.1 antibody, the 15D12.2 antibody, the 1A4 antibody, the 3E1 antibody, the 2F10 antibody, the Clone 16 germlined antibody, the Clone 16 antibody, or an antigen-binding fragment thereof if the amino acid sequence of the ErbB3 in the biological sample comprises at least one such amino acid substitution or deletion.

5.5.2 Routes of Administration and Dosages

Methods of preparing and subject an antibody described herein (e.g., in Section 5.1) or an antigen-binding fragment thereof, or an antibody conjugate thereof (e.g., an antibody conjugate described in Section 5.2) to a subject in need thereof are well known to or are readily determined by those skilled in the art. The route of administration of the antibody described herein (e.g., in Section 5.1) or antigen-binding fragment thereof, or the antibody conjugate thereof (e.g., an antibody conjugate described in Section 5.2), can be, for example, oral, parenteral, by inhalation or topical. The term parenteral as used herein includes, e.g., intravenous, intraarterial, intraperitoneal, intramuscular, subcutaneous, rectal, or vaginal administration. However, in other methods compatible with the teachings herein, an antibody described herein (e.g., in Section 5.1) or an antigen-binding fragment thereof, or an antibody conjugate thereof (e.g., an antibody conjugate described in Section 5.2) can be delivered directly to the site of the adverse cellular population thereby increasing the exposure of the diseased tissue to the therapeutic agent.

In certain aspects, an antibody described herein (e.g., in Section 5.1) or an antigen-binding fragment thereof, or an antibody conjugate thereof (e.g., an antibody conjugate described in Section 5.2) can be formulated for local administration or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

As discussed herein, an antibody described herein (e.g., in Section 5.1) or an antigen-binding fragment thereof, or an antibody conjugate thereof (e.g., an antibody conjugate described in Section 5.2) can be administered in a pharmaceutically effective amount for the in vivo treatment of ErbB-expressing cell-mediated diseases such as certain types of cancers.

Parenteral formulations can be a single bolus dose, an infusion or a loading bolus dose followed with a maintenance dose. These compositions can be administered at specific fixed or variable intervals, e.g., once a day, or on an "as needed" basis.

The composition can be administered as a single dose, multiple doses or over an established period of time in an infusion. Dosage regimens also can be adjusted to provide the optimum desired response (e.g., a therapeutic or prophylactic response).

Therapeutically effective doses of the compositions of the present invention, for treatment of ErbB-expressing cell-mediated diseases such as certain types of cancers including e.g., colon cancer, lung cancer, gastric cancer, head and neck squamous cells cancer, melanoma, pancreatic cancer, prostate cancer, and breast cancer, vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages can be titrated using routine methods known to those of skill in the art to optimize safety and efficacy.

The amount of an antibody described herein (e.g., in Section 5.1) or an antigen-binding fragment thereof, or an antibody conjugate thereof (e.g., an antibody conjugate described in Section 5.2) to be administered to a subject can be determined by the skilled artisan (e.g., a physician). Factors influencing the mode of administration and the respective amount of an antibody described herein (e.g., in Section 5.1) or an antigen-binding fragment thereof, or an antibody conjugate thereof (e.g., an antibody conjugate described in Section 5.2), include, but are not limited to, the severity of the disease, the history of the disease, and the age, height, weight, health, and physical condition of the individual undergoing therapy. Similarly, the amount of an antibody described herein (e.g., in Section 5.1) or an antigen-binding fragment thereof, or an antibody conjugate thereof (e.g., an antibody conjugate described in Section 5.2) to be administered will be dependent upon the mode of administration and whether the subject will undergo a single dose or multiple doses of this agent.

The pharmaceutical compositions, in another embodiment, provide a dosage of about 50 mg of antibody per kilogram of body weight for administration over a period of time, e.g., every day or few days, every week, every 2 weeks, or every 3 weeks.

5.6 Combination Therapy

In certain aspects, provided herein is the administration of an antibody described herein thereof (see, e.g., Section 5.1) or an antigen-binding fragment thereof, or an antibody conjugate described herein (e.g., in Section 5.2) in combination at least one other therapy. The an antibody described herein thereof (see, e.g., Section 5.1) or antigen-binding fragment thereof, or the antibody conjugate described herein (e.g., in Section 5.2) and the at least one other therapy can be administered together in a single composition or can be administered in separate compositions. As used herein, the term "in combination" in the context of the administration of other therapies refers to the use of more than one therapy. The use of the term "in combination" does not restrict the order in which therapies are administered. The therapies may be administered, e.g., serially, sequentially, concurrently, or concomitantly.

An antibody described herein thereof (see, e.g., Section 5.1) or an antigen-binding fragment thereof, or an antibody conjugate described herein (e.g., in Section 5.2) can be used in combination with any known therapies for cancer, including any agent or combination of agents that are known to be useful, or which have been used or are currently in use, for treatment of cancer, e.g., colon cancer, lung cancer, gastric cancer, head and neck squamous cells cancer, and breast cancer. The second agent or combination of agents of the pharmaceutical combination formulation or dosing regimen preferably has complementary activities to the antibody or antigen-binding fragment, or the antibody conjugate such that they do not adversely affect each other.

5.7 Diagnostic Uses

In another aspect, provided herein is a diagnostic method useful during diagnosis of ErbB-expressing cell-mediated diseases such as certain types of cancer including, e.g., colon cancer, lung cancer, gastric cancer, head and neck squamous cells cancer, melanoma, pancreatic cancer, prostate cancer, and breast cancer, which involves measuring the expression level of ErbB protein or transcript in tissue or other cells or body fluid from an individual and comparing the measured expression level with a standard ErbB expression level in normal tissue or body fluid, whereby an increase in the expression level compared to the standard is indicative of a disorder.

An antibody described herein thereof (see, e.g., Section 5.1) or an antigen-binding fragment thereof can be used to assay ErbB protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin, and can be used to label an antibody described herein thereof (see, e.g., Section 5.1) or an antigen-binding fragment thereof. Suitable assays are described in more detail elsewhere herein.

As used herein, "assaying the expression level of ErbB polypeptide" is intended qualitatively or quantitatively measuring or estimating the level of ErbB polypeptide in a first biological sample either directly (e.g., by determining or estimating absolute protein level) or relatively (e.g., by comparing to the disease associated polypeptide level in a second biological sample). ErbB polypeptide expression level in the first biological sample can be measured or estimated and compared to a standard ErbB polypeptide level, the standard being taken from a second biological sample obtained from an individual not having the disorder or being determined by averaging levels from a population of individuals not having the disorder. As will be appreciated in the art, once the "standard" ErbB polypeptide level is known, it can be used repeatedly as a standard for comparison.

Also provided herein is a diagnostic method useful during diagnosis of ErbB-expressing cell-mediated diseases such as certain types of cancer including, e.g., colon cancer, lung cancer, gastric cancer, head and neck squamous cells cancer, melanoma, pancreatic cancer, prostate cancer, and breast cancer, which involves measuring the activity level of ErbB protein in tissue or other cells or body fluid from an individual and comparing the measured activity level with a standard ErbB activity level in normal tissue or body fluid, whereby an increase in the activity level compared to the standard is indicative of a disorder.

As used herein, the term "assaying the activity level of ErbB protein" refers to qualitatively or quantitatively measuring or estimating the activity of ErbB protein in a first biological sample either directly (e.g., by determining or estimating absolute activity level) or relatively (e.g., by comparing to the activity level in a second biological sample). ErbB protein activity level in the first biological sample can be measured or estimated and compared to a standard ErbB protein activity, the standard being taken from a second biological sample obtained from an individual not having the disorder or being determined by averaging levels from a population of individuals not having the disorder or from an individual prior to treatment. As will be appreciated in the art, once the "standard" ErbB protein activity level is known, it can be used repeatedly as a standard for comparison. In certain aspects, the activity level of ErbB in a biological sample is measured or estimated or compared by detecting phosphorylated ErbB in a biological sample. In a specific aspect, the activity level of ErbB in a biological sample is measured or estimated or compared by detecting phosphorylated ErbB3 in a skin biopsy, wherein the skin is stimulated with heregulin prior to or after biopsy.

As used herein, the term "biological sample" refers to any biological sample obtained from a subject, cell line, tissue, or other source of cells potentially expressing ErbB3. Methods for obtaining tissue biopsies and body fluids from animals (e.g., humans) are well known in the art. Biological samples include cancer cells and tumor samples.

In some aspects, the bioactivity of an antibody described herein thereof (see, e.g., Section 5.1) or an antigen-binding fragment thereof administered to a subject can be detected using an ex vivo assay. In particular aspects, the ex vivo assay comprises detecting the level of phosphorylated ErbB in a skin biopsy, wherein the skin is stimulated with neuregulin prior to or after biopsy. In a specific aspect, matched skin biopsies are taken from a subject that has been administered an antibody described herein thereof (see, e.g., Section 5.1) or an antigen-binding fragment thereof. In a specific aspect, neuregulin is injected under a first area of the skin and a control buffer is injected under a second area of the skin of a subject administered an antibody described herein thereof (see, e.g., Section 5.1) or an antigen-binding fragment thereof, wherein after a desired amount of time (e.g., 10-60 minutes) a biopsy is taken from the first and second areas of the skin. In an alternative aspect, a first skin biopsy is treated with neuregulin and a second skin biopsy is treated with a control buffer, wherein the first and the second biopsies are matched skin biopsies taken from a subject that has been administered an antibody described herein thereof (see, e.g., Section 5.1) or an antigen-binding fragment thereof. In another specific aspect, the level of phosphorylated ErbB is detected in the skin biopsies. In certain aspects, the difference in the level of phosphorylated ErbB between the first (neuregulin treated) and the second (control buffer treated) biopsy is determined. In certain aspects, the skin biopsy is homogenized and the level of phosphorylated ErbB is detected by ELISA. In still other aspects, the levels of phosphorylated ErbB in the skin biopsies from a subject that has been administered an antibody described herein thereof (see, e.g., Section 5.1) or an antigen-binding fragment thereof is compared to the levels of phosphorylated ErbB in skin biopsies from a control subject that has not been administered the antibody described herein thereof (see, e.g., Section 5.1) or antigen-binding fragment thereof, wherein a reduction in the level of phosphorylated ErbB in the skin biopsies of the subject that has been administered the antibody described herein thereof (see, e.g., Section 5.1) or antigen-binding fragment thereof is a measure of the bioactivity of the antibody described herein thereof (see, e.g., Section 5.1) or antigen-binding fragment thereof. In alternative aspects, the levels of phosphorylated ErbB in the skin biopsies from a subject that has been administered the antibody described herein thereof (see, e.g., Section 5.1) or antigen-binding fragment thereof is compared to the levels of phosphorylated ErbB in skin biopsies from the same subject taken prior to the administration of the antibody described herein thereof (see, e.g., Section 5.1) or antigen-binding fragment thereof, wherein a reduction in the level of phosphorylated ErbB in the skin biopsies of the subject after administration of the antibody described herein thereof (see, e.g., Section 5.1) or antigen-binding fragment thereof is a measure of bioactivity of the antibody described herein thereof (see, e.g., Section 5.1) or antigen-binding fragment thereof.

A further aspect is the use of an antibody described herein thereof (see, e.g., Section 5.1) or an antigen-binding fragment thereof for diagnostic monitoring of protein levels in tissue as part of a clinical testing procedure, e.g., to determine the efficacy of a given treatment regimen. For example, detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

In one embodiment, monitoring of a condition described herein (e.g., a condition involving ErbB and/or abnormal ErbB signaling), such as ErbB-expressing cell-mediated diseases such as certain types of cancer including, e.g., colon cancer, lung cancer, gastric cancer, head and neck squamous cells cancer, melanoma, pancreatic cancer, prostate cancer, and breast cancer, is carried out by repeating the method for diagnosing for a period of time after initial diagnosis, and wherein an antibody described herein thereof (see, e.g., Section 5.1) or an antigen-binding fragment thereof is utilized.

Presence of the labeled an antibody described herein thereof (see, e.g., Section 5.1) or an antigen-binding fragment thereof can be detected in the subject using methods known in the art for in vivo scanning Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

5.8 Kits

Provided herein are kits comprising one or more antibodies described herein, or antigen-binding fragments thereof, or conjugates thereof. In a specific embodiment, provided herein is a pharmaceutical pack or kit comprising one or more containers filled with one or more of the ingredients of the pharmaceutical compositions described herein, such as one or more antibodies provided herein or an antigen-binding fragment thereof. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided herein are kits that can be used in the above methods. In one embodiment, a kit comprises an antibody described herein, preferably a purified antibody, in one or more containers. In a specific embodiment, kits described herein contain a substantially isolated ErbB antigen (e.g., the extracellular domain of ErbB) as a control. In another specific embodiment, the kits described herein further comprise a control antibody which does not react with an ErbB antigen. In another specific embodiment, kits described herein contain one or more elements for detecting the binding of a modified antibody to an ErbB antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized ErbB antigen. The ErbB antigen provided in the kit can also be attached to a solid support. In a more specific embodiment, the detecting means of the above described kit includes a solid support to which an ErbB antigen is attached. Such a kit can also include a non-attached reporter-labeled anti-human antibody or anti-mouse/rat antibody. In this embodiment, binding of the antibody to the ErbB antigen can be detected by binding of the said reporter-labeled antibody.

The following examples are offered by way of illustration and not by way of limitation.

6. EXAMPLES

The examples in this section (i.e., Section 6) are offered by way of illustration, and not by way of limitation.

Introduction to Examples 1-4

The 2C2 antibody (see, WO 2013/078191) is an anti-ErbB3 antibody that can inhibit ligand-dependent and ligand-independent activation of ErbB3. The examples presented herein utilize structural analysis using X-ray crystallography of the 2C2 Fab in complex with the extracellular domain of human ErbB3 to characterize the epitope binding region of the 2C2 antibody and to elucidate a structural basis for the ability of the 2C2 antibody to inhibit ligand-dependent and ligand-independent activation of human ErbB3. Briefly, the data presented herein demonstrate that 2C2 binds to ErbB3 domain II and domain II, including the domain II/domain III hinge region. Thus, without wishing to be bound by any particular theory or mechanism, the results presented herein indicate that 2C2 binds to and wedges itself in the boundary between ErbB3 domains II and III (the domain II/domain III hinge region), thereby succeeding in restricting ErbB3 to an auto-inhibited configuration by hindering a crucial conformational change that is required for both ligand-dependent and ligand-independent ErbB3 activation.

The results presented herein, therefore, identify a specific structural region within ErbB3 that can be immunologically targeted to successfully inhibit both ligand-dependent and ligand-independent activation of ErbB3. Not only do the examples presented herein reveal this crucial ErbB3 structural region, but they also demonstrate the successful production of new antibodies that specifically target this region and bind to the region with extremely high affinity.

Moreover, the examples presented herein also demonstrate that the general architecture of the ErbB3 epitope and structural region identified and shown herein to be important for ligand-dependent and ligand-independent ErbB3 activation is conserved among ErbB members. Thus, these data indicate that antibodies directed against particular regions of other ErbBs, such as ErbB1 (EGFR) and ErbB4, can be generated and utilized to inhibit ligand-dependent and ligand-independent activation of these ErbB members as well.

6.1 Example 1. The Crystal Structure of the 2C2/ErbB3 Extracellular Domain Complex 6.1.1 Introduction ErbB3 can be activated in a ligand-dependent and/or a ligand-independent mechanism (FIG. 1). This example uses X-ray crystallography of the 2C2 Fab in complex with the extracellular domain of human ErbB3 and other experimental techniques to characterize the epitope binding region of the 2C2 antibody. In particular, the example identifies the human ErbB3 amino acid residues that are in contact with amino acid residues in the variable heavy and variable light chain regions of 2C2. In particular, this example demonstrates that 2C2-YTE binds to amino acid residues in domains II and III of ErbB3 and uses this data to elucidate a structural basis for the ability to the 2C2 antibody to inhibit ligand-dependent and ligand-independent activation of human ErbB3. Briefly, the data presented herein demonstrate that 2C2 binds to ErbB3 domain II and domain III, including the domain II/domain III hinge region. Without wishing to be bound by any particular theory or mechanism, these data indicate that 2C2 binds to and wedges itself in the boundary between ErbB3 domains II and III (the domain II/domain III hinge region), thereby succeeding in restricting ErbB3 to an auto-inhibited configuration by hindering a crucial conformational change that is required for both ligand-dependent and ligand-independent ErbB3 activation.

6.1.2 Materials and Methods

Nomenclature Note

The amino acid sequences of the antibodies referred to as "2C2" and "2C2-YTE" in WO 2013/078191 differ from each other only within their constant regions. As such, the amino acid sequence of the 2C2 Fab and the corresponding amino acid sequences of 2C2 and 2C2-YTE (including the variable light and variable heavy chain sequences) are all identical to each other. For ease of reference, therefore, while the whole antibody used in the examples was the 2C2-YTE antibody, it is referred to within the examples as "2C2".

Protein Purification and Crystallography Methods.

ErbB3 extracellular ligand binding domain with C-terminal hexa-histidine tag was cloned into pFastbac1. High-titer Sf9 cells infected with the bacmid were used to infect Sf9 cells in sf900II serum free media (Invitrogen). The medium was collected 5 days after infection and incubated with Ni-NTA agarose (Qiagen, 2 mL per a liter medium) overnight at 4° C. The protein was eluted from the beads with 300 mM imidazole and dialyzed against 20 mM Tris pH 8.0. The protein was then de-glycosylated and subjected to an anion exchange chromatography (MonoQ HR, GE healthcare). The DNA sequence for 2C2 Fab was optimized for *E. coli* expression and synthesized, and the sequences for heavy chain and light chain were cloned into a vector pET26b (Novagen) each containing pelB signal peptide for periplasmic localization. The vector was transformed into BL21(DE3), and single colony was grown in LB medium and induced with 0.5 mM IPTG at 20° C. for 16 hours. The cell pellet was lysed with French Press at 15,000 psi, and the supernatant, after centrifugation at 25,000×g, was incubated with protein A agarose (Invitrogen) for 2 hours at 4° C. The resin was washed with PBS and the protein was eluted with 100 mM Glycine-HCl, pH 3.5 and immediately neutralized with 100 mM Tris, pH 8.0. The protein was then subject to a cation exchange chromatography (MonoS HR, GE healthcare) and the fractions containing the equimolar amounts of heavy chain and light chain were combined and concentrated. The purity and homogeneity of each purified protein preparations were assessed by denatured SDS-PAGE.

Purified ErbB3 ectodomain and 2C2 Fab were mixed and incubated for at least an hour at 4° C. before loading to a size exclusion chromatography column (Superdex 200 HR, GE healthcare) equilibrated in 20 mM Tris and 100 mM NaCl at pH 8.0, to separate excess Fab.

The crystals of the complex between the ErbB3 extracellular domain and Fab fragment of 2C2 were grown at 294° K using a hanging drop vapor diffusion method from the drops containing equal volumes of the protein solution and reservoir containing 18% PEG 3,350, 0.2 M di-ammonium citrate hexahydrate, and 0.2 M sodium thiocyanate. The crystals were cryoprotected by slowly transferring to artificial mother liquor supplemented with 30% PEG 400 and flash-cooled in liquid nitrogen.

The X-ray diffraction data were obtained at the Advanced Photon Source (Argonne National Laboratory) beamline 24-ID-E, and processed and scaled to 3.04 Å using XDS (Kabsch, W. (2010). Xds. Acta Crystallogr D Biol Crystallogr 66, 125-132). The crystal has a space group of P1, with the cell unit parameter of a=84.18, b=126.96, c=137.92, and α=87.11, β=85.5, γ=89.93, containing 4 complex molecules per asymmetric unit. The structure was solved by molecular replacement (PHASER) using coordinates from the ErbB3 extracellular domain (4LEO.pdb) and a Fab fragment (4LEO.pdb) and refined with Refmac and PHENIX iteratively while inspected manually using Coot.

Fluorescently Labeled 2C2 Binding Assays

2C2 was labeled with Alexa-647 at a molar loading ratio of <3 dye/mAb. Labeled 2C2 was titrated on BaF3 cells engineered to co-express ErbB2 and ErbB3. The incubation was performed in FACS buffer (PBS+2% newborn calf serum) on ice for 4 hours to prevent receptor internalization. Cells were washed twice with FACS buffer, and were subsequently incubated with the 7-AAD vital dye to allow gating of live cells. Mean cell fluorescence was measured using an Accuri C6 Flow cytometer. Background-subtracted mean fluorescence intensity was plotted as a function of antibody concentration. The data were fit to a single-site binding isotherm using GraphPad Prism, from which the apparent Kd values were determined.

ELISA Assays Assessing Binding of 2C2 to ErbB3-ECD or a Domain Thereof

Each His-tagged domain in ErbB3 (domain I, II, III, and IV) was expressed in baculovirus-infected Sf9 cells and purified from conditioned media using metal affinity chromatography followed by size-exclusion chromatography. Each purified domain (as well as the full his-tagged ErbB3 extracellular domain) was coated on ELISA plates. After blocking with 5% BSA in TBST, 2C2 was titrated and incubated for 1 hour. The plates were washed with TBST and incubated with an HRP-conjugated anti-human secondary antibody. The plates were washed again and read after incubation with WestPico Chemiluminescent Substrate. Binding data were plotted as a function of the log-transformed concentration of 2C2 concentration. Data were fit to a non-linear regression agonist equation with a floating Hill slope.

Neuregulin Binding Assays

Neuregulin1-beta1 was labeled with Alexa-647 (Nrg-647) at a molar loading ratio of 0.5 dye/mAb. Nrg-647 was titrated on BaF3 cells engineered to co-express ErbB2 and ErbB3, which were either untreated, or pre-incubated with 10 nM 2C2 for 1 hour. The incubations were performed in FACS buffer (PBS+2% newborn calf serum) on ice for 1 hour to prevent receptor internalization. Cells were washed twice with FACS buffer, and were subsequently incubated with the 7-AAD vital dye to allow gating of live cells. Mean cell fluorescence was measured using an Accuri C6 Flow cytometer. Background-subtracted mean fluorescence intensity was plotted as a function of Nrg-647 concentration. The data were fit to a two-site binding isotherm using GraphPad Prism.

Binding Affinity Measurements

Surface plasmon resonance (SPR) experiments were performed using a BIAcore T100 instrument (GE Healthcare) at 25° C. (Keck Foundation Biotechnology Resource Laboratory, Yale University). The Fab fragment of 2C2 was immobilized on a CM5 BIAcore sensor chip using a standard amine coupling method. Surfaces with three different concentrations of Fab were generated by varying the contact time of the Fab solution in 10 mM sodium acetate buffer at pH 5.5. A titration of purified ErbB3-ECD or ErbB3 domain III was flowed over the sensor chip with the immobilized Fab fragment of 2C2. Acquired data were analyzed using the evaluation software supplied with the BIAcore T100 instrument.

6.1.3 Results

Analysis of 2C2 Binding Affinity for ErbB3

Figure 2:
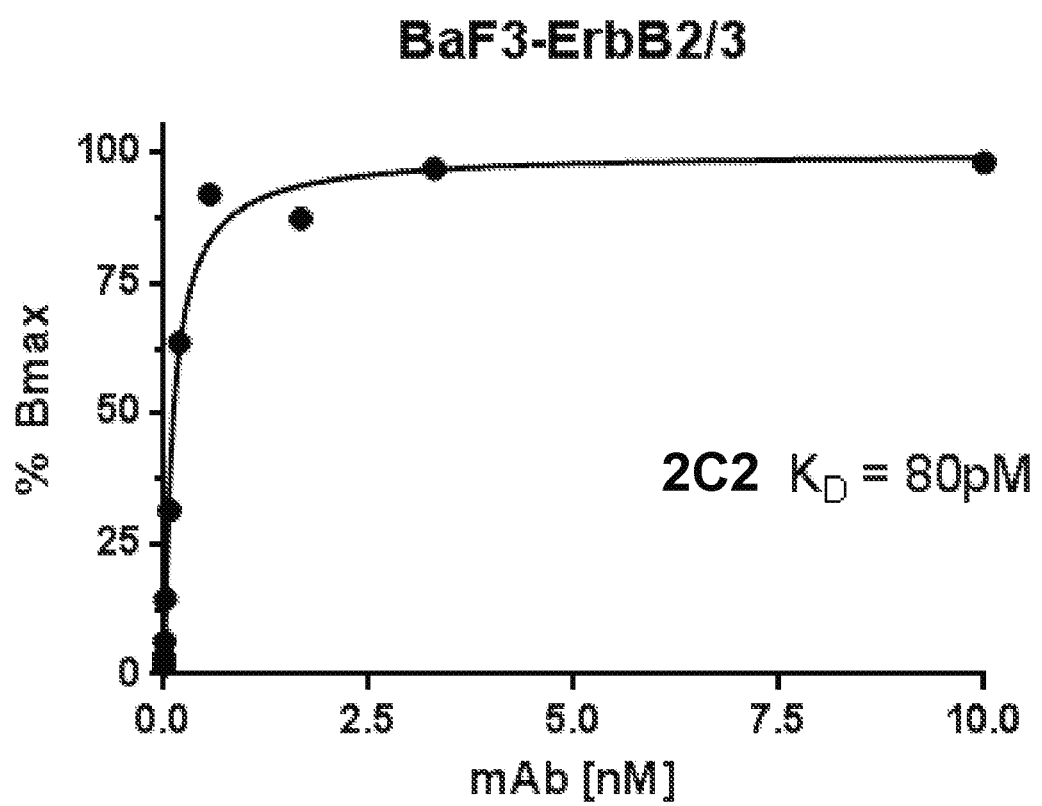

In order to determine the affinity of 2C2 for cell-surface expressed ErbB3, 2C2 was fluorescently labeled with Alexa-647 and was titrated on BaF3 cells engineered to co-express ErbB2 and ErbB3. Titration was performed on ice to prevent receptor internalization. FACS analysis of fluorescently labeled 2C2 bound to ErbB3 was subsequently performed. To obtain the apparent $K_D$ for 2C2 and ErbB3, the background-subtracted mean fluorescence intensity was plotted as a function of antibody concentration and data fit to a single-site binding isotherm (FIG. 2). This analysis yielded an apparent $K_D$ of 80 pM, demonstrating strong binding interaction between 2C2 and cell-surface expressed ErbB3.

2C2 Binds Primarily to Domain III in ErbB3

Figure 3:
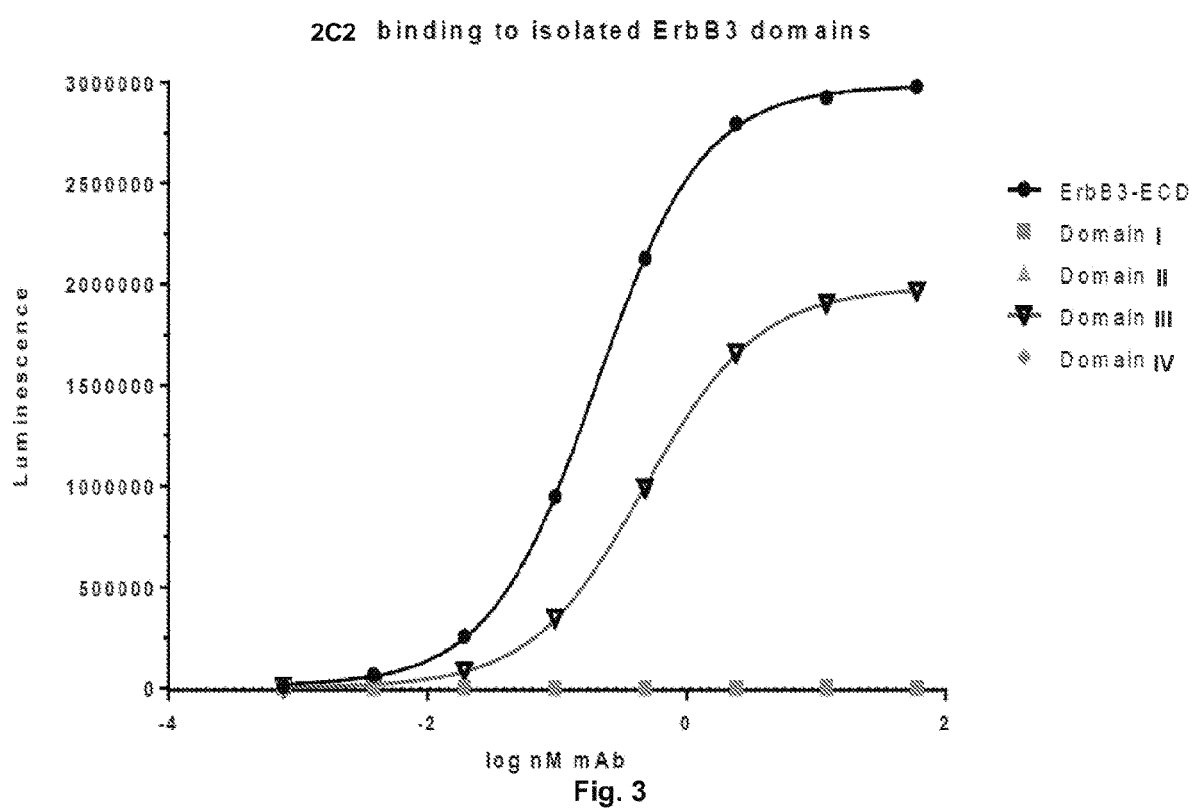

ELISA assays were performed to elucidate the location of 2C2 binding to ErbB3. His-tagged ErbB3 extracellular domain, domain I, domain II, domain III, and domain IV expressing baculoviruses were utilized to infect Sf9 cells, conditioned media was harvested, and the individual ErbB3 constructs were purified. To assess the ability of 2C2 to bind these individual ErbB3 domains, or ErbB3 extracellular domain, ELISA plates were individually coated with His-tagged ErbB3 constructs and used for 2C2 titration. Following incubation with a secondary HRP-conjugated anti-human antibody, the luminescent readout was plotted as a function of the log of 2C2 concentration and data were fitted to a four-parameter sigmoidal equation. These data demonstrate that 2C2 binds to the ErbB3 extracellular domain and domain III, while binding between 2C2 and domains I, II, and IV was below the level of detection (FIG. 3). Taken together, these data demonstrate that domain III contains the majority of the epitope that is recognized by 2C2.

2C2 Binds to a Unique Epitope in ErbB3 Domain III

To further investigate the mechanism of 2C2 binding to domain III of ErbB3, crystallography analyses were performed on the ErbB3 ectodomain bound to 2C2 Fab. His-tagged ErbB3 extracellular domain was baculovirus expressed in Sf9 cells and subsequently deglycosylated and purified. The 2C2 Fab DNA sequence was optimized, expressed in *E. coli*, and the heavy chain and light chain were purified and combined in equimolar amounts. Purified ErbB3 ectodomain and 2C2 Fab were incubated and excess Fab was removed by size exclusion chromatography. Crystals of the complex were grown at 294K, cryoprotected, and X-ray diffraction data were obtained as described in the materials and methods above.

Figure 4:
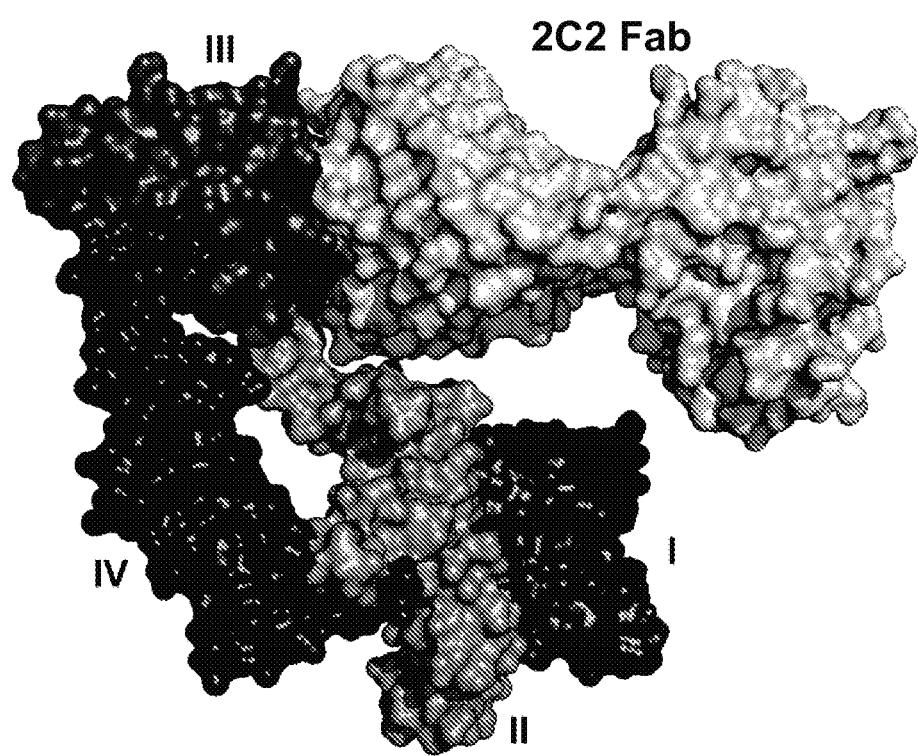
Figure 5A:
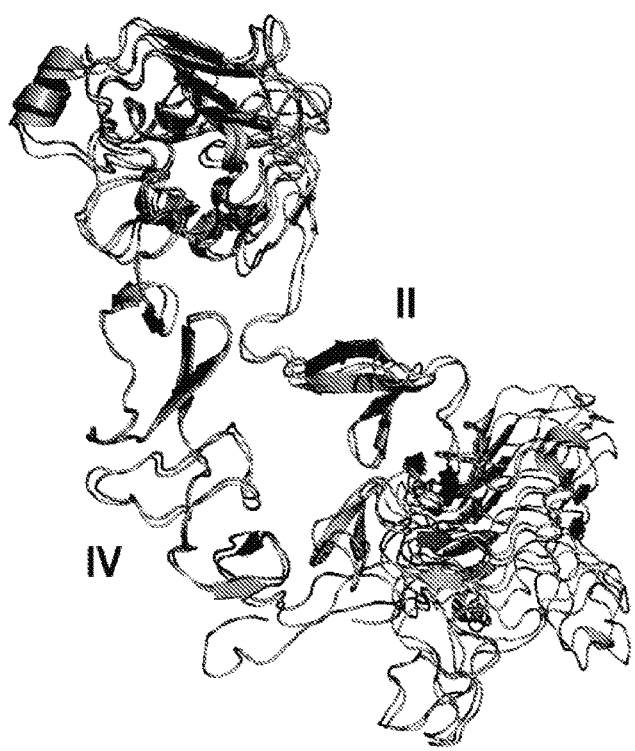
Figure 5B:
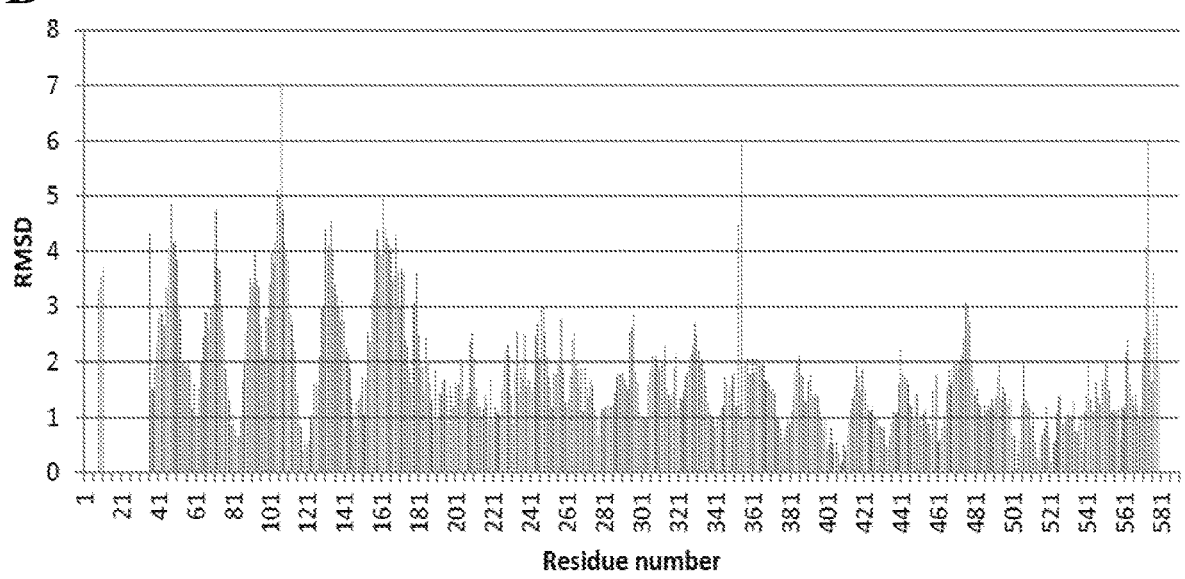

Analysis of a space-filling model of the X-ray diffraction data demonstrates binding of 2C2 to the side of ErbB3 domain III (FIG. 4). Further, interaction of 2C2 with this unique domain III epitope promotes or is associated with further intra-ErbB3 contacts between ErbB3 domains II and IV. These intra-ErbB3 points of contact between ErbB3 domains II and IV result in an overall tethered configuration of the receptor, indicating that the receptor is restricted to its auto-inhibited state. The Neuregulin binding sites in ErbB3 domains I and III are far apart from one another on 2C2-bound ErbB3. Furthermore, structure comparison reveals a high degree of similarity between the 2C2 Fab-bound ErbB3 ECD and the inactive ErbB3 ECD (PDB ID: 1M6B) (FIG. 5A-C). Taken together, these data identify a novel location in the domain III of ErbB3 that, when bound by antibody, mediates restriction of the ErbB3 receptor into an inactive state, thereby allowing for the inhibition of both ligand-dependent and ligand-independent ErbB3 receptor activation.

2C2-ErbB3 Interaction Inhibits Neuregulin Binding

Figure 6:
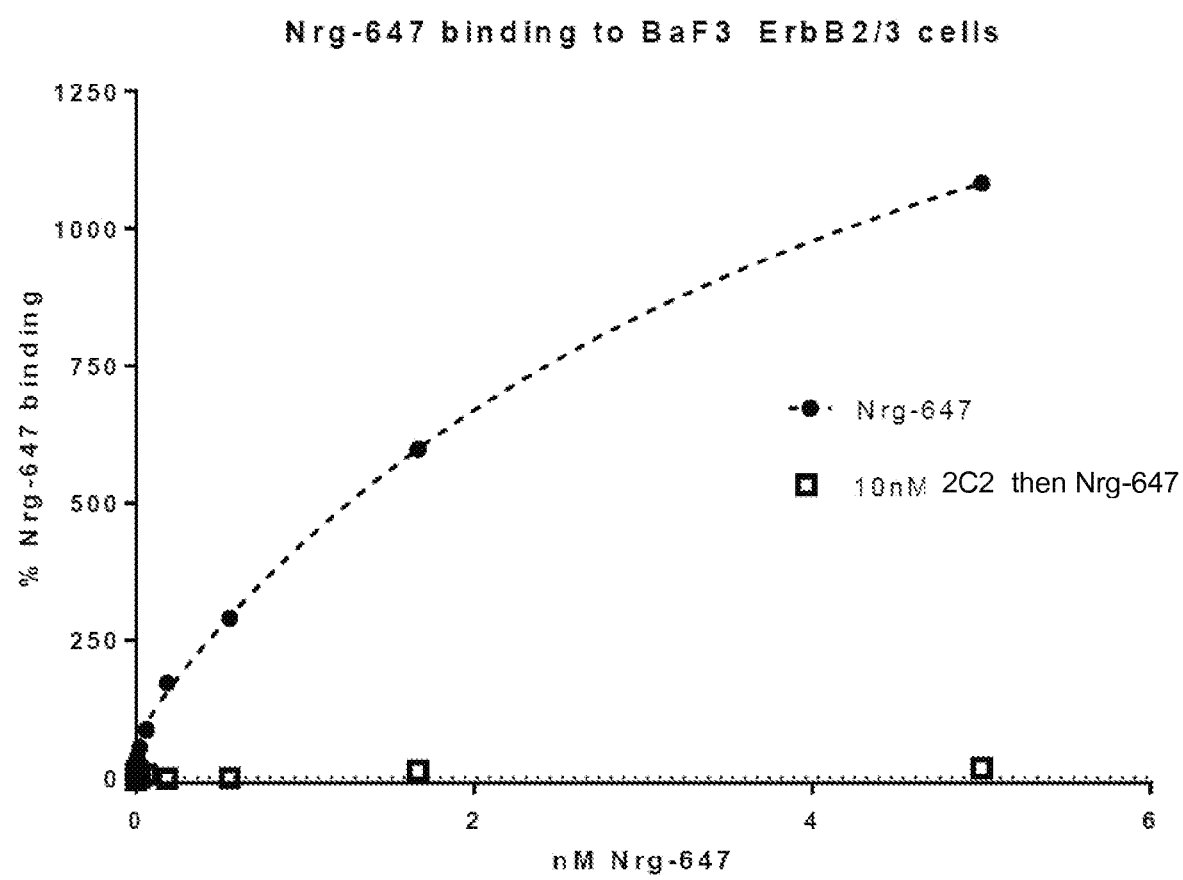

Given the distance between the Neuregulin binding sites in domains I and III of the 2C2-bound ErbB3 ECD, the impact of 2C2 on Neuregulin binding to ErbB3 was assessed. To this end, Neuregulin1-beta1 was labeled with Alexa-647 (Nrg-647) and titrated on BaF3 cells engineered to co-express ErbB2 and ErbB3, which were either untreated or pre-incubated with 2C2. Titration was performed on ice to prevent receptor internalization and FACS analysis of Nrg-647 bound to the cells was subsequently performed. The background-subtracted mean fluorescence intensity was plotted as a function of Nrg-647 concentration and the data were fit to a two-site binding isotherm. Neuregulin binds with high affinity in the absence of 2C2 pre-incubation (FIG. 6, circles), while pre-incubation of ErbB2- and ErbB3-expressing cells with 2C2 completely abrogated Nrg-647 binding (FIG. 6, squares). These data indicate that 2C2 is capable of inhibiting ligand binding to ErbB3, and as a consequence, ligand-dependent ErbB3 activation and signaling.

Figure 7:
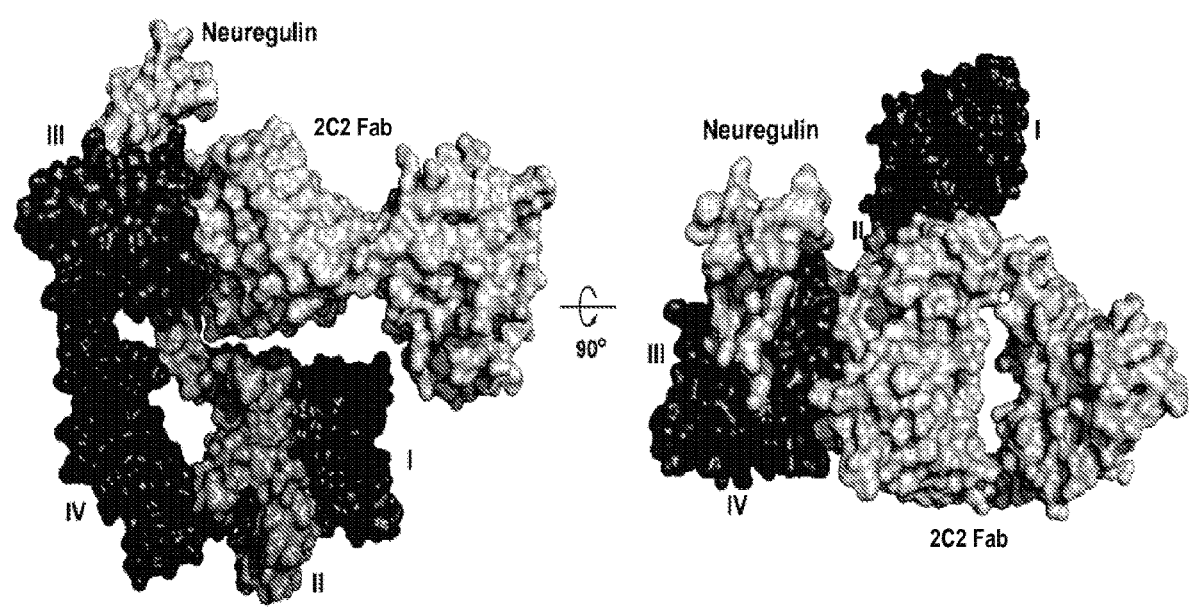

To further investigate the impact of 2C2 on Neuregulin binding to ErbB3, the structure of ligand-bound ErbB4 domain III (PDB ID: 3U7U) was superimposed on the structure of 2C2-bound to ErbB3 ECD. Surprisingly, despite the finding that 2C2 is able to ablate ligand binding to ErbB3 (FIG. 6), the Neuregulin binding site is not occluded by 2C2 (FIG. 7). Rather, the data indicate that 2C2 binding interferes with the conformational change in ErbB3 required to bring domains I and III into close proximity to allow for ligand binding to take place.

2C2 Interacts with the Domain II-III Hinge

Figure 8:
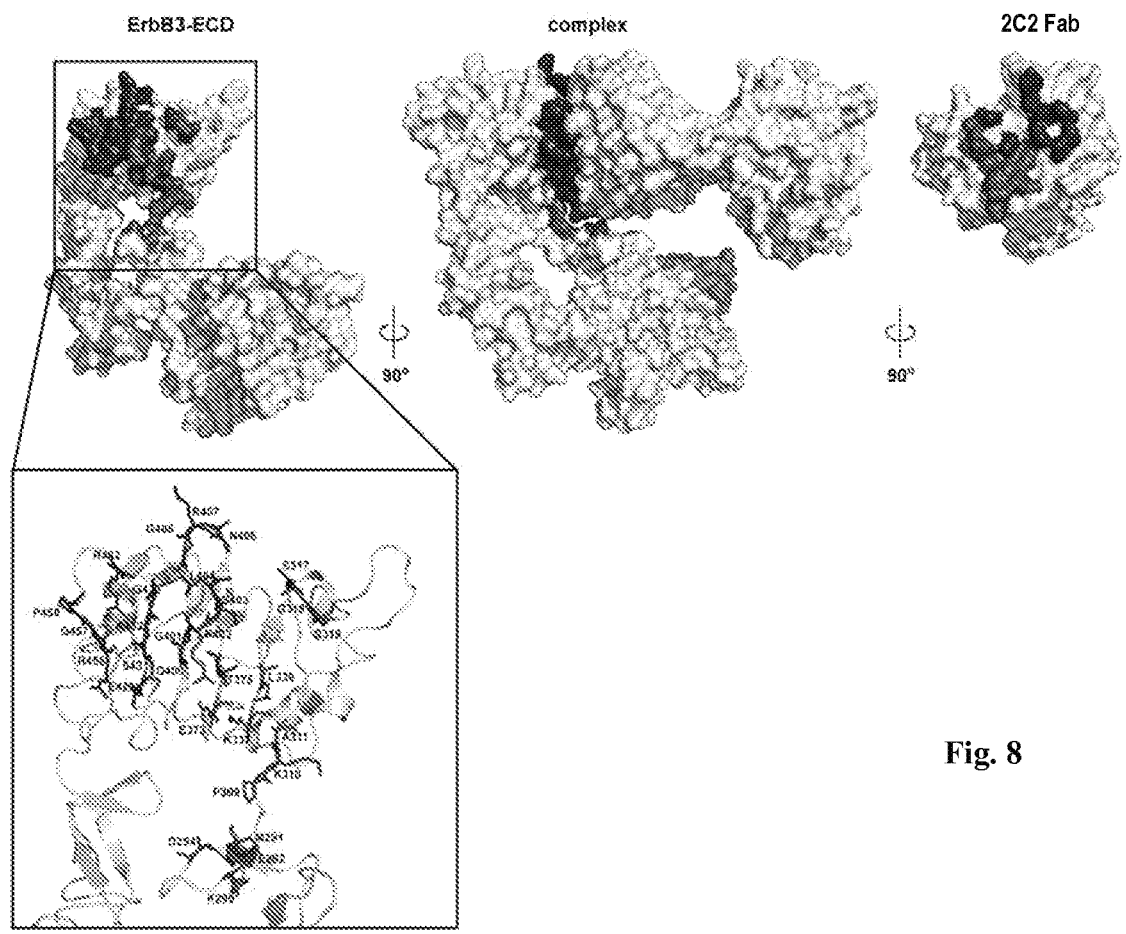
Figure 9:
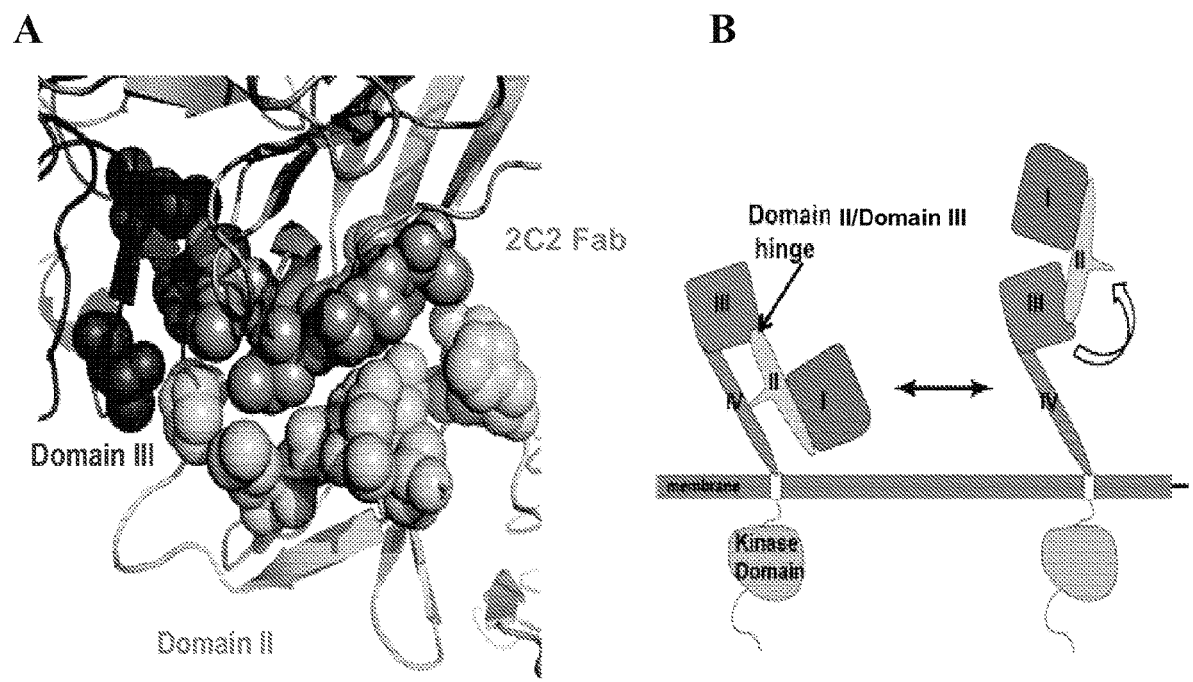

The X-Ray diffraction data was further analyzed to elucidate the contribution of both the light and the heavy chains to receptor binding. Both the heavy and light chains make robust contributions to ErbB3 binding (FIG. 8, Table 23. and Table 24). While the heavy chain binds entirely to domain III, the light chain binds to both domains II and III. Furthermore, the light chain makes several points of contact with the hinge region uniting domains II and III (the domain II/domain III hinge region) (FIG. 9A). The flexibility (or rigidity) imparted to ErbB3 by a hinge in the boundary between domains II and III is thought to be a key regulator of the receptor's ability to adopt an extended, ligand binding-competent conformation. The unique binding of the 2C2 light chain to a string of amino acids in the hinge region actively prevents the receptor from releasing itself from an auto-inhibited state (FIG. 9B).

TABLE 23

Contacts between ErbB3 ECD and 2C2 variable heavy chain region ("$V_H$") found in the crystal structure. Amino acid residues from ErbB3 ECD that contain at least one atom within 5Å of amino acid residues from 2C2 $V_H$ are listed. Amino acid numbers correspond to the mature numbering for ErbB3. See FIG. 16.

| ErbB3 ECD | | | 2C2 $V_H$ | | |
|---|---|---|---|---|---|
| Residue | Number | Domain | Residue | Number | CDR |
| Ser | 317 | 3 | Leu | 101 | 3 |
| Gly | 318 | 3 | Leu | 101 | 3 |
| Thr | 375 | 3 | Asp | 103 | 3 |
| Gly | 400 | 3 | Tyr | 33 | 1 |
| Gly | 401 | 3 | Tyr | 31 | 1 |
|  |  |  | Tyr | 33 | 1 |

TABLE 23-continued

Contacts between ErbB3 ECD and 2C2 variable heavy chain region ("$V_H$") found in the crystal structure. Amino acid residues from ErbB3 ECD that contain at least one atom within 5Å of amino acid residues from 2C2 $V_H$ are listed. Amino acid numbers correspond to the mature numbering for ErbB3. See FIG. 16.

| ErbB3 ECD | | | 2C2 $V_H$ | | |
|---|---|---|---|---|---|
| Residue | Number | Domain | Residue | Number | CDR |
| Arg | 402 | 3 | Tyr | 31 | 1 |
|  |  |  | Tyr | 33 | 1 |
|  |  |  | Val | 99 | 3 |
|  |  |  | Leu | 101 | 3 |
|  |  |  | Asp | 103 | 3 |
| Ser | 403 | 3 | Leu | 101 | 3 |
| Leu | 404 | 3 | Tyr | 31 | 1 |
|  |  |  | Ser | 53 | 2 |
| Asn | 406 | 3 | Tyr | 31 | 1 |
| Arg | 407 | 3 | Tyr | 31 | 1 |
| Gly | 408 | 3 | Tyr | 31 | 1 |
| Glu | 429 | 3 | Val | 57 | 2 |
| Ser | 431 | 3 | Tyr | 33 | 1 |
|  |  |  | Gly | 56 | 2 |
|  |  |  | Val | 57 | 2 |
| Ala | 432 | 3 | Tyr | 33 | 1 |
|  |  |  | Gly | 52 | 2 |
|  |  |  | Ser | 53 | 2 |
|  |  |  | Ser | 54 | 2 |
| Gly | 433 | 3 | Ser | 53 | 2 |
|  |  |  | Ser | 54 | 2 |
| Arg | 456 | 3 | Ser | 54 | 2 |
|  |  |  | Gly | 56 | 2 |
|  |  |  | Val | 57 | 2 |
|  |  |  | Thr | 58 | 2 |
| Gly | 457 | 3 | Ser | 54 | 2 |
|  |  |  | Gly | 55 | 2 |
|  |  |  | Gly | 56 | 2 |
|  |  |  | Val | 57 | 2 |
| Pro | 458 | 3 | Ser | 54 | 2 |
|  |  |  | Gly | 55 | 2 |
| Arg | 462 | 3 | Ser | 54 | 2 |

TABLE 24

Contacts between ErbB3 ECD and 2C2 variable light chain region ("$V_L$") found in the crystal structure. Amino acid residues from ErbB3 ECD that contain at least one atom within 5Å of amino acid residues from 2C2 $V_L$ are listed. Amino acid numbers correspond to the mature numbering for ErbB3. See FIG. 16.

| ErbB3 ECD | | | 2C2 $V_L$ | | |
|---|---|---|---|---|---|
| Residue | Number | Domain | Residue | Number | CDR |
| Met | 291 | 2 | Leu | 26 | 1 |
| Glu | 292 | 2 | Leu | 26 | 1 |
| Asp | 294 | 2 | Ser | 25 | 1 |
| Lys | 299 | 2 | Ser | 25 | 1 |
| *Pro | 309 | 2 | Leu | 26 | 1 |
|  |  |  | Leu | 31 | 1 |
| *Lys | 310 | 3 | Leu | 31 | 1 |
| *Ala | 311 | 3 | Gly | 30 | 1 |
|  |  |  | Leu | 31 | 1 |
| Gly | 318 | 3 | Arg | 51 | 2 |
| Ser | 319 | 3 | Arg | 51 | 2 |
| Lys | 337 | 3 | Leu | 31 | 1 |
|  |  |  | Asn | 32 | 1 |
|  |  |  | Asp | 94 | 3 |
| Leu | 339 | 3 | Leu | 31 | 1 |
|  |  |  | Asn | 32 | 1 |
|  |  |  | Tyr | 33 | 1 |
| Glu | 373 | 3 | Asp | 94 | 3 |
| Arg | 402 | 3 | Asn | 32 | 1 |
|  |  |  | Trp | 92 | 3 |

*denotes ErbB3 domain II/domain III hinge region residues

2C2 Exhibits Optimal Binding with ErbB3

Figure 10:
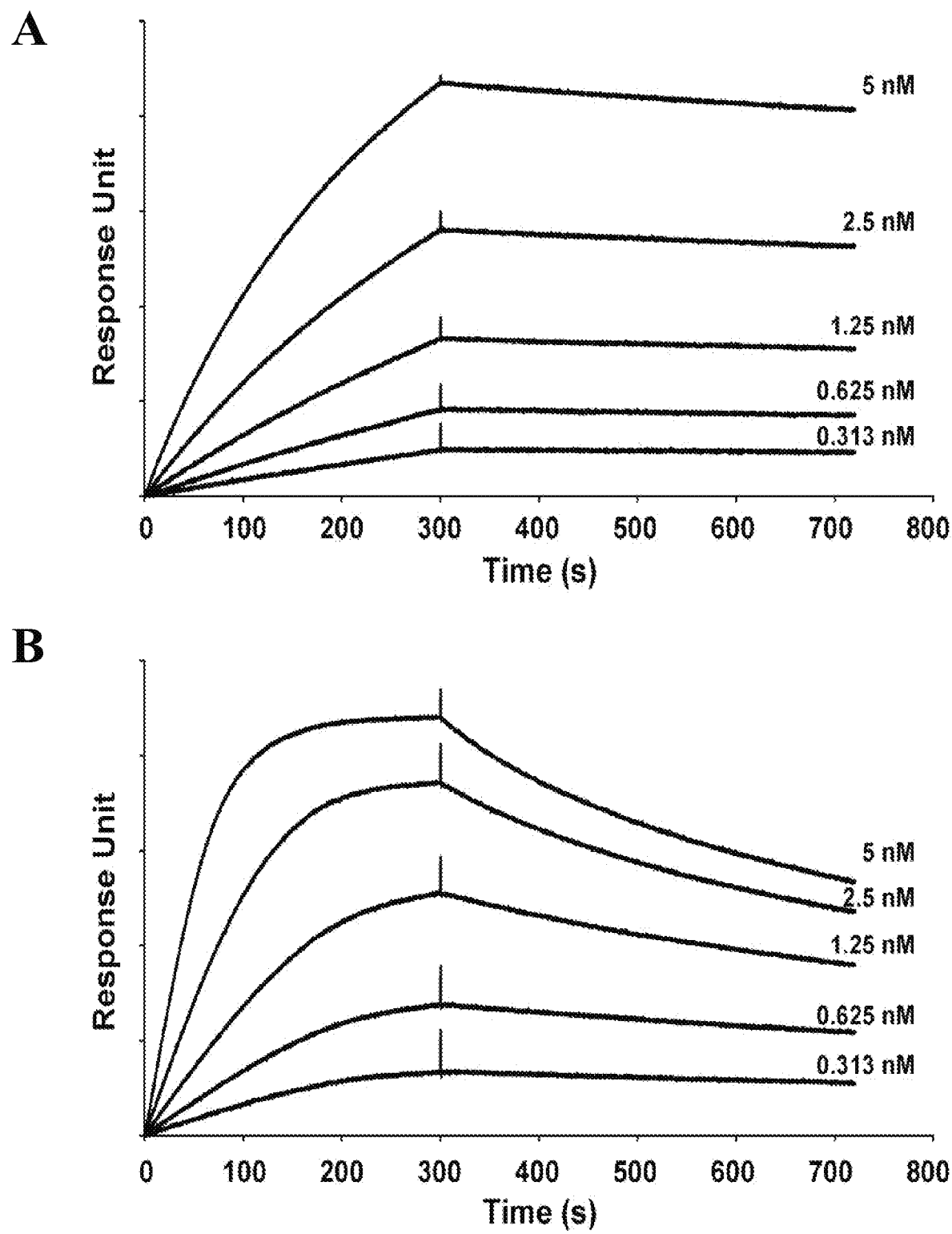

The interaction between 2C2 and domains II and III of ErbB3 elucidated from the structural analyses (FIGS. 8 and 9A-B) may contribute positively towards the binding affinity of the complex. To investigate the contribution of domains II and III to the binding affinity of the complex, surface plasmon resonance experiments were performed. A titration of purified ErbB3-ECD or ErbB3 domain III was flowed over 2C2 Fab immobilized on a sensor chip. The resulting data demonstrate that the off-rate of ErbB3-ECD is markedly slower than that of ErbB3-domain III, resulting in an overall two-fold higher affinity for ErbB3-ECD (FIGS. 10A and 10B, respectively, and Table 25). Taken together, these data demonstrate that 2C2 binds with high affinity to both ErbB3-ECD and purified ErbB3 domain III, but with a higher affinity to the ErbB3-ECD than isolated domain III, in agreement with the results presented above (see FIG. 3).

TABLE 25

Binding affinity of 2C2 Fab and ErbB3 ECD and domain III.

| | $K_D$, × $10^{-9}$M | $k_{on}$ ($M^{-1}s^{-1}$) | $k_{off}$ ($s^{-1}$) |
|---|---|---|---|
| ErbB3 ECD | 0.1661 ± 0.006 | 9.40 × $10^5$ | 1.56 × $10^{-4}$ |
| ErbB3 domain III | 0.3774 ± 0.030 | 4.65 × $10^6$ | 1.74 × $10^{-3}$ |

6.1.4 Discussion

This example demonstrates that 2C2 binds to specific amino acid residues within domainII, domain III, and the domain II/domain III hinge region. Without being bound by any theory, the data indicate that binding of antibodies that target the region of ErbB3 bound by 2C2 restrict ErbB3 to an auto-inhibited conformation, and prevent the receptor from entering the extended state required for both ligand binding, and receptor dimerization. Thus, the results presented herein identify a particular structural region within ErbB3 that, when bound by antibody, can inhibit ErbB3 signaling irrespective of its mechanism of activation, that is, can inhibit both ligand-dependent and ligand-independent ErbB3 activation.

6.2 Example 2. Generation of Antibodies that Target with High Affinity the Structural Region of ErbB3 Important for Ligand-Dependent and Ligand-Independent Receptor Activation 6.2.1 Introduction.

This example describes the successful use of the data presented above to generate antibodies targeting the structural region of ErbB3 identified in the previous example to be important for ligand-dependent and ligand-independent ErbB3 receptor activation. Importantly, these new antibodies actually bind this region with substantially higher affinity than the 2C2 antibody.

6.2.2 Materials and Methods

Preparation of 2C2 Fab Variants

The DNA sequence of the plasmid for the expression of 2C2 Fab was modified by introducing the new mutations using the QuikChange mutagenesis method. The plasmids containing the new DNA sequences were transformed into BL21(DE3). Single colonies were grown in LB media and the protein was induced with 0.4 mM IPTG for 16 hours at 18 degrees. The bacterial cells were lysed and the 2C2 Fab variants were purified employing protein A agarose (Invitrogen).

Binding Affinity Measurements

Surface plasmon resonance (SPR) experiments were performed using a BIAcore T100 instrument (GE Healthcare) at 25° C. (Keck Foundation Biotechnology Resource Laboratory, Yale University). The Fab fragment of 2C2 and two Fab variants in the light chain CDR1, namely S23R and S25H, were immobilized on a CM5 BIAcore sensorchip using a standard amine coupling method. A series of solutions of ErbB3-ECD with various concentrations was passed over the sensor chip containing the immobilized Fabs. A dissociation time of 4800 seconds was used to monitor the difference in off rate for each measurement, which was done in triplicate. Acquired data were analyzed using the evaluation software supplied with the BiaCore T100 instrument.

6.2.3 Results

2C2 Mutations to Designed to Enhance its Affinity for ErbB3

The data presented in the previous example was used to selectively choose mutations to introduce within the 2C2 heavy chain and/or light chain amino acid sequences to design antibodies that maximize interactions and improve complementarity with the domain II/domain III hinge region in ErbB3. See Table 26.

To assess such antibodies, Fabs expressed in E. coli are tested for enhanced binding to ErbB3 using standard ELISA, Surface Plasmon Resonance (SPR), kinetic exclusion assay (Kinexa), or flow cytometry methods. The ELISA, SPR and flow cytometry assays are performed as described in Section 6.1.2 or 6.2.2, supra. Antibodies that display enhanced binding in a Fab format are then converted to full IgG1 antibodies, and the increased avidity effect is measured using the same assays. In addition, their effect on inhibiting ErbB3 activation is assessed in cell-based phosphorylation and proliferative assays.

TABLE 26

ErbB3 affinity-enhancing 2C2 mutations

| 2C2 amino acid | Mutation | CDR | $V_H/V_L$ |
|---|---|---|---|
| S25 | N/T/D/R/K/H | 1 | L |
| S23 | N/D/E/Q/H/K/R | 1 | L |
| V57 | Q/T/S/N | 2 | H |
| L26 | F/Y/M/I | 1 | L |
| F101 | R/Q/L/M/I/W/Y | 3 | H |
| L31 | M | 1 | L |
| D94 | N/H | 3 | L |
| S53 | T | 2 | H |

Accordingly the 2C2 variants were generated by modifying amino acid residues in light chain CDR that make contact with D2 to extend the interactions between the antibody and ErbB3-ECD.

Enhanced Binding Affinity Antibodies

Figure 11:
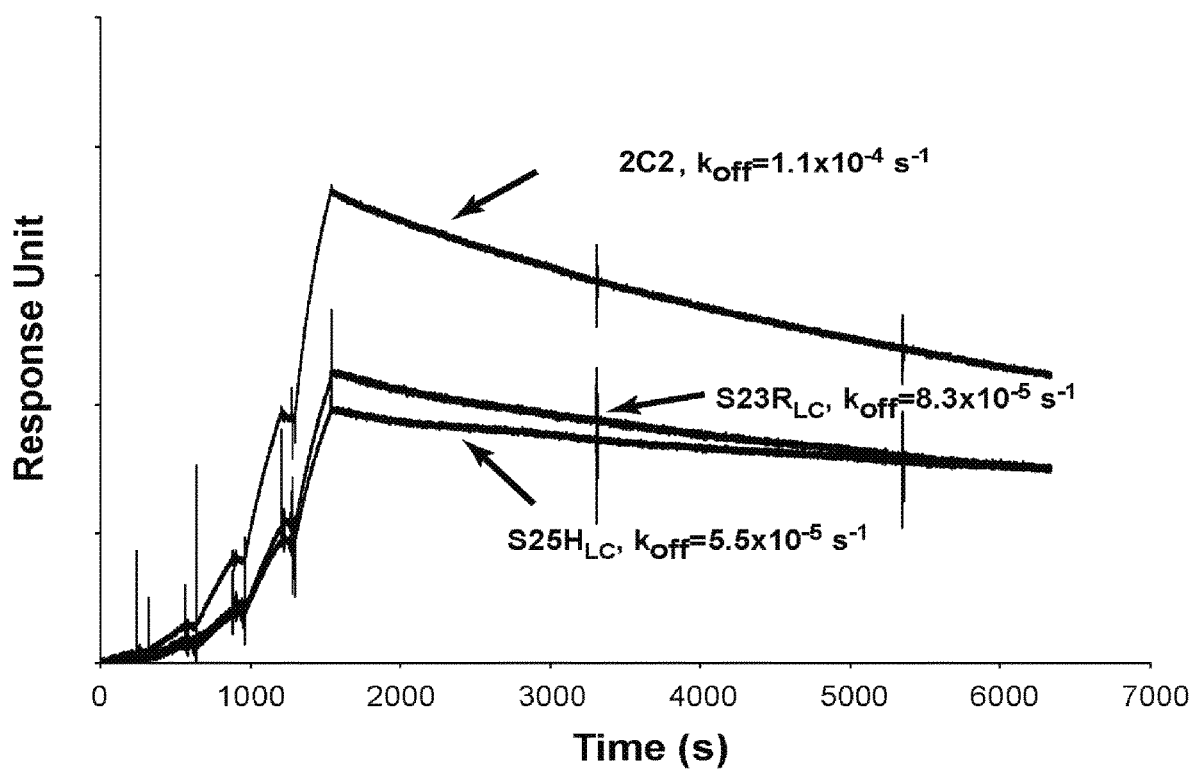

Amino acid residues 23 and 25 in the 2C2 light chain, which were shown in the previous example to be proximal to domain II in ErbB3, were modified to extend their interactions. Based on the crystal structure of ErbB3 ECD-2C2 Fab complex, elucidated as discussed in the previous example, substitution of a serine for a histidine at amino acid residue 25 (S25H) of the 2C2 light chain was predicted to introduce salt bridge or hydrogen bond interactions with ErbB3 D294. The antibody containing this mutation is referred to herein as "S25H antibody", and its Fab fragment is referred to herein as "S25H Fab". Likewise, the crystal structure data was used to predict that substitution of a serine for an arginine at amino acid residue 23 (S23R) of the 2C2 light chain was predicted to introduce hydrogen bonds with ErbB3 N274. The antibody containing this mutation is referred to herein as "S23R antibody", and its Fab fragment is referred to herein as "S23R Fab". The off-rate obtained by fitting the surface Plasmon resonance sensorgrams using 1:1 binding model indicated that both S23R and S25H substantially improved the binding of the antibody by decreasing the off-rate (FIG. 11).

6.3 Example 3. 2C2 is Capable of Binding to Most Recurring Oncogenic Mutations in the ErbB3 Ectodomain

6.3.1 Introduction.

Numerous mutations in ErbB3 have been linked to cancer (Jaiswal et al. Oncogenic ERBB3 mutations in human cancers. Cancer Cell, 2013, 23:603-317). As such, this example investigates the therapeutic capacity of antibodies that target and bind to the 2C2-binding region of ErbB3 in the context of oncogenic ErbB3 mutations.

6.3.2 Materials and Methods

Flow-Cytometry Competition Assay

His-tagged ErbB3 ectodomain variants were expressed in baculovirus-infected Sf9 cells and purified by metal affinity chromatography followed by size exclusion chromatography. A titration of each ErbB3 mutant was co-incubated with 10 nM of Alexa-647 conjugated 2C2 for 1 hour at room temperature. The mixtures were then added to T47D cells which endogenously express ErbB3 and allowed to bind for 1 hour on ice. The cells were washed in FACS buffer (PBS+2% newborn calf serum) and fluorescence measured with an Accuri C6 Flow cytometer. Data are reported as the background-subtracted mean fluorescent intensity of each sample.

ELISA Assays

Each His-tagged ErbB3 variant was expressed in baculovirus-infected Sf9 cells and purified from conditioned media using metal affinity chromatography followed by size-exclusion chromatography. Each purified variant (as well as the control his-tagged ErbB3 extracellular domain) was coated on ELISA plates. After blocking with 5% BSA in TBST, 2C2 was titrated and incubated for 1 hour. The plates were washed with TBST and incubated with an HRP-conjugated anti-human secondary antibody. The plates were washed again and read after incubation with WestPico Chemiluminescent Substrate. Binding data were plotted as a function of the log-transformed concentration of 2C2 concentration. Data were fit to a non-linear regression agonist equation with a floating Hill slope.

6.3.3 Results

2C2 Binds to Specific ErbB3 Oncogenic Mutations

Figure 12A:
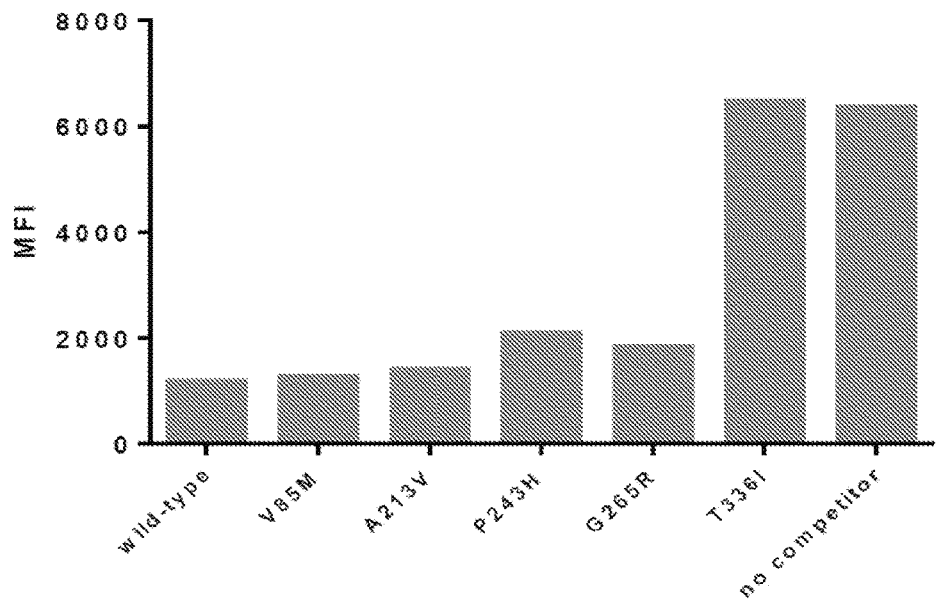

To assess the ability of 2C2 to bind to recurring oncogenic mutations, individual baculovirus-expressed His-tagged ErbB3 variants encoding oncogenic mutations were generated and purified from infected Sf9 cells (Table 27). A titration of each purified ErbB3 mutant was subsequently incubated with fluorescently conjugated 2C2. The mixtures were then incubated with T47D cells endogenously expressing ErbB3 to assess the ability of the purified ErbB3 mutant to compete off binding of fluorescently-labeled 2C2 to cell surface expressed ErbB3. FACS analysis of the mean fluorescent intensity of each sample reveals that each of the mutants, with the exception of T336I, was able to bind to and compete 2C2 off the cell surface (FIG. 12A).

TABLE 27

|  | Mature | Immature |
|---|---|---|
| Mutant1 | V85M | V104M |
| Mutant2 | A213V | A232V |
| Mutant3 | P243H | P262H |
| Mutant4 | G265R | G284R |
| Mutant5 | T336I | T355I |

Figure 12B:
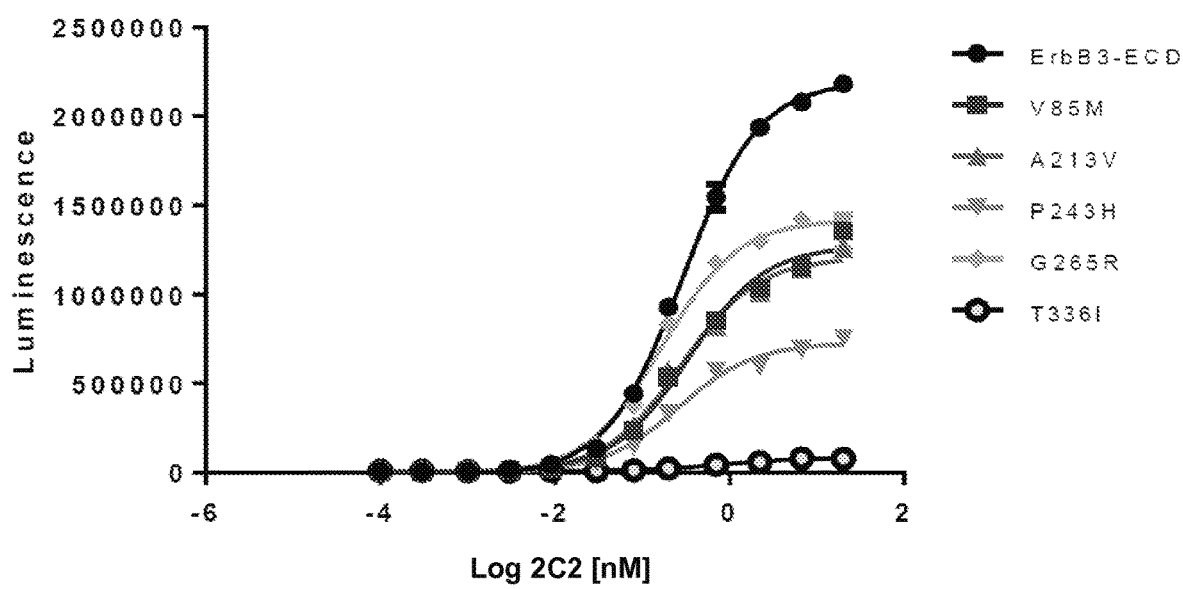

The same experiment was performed via solid-state ELISA, wherein the purified ErbB3 mutants were immobilized on ELISA plates and incubated with titrated 2C2 prior to incubation with an HRP-conjugated anti-human secondary antibody. ELISA binding data reflects the same trends observed in FIG. 12A, wherein each of the generated ErbB3 mutants, with the exception of T336I was capable of binding to 2C2 (FIG. 12B). Taken together, these data importantly demonstrate that 2C2, therefore, and antibodies that bind to the same ErbB3 region as 2C2, retain the ability to bind to ErbB3 even in the context of specific oncogenic mutations. These results also identify mutations (e.g., T336I) that can be useful in diagnostic assays and therapeutic regimens as described herein.

6.4 Example 4. Inhibition of Ligand-Dependent and Ligand-Independent ErbB1 (EGFR) and ErbB4 Activation

6.4.1 Introduction.

This example demonstrates that the general architecture of the ErbB3 2C2 epitope and structural binding region identified and shown herein to be important for ligand-dependent and ligand-independent ErbB3 activation is conserved among ErbB members. Thus, the data presented herein indicate that antibodies directed against corresponding regions of other ErbBs, such as ErbB1 (EGFR) and ErbB4, can be generated and utilized to inhibit ligand-dependent and ligand-independent activation of these ErbB members as well.

6.4.2 Materials and Methods

Sequence Alignment

The amino acid sequence of ErbB3-ECD was aligned to the amino acid sequences of EGFR and ErbB4 using Clustal Omega (provided by the European Bioinformatics Institute).

Crystal Structure Modeling

Atomic coordinates of ErbB3-ECD from the structure of ErbB3-ECD:Fab 2C2 complex were aligned to the coordinates of extracellular domain of EGFR (PDB ID: 1YY9) or ErbB4 (PDB ID: 2AHX) using Pymol.

6.4.3 Results

Figure 13A:
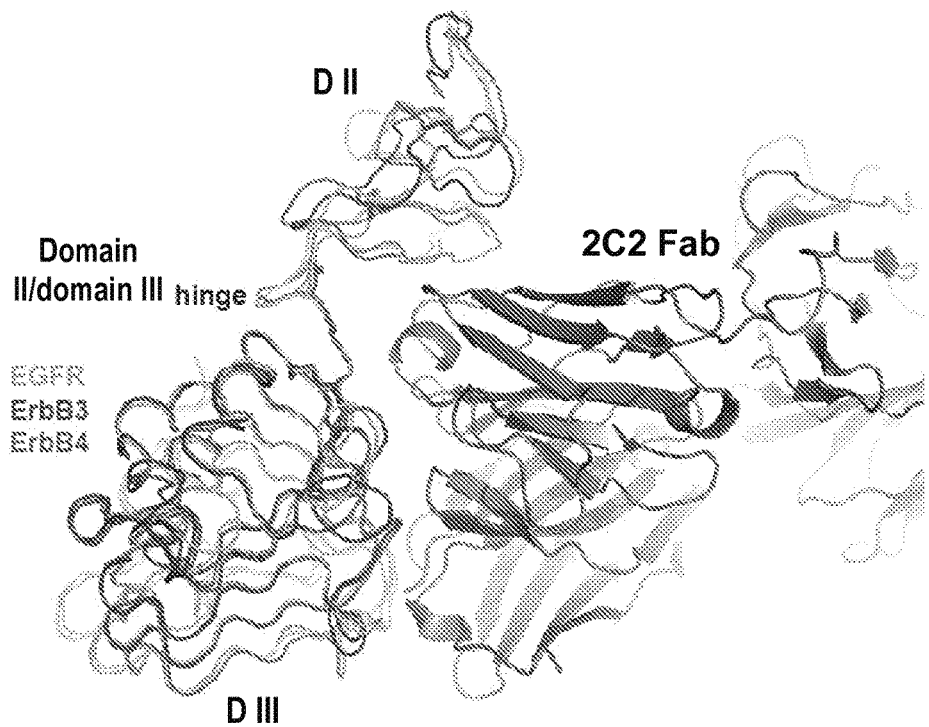
Figure 13B:
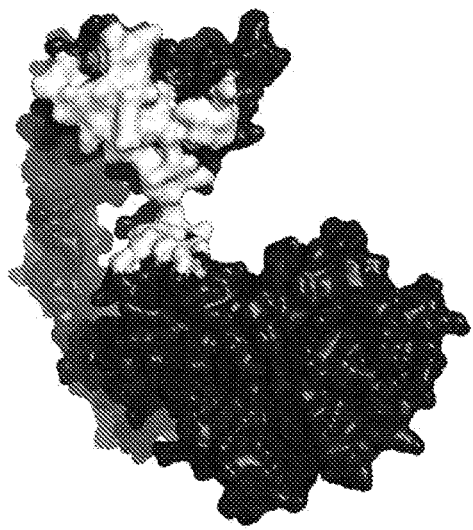
Figure 13C:
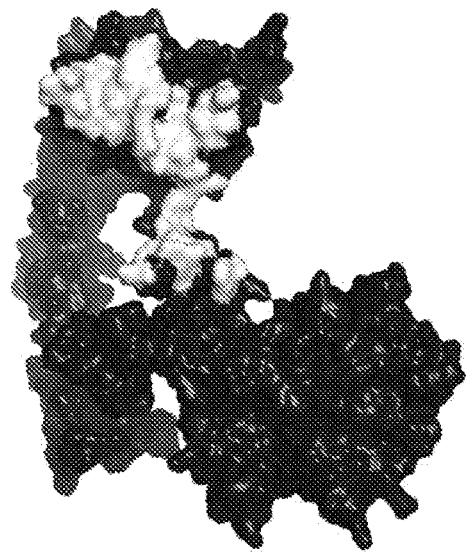

To investigate whether the ErbB3 2C2 epitope identified herein might also be present in other ErbB receptors, the crystal structures of ErbB3, ErbB1 (EGFR) and ErbB4 were compared. Superimposition of the inactive crystal structures of EGFR, ErbB3, and ErbB4, centered on domain III, reveals that the general 2C2 epitope architecture is conserved amongst these ErbB receptors (FIG. 13A-C). Furthermore, structural analyses identified several residues in both EGFR and ErbB4 that can make contact with 2C2 in a manner analogous to 2C2's binding to ErbB3 (Table 28; mature receptor amino acid numbering used). Additionally, sequence alignment of EGFR, ErbB3, and ErbB4, centered on the 2C2 binding epitope, demonstrates high sequence identity, particularly between ErbB3 and ErbB4 (FIG. 14). This conservation indicates that a biologic agent(s), such as an antibody(ies) targeted to a 2C2-like epitope of EGFR and/or ErbB4 can be used to inhibit ligand-dependent and ligand-independent activation involving ErbBs such as EGFR and/or ErbB4.

Antibody variants of 2C2 designed to enhance the affinity for EGFR and/or ErbB4 are described in Table 29. Assays described in Section 6.1.2, supra, are performed to evaluate antibody binding to ErbB3, EGFR, and ErbB4 binding and the ability of the antibodies to inhibit ligand-dependent and ligand-independent activation.

TABLE 28

| EGFR | | | ErbB4 | | |
|---|---|---|---|---|---|
| N274 | V312 | G404 | H270 | D310 | V401 |
| A286 | N314 | R405 | N271 | G313 | L403 |
| C287 | I318 | T406 | M288 | T314 | S405 |
| A289 | G319 | K407 | E289 | G315 | G406 |
| S291 | E320 | Q411 | V290 | M318 | S429 |
| Y292 | K322 | E431 | E291 | K336 | A430 |
| E293 | S340 | S433 | E292 | N338 | G431 |
| M294 | S342 | D434 | N293 | G339 | N432 |
| E295 | G343 | G458 | K296 | N340 | S454 |
| C302 | D344 | T459 | C301 | E372 | T455 |
| C309 | T378 | S460 | C305 | T374 | I456 |

TABLE 28-continued

| EGFR | | | ErbB4 | | |
|---|---|---|---|---|---|
| R310 | G379 | G461 | P306 | G399 | N457 |
| K311 | R403 | Q462 | K307 | G400 | Q458 |
|  |  |  | A308 | R401 |  |

TABLE 29

ErbB affinity-enhancing 2C2 mutations

| 2C2 amino acid | Mutation | VH/VL | ErbB receptor Affected |
|---|---|---|---|
| L31 | S/A/G/V | VL | EGFR |
| R51 | F/Y/H/A/L/I/V | VL | EGFR |
| Y31 | S/A/G | VH | EGFR |
| Y33 | F/I/V/L/A | VL | ErbB4 |
| Any 1 or more of S53, S54, G55, G56, and V57 | Delete | VH | EGFR/ErbB4 |

TABLE 30

Sequences referred to herein.

SEQ ID NO 1
Sequence
LEEKKVCQGTSNKLTQLGTFEDHFLSLQRMFNNCEVVLGNLEITYVQRNYD
LSFLKTIQEVAGYVLIALNTVERIPLENLQIIRGNMYYENSYALAVLSNYDAN
KTGLKELPMRNLQEILHGAVRFSNNPALCNVESIQWRDIVSSDFLSNMSMDF
QNHLGSCQKCDPSCPNGSCWGAGEENCQKLTKIICAQQCSGRCRGKSPSDCC
HNQCAAGCTGPRESDCLVCRKFRDEATCKDTCPPLMLYNPTTYQMDVNPEG
KYSFGATCVKKCPRNYVVTDHGSCVRACGADSYEMEEDGVRKCKKCEGPC
RKVCNGIGIGEFKDSLSINATNIKHFKNCTSISGDLHILPVAFRGDSFTHTPPLD
PQELDILKTVKEITGFLLIQAWPENRTDLHAFENLEIIRGRTKQHGQFSLAVVS
LNITSLGLRSLKEISDGDVIISGNKNLCYANTINWKKLFGTSGQKTKIISNRGE
NSCKATGQVCHALCSPEGCWGPEPRDCVSCRNVSRGRECVDKCNLLEGEPR
EFVENSECIQCHPECLPQAMNITCTGRGPDNCIQCAHYIDGPHCVKTCPAGV
MGENNTLVWKYADAGHVCHLCHPNCTYGCTGPGLEGCPTNGPKIPSIATGM
VGALLLLLVVALGIGLFMRRRHIVRKRTLRRLLQERELVEPLTPSGEAPNQAL
LRILKETEFKKIKVLGSGAFGTVYKGLWIPEGEKVKIPVAIKELREATSPKAN
KEILDEAYVMASVDNPHVCRLLGICLTSTVQLITQLMPFGCLLDYVREHKDN
IGSQYLLNWCVQIAKGMNYLEDRRLVHRDLAARNVLVKTPQHVKITDFGLA
KLLGAEEKEYHAEGGKVPIKWMALESILHRIYTHQSDVWSYGVTVWELMTF
GSKPYDGIPASEISSILEKGERLPQPPICTIDVYMIMVKCWMIDADSRPKFRELI
IEFSKMARDPQRYLVIQGDERMHLPSPTDSNFYRALMDEEDMDDVVDADEY
LIPQQGFFSSPSTSRTPLLSSLSATSNNSTVACIDRNGLQSCPIKEDSFLQRYSS
DPTGALTEDSIDDTFLPVPEYINQSVPKRPAGSVQNPVYHNQPLNPAPSRDPH
YQDPHSTAVGNPEYLNTVQPTCVNSTFDSPAHWAQKGSHQISLDNPDYQQD
FFPKEAKPNGIFKGSTAENAEYLRVAPQSSEFIGA SEQ ID NO 2
Sequence
SEVGNSQAVCPGTLNGLSVTGDAENQYQTLYKLYERCEVVMGNLEIVLTGH
NADLSFLQWIREVTGYVLVAMNEFSTLPLPNLRVVRGTQVYDGKFAIFVML
NYNTNSSHALRQLRLTQLTEILSGGVYIEKNDKLCHMDTIDWRDIVRDRDAE
IVVKDNGRSCPPCHEVCKGRCWGPGSEDCQTLTKTICAPQCNGHCFGPNPNQ
CCHDECAGGCSGPQDTDCFACRHFNDSGACVPRCPQPLVYNKLTFQLEPNP
HTKYQYGGVCVASCPHNFVVDQTSCVRACPPDKMEVDKNGLKMCEPCGGL
CPKACEGTGSGSRFQTVDSSNIDGFVNCTKILGNLDFLITGLNGDPWHKIPAL
DPEKLNVFRTVREITGYLNIQSWPPHMHNFSVFSNLTTIGGRSLYNRGFSLLI
MKNLNVTSLGFRSLKEISAGRIYISANRQLCYHHSLNWTKVLRGPTEERLDIK
HNRPRRDCVAEGKVCDPLCSSGGCWGPGPGQCLSCRNYSRGGVCVTHCNFL
NGEPREFAHEAECFSCHPECQPMEGTATCNGSGSDTCAQCAHFRDGPHCVSS
CPHGVLGAKGPIYKYPDVQNECRPCHENCTQGCKGPELQDCLGQTLVLIGKT
HLTMALTVIAGLVVIFMMLGGTFLYWRGRRIQNKRAMRRYLERGESIEPLDP
SEKANKVLARIFKETELRKLKVLGSGVFGTVHKGVWIPEGESIKIPVCIKVIED
KSGRQSFQAVTDHMLAIGSLDHAHIVRLLGLCPGSSLQLVTQYLPLGSLLDH
VRQHRGALGPQLLLNWGVQIAKGMYYLEEHGMVHRNLAARNVLLKSPSQV
QVADFGVADLLPPDDKQLLYSEAKTPIKWMALESIHFGKYTHQSDVWSYGV
TVWELMTFGAEPYAGLRLAEVPDLLEKGERLAQPQICTIDVYMVMVKCWMI
DENIRPTFKELANEFTRMARDPPRYLVIKRESGPGIAPGPEPHGLTNKKLEEV
ELEPELDLDLDLEAEEDNLATTTLGSALSLPVGTLNRPRGSQSLLSPSSGYMP
MNQGNLGESCQESAVSGSSERCPRPVSLHPMPRGCLASESSEGHVTGSEAEL TABLE 30-continued Sequences referred to herein.

| SEQ ID NO | Sequence |
|---|---|
| | QEKVSMCRSRSRSRSPRPRGDSAYHSQRHSLLTPVTPLSPPGLEEEDVNGYV MPDTHLKGTPSSREGTLSSVGLSSVLGTEEEDEDEEYEYMNRRRRHSPPHPPR PSSLEELGYEYMDVGSDLSASLGSTQSCPLHPVPIMPTAGTTPDEDYEYMNR QRDGGGPGGDYAAMGACPASEQGYEEMRAFQGPGHQAPHVHYARLKTLRS LEATDSAFDNPDYWHSRLFPKANAQRT |
| 3 | QSVCAGTENKLSSLSDLEQQYRALRKYYENCEVVMGNLEITSIEHNRDLSFL RSVREVTGYVLVALNQFRYLPLENLRIIRGTKLYEDRYALAIFLNYRKDGNF GLQELGLKNLTEILNGGVYVDQNKFLCYADTIHWQDIVRNPWPSNLTLVSTN GSSSGCGRCHKSCTGRCWGPTENHCQTLTRTVCAEQCDGRCYGPYVSDCCHR ECAGGCSGPKDTDCFACMNFNDSGACVTQCPQTFVYNPTTFQLEHNFNAKY TYGAFCVKKCPHNFVVDSSSCVRACPSSKMEVEENGIKMCKPCTDICPKACD GIGTGSLMSAQTVDSSNIDKFINCTKINGNLIFLVTGIHGDPYNAIEAIDPEKLN VFRTVREITGFLNIQSWPPNMTDFSVFSNLVTIGGRVLYSGLSLLILKQQGITS LQFQSLKEISAGNIYITDNSNLCYYHTINWTTLFSTINQRIVIRDNRKAENCTA EGMVCNHLCSSDGCWGPGPDQCLSCRRFSRGRICIESCNLYDGEFREFENGSI CVECDPQCEKMEDGLLTCHGPGPDNCTKCSHFKDGPNCVEKCPDGLQGANS FIFKYADPDRECHPCHPNCTQGCNGPTSHDCIYYPWTGHSTLPQHARTPLIAA GVIGGLFILVIVGLTFAVYVRRKSIKKKRALRRFLETELVEPLTPSGTAPNQAQ LRILKETELKRVKVLGSGAFGTVYKGIWVPEGETVKIPVAIKILNETTGPKAN VEFMDEALIMASMDHPHLVRLLGVCLSPTIQLVTQLMPHGCLLEYVHEHKD NIGSQLLLNWCVQIAKGMMYLEERRLVHRDLAARNVLVKSPNHVKITDPGL ARLLEGDEKEYNADGGKMPIKWMALECIHYRKFTHQSDVWSYGVTIWELM TFGGKPYDGIPTREIPDLLEKGERLPQPPICTIDVYMVMVKCWMIDADSRPKF KELAAEFSRMARDPQRYLVIQGDDRMKLPSPNDSKFFQNLLDEEDLEDMMD AEEYLVPQAFNIPPPIYTSRARIDSNRSEIGHSPPPAYTPMSGNQFVYRDGGFA AEQGVSVPYRAPTSTIPEAPVAQGATAEIFDDSCCNGTLRKPVAPHVQEDSST QRYSADPTVFAPERSPRGELDEEGYMTPMRDKPKQEYLNPVEENPFVSRRKN GDLQALDNPEYHNASNGPPKAEDEYVNEPLYLNTFANTLGKAEYLKNNILS MPEKAKKAFDNPDYWNHSLPPRSTLQHPDYLQEYSTKYFYKQNGRIRPIVAE NPEYLSEFSLKPGTVLPPPPYRHRNTVV |
| 4 | EVQLLESGGGLVQPGGSLRLSCAASGFTFSYYYMQWVRQAPGKGLEWVSYI GSSGGVTNYADSVKGRFTISRDNSKNTLYLQMNSLRAEDTAVYYCARVGLG DAFDIWGQGTMVTVSS |
| 5 | QSVLTQPPSASGTPGQRVTISCSGSLSNIGLNYVSWYQQLPGTAPKLLISRNN QRPSGVPDRFSGSKSGTSASLAISGLRSEDEADYYCAAWDDSPPGEAFGGGT KLTVL |
| 6 | YYYMQ |
| 7 | YIGSSGGVTNYADSVKG |
| 8 | VGLGDAFDI |
| 9 | SGSLSNIGLNYVS |
| 10 | RNNQRPS |
| 11 | AAWDDSPPGEA |
| 12 | GFTFSYYYM |
| 13 | GSSGG |
| 14 | VGLGDAFDI |
| 15 | SGSLSNIGLNYVS |
| 16 | RNNQRPS |
| 17 | AAWDDSPPGEA |
| 18 | GFTFSYYY |
| 19 | IGSSGGVT |
| 20 | ARVGLGDAFDI |
| 21 | LSNIGLNY |
| 22 | RNN |
| 23 | AAWDDSPPGEA |

TABLE 30-continued

Sequences referred to herein.

| SEQ ID NO | Sequence |
|---|---|
| 24 | YIGX₁SGGX₂TNYADSVKG, wherein X₁ represents amino acid residues S or T and X₂ represents amino acid residues V, Q, T, S, or N |
| 25 | GXSGG, wherein X represents amino acid residues S or T |
| 26 | IGX₁SGGX₂T, wherein X₁ represents amino acid residues S or T and X₂ represents amino acid residues V, Q, T, S, or N |
| 27 | VGXGDAFDI, wherein X represents amino acid residues R, Q, L, M, I, W, or Y |
| 28 | VGXGDAFDI, wherein X represents amino acid residues R, Q, L, M, I, W, or Y |
| 29 | ARVGXGDAFDI, wherein X represents amino acid residues R, Q, L, M, I, W, or Y |
| 30 | X₁GX₂X₃SNIGX₄NYVS, wherein X₁ represents amino acid residues S, N, D, E, Q, H, R or K; X₂ represents amino acid residues S, N, T, D, R, K, H, F, or Y; X₃ represents amino acid residues L, F, Y, M, or I; and X₄ represents amino acid residues L or M |
| 31 | X₁GX₂X₃SNIGX₄NYVS, wherein X₁ represents amino acid residues S, N, D, E, Q, H, R or K; X₂ represents amino acid residues S, N, T, D, R, K, H, F, or Y; X₃ represents amino acid residues L, F, Y, M, or I, and X₄ represents amino acid residues L or M |
| 32 | X₁SNIGX₂NY, wherein X₁ represents amino acid residues L, F, Y, M, or I, and X₂ represents amino acid residues L or M |
| 33 | AAWDXSPPGEA, wherein X represents amino acid residues D, N, or H |
| 34 | AAWDXSPPGEA, wherein X represents amino acid residues D, N, or H |
| 35 | AAWDXSPPGEA, wherein X represents amino acid residues D, N, or H |
| 36 | XGSLSNIGLNYVS, wherein X is R, N, D, E, Q, or H |
| 37 | XGSLSNIGLNYVS, wherein X is R, N, D, E, Q, or H |
| 38 | SGXLSNIGLNYVS, wherein X is H, N, T, D, R, L, F, or Y |
| 39 | SGXLSNIGLNYVS, wherein X is H, N, T, D, R, L, F, or Y |
| 40 | SGSXSNIGLNYVS, wherein X is I, M, F, or Y |
| 41 | SGSXSNIGLNYVS, wherein X is I, M, F, or Y |
| 42 | XSNIGLNY, wherein X is I, M, F, or Y |
| 43 | X₁GX₂LSNIGLNYVS, wherein X₁ is R, N, E, Q, H, or K and X₂ is H, N, T, D, R, L, F or Y |
| 44 | X₁GX₂LSNIGLNYVS, wherein X₁ is R, N, E, Q, H, or K and X₂ is H, N, T, D, R, L, F or Y |
| 45 | YIGSSGGVTNYADSXKG, wherein X is Q, T, S or N |
| 46 | XGSLSNIGLNYVS, wherein X is R, N, E, Q, H, or K |
| 47 | XGSLSNIGLNYVS, wherein X is R, N, E, Q, H, or K |
| 48 | X₁GSX₂SNIGLNYVS, wherein X₁ is R, N, E, Q, H, or K and X₂ is I, M, F or Y |
| 49 | X₁GSX₂SNIGLNYVS, wherein X₁ is R, N, E, Q, H, or K and X₂ is I, M, F or Y |
| 50 | SGX₁X₂SNIGLNYVS, wherein X₁ is H, N, T, D, R, L, F or Y and X₂ is I, M, F or Y |
| 51 | SGX₁X₂SNIGLNYVS, wherein X₁ is H, N, T, D, R, L, F or Y and X₂ is I, M, F or Y |
| 52 | X₁GX₂LSNIGLNYVS, wherein X₁ is R, N, D, E, Q, H, or K, X₂ is H, N, T, D, R, L, F or Y |
| 53 | X₁GX₂LSNIGLNYVS, wherein X₁ is R, N, D, E, Q, H, or K, X₂ is H, N, T, D, R, L, F or Y |

TABLE 30-continued

Sequences referred to herein.

| SEQ ID NO | Sequence |
|---|---|
| 54 | $X_1GX_2X_3$SNIGLNYVS, wherein $X_1$ is R, N, D, E, Q, H or K, $X_2$ is H, N, T, D, R, L, F or Y and $X_3$ is I, M, F or Y |
| 55 | $X_1GX_2X_3$SNIGLNYVS, wherein $X_1$ is R, N, D, E, Q, H or K, $X_2$ is H, N, T, D, R, L, F or Y and $X_3$ is I, M, F or Y |
| 56 | XYYMQ, wherein X represents amino acid residues Y, S, A, or G |
| 57 | GFTFSXYYM, wherein X is Y, S, A, or G |
| 58 | GFTFSXYY, wherein X represents amino acid residues Y, S, A, or G |
| 59 | SGSLSNIGXNYVS, wherein X represents amino acid residues L, S, A, G or V |
| 60 | SGSLSNIGXNYVS, wherein X represents amino acid residues L, S, A, G or V |
| 61 | LSNIGXNY, wherein X represents amino acid residues L, S, A, G or V |
| 62 | XNNQRPS, wherein X represents amino acid residues R, F, Y, H, A, L, I or V |
| 63 | XNNQRPS, wherein X represents amino acid residues R, F, Y, H, A, L, I or V |
| 64 | XNN, wherein X represents amino acid residues R, F, Y, H, A, L, I or V |
| 65 | XYYMQ, wherein X is S, A, or G |
| 66 | GFTFSXYYM, wherein X is S, A, or G |
| 67 | GFTFSXYY, wherein X is S, A, or G |
| 68 | SGSLSNIGXNYVS, wherein X is S, A, G, or V |
| 69 | SGSLSNIGXNYVS, wherein X is S, A, G, or V |
| 70 | LSNIGXNY, wherein X is S, A, G, or V |
| 71 | XNNQRPS, wherein X is F, Y, H, A, L, I, or V |
| 72 | XNNQRPS, wherein X is F, Y, H, A, L, I, or V |
| 73 | XNN, wherein X is F, Y, H, A, L, I, or V |
| 74 | SGSLSNIGLNXVS, wherein X is Y, F, I, V, L or A |
| 75 | SGSLSNIGLNXVS, wherein X is Y, F, I, V, L or A |
| 76 | LSNIGLNX, wherein X is Y, F, I, V, L or A |
| 77 | QSVLTQPPSASGTPGQRVTISC |
| 78 | WYQQLPGTAPKLLIS |
| 79 | GVPDRFSGSKSGX$_1$X$_2$ASLAISGLRSEDEADYYC, wherein $X_1$ is T, N or Y and $X_2$ is S, N, H, Y, K or R |
| 80 | FGGGTKLTVLGQPKAAPSVTL |
| 81 | EVQLLESGGGLVQPGGSLRLSCAASGFTFS |
| 82 | WVRQAPGKGLEWVS |
| 83 | RFTISRDNSKNTLYLQMNSLRAEDTAVYYCAR |
| 84 | WGQGTMVTVSS |
| 85 | QSVLTQPPSASGTPGQRVTISC |
| 86 | WYQQLPGTAPKLLIS |
| 87 | GVPDRFSGSKSGX$_1$X$_2$ASLAISGLRSEDEADYYC, wherein $X_1$ is T, N or Y and $X_2$ is S, N, H, Y, K or R |
| 88 | FGGGTKLTV |
| 89 | EVQLLESGGGLVQPGGSLRLSCAAS |

TABLE 30-continued

Sequences referred to herein.

| SEQ ID NO | Sequence |
|---|---|
| 90 | QWVRQAPGKGLEWVSYI |
| 91 | VTNYADSX$_1$KGRFTISRDNSKNTLYLQMNSLRAEDTAVYYCAR, wherein X$_1$ is V, Q, T, S, or N |
| 92 | WGQGTMVTVSS |
| 93 | QSVLTQPPSASGTPGQRVTISCX$_1$GX$_2$, wherein X$_1$ is S, R, N, D, E, Q, or H, and X$_2$ is S, H, N, T, D, R, L, F, or Y |
| 94 | VSWYQQLPGTAPKLLIS |
| 95 | QRPSGVPDRFSGSKSGX$_1$X$_2$ASLAISGLRSEDEADYYC, wherein X$_1$ is T, N or Y and X$_2$ is S, N, H, Y, K or R |
| 96 | FGGGTKLTVL |
| 97 | EVQLLESGGGLVQPGGSLRLSCAAS |
| 98 | MQWVRQAPGKGLEWVSY |
| 99 | NYADSX$_1$KGRFTISRDNSKNTLYLQMNSLRAEDTAVYYC wherein X$_1$ is V, Q, T, S, or N |
| 100 | WGQGTMVTVSS |
| 101 | QSVLTQPPSASGTPGQRVTISCXGSLSNIGLNYVSWYQQLPGTAPKLLISRNN QRPSGVPDRFSGSKSGTSASLAISGLRSEDEADYYCAAWDDSPPGEAFGGGT KLTVL, wherein X is R, N, D, E, Q, or H |
| 102 | QSVLTQPPSASGTPGQRVTISCSGXLSNIGLNYVSWYQQLPGTAPKLLISRNN QRPSGVPDRFSGSKSGTSASLAISGLRSEDEADYYCAAWDDSPPGEAFGGGT KLTVL, wherein X is H, N, T, D, R, L, F, or Y |
| 103 | EVQLLESGGGLVQPGGSLRLSCAASGFTFSYYYMQWVRQAPGKGLEWVSYI GSSGGVTNYADSXKGRFTISRDNSKNTLYLQMNSLRAEDTAVYYCARVGLG DAFDIWGQGTMVTVSS, wherein X is Q, T, S, or N |
| 104 | QSVLTQPPSASGTPGQRVTISCSGSXSNIGLNYVSWYQQLPGTAPKLLISRNN QRPSGVPDRFSGSKSGTSASLAISGLRSEDEADYYCAAWDDSPPGEAFGGGT KLTVL, wherein X is I, M, F, or Y |
| 105 | QSVLTQPPSASGTPGQRVTISCX$_1$GX$_2$LSNIGLNYVSWYQQLPGTAPKLLISRN NQRPSGVPDRFSGSKSGTSASLAISGLRSEDEADYYCAAWDDSPPGEAFGGG TKLTVL, wherein X$_1$ is R, N, E, Q, H, or K, and X$_2$ is H, N, T, D, R, L, F, or Y |
| 106 | QSVLTQPPSASGTPGQRVTISCXGSLSNIGLNYVSWYQQLPGTAPKLLISRNN QRPSGVPDRFSGSKSGTSASLAISGLRSEDEADYYCAAWDDSPPGEAFGGGT KLTVL, wherein X is R, N, E, Q, H, or K |
| 107 | QSVLTQPPSASGTPGQRVTISCX$_1$GSX$_2$SNIGLNYVSWYQQLPGTAPKLLISRN NQRPSGVPDRFSGSKSGTSASLAISGLRSEDEADYYCAAWDDSPPGEAFGGG TKLTVL, wherein X$_1$ is R, N, E, Q, H, or K and wherein X$_2$ is I, M, F, or Y |
| 108 | QSVLTQPPSASGTPGQRVTISCSGX$_1$X$_2$SNIGLNYVSWYQQLPGTAPKLLISRN NQRPSGVPDRFSGSKSGTSASLAISGLRSEDEADYYCAAWDDSPPGEAFGGG TKLTVL, wherein X$_1$ is H, N, T, D, R, L, F, or Y, and X$_2$ is I, M, F, or Y |
| 109 | QSVLTQPPSASGTPGQRVTISCX$_1$GX$_2$LSNIGLNYVSWYQQLPGTAPKLLISRN NQRPSGVPDRFSGSKSGTSASLAISGLRSEDEADYYCAAWDDSPPGEAFGGG TKLTVL, wherein X$_1$ is R, N, D, E, Q, H, or K, and X$_2$ is H, N, T, D, R, L, F, or Y |
| 110 | QSVLTQPPSASGTPGQRVTISCX$_1$GX$_2$X$_3$SNIGLNYVSWYQQLPGTAPKLLISR NNQRPSGVPDRFSGSKSGTSASLAISGLRSEDEADYYCAAWDDSPPGEAFGG GTKLTVL, wherein X$_1$ is R, N, D, E, Q, H, or K, X$_2$ is H, N, T, D, R, L, F, or Y, and X$_3$ is I, M, F, or Y |
| 111 | EVQLLESGGGLVQPGGSLRLSCAASGFTFSXYYMQWVRQAPGKGLEWVSYI GSSGGVTNYADSVKGRFTISRDNSKNTLYLQMNSLRAEDTAVYYCARVGLG DAFDIWGQGTMVTVSS, wherein X is S, A, or G |
| 112 | QSVLTQPPSASGTPGQRVTISCSGSLSNIGLNYVSWYQQLPGTAPKLLISRNN QRPSGVPDRFSGSKSGX$_1$X$_2$ASLAISGLRSEDEADYYCAAWDDSPPGEAFGGG TKLTVL, wherein X$_1$ is N, H, Y, K, or R, and X$_2$ is N or Y |

TABLE 30-continued

Sequences referred to herein.

| SEQ ID NO | Sequence |
|---|---|
| 113 | QSVLTQPPSASGTPGQRVTISCSGSLSNIGLNYVSWYQQLPGTAPKLLISXNN QRPSGVPDRFSGSKSGTSASLAISGLRSEDEADYYCAAWDDSPPGEAFGGGT KLTVL, wherein X is F, Y, H, A, L, I, or V |
| 114 | QSVLTQPPSASGTPGQRVTISCSGSLSNIGX$_1$NYVSWYQQLPGTAPKLLISX$_2$N NQRPSGVPDRFSGSKSGTSASLAISGLRSEDEADYYCAAWDDSPPGEAFGGG TKLTVL, wherein X$_1$ is S, A, G, or V and X$_2$ is F, Y, H, A, L, I, or V |
| 115 | QSVLTQPPSASGTPGQRVTISCSGSLSNIGXNYVSWYQQLPGTAPKLLISRNN QRPSGVPDRFSGSKSGTSASLAISGLRSEDEADYYCAAWDDSPPGEAFGGGT KLTVL, wherein X is S, A, G, or V |
| 116 | EVQLLESGGGLVQPGGSLRLSCAASGFTFSXYYMQWVRQAPGKGLEWVSYI GSSGGVTNYADSVKGRFTISRDNSKNTLYLQMNSLRAEDTAVYYCARVGLG DAFDIWGQGTMVTVSS, wherein X is S, A, or G, or V |
| 117 | QSVLTQPPSASGTPGQRVTISCSGSLSNIGLNXVSWYQQLPGTAPKLLISRNN QRPSGVPDRFSGSKSGTSASLAISGLRSEDEADYYCAAWDDSPPGEAFGGGT KLTVL, wherein X is Y, F, I, V, L, or A. |
| 118 | QSVLTQPPSASGTPGQRVTISCSGSLSNIGLNYVSWYQQLPGTAPKLLISRNN QRPSGVPDRFSGSKSGX$_1$X$_2$ASLAISGLRSEDEADYYCAAWDDSPPGEAFGGG TKLTVL, wherein X$_1$ is T, N or Y and X$_2$ is S, N, H, Y, K or R |
| 119 | MSERKEGRGKGKGKKKERGSGKKPESAAGSQSPALPPRLKEMKSQESAAGS KLVLRCETSSEYSSLRFKWFKNGNELNRKNKPQNIKIQKKPGKSELRINKASL ADSGEYMCKVISKLGNDSASANITIVESNEIITGMPASTEGAYVSSESPIRISVS TEGANTSSSTSTSTTGTSHLVKCAEKEKTFCVNGGECFMVKDLSNPSRYLCK CPNEFTGDRCQNYVMASFYKHLGIEFMEAEELYQKRVLTITGICIALLVVGIM CVVAYCKTKKQRKKLHDRLRQSLRSERNNMMNIANGPHHPNPPPENVQLV NQYVSKNVISSEHIVEREAETSFSTSHYTSTAHHSTTVTQTPSHSWSNGHTESI LSESHSVIVMSSVENSRHSSPTGGPRGRLNGTGGPRECNSFLRHARETPDSYR DSPHSERYVSAMTTPARMSPVDFHTPSSPKSPPSEMSPPVSSMTVSMPSMAVS PFMEEERPLLLVTPPRLREKKFDHHPQQFSSFHHNPAHDSNSLPASPLRIVEDE EYETTQEYEPAQEPVKKLANSRRAKRTKPNGHIANRLEVDSNTSSQSSNSESE TEDERVGEDTPFLGIQNPLAASLEATPAFRLADSRTNPAGRFSTQEEIQARLSS VIANQDPIAV |

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

What is claimed:

1. An isolated antibody or fragment thereof that binds to ErbB3, wherein the antibody or fragment thereof comprises:
  (a) a variable heavy chain region (VH) complementarity determining region (CDR)1 comprising the following amino acid sequence: YYYMQ (SEQ ID NO: 6);
  (b) a VH CDR2 comprising the following amino acid sequence: YIGSSGGVTNYADSVKG (SEQ ID NO: 7);
  (c) a VH CDR3 comprising the following amino acid sequence: VGLGDAFDI (SEQ ID NO: 8);
  (d) a variable light chain region (VL) CDR1 comprising the following amino acid sequence: $X_4GX_5LSNIGLNYVS$ (SEQ ID NO: 30);
  (e) a VL CDR2 comprising the following amino acid sequence: RNNQRPS (SEQ ID NO: 10); and
  (f) a VL CDR3 comprising the following amino acid sequence: AAWDDSPPGEA (SEQ ID NO: 11);
wherein $X_4$ represents amino acid residue R and $X_5$ represents amino acid residue H.

2. The antibody or fragment thereof of claim 1, wherein the antibody is a bispecific antibody or dual specificity antibody.

3. The antibody or fragment thereof of claim 1, wherein the antibody is a humanized antibody.

4. The antibody or fragment thereof of claim 1, wherein the antibody is a monoclonal antibody.

5. An isolated antibody or fragment thereof that binds to ErbB3, wherein the antibody or fragment thereof comprises:
  (a) a variable heavy chain region (VH) complementarity determining region (CDR)1 comprising the following amino acid sequence: YYYMQ (SEQ ID NO: 6);
  (b) a VH CDR2 comprising the following amino acid sequence: YIGSSGGVTNYADSVKG (SEQ ID NO: 7);
  (c) a VH CDR3 comprising the following amino acid sequence: VGLGDAFDI (SEQ ID NO: 8);
  (d) a variable light chain region (VL) CDR1 comprising the following amino acid sequence: $X_4GX_5LSNIGLNYVS$ (SEQ ID NO: 30);
  (e) a VL CDR2 comprising the following amino acid sequence: RNNQRPS (SEQ ID NO: 10); and
  (f) a VL CDR3 comprising the following amino acid sequence: AAWDDSPPGEA (SEQ ID NO: 11);
wherein $X_4$ represents amino acid residue R and $X_5$ represents amino acid residue S.

6. The antibody or fragment thereof of claim 5, wherein the antibody is a bispecific antibody or dual specificity antibody.

7. The antibody or fragment thereof of claim 5, wherein the antibody is a humanized antibody.

8. The antibody or fragment thereof of claim 5, wherein the antibody is a monoclonal antibody.

9. An isolated antibody or fragment thereof that binds to ErbB3, wherein the antibody or fragment thereof comprises:
  (a) a variable heavy chain region (VH) complementarity determining region (CDR)1 comprising the following amino acid sequence: YYYMQ (SEQ ID NO: 6);
  (b) a VH CDR2 comprising the following amino acid sequence: YIGSSGGVTNYADSVKG (SEQ ID NO: 7);
  (c) a VH CDR3 comprising the following amino acid sequence: VGLGDAFDI (SEQ ID NO: 8);
  (d) a variable light chain region (VL) CDR1 comprising the following amino acid sequence: $X_4GX_5LSNIGLNYVS$ (SEQ ID NO: 30);
  (e) a VL CDR2 comprising the following amino acid sequence: RNNQRPS (SEQ ID NO: 10); and
  (f) a VL CDR3 comprising the following amino acid sequence: AAWDDSPPGEA (SEQ ID NO: 11);
wherein $X_4$ represents amino acid residue S and $X_5$ represents amino acid residue H.

10. The antibody or fragment thereof of claim 9, wherein the antibody is a bispecific antibody or dual specificity antibody.

11. The antibody or fragment thereof of claim 9, wherein the antibody is a humanized antibody.

12. The antibody or fragment thereof of claim 9, wherein the antibody is a monoclonal antibody.

* * * * *

SEQUENCE LISTING

```
<160> NUMBER OF SEQ ID NOS: 119

<210> SEQ ID NO 1
<211> LENGTH: 1186
<212> TYPE: PRT
<213> ORGANISM: Homo sapiens
<220> FEATURE:
<223> OTHER INFORMATION: an exemplary amino acid sequence of mature
      human ErbB1 corresponding to amino acid 25 to 1,210 of Genbank
      accession number NP_005219.2

<400> SEQUENCE: 1

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30
```

```
Asn Cys Glu Val Val Leu Gly Asn Leu Glu Ile Thr Tyr Val Gln Arg
         35                  40                  45

Asn Tyr Asp Leu Ser Phe Leu Lys Thr Ile Gln Glu Val Ala Gly Tyr
 50                  55                  60

Val Leu Ile Ala Leu Asn Thr Val Glu Arg Ile Pro Leu Glu Asn Leu
 65                  70                  75                  80

Gln Ile Ile Arg Gly Asn Met Tyr Tyr Glu Asn Ser Tyr Ala Leu Ala
                 85                  90                  95

Val Leu Ser Asn Tyr Asp Ala Asn Lys Thr Gly Leu Lys Glu Leu Pro
                100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
                180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
                260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
                340                 345                 350

Arg Gly Asp Ser Phe Thr His Thr Pro Pro Leu Asp Pro Gln Glu Leu
        355                 360                 365

Asp Ile Leu Lys Thr Val Lys Glu Ile Thr Gly Phe Leu Leu Ile Gln
370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
                420                 425                 430

Ser Asp Gly Asp Val Ile Ile Ser Gly Asn Lys Asn Leu Cys Tyr Ala
        435                 440                 445
```

```
Asn Thr Ile Asn Trp Lys Lys Leu Phe Gly Thr Gly Gln Lys Thr
450                 455                 460
Lys Ile Ile Ser Asn Arg Gly Glu Asn Ser Cys Lys Ala Thr Gly Gln
465                 470                 475                 480
Val Cys His Ala Leu Cys Ser Pro Glu Gly Cys Trp Gly Pro Glu Pro
                485                 490                 495
Arg Asp Cys Val Ser Cys Arg Asn Val Ser Arg Gly Arg Glu Cys Val
                500                 505                 510
Asp Lys Cys Asn Leu Leu Glu Gly Glu Pro Arg Glu Phe Val Glu Asn
                515                 520                 525
Ser Glu Cys Ile Gln Cys His Pro Glu Cys Leu Pro Gln Ala Met Asn
530                 535                 540
Ile Thr Cys Thr Gly Arg Gly Pro Asp Asn Cys Ile Gln Cys Ala His
545                 550                 555                 560
Tyr Ile Asp Gly Pro His Cys Val Lys Thr Cys Pro Ala Gly Val Met
                565                 570                 575
Gly Glu Asn Asn Thr Leu Val Trp Lys Tyr Ala Asp Ala Gly His Val
                580                 585                 590
Cys His Leu Cys His Pro Asn Cys Thr Tyr Gly Cys Thr Gly Pro Gly
                595                 600                 605
Leu Glu Gly Cys Pro Thr Asn Gly Pro Lys Ile Pro Ser Ile Ala Thr
                610                 615                 620
Gly Met Val Gly Ala Leu Leu Leu Leu Leu Val Ala Leu Gly Ile
625                 630                 635                 640
Gly Leu Phe Met Arg Arg Arg His Ile Val Arg Lys Arg Thr Leu Arg
                645                 650                 655
Arg Leu Leu Gln Glu Arg Glu Leu Val Glu Pro Leu Thr Pro Ser Gly
                660                 665                 670
Glu Ala Pro Asn Gln Ala Leu Leu Arg Ile Leu Lys Glu Thr Glu Phe
                675                 680                 685
Lys Lys Ile Lys Val Leu Gly Ser Gly Ala Phe Gly Thr Val Tyr Lys
690                 695                 700
Gly Leu Trp Ile Pro Glu Gly Glu Lys Val Lys Ile Pro Val Ala Ile
705                 710                 715                 720
Lys Glu Leu Arg Glu Ala Thr Ser Pro Lys Ala Asn Lys Glu Ile Leu
                725                 730                 735
Asp Glu Ala Tyr Val Met Ala Ser Val Asp Asn Pro His Val Cys Arg
                740                 745                 750
Leu Leu Gly Ile Cys Leu Thr Ser Thr Val Gln Leu Ile Thr Gln Leu
                755                 760                 765
Met Pro Phe Gly Cys Leu Leu Asp Tyr Val Arg Glu His Lys Asp Asn
770                 775                 780
Ile Gly Ser Gln Tyr Leu Leu Asn Trp Cys Val Gln Ile Ala Lys Gly
785                 790                 795                 800
Met Asn Tyr Leu Glu Asp Arg Arg Leu Val His Arg Asp Leu Ala Ala
                805                 810                 815
Arg Asn Val Leu Val Lys Thr Pro Gln His Val Lys Ile Thr Asp Phe
                820                 825                 830
Gly Leu Ala Lys Leu Leu Gly Ala Glu Glu Lys Glu Tyr His Ala Glu
                835                 840                 845
Gly Gly Lys Val Pro Ile Lys Trp Met Ala Leu Glu Ser Ile Leu His
                850                 855                 860
Arg Ile Tyr Thr His Gln Ser Asp Val Trp Ser Tyr Gly Val Thr Val
```

```
                865                 870                 875                 880
Trp Glu Leu Met Thr Phe Gly Ser Lys Pro Tyr Asp Gly Ile Pro Ala
                    885                 890                 895

Ser Glu Ile Ser Ser Ile Leu Glu Lys Gly Glu Arg Leu Pro Gln Pro
                900                 905                 910

Pro Ile Cys Thr Ile Asp Val Tyr Met Ile Met Val Lys Cys Trp Met
                915                 920                 925

Ile Asp Ala Asp Ser Arg Pro Lys Phe Arg Glu Leu Ile Ile Glu Phe
                930                 935                 940

Ser Lys Met Ala Arg Asp Pro Gln Arg Tyr Leu Val Ile Gln Gly Asp
945                 950                 955                 960

Glu Arg Met His Leu Pro Ser Pro Thr Asp Ser Asn Phe Tyr Arg Ala
                965                 970                 975

Leu Met Asp Glu Glu Asp Met Asp Asp Val Val Asp Ala Asp Glu Tyr
                980                 985                 990

Leu Ile Pro Gln Gln Gly Phe Phe Ser Ser Pro Ser Thr Ser Arg Thr
                995                 1000                1005

Pro Leu Leu Ser Ser Leu Ser Ala Thr Ser Asn Asn Ser Thr Val Ala
            1010                1015                1020

Cys Ile Asp Arg Asn Gly Leu Gln Ser Cys Pro Ile Lys Glu Asp Ser
1025                1030                1035                1040

Phe Leu Gln Arg Tyr Ser Ser Asp Pro Thr Gly Ala Leu Thr Glu Asp
                1045                1050                1055

Ser Ile Asp Asp Thr Phe Leu Pro Val Pro Glu Tyr Ile Asn Gln Ser
                1060                1065                1070

Val Pro Lys Arg Pro Ala Gly Ser Val Gln Asn Pro Val Tyr His Asn
                1075                1080                1085

Gln Pro Leu Asn Pro Ala Pro Ser Arg Asp Pro His Tyr Gln Asp Pro
                1090                1095                1100

His Ser Thr Ala Val Gly Asn Pro Glu Tyr Leu Asn Thr Val Gln Pro
1105                1110                1115                1120

Thr Cys Val Asn Ser Thr Phe Asp Ser Pro Ala His Trp Ala Gln Lys
                1125                1130                1135

Gly Ser His Gln Ile Ser Leu Asp Asn Pro Asp Tyr Gln Gln Asp Phe
                1140                1145                1150

Phe Pro Lys Glu Ala Lys Pro Asn Gly Ile Phe Lys Gly Ser Thr Ala
                1155                1160                1165

Glu Asn Ala Glu Tyr Leu Arg Val Ala Pro Gln Ser Ser Glu Phe Ile
                1170                1175                1180

Gly Ala
1185

<210> SEQ ID NO 2
<211> LENGTH: 1323
<212> TYPE: PRT
<213> ORGANISM: Homo sapiens
<220> FEATURE:
<223> OTHER INFORMATION: exemplary amino acid sequence of mature human
      ErbB3, corresponding to amino acids 20 to 1,342 of Genbank
      accession number NP_001973.2

<400> SEQUENCE: 2

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
                20                  25                  30
```

-continued

```
Leu Tyr Glu Arg Cys Glu Val Met Gly Asn Leu Glu Ile Val Leu
         35                  40                  45

Thr Gly His Asn Ala Asp Leu Ser Phe Leu Gln Trp Ile Arg Glu Val
 50                  55                  60

Thr Gly Tyr Val Leu Val Ala Met Asn Glu Phe Ser Thr Leu Pro Leu
 65                  70                  75                  80

Pro Asn Leu Arg Val Val Arg Gly Thr Gln Val Tyr Asp Gly Lys Phe
                 85                  90                  95

Ala Ile Phe Val Met Leu Asn Tyr Asn Thr Asn Ser Ser His Ala Leu
                100                 105                 110

Arg Gln Leu Arg Leu Thr Gln Leu Thr Glu Ile Leu Ser Gly Gly Val
                115                 120                 125

Tyr Ile Glu Lys Asn Asp Lys Leu Cys His Met Asp Thr Ile Asp Trp
        130                 135                 140

Arg Asp Ile Val Arg Asp Arg Asp Ala Glu Ile Val Val Lys Asp Asn
145                 150                 155                 160

Gly Arg Ser Cys Pro Pro Cys His Glu Val Cys Lys Gly Arg Cys Trp
                    165                 170                 175

Gly Pro Gly Ser Glu Asp Cys Gln Thr Leu Thr Lys Thr Ile Cys Ala
                180                 185                 190

Pro Gln Cys Asn Gly His Cys Phe Gly Pro Asn Pro Asn Gln Cys Cys
            195                 200                 205

His Asp Glu Cys Ala Gly Gly Cys Ser Gly Pro Gln Asp Thr Asp Cys
        210                 215                 220

Phe Ala Cys Arg His Phe Asn Asp Ser Gly Ala Cys Val Pro Arg Cys
225                 230                 235                 240

Pro Gln Pro Leu Val Tyr Asn Lys Leu Thr Phe Gln Leu Glu Pro Asn
                245                 250                 255

Pro His Thr Lys Tyr Gln Tyr Gly Gly Val Cys Val Ala Ser Cys Pro
                260                 265                 270

His Asn Phe Val Val Asp Gln Thr Ser Cys Val Arg Ala Cys Pro Pro
            275                 280                 285

Asp Lys Met Glu Val Asp Lys Asn Gly Leu Lys Met Cys Glu Pro Cys
    290                 295                 300

Gly Gly Leu Cys Pro Lys Ala Cys Glu Gly Thr Gly Ser Gly Ser Arg
305                 310                 315                 320

Phe Gln Thr Val Asp Ser Ser Asn Ile Asp Gly Phe Val Asn Cys Thr
                325                 330                 335

Lys Ile Leu Gly Asn Leu Asp Phe Leu Ile Thr Gly Leu Asn Gly Asp
                340                 345                 350

Pro Trp His Lys Ile Pro Ala Leu Asp Pro Glu Lys Leu Asn Val Phe
            355                 360                 365

Arg Thr Val Arg Glu Ile Thr Gly Tyr Leu Asn Ile Gln Ser Trp Pro
370                 375                 380

Pro His Met His Asn Phe Ser Val Phe Ser Asn Leu Thr Thr Ile Gly
385                 390                 395                 400

Gly Arg Ser Leu Tyr Asn Arg Gly Phe Ser Leu Leu Ile Met Lys Asn
                405                 410                 415

Leu Asn Val Thr Ser Leu Gly Phe Arg Ser Leu Lys Glu Ile Ser Ala
            420                 425                 430

Gly Arg Ile Tyr Ile Ser Ala Asn Arg Gln Leu Cys Tyr His His Ser
        435                 440                 445
```

```
Leu Asn Trp Thr Lys Val Leu Arg Gly Pro Thr Glu Arg Leu Asp
450                 455                 460

Ile Lys His Asn Arg Pro Arg Asp Cys Val Ala Glu Gly Lys Val
465                 470                 475                 480

Cys Asp Pro Leu Cys Ser Ser Gly Gly Cys Trp Gly Pro Gly Pro
                485                 490                 495

Gln Cys Leu Ser Cys Arg Asn Tyr Ser Arg Gly Gly Val Cys Val Thr
                500                 505                 510

His Cys Asn Phe Leu Asn Gly Glu Pro Arg Glu Phe Ala His Glu Ala
                515                 520                 525

Glu Cys Phe Ser Cys His Pro Glu Cys Gln Pro Met Glu Gly Thr Ala
530                 535                 540

Thr Cys Asn Gly Ser Gly Ser Asp Thr Cys Ala Gln Cys Ala His Phe
545                 550                 555                 560

Arg Asp Gly Pro His Cys Val Ser Ser Cys Pro His Gly Val Leu Gly
                565                 570                 575

Ala Lys Gly Pro Ile Tyr Lys Tyr Pro Asp Val Gln Asn Glu Cys Arg
                580                 585                 590

Pro Cys His Glu Asn Cys Thr Gln Gly Cys Lys Gly Pro Glu Leu Gln
                595                 600                 605

Asp Cys Leu Gly Gln Thr Leu Val Leu Ile Gly Lys Thr His Leu Thr
610                 615                 620

Met Ala Leu Thr Val Ile Ala Gly Leu Val Val Ile Phe Met Met Leu
625                 630                 635                 640

Gly Gly Thr Phe Leu Tyr Trp Arg Gly Arg Arg Ile Gln Asn Lys Arg
                645                 650                 655

Ala Met Arg Arg Tyr Leu Glu Arg Gly Glu Ser Ile Glu Pro Leu Asp
                660                 665                 670

Pro Ser Glu Lys Ala Asn Lys Val Leu Ala Arg Ile Phe Lys Glu Thr
                675                 680                 685

Glu Leu Arg Lys Leu Lys Val Leu Gly Ser Gly Val Phe Gly Thr Val
690                 695                 700

His Lys Gly Val Trp Ile Pro Glu Gly Glu Ser Ile Lys Ile Pro Val
705                 710                 715                 720

Cys Ile Lys Val Ile Glu Asp Lys Ser Gly Arg Gln Ser Phe Gln Ala
                725                 730                 735

Val Thr Asp His Met Leu Ala Ile Gly Ser Leu Asp His Ala His Ile
                740                 745                 750

Val Arg Leu Leu Gly Leu Cys Pro Gly Ser Ser Leu Gln Leu Val Thr
                755                 760                 765

Gln Tyr Leu Pro Leu Gly Ser Leu Leu Asp His Val Arg Gln His Arg
770                 775                 780

Gly Ala Leu Gly Pro Gln Leu Leu Leu Asn Trp Gly Val Gln Ile Ala
785                 790                 795                 800

Lys Gly Met Tyr Tyr Leu Glu Glu His Gly Met Val His Arg Asn Leu
                805                 810                 815

Ala Ala Arg Asn Val Leu Leu Lys Ser Pro Ser Gln Val Gln Val Ala
                820                 825                 830

Asp Phe Gly Val Ala Asp Leu Leu Pro Pro Asp Lys Gln Leu Leu
                835                 840                 845

Tyr Ser Glu Ala Lys Thr Pro Ile Lys Trp Met Ala Leu Glu Ser Ile
850                 855                 860

His Phe Gly Lys Tyr Thr His Gln Ser Asp Val Trp Ser Tyr Gly Val
```

-continued

```
                865                 870                 875                 880
            Thr Val Trp Glu Leu Met Thr Phe Gly Ala Glu Pro Tyr Ala Gly Leu
                            885                 890                 895

Arg Leu Ala Glu Val Pro Asp Leu Leu Glu Lys Gly Glu Arg Leu Ala
                            900                 905                 910

Gln Pro Gln Ile Cys Thr Ile Asp Val Tyr Met Val Met Val Lys Cys
                            915                 920                 925

Trp Met Ile Asp Glu Asn Ile Arg Pro Thr Phe Lys Glu Leu Ala Asn
                            930                 935                 940

Glu Phe Thr Arg Met Ala Arg Asp Pro Pro Arg Tyr Leu Val Ile Lys
            945                 950                 955                 960

Arg Glu Ser Gly Pro Gly Ile Ala Pro Gly Pro Glu Pro His Gly Leu
                            965                 970                 975

Thr Asn Lys Lys Leu Glu Glu Val Glu Leu Glu Pro Glu Leu Asp Leu
                            980                 985                 990

Asp Leu Asp Leu Glu Ala Glu Glu Asp Asn Leu Ala Thr Thr Thr Leu
                            995                 1000                1005

Gly Ser Ala Leu Ser Leu Pro Val Gly Thr Leu Asn Arg Pro Arg Gly
                            1010                1015                1020

Ser Gln Ser Leu Leu Ser Pro Ser Ser Gly Tyr Met Pro Met Asn Gln
            1025                1030                1035                1040

Gly Asn Leu Gly Glu Ser Cys Gln Glu Ser Ala Val Ser Gly Ser Ser
                            1045                1050                1055

Glu Arg Cys Pro Arg Pro Val Ser Leu His Pro Met Pro Arg Gly Cys
                            1060                1065                1070

Leu Ala Ser Glu Ser Ser Glu Gly His Val Thr Gly Ser Glu Ala Glu
                            1075                1080                1085

Leu Gln Glu Lys Val Ser Met Cys Arg Ser Arg Ser Arg Ser Arg Ser
                            1090                1095                1100

Pro Arg Pro Arg Gly Asp Ser Ala Tyr His Ser Gln Arg His Ser Leu
            1105                1110                1115                1120

Leu Thr Pro Val Thr Pro Leu Ser Pro Pro Gly Leu Glu Glu Glu Asp
                            1125                1130                1135

Val Asn Gly Tyr Val Met Pro Asp Thr His Leu Lys Gly Thr Pro Ser
                            1140                1145                1150

Ser Arg Glu Gly Thr Leu Ser Ser Val Gly Leu Ser Ser Val Leu Gly
                            1155                1160                1165

Thr Glu Glu Glu Asp Glu Asp Glu Glu Tyr Glu Tyr Met Asn Arg Arg
                            1170                1175                1180

Arg Arg His Ser Pro Pro His Pro Pro Arg Pro Ser Ser Leu Glu Glu
            1185                1190                1195                1200

Leu Gly Tyr Glu Tyr Met Asp Val Gly Ser Asp Leu Ser Ala Ser Leu
                            1205                1210                1215

Gly Ser Thr Gln Ser Cys Pro Leu His Pro Val Pro Ile Met Pro Thr
                            1220                1225                1230

Ala Gly Thr Thr Pro Asp Glu Asp Tyr Glu Tyr Met Asn Arg Gln Arg
                            1235                1240                1245

Asp Gly Gly Gly Pro Gly Gly Asp Tyr Ala Ala Met Gly Ala Cys Pro
            1250                1255                1260

Ala Ser Glu Gln Gly Tyr Glu Glu Met Arg Ala Phe Gln Gly Pro Gly
            1265                1270                1275                1280

His Gln Ala Pro His Val His Tyr Ala Arg Leu Lys Thr Leu Arg Ser
                            1285                1290                1295
```

-continued

```
Leu Glu Ala Thr Asp Ser Ala Phe Asp Asn Pro Asp Tyr Trp His Ser
            1300                1305                1310
Arg Leu Phe Pro Lys Ala Asn Ala Gln Arg Thr
        1315                1320
```

<210> SEQ ID NO 3
<211> LENGTH: 1283
<212> TYPE: PRT
<213> ORGANISM: Homo sapiens
<220> FEATURE:
<223> OTHER INFORMATION: exemplary amino acid sequence of mature human
      ErbB4 corresponding to amino acids 26 to 1,308 of Genbank
      accession number NP_005226.1

<400> SEQUENCE: 3

```
Gln Ser Val Cys Ala Gly Thr Glu Asn Lys Leu Ser Ser Leu Ser Asp
1               5                   10                  15
Leu Glu Gln Gln Tyr Arg Ala Leu Arg Lys Tyr Tyr Glu Asn Cys Glu
            20                  25                  30
Val Val Met Gly Asn Leu Glu Ile Thr Ser Ile Glu His Asn Arg Asp
        35                  40                  45
Leu Ser Phe Leu Arg Ser Val Arg Glu Val Thr Gly Tyr Val Leu Val
    50                  55                  60
Ala Leu Asn Gln Phe Arg Tyr Leu Pro Leu Glu Asn Leu Arg Ile Ile
65                  70                  75                  80
Arg Gly Thr Lys Leu Tyr Glu Asp Arg Tyr Ala Leu Ala Ile Phe Leu
                85                  90                  95
Asn Tyr Arg Lys Asp Gly Asn Phe Gly Leu Gln Glu Leu Gly Leu Lys
            100                 105                 110
Asn Leu Thr Glu Ile Leu Asn Gly Gly Val Tyr Val Asp Gln Asn Lys
        115                 120                 125
Phe Leu Cys Tyr Ala Asp Thr Ile His Trp Gln Asp Ile Val Arg Asn
    130                 135                 140
Pro Trp Pro Ser Asn Leu Thr Leu Val Ser Thr Asn Gly Ser Ser Gly
145                 150                 155                 160
Cys Gly Arg Cys His Lys Ser Cys Thr Gly Arg Cys Trp Gly Pro Thr
                165                 170                 175
Glu Asn His Cys Gln Thr Leu Thr Arg Thr Val Cys Ala Glu Gln Cys
            180                 185                 190
Asp Gly Arg Cys Tyr Gly Pro Tyr Val Ser Asp Cys Cys His Arg Glu
        195                 200                 205
Cys Ala Gly Gly Cys Ser Gly Pro Lys Asp Thr Asp Cys Phe Ala Cys
    210                 215                 220
Met Asn Phe Asn Asp Ser Gly Ala Cys Val Thr Gln Cys Pro Gln Thr
225                 230                 235                 240
Phe Val Tyr Asn Pro Thr Thr Phe Gln Leu Glu His Asn Phe Asn Ala
                245                 250                 255
Lys Tyr Thr Tyr Gly Ala Phe Cys Val Lys Lys Cys Pro His Asn Phe
            260                 265                 270
Val Val Asp Ser Ser Ser Cys Val Arg Ala Cys Pro Ser Ser Lys Met
        275                 280                 285
Glu Val Glu Glu Asn Gly Ile Lys Met Cys Lys Pro Cys Thr Asp Ile
    290                 295                 300
Cys Pro Lys Ala Cys Asp Gly Ile Gly Thr Gly Ser Leu Met Ser Ala
305                 310                 315                 320
```

```
Gln Thr Val Asp Ser Ser Asn Ile Asp Lys Phe Ile Asn Cys Thr Lys
                325                 330                 335

Ile Asn Gly Asn Leu Ile Phe Leu Val Thr Gly Ile His Gly Asp Pro
            340                 345                 350

Tyr Asn Ala Ile Glu Ala Ile Asp Pro Glu Lys Leu Asn Val Phe Arg
        355                 360                 365

Thr Val Arg Glu Ile Thr Gly Phe Leu Asn Ile Gln Ser Trp Pro Pro
    370                 375                 380

Asn Met Thr Asp Phe Ser Val Phe Ser Asn Leu Val Thr Ile Gly Gly
385                 390                 395                 400

Arg Val Leu Tyr Ser Gly Leu Ser Leu Leu Ile Leu Lys Gln Gln Gly
                405                 410                 415

Ile Thr Ser Leu Gln Phe Gln Ser Leu Lys Glu Ile Ser Ala Gly Asn
            420                 425                 430

Ile Tyr Ile Thr Asp Asn Ser Asn Leu Cys Tyr Tyr His Thr Ile Asn
        435                 440                 445

Trp Thr Thr Leu Phe Ser Thr Ile Asn Gln Arg Ile Val Ile Arg Asp
    450                 455                 460

Asn Arg Lys Ala Glu Asn Cys Thr Ala Glu Gly Met Val Cys Asn His
465                 470                 475                 480

Leu Cys Ser Ser Asp Gly Cys Trp Gly Pro Gly Pro Asp Gln Cys Leu
                485                 490                 495

Ser Cys Arg Arg Phe Ser Arg Gly Arg Ile Cys Ile Glu Ser Cys Asn
            500                 505                 510

Leu Tyr Asp Gly Glu Phe Arg Glu Phe Glu Asn Gly Ser Ile Cys Val
        515                 520                 525

Glu Cys Asp Pro Gln Cys Glu Lys Met Glu Asp Gly Leu Leu Thr Cys
    530                 535                 540

His Gly Pro Gly Pro Asp Asn Cys Thr Lys Cys Ser His Phe Lys Asp
545                 550                 555                 560

Gly Pro Asn Cys Val Glu Lys Cys Pro Asp Gly Leu Gln Gly Ala Asn
                565                 570                 575

Ser Phe Ile Phe Lys Tyr Ala Asp Pro Asp Arg Glu Cys His Pro Cys
            580                 585                 590

His Pro Asn Cys Thr Gln Gly Cys Asn Gly Pro Thr Ser His Asp Cys
        595                 600                 605

Ile Tyr Tyr Pro Trp Thr Gly His Ser Thr Leu Pro Gln His Ala Arg
    610                 615                 620

Thr Pro Leu Ile Ala Ala Gly Val Ile Gly Gly Leu Phe Ile Leu Val
625                 630                 635                 640

Ile Val Gly Leu Thr Phe Ala Val Tyr Val Arg Arg Lys Ser Ile Lys
                645                 650                 655

Lys Lys Arg Ala Leu Arg Arg Phe Leu Glu Thr Glu Leu Val Glu Pro
            660                 665                 670

Leu Thr Pro Ser Gly Thr Ala Pro Asn Gln Ala Gln Leu Arg Ile Leu
        675                 680                 685

Lys Glu Thr Glu Leu Lys Arg Val Lys Val Leu Gly Ser Gly Ala Phe
    690                 695                 700

Gly Thr Val Tyr Lys Gly Ile Trp Val Pro Glu Gly Glu Thr Val Lys
705                 710                 715                 720

Ile Pro Val Ala Ile Lys Ile Leu Asn Glu Thr Thr Gly Pro Lys Ala
                725                 730                 735

Asn Val Glu Phe Met Asp Glu Ala Leu Ile Met Ala Ser Met Asp His
```

-continued

```
                740                 745                 750
Pro His Leu Val Arg Leu Leu Gly Val Cys Leu Ser Pro Thr Ile Gln
            755                 760                 765
Leu Val Thr Gln Leu Met Pro His Gly Cys Leu Leu Glu Tyr Val His
            770                 775                 780
Glu His Lys Asp Asn Ile Gly Ser Gln Leu Leu Leu Asn Trp Cys Val
785                 790                 795                 800
Gln Ile Ala Lys Gly Met Met Tyr Leu Glu Glu Arg Arg Leu Val His
                805                 810                 815
Arg Asp Leu Ala Ala Arg Asn Val Leu Val Lys Ser Pro Asn His Val
            820                 825                 830
Lys Ile Thr Asp Phe Gly Leu Ala Arg Leu Leu Glu Gly Asp Glu Lys
            835                 840                 845
Glu Tyr Asn Ala Asp Gly Gly Lys Met Pro Ile Lys Trp Met Ala Leu
            850                 855                 860
Glu Cys Ile His Tyr Arg Lys Phe Thr His Gln Ser Asp Val Trp Ser
865                 870                 875                 880
Tyr Gly Val Thr Ile Trp Glu Leu Met Thr Phe Gly Gly Lys Pro Tyr
                885                 890                 895
Asp Gly Ile Pro Thr Arg Glu Ile Pro Asp Leu Leu Glu Lys Gly Glu
            900                 905                 910
Arg Leu Pro Gln Pro Pro Ile Cys Thr Ile Asp Val Tyr Met Val Met
            915                 920                 925
Val Lys Cys Trp Met Ile Asp Ala Asp Ser Arg Pro Lys Phe Lys Glu
            930                 935                 940
Leu Ala Ala Glu Phe Ser Arg Met Ala Arg Asp Pro Gln Arg Tyr Leu
945                 950                 955                 960
Val Ile Gln Gly Asp Asp Arg Met Lys Leu Pro Ser Pro Asn Asp Ser
                965                 970                 975
Lys Phe Phe Gln Asn Leu Leu Asp Glu Glu Asp Leu Glu Asp Met Met
                980                 985                 990
Asp Ala Glu Glu Tyr Leu Val Pro Gln Ala Phe Asn Ile Pro Pro Pro
            995                 1000                1005
Ile Tyr Thr Ser Arg Ala Arg Ile Asp Ser Asn Arg Ser Glu Ile Gly
            1010                1015                1020
His Ser Pro Pro Pro Ala Tyr Thr Pro Met Ser Gly Asn Gln Phe Val
1025                1030                1035                1040
Tyr Arg Asp Gly Gly Phe Ala Ala Glu Gln Gly Val Ser Val Pro Tyr
                1045                1050                1055
Arg Ala Pro Thr Ser Thr Ile Pro Glu Ala Pro Val Ala Gln Gly Ala
            1060                1065                1070
Thr Ala Glu Ile Phe Asp Asp Ser Cys Cys Asn Gly Thr Leu Arg Lys
            1075                1080                1085
Pro Val Ala Pro His Val Gln Glu Asp Ser Ser Thr Gln Arg Tyr Ser
            1090                1095                1100
Ala Asp Pro Thr Val Phe Ala Pro Glu Arg Ser Pro Arg Gly Glu Leu
1105                1110                1115                1120
Asp Glu Glu Gly Tyr Met Thr Pro Met Arg Asp Lys Pro Lys Gln Glu
                1125                1130                1135
Tyr Leu Asn Pro Val Glu Glu Asn Pro Phe Val Ser Arg Arg Lys Asn
                1140                1145                1150
Gly Asp Leu Gln Ala Leu Asp Asn Pro Glu Tyr His Asn Ala Ser Asn
            1155                1160                1165
```

-continued

```
Gly Pro Pro Lys Ala Glu Asp Glu Tyr Val Asn Glu Pro Leu Tyr Leu
    1170                1175                1180

Asn Thr Phe Ala Asn Thr Leu Gly Lys Ala Glu Tyr Leu Lys Asn Asn
        1185                1190                1195                1200

Ile Leu Ser Met Pro Glu Lys Ala Lys Lys Ala Phe Asp Asn Pro Asp
                1205                1210                1215

Tyr Trp Asn His Ser Leu Pro Pro Arg Ser Thr Leu Gln His Pro Asp
            1220                1225                1230

Tyr Leu Gln Glu Tyr Ser Thr Lys Tyr Phe Tyr Lys Gln Asn Gly Arg
        1235                1240                1245

Ile Arg Pro Ile Val Ala Glu Asn Pro Glu Tyr Leu Ser Glu Phe Ser
    1250                1255                1260

Leu Lys Pro Gly Thr Val Leu Pro Pro Pro Tyr Arg His Arg Asn
1265                1270                1275                1280

Thr Val Val

<210> SEQ ID NO 4
<211> LENGTH: 118
<212> TYPE: PRT
<213> ORGANISM: Homo sapiens
<220> FEATURE:
<223> OTHER INFORMATION: VH domain

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Tyr Met Gln Trp Val Arg Gln Ala Pro Gly Lys Gly Leu Glu Trp Val
        35                  40                  45

Ser Tyr Ile Gly Ser Ser Gly Gly Val Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Val Gly Leu Gly Asp Ala Phe Asp Ile Trp Gly Gln Gly Thr
        100                 105                 110

Met Val Thr Val Ser Ser
        115

<210> SEQ ID NO 5
<211> LENGTH: 110
<212> TYPE: PRT
<213> ORGANISM: Homo sapiens
<220> FEATURE:
<223> OTHER INFORMATION: VL domain

<400> SEQUENCE: 5

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Leu Asn
            20                  25                  30

Tyr Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60
```

```
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Pro
                 85                  90                  95

Pro Gly Glu Ala Phe Gly Gly Gly Thr Lys Leu Thr Val Leu
            100                 105                 110

<210> SEQ ID NO 6
<211> LENGTH: 5
<212> TYPE: PRT
<213> ORGANISM: Artificial Sequence
<220> FEATURE:
<223> OTHER INFORMATION: VH CDR1 according to Kabat system

<400> SEQUENCE: 6

Tyr Tyr Tyr Met Gln
 1               5

<210> SEQ ID NO 7
<211> LENGTH: 17
<212> TYPE: PRT
<213> ORGANISM: Artificial Sequence
<220> FEATURE:
<223> OTHER INFORMATION: VH CDR2 according to Kabat system

<400> SEQUENCE: 7

Tyr Ile Gly Ser Ser Gly Gly Val Thr Asn Tyr Ala Asp Ser Val Lys
 1               5                  10                  15

Gly

<210> SEQ ID NO 8
<211> LENGTH: 9
<212> TYPE: PRT
<213> ORGANISM: Artificial Sequence
<220> FEATURE:
<223> OTHER INFORMATION: VH CDR3 according to Kabat system

<400> SEQUENCE: 8

Val Gly Leu Gly Asp Ala Phe Asp Ile
 1               5

<210> SEQ ID NO 9
<211> LENGTH: 13
<212> TYPE: PRT
<213> ORGANISM: Artificial Sequence
<220> FEATURE:
<223> OTHER INFORMATION: VL CDR1 according to Kabat system

<400> SEQUENCE: 9

Ser Gly Ser Leu Ser Asn Ile Gly Leu Asn Tyr Val Ser
 1               5                  10

<210> SEQ ID NO 10
<211> LENGTH: 7
<212> TYPE: PRT
<213> ORGANISM: Artificial Sequence
<220> FEATURE:
<223> OTHER INFORMATION: VL CDR2 according to Kabat system

<400> SEQUENCE: 10

Arg Asn Asn Gln Arg Pro Ser
 1               5

<210> SEQ ID NO 11
```

```
<211> LENGTH: 11
<212> TYPE: PRT
<213> ORGANISM: Artificial Sequence
<220> FEATURE:
<223> OTHER INFORMATION: VL CDR3 according to Kabat system

<400> SEQUENCE: 11

Ala Ala Trp Asp Asp Ser Pro Pro Gly Glu Ala
1               5                   10

<210> SEQ ID NO 12
<211> LENGTH: 9
<212> TYPE: PRT
<213> ORGANISM: Artificial Sequence
<220> FEATURE:
<223> OTHER INFORMATION: VH CDR1 according to Chothia system

<400> SEQUENCE: 12

Gly Phe Thr Phe Ser Tyr Tyr Tyr Met
1               5

<210> SEQ ID NO 13
<211> LENGTH: 5
<212> TYPE: PRT
<213> ORGANISM: Artificial Sequence
<220> FEATURE:
<223> OTHER INFORMATION: VH CDR2 according to Chothia system

<400> SEQUENCE: 13

Gly Ser Ser Gly Gly
1               5

<210> SEQ ID NO 14
<211> LENGTH: 9
<212> TYPE: PRT
<213> ORGANISM: Artificial Sequence
<220> FEATURE:
<223> OTHER INFORMATION: VH CDR3 according to Chothia system

<400> SEQUENCE: 14

Val Gly Leu Gly Asp Ala Phe Asp Ile
1               5

<210> SEQ ID NO 15
<211> LENGTH: 13
<212> TYPE: PRT
<213> ORGANISM: Artificial Sequence
<220> FEATURE:
<223> OTHER INFORMATION: VL CDR1 according to Chothia system

<400> SEQUENCE: 15

Ser Gly Ser Leu Ser Asn Ile Gly Leu Asn Tyr Val Ser
1               5                   10

<210> SEQ ID NO 16
<211> LENGTH: 7
<212> TYPE: PRT
<213> ORGANISM: Artificial Sequence
<220> FEATURE:
<223> OTHER INFORMATION: VL CDR2 according to Chothia system

<400> SEQUENCE: 16

Arg Asn Asn Gln Arg Pro Ser
1               5

<210> SEQ ID NO 17
<211> LENGTH: 11
```

```
<212> TYPE: PRT
<213> ORGANISM: Artificial Sequence
<220> FEATURE:
<223> OTHER INFORMATION: VL CDR3 according to Chothia system

<400> SEQUENCE: 17

Ala Ala Trp Asp Asp Ser Pro Pro Gly Glu Ala
1               5                   10

<210> SEQ ID NO 18
<211> LENGTH: 8
<212> TYPE: PRT
<213> ORGANISM: Artificial Sequence
<220> FEATURE:
<223> OTHER INFORMATION: VH CDR1 according to IMGT system

<400> SEQUENCE: 18

Gly Phe Thr Phe Ser Tyr Tyr Tyr
1               5

<210> SEQ ID NO 19
<211> LENGTH: 8
<212> TYPE: PRT
<213> ORGANISM: Artificial Sequence
<220> FEATURE:
<223> OTHER INFORMATION: VH CDR2 according to IMGT system

<400> SEQUENCE: 19

Ile Gly Ser Ser Gly Gly Val Thr
1               5

<210> SEQ ID NO 20
<211> LENGTH: 11
<212> TYPE: PRT
<213> ORGANISM: Artificial Sequence
<220> FEATURE:
<223> OTHER INFORMATION: VH CDR3 according to IMGT system

<400> SEQUENCE: 20

Ala Arg Val Gly Leu Gly Asp Ala Phe Asp Ile
1               5                   10

<210> SEQ ID NO 21
<211> LENGTH: 8
<212> TYPE: PRT
<213> ORGANISM: Artificial Sequence
<220> FEATURE:
<223> OTHER INFORMATION: VL CDR2 according to IMGT system

<400> SEQUENCE: 21

Leu Ser Asn Ile Gly Leu Asn Tyr
1               5

<210> SEQ ID NO 22
<211> LENGTH: 3
<212> TYPE: PRT
<213> ORGANISM: Artificial Sequence
<220> FEATURE:
<223> OTHER INFORMATION: VL CDR3 according to IMGT system

<400> SEQUENCE: 22

Arg Asn Asn
1

<210> SEQ ID NO 23
<211> LENGTH: 11
<212> TYPE: PRT
```

```
<213> ORGANISM: Artificial Sequence
<220> FEATURE:
<223> OTHER INFORMATION: VL CDR3 according to IMGT system

<400> SEQUENCE: 23

Ala Ala Trp Asp Asp Ser Pro Pro Gly Glu Ala
1               5                   10

<210> SEQ ID NO 24
<211> LENGTH: 17
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 4
<223> OTHER INFORMATION: Xaa = Ser or Thr
<220> FEATURE:
<221> NAME/KEY: VARIANT
<222> LOCATION: 8
<223> OTHER INFORMATION: Xaa = Val, Gln, Thr, Ser or Asn

<400> SEQUENCE: 24

Tyr Ile Gly Xaa Ser Gly Gly Xaa Thr Asn Tyr Ala Asp Ser Val Lys
1               5                   10                  15

Gly

<210> SEQ ID NO 25
<211> LENGTH: 5
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 2
<223> OTHER INFORMATION: Xaa = Ser or Thr

<400> SEQUENCE: 25

Gly Xaa Ser Gly Gly
1               5

<210> SEQ ID NO 26
<211> LENGTH: 8
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 3
<223> OTHER INFORMATION: Xaa = Ser or Thr
<220> FEATURE:
<221> NAME/KEY: VARIANT
<222> LOCATION: 7
<223> OTHER INFORMATION: Xaa = Val, Gln, Thr, Ser or Asn

<400> SEQUENCE: 26

Ile Gly Xaa Ser Gly Gly Xaa Thr
1               5

<210> SEQ ID NO 27
<211> LENGTH: 9
<212> TYPE: PRT
<213> ORGANISM: Artificial Sequence
<220> FEATURE:
<223> OTHER INFORMATION: VH CDR3
<220> FEATURE:
<221> NAME/KEY: VARIANT
```

```
<222> LOCATION: 3
<223> OTHER INFORMATION: Xaa = Arg, Gln, Leu, Met, Ile, Trp or Tyr

<400> SEQUENCE: 27

Val Gly Xaa Gly Asp Ala Phe Asp Ile
1               5

<210> SEQ ID NO 28
<211> LENGTH: 9
<212> TYPE: PRT
<213> ORGANISM: Artificial Sequence
<220> FEATURE:
<223> OTHER INFORMATION: VH CDR3
<220> FEATURE:
<221> NAME/KEY: VARIANT
<222> LOCATION: 3
<223> OTHER INFORMATION: Xaa = Arg, Gln, Leu, Met, Ile, Trp or Tyr

<400> SEQUENCE: 28

Val Gly Xaa Gly Asp Ala Phe Asp Ile
1               5

<210> SEQ ID NO 29
<211> LENGTH: 11
<212> TYPE: PRT
<213> ORGANISM: Artificial Sequence
<220> FEATURE:
<223> OTHER INFORMATION: VH CDR3
<220> FEATURE:
<221> NAME/KEY: VARIANT
<222> LOCATION: 5
<223> OTHER INFORMATION: Xaa = Arg, Gln, Leu, Met, Ile, Trp or Tyr

<400> SEQUENCE: 29

Ala Arg Val Gly Xaa Gly Asp Ala Phe Asp Ile
1               5                   10

<210> SEQ ID NO 30
<211> LENGTH: 13
<212> TYPE: PRT
<213> ORGANISM: Artificial Sequence
<220> FEATURE:
<223> OTHER INFORMATION: VL CDR1
<220> FEATURE:
<221> NAME/KEY: VARIANT
<222> LOCATION: 1
<223> OTHER INFORMATION: Xaa = Ser, Asn, Asp, Glu, Gln, His, Arg or Lys
<220> FEATURE:
<221> NAME/KEY: VARIANT
<222> LOCATION: 3
<223> OTHER INFORMATION: Xaa = Ser, Asn, Thr, Asp, Arg, Lys, His, Phe or
    Tyr
<220> FEATURE:
<221> NAME/KEY: VARIANT
<222> LOCATION: 4
<223> OTHER INFORMATION: Xaa = Leu, Phe, Tyr, Met or Ile
<220> FEATURE:
<221> NAME/KEY: VARIANT
<222> LOCATION: 9
<223> OTHER INFORMATION: Xaa = Leu or Met

<400> SEQUENCE: 30

Xaa Gly Xaa Xaa Ser Asn Ile Gly Xaa Asn Tyr Val Ser
1               5                   10

<210> SEQ ID NO 31
<211> LENGTH: 13
<212> TYPE: PRT
<213> ORGANISM: Artificial Sequence
<220> FEATURE:
<223> OTHER INFORMATION: VL CDR1
```

```
<220> FEATURE:
<221> NAME/KEY: VARIANT
<222> LOCATION: 1
<223> OTHER INFORMATION: Xaa = Ser, Asn, Asp, Glu, Gln, His, Arg or Lys
<220> FEATURE:
<221> NAME/KEY: VARIANT
<222> LOCATION: 3
<223> OTHER INFORMATION: Xaa = Ser, Asn, Thr, Asp, Arg, Lys, His, Phe or
      Tyr
<220> FEATURE:
<221> NAME/KEY: VARIANT
<222> LOCATION: 4
<223> OTHER INFORMATION: Xaa = Leu, Phe, Tyr, Met or Ile
<220> FEATURE:
<221> NAME/KEY: VARIANT
<222> LOCATION: 9
<223> OTHER INFORMATION: Xaa = Leu or Met

<400> SEQUENCE: 31

Xaa Gly Xaa Xaa Ser Asn Ile Gly Xaa Asn Tyr Val Ser
1               5                   10

<210> SEQ ID NO 32
<211> LENGTH: 8
<212> TYPE: PRT
<213> ORGANISM: Artificial Sequence
<220> FEATURE:
<223> OTHER INFORMATION: VL CDR1
<220> FEATURE:
<221> NAME/KEY: VARIANT
<222> LOCATION: 1
<223> OTHER INFORMATION: Xaa = Leu, Phe, Tyr, Met or Ile
<220> FEATURE:
<221> NAME/KEY: VARIANT
<222> LOCATION: 6
<223> OTHER INFORMATION: Xaa = Leu or Met

<400> SEQUENCE: 32

Xaa Ser Asn Ile Gly Xaa Asn Tyr
1               5

<210> SEQ ID NO 33
<211> LENGTH: 11
<212> TYPE: PRT
<213> ORGANISM: Artificial Sequence
<220> FEATURE:
<223> OTHER INFORMATION: VL CDR3
<220> FEATURE:
<221> NAME/KEY: VARIANT
<222> LOCATION: 5
<223> OTHER INFORMATION: Xaa = Asp, Asn or His

<400> SEQUENCE: 33

Ala Ala Trp Asp Xaa Ser Pro Pro Gly Glu Ala
1               5                   10

<210> SEQ ID NO 34
<211> LENGTH: 11
<212> TYPE: PRT
<213> ORGANISM: Artificial Sequence
<220> FEATURE:
<223> OTHER INFORMATION: VL CDR3
<220> FEATURE:
<221> NAME/KEY: VARIANT
<222> LOCATION: 5
<223> OTHER INFORMATION: Xaa = Asp, Asn or His

<400> SEQUENCE: 34

Ala Ala Trp Asp Xaa Ser Pro Pro Gly Glu Ala
1               5                   10
```

```
<210> SEQ ID NO 35
<211> LENGTH: 11
<212> TYPE: PRT
<213> ORGANISM: Artificial Sequence
<220> FEATURE:
<223> OTHER INFORMATION: VL CDR3
<220> FEATURE:
<221> NAME/KEY: VARIANT
<222> LOCATION: 5
<223> OTHER INFORMATION: Xaa = Asp, Asn or His

<400> SEQUENCE: 35

Ala Ala Trp Asp Xaa Ser Pro Pro Gly Glu Ala
1               5                   10

<210> SEQ ID NO 36
<211> LENGTH: 13
<212> TYPE: PRT
<213> ORGANISM: Artificial Sequence
<220> FEATURE:
<223> OTHER INFORMATION: VL CDR1 defined by Kabat system
<220> FEATURE:
<221> NAME/KEY: VARIANT
<222> LOCATION: 1
<223> OTHER INFORMATION: Xaa = Arg, Asn, Asp, Glu, Gln or His

<400> SEQUENCE: 36

Xaa Gly Ser Leu Ser Asn Ile Gly Leu Asn Tyr Val Ser
1               5                   10

<210> SEQ ID NO 37
<211> LENGTH: 13
<212> TYPE: PRT
<213> ORGANISM: Artificial Sequence
<220> FEATURE:
<223> OTHER INFORMATION: VL CDR1 defined by Chothia system
<220> FEATURE:
<221> NAME/KEY: VARIANT
<222> LOCATION: 1
<223> OTHER INFORMATION: Xaa = Arg, Asn, Asp, Glu, Gln or His

<400> SEQUENCE: 37

Xaa Gly Ser Leu Ser Asn Ile Gly Leu Asn Tyr Val Ser
1               5                   10

<210> SEQ ID NO 38
<211> LENGTH: 13
<212> TYPE: PRT
<213> ORGANISM: Artificial Sequence
<220> FEATURE:
<223> OTHER INFORMATION: VL CDR1 defined by Kabat system
<220> FEATURE:
<221> NAME/KEY: VARIANT
<222> LOCATION: 3
<223> OTHER INFORMATION: Xaa = His, Asn, Thr, Asp, Arg, Leu, Phe or Tyr

<400> SEQUENCE: 38

Ser Gly Xaa Leu Ser Asn Ile Gly Leu Asn Tyr Val Ser
1               5                   10

<210> SEQ ID NO 39
<211> LENGTH: 13
<212> TYPE: PRT
<213> ORGANISM: Artificial Sequence
<220> FEATURE:
<223> OTHER INFORMATION: VL CDR1 defined by Chothia system
<220> FEATURE:
<221> NAME/KEY: VARIANT
<222> LOCATION: 3
<223> OTHER INFORMATION: Xaa = His, Asn, Thr, Asp, Arg, Leu, Phe or Tyr
```

```
<400> SEQUENCE: 39

Ser Gly Xaa Leu Ser Asn Ile Gly Leu Asn Tyr Val Ser
1               5                   10

<210> SEQ ID NO 40
<211> LENGTH: 13
<212> TYPE: PRT
<213> ORGANISM: Artificial Sequence
<220> FEATURE:
<223> OTHER INFORMATION: VL CDR1 defined by Kabat system
<220> FEATURE:
<221> NAME/KEY: VARIANT
<222> LOCATION: 4
<223> OTHER INFORMATION: Xaa = Ile, Met, Phe or Tyr

<400> SEQUENCE: 40

Ser Gly Ser Xaa Ser Asn Ile Gly Leu Asn Tyr Val Ser
1               5                   10

<210> SEQ ID NO 41
<211> LENGTH: 13
<212> TYPE: PRT
<213> ORGANISM: Artificial Sequence
<220> FEATURE:
<223> OTHER INFORMATION: VL CDR1 defined by Chothia system
<220> FEATURE:
<221> NAME/KEY: VARIANT
<222> LOCATION: 4
<223> OTHER INFORMATION: Xaa = Ile, Met, Phe or Tyr

<400> SEQUENCE: 41

Ser Gly Ser Xaa Ser Asn Ile Gly Leu Asn Tyr Val Ser
1               5                   10

<210> SEQ ID NO 42
<211> LENGTH: 8
<212> TYPE: PRT
<213> ORGANISM: Artificial Sequence
<220> FEATURE:
<223> OTHER INFORMATION: VL CDR1 defined by IMGT system
<220> FEATURE:
<221> NAME/KEY: VARIANT
<222> LOCATION: 1
<223> OTHER INFORMATION: Xaa = Ile, Met, Phe or Tyr

<400> SEQUENCE: 42

Xaa Ser Asn Ile Gly Leu Asn Tyr
1               5

<210> SEQ ID NO 43
<211> LENGTH: 13
<212> TYPE: PRT
<213> ORGANISM: Artificial Sequence
<220> FEATURE:
<223> OTHER INFORMATION: VL CDR1 defined by Kabat system
<220> FEATURE:
<221> NAME/KEY: VARIANT
<222> LOCATION: 1
<223> OTHER INFORMATION: Xaa = Arg, Asn, Glu, Gln, His or Lys
<220> FEATURE:
<221> NAME/KEY: VARIANT
<222> LOCATION: 3
<223> OTHER INFORMATION: Xaa = His, Asn, Thr, Asp, Arg, Leu, Phe or Tyr

<400> SEQUENCE: 43

Xaa Gly Xaa Leu Ser Asn Ile Gly Leu Asn Tyr Val Ser
1               5                   10

<210> SEQ ID NO 44
```

```
<211> LENGTH: 13
<212> TYPE: PRT
<213> ORGANISM: Artificial Sequence
<220> FEATURE:
<223> OTHER INFORMATION: VL CDR1 defined by Chothia system
<220> FEATURE:
<221> NAME/KEY: VARIANT
<222> LOCATION: 1
<223> OTHER INFORMATION: Xaa = Arg, Asn, Glu, Gln, His or Lys
<220> FEATURE:
<221> NAME/KEY: VARIANT
<222> LOCATION: 3
<223> OTHER INFORMATION: Xaa = His, Asn, Thr, Asp, Arg, Leu, Phe or Tyr

<400> SEQUENCE: 44

Xaa Gly Xaa Leu Ser Asn Ile Gly Leu Asn Tyr Val Ser
1               5                   10

<210> SEQ ID NO 45
<211> LENGTH: 17
<212> TYPE: PRT
<213> ORGANISM: Artificial Sequence
<220> FEATURE:
<223> OTHER INFORMATION: VH CDR2 defined by Kabat system
<220> FEATURE:
<221> NAME/KEY: VARIANT
<222> LOCATION: 15
<223> OTHER INFORMATION: Xaa = Gln, Thr, Ser or Asn

<400> SEQUENCE: 45

Tyr Ile Gly Ser Ser Gly Gly Val Thr Asn Tyr Ala Asp Ser Xaa Lys
1               5                   10                  15
Gly

<210> SEQ ID NO 46
<211> LENGTH: 13
<212> TYPE: PRT
<213> ORGANISM: Artificial Sequence
<220> FEATURE:
<223> OTHER INFORMATION: VL CDR1 defined by Kabat system
<220> FEATURE:
<221> NAME/KEY: VARIANT
<222> LOCATION: 1
<223> OTHER INFORMATION: Xaa = Arg, Asn, Glu, Gln, His or Lys

<400> SEQUENCE: 46

Xaa Gly Ser Leu Ser Asn Ile Gly Leu Asn Tyr Val Ser
1               5                   10

<210> SEQ ID NO 47
<211> LENGTH: 13
<212> TYPE: PRT
<213> ORGANISM: Artificial Sequence
<220> FEATURE:
<223> OTHER INFORMATION: VL CDR1 defined by Chothia system
<220> FEATURE:
<221> NAME/KEY: VARIANT
<222> LOCATION: 1
<223> OTHER INFORMATION: Xaa = Arg, Asn, Glu, Gln, His or Lys

<400> SEQUENCE: 47

Xaa Gly Ser Leu Ser Asn Ile Gly Leu Asn Tyr Val Ser
1               5                   10

<210> SEQ ID NO 48
<211> LENGTH: 13
<212> TYPE: PRT
<213> ORGANISM: Artificial Sequence
<220> FEATURE:
<223> OTHER INFORMATION: VL CDR1 defined by Kabat system
```

```
<220> FEATURE:
<221> NAME/KEY: VARIANT
<222> LOCATION: 1
<223> OTHER INFORMATION: Xaa = Arg, Asn, Glu, Gln, His or Lys
<220> FEATURE:
<221> NAME/KEY: VARIANT
<222> LOCATION: 4
<223> OTHER INFORMATION: Xaa = Ile, Met, Phe or Tyr

<400> SEQUENCE: 48

Xaa Gly Ser Xaa Ser Asn Ile Gly Leu Asn Tyr Val Ser
1               5                   10

<210> SEQ ID NO 49
<211> LENGTH: 13
<212> TYPE: PRT
<213> ORGANISM: Artificial Sequence
<220> FEATURE:
<223> OTHER INFORMATION: VL CDR1 defined by Chothia system
<220> FEATURE:
<221> NAME/KEY: VARIANT
<222> LOCATION: 1
<223> OTHER INFORMATION: Xaa = Arg, Asn, Glu, Gln, His or Lys
<220> FEATURE:
<221> NAME/KEY: VARIANT
<222> LOCATION: 4
<223> OTHER INFORMATION: Xaa = Ile, Met, Phe or Tyr

<400> SEQUENCE: 49

Xaa Gly Ser Xaa Ser Asn Ile Gly Leu Asn Tyr Val Ser
1               5                   10

<210> SEQ ID NO 50
<211> LENGTH: 13
<212> TYPE: PRT
<213> ORGANISM: Artificial Sequence
<220> FEATURE:
<223> OTHER INFORMATION: VL CDR1 defined by Kabat system
<220> FEATURE:
<221> NAME/KEY: VARIANT
<222> LOCATION: 3
<223> OTHER INFORMATION: Xaa = His, Asn, Thr, Asp, Arg, Leu, Phe or Tyr
<220> FEATURE:
<221> NAME/KEY: VARIANT
<222> LOCATION: 4
<223> OTHER INFORMATION: Xaa = Ile, Met, Phe or Tyr

<400> SEQUENCE: 50

Ser Gly Xaa Xaa Ser Asn Ile Gly Leu Asn Tyr Val Ser
1               5                   10

<210> SEQ ID NO 51
<211> LENGTH: 13
<212> TYPE: PRT
<213> ORGANISM: Artificial Sequence
<220> FEATURE:
<223> OTHER INFORMATION: VL CDR1 defined by Chothia system
<220> FEATURE:
<221> NAME/KEY: VARIANT
<222> LOCATION: 3
<223> OTHER INFORMATION: Xaa = His, Asn, Thr, Asp, Arg, Leu, Phe or Tyr
<220> FEATURE:
<221> NAME/KEY: VARIANT
<222> LOCATION: 4
<223> OTHER INFORMATION: Xaa = Ile, Met, Phe or Tyr

<400> SEQUENCE: 51

Ser Gly Xaa Xaa Ser Asn Ile Gly Leu Asn Tyr Val Ser
1               5                   10

<210> SEQ ID NO 52
```

```
<211> LENGTH: 13
<212> TYPE: PRT
<213> ORGANISM: Artificial Sequence
<220> FEATURE:
<223> OTHER INFORMATION: VL CDR1 defined by Kabat system
<220> FEATURE:
<221> NAME/KEY: VARIANT
<222> LOCATION: 1
<223> OTHER INFORMATION: Xaa = Arg, Asn, Glu, Gln, His or Lys
<220> FEATURE:
<221> NAME/KEY: VARIANT
<222> LOCATION: 3
<223> OTHER INFORMATION: Xaa = His, Asn, Thr, Asp, Arg, Leu, Phe or Tyr

<400> SEQUENCE: 52

Xaa Gly Xaa Leu Ser Asn Ile Gly Leu Asn Tyr Val Ser
1               5                   10

<210> SEQ ID NO 53
<211> LENGTH: 13
<212> TYPE: PRT
<213> ORGANISM: Artificial Sequence
<220> FEATURE:
<223> OTHER INFORMATION: VL CDR1 defined by Chothia system
<220> FEATURE:
<221> NAME/KEY: VARIANT
<222> LOCATION: 1
<223> OTHER INFORMATION: Xaa = Arg, Asn, Glu, Gln, His or Lys
<220> FEATURE:
<221> NAME/KEY: VARIANT
<222> LOCATION: 3
<223> OTHER INFORMATION: Xaa = His, Asn, Thr, Asp, Arg, Leu, Phe or Tyr

<400> SEQUENCE: 53

Xaa Gly Xaa Leu Ser Asn Ile Gly Leu Asn Tyr Val Ser
1               5                   10

<210> SEQ ID NO 54
<211> LENGTH: 13
<212> TYPE: PRT
<213> ORGANISM: Artificial Sequence
<220> FEATURE:
<223> OTHER INFORMATION: VL CDR1 defined by Kabat system
<220> FEATURE:
<221> NAME/KEY: VARIANT
<222> LOCATION: 1
<223> OTHER INFORMATION: Xaa = Arg, Asn, Glu, Gln, His or Lys
<220> FEATURE:
<221> NAME/KEY: VARIANT
<222> LOCATION: 3
<223> OTHER INFORMATION: Xaa = His, Asn, Thr, Asp, Arg, Leu, Phe or Tyr
<220> FEATURE:
<221> NAME/KEY: VARIANT
<222> LOCATION: 4
<223> OTHER INFORMATION: Xaa = Ile, Met, Phe or Tyr

<400> SEQUENCE: 54

Xaa Gly Xaa Xaa Ser Asn Ile Gly Leu Asn Tyr Val Ser
1               5                   10

<210> SEQ ID NO 55
<211> LENGTH: 13
<212> TYPE: PRT
<213> ORGANISM: Artificial Sequence
<220> FEATURE:
<223> OTHER INFORMATION: VL CDR1 defined by Chothia system
<220> FEATURE:
<221> NAME/KEY: VARIANT
<222> LOCATION: 1
<223> OTHER INFORMATION: Xaa = Arg, Asn, Glu, Gln, His or Lys
<220> FEATURE:
<221> NAME/KEY: VARIANT
<222> LOCATION: 3
```

```
<223> OTHER INFORMATION: Xaa = His, Asn, Thr, Asp, Arg, Leu, Phe or Tyr
<220> FEATURE:
<221> NAME/KEY: VARIANT
<222> LOCATION: 4
<223> OTHER INFORMATION: Xaa = Ile, Met, Phe or Tyr

<400> SEQUENCE: 55

Xaa Gly Xaa Xaa Ser Asn Ile Gly Leu Asn Tyr Val Ser
 1               5                  10

<210> SEQ ID NO 56
<211> LENGTH: 5
<212> TYPE: PRT
<213> ORGANISM: Artificial Sequence
<220> FEATURE:
<223> OTHER INFORMATION: VH CDR1
<220> FEATURE:
<221> NAME/KEY: VARIANT
<222> LOCATION: 1
<223> OTHER INFORMATION: Xaa = Tyr, Ser, Ala or Gly

<400> SEQUENCE: 56

Xaa Tyr Tyr Met Gln
 1               5

<210> SEQ ID NO 57
<211> LENGTH: 9
<212> TYPE: PRT
<213> ORGANISM: Artificial Sequence
<220> FEATURE:
<223> OTHER INFORMATION: VH CDR1
<220> FEATURE:
<221> NAME/KEY: VARIANT
<222> LOCATION: 6
<223> OTHER INFORMATION: Xaa = Tyr, Ser, Ala or Gly

<400> SEQUENCE: 57

Gly Phe Thr Phe Ser Xaa Tyr Tyr Met
 1               5

<210> SEQ ID NO 58
<211> LENGTH: 8
<212> TYPE: PRT
<213> ORGANISM: Artificial Sequence
<220> FEATURE:
<223> OTHER INFORMATION: VH CDR1
<220> FEATURE:
<221> NAME/KEY: VARIANT
<222> LOCATION: 6
<223> OTHER INFORMATION: Xaa = Tyr, Ser, Ala or Gly

<400> SEQUENCE: 58

Gly Phe Thr Phe Ser Xaa Tyr Tyr
 1               5

<210> SEQ ID NO 59
<211> LENGTH: 13
<212> TYPE: PRT
<213> ORGANISM: Artificial Sequence
<220> FEATURE:
<223> OTHER INFORMATION: VL CDR1
<220> FEATURE:
<221> NAME/KEY: VARIANT
<222> LOCATION: 9
<223> OTHER INFORMATION: Xaa = Leu, Ser, Als, Gly or Val

<400> SEQUENCE: 59

Ser Gly Ser Leu Ser Asn Ile Gly Xaa Asn Tyr Val Ser
 1               5                  10
```

```
<210> SEQ ID NO 60
<211> LENGTH: 13
<212> TYPE: PRT
<213> ORGANISM: Artificial Sequence
<220> FEATURE:
<223> OTHER INFORMATION: VL CDR1
<220> FEATURE:
<221> NAME/KEY: VARIANT
<222> LOCATION: 9
<223> OTHER INFORMATION: Xaa = Leu, Ser, Als, Gly or Val

<400> SEQUENCE: 60

Ser Gly Ser Leu Ser Asn Ile Gly Xaa Asn Tyr Val Ser
1               5                   10

<210> SEQ ID NO 61
<211> LENGTH: 8
<212> TYPE: PRT
<213> ORGANISM: Artificial Sequence
<220> FEATURE:
<223> OTHER INFORMATION: VL CDR1
<220> FEATURE:
<221> NAME/KEY: VARIANT
<222> LOCATION: 6
<223> OTHER INFORMATION: Xaa = Leu, Ser, Als, Gly or Val

<400> SEQUENCE: 61

Leu Ser Asn Ile Gly Xaa Asn Tyr
1               5

<210> SEQ ID NO 62
<211> LENGTH: 7
<212> TYPE: PRT
<213> ORGANISM: Artificial Sequence
<220> FEATURE:
<223> OTHER INFORMATION: VL CDR2
<220> FEATURE:
<221> NAME/KEY: VARIANT
<222> LOCATION: 1
<223> OTHER INFORMATION: Xaa = Arg, Phe, Tyr, His, Ala, Leu, Ile or Val

<400> SEQUENCE: 62

Xaa Asn Asn Gln Arg Pro Ser
1               5

<210> SEQ ID NO 63
<211> LENGTH: 7
<212> TYPE: PRT
<213> ORGANISM: Artificial Sequence
<220> FEATURE:
<223> OTHER INFORMATION: VL CDR2
<220> FEATURE:
<221> NAME/KEY: VARIANT
<222> LOCATION: 1
<223> OTHER INFORMATION: Xaa = Arg, Phe, Tyr, His, Ala, Leu, Ile or Val

<400> SEQUENCE: 63

Xaa Asn Asn Gln Arg Pro Ser
1               5

<210> SEQ ID NO 64
<211> LENGTH: 3
<212> TYPE: PRT
<213> ORGANISM: Artificial Sequence
<220> FEATURE:
<223> OTHER INFORMATION: VL CDR2
<220> FEATURE:
<221> NAME/KEY: VARIANT
<222> LOCATION: 1
<223> OTHER INFORMATION: Xaa = Arg, Phe, Tyr, His, Ala, Leu, Ile or Val
```

-continued

<400> SEQUENCE: 64

Xaa Asn Asn
1

<210> SEQ ID NO 65
<211> LENGTH: 5
<212> TYPE: PRT
<213> ORGANISM: Artificial Sequence
<220> FEATURE:
<223> OTHER INFORMATION: VH CDR1 defined by Kabat system
<220> FEATURE:
<221> NAME/KEY: VARIANT
<222> LOCATION: 1
<223> OTHER INFORMATION: Xaa = Ser, Ala or Gly

<400> SEQUENCE: 65

Xaa Tyr Tyr Met Gln
1               5

<210> SEQ ID NO 66
<211> LENGTH: 9
<212> TYPE: PRT
<213> ORGANISM: Artificial Sequence
<220> FEATURE:
<223> OTHER INFORMATION: VH CDR1 defined by Chothia system
<220> FEATURE:
<221> NAME/KEY: VARIANT
<222> LOCATION: 6
<223> OTHER INFORMATION: Xaa = Ser, Ala or Gly

<400> SEQUENCE: 66

Gly Phe Thr Phe Ser Xaa Tyr Tyr Met
1               5

<210> SEQ ID NO 67
<211> LENGTH: 8
<212> TYPE: PRT
<213> ORGANISM: Artificial Sequence
<220> FEATURE:
<223> OTHER INFORMATION: VH CDR1 defined by IMGT system
<220> FEATURE:
<221> NAME/KEY: VARIANT
<222> LOCATION: 6
<223> OTHER INFORMATION: Xaa = Ser, Ala or Gly

<400> SEQUENCE: 67

Gly Phe Thr Phe Ser Xaa Tyr Tyr
1               5

<210> SEQ ID NO 68
<211> LENGTH: 13
<212> TYPE: PRT
<213> ORGANISM: Artificial Sequence
<220> FEATURE:
<223> OTHER INFORMATION: VL CDR1 defined by Kabat system
<220> FEATURE:
<221> NAME/KEY: VARIANT
<222> LOCATION: 9
<223> OTHER INFORMATION: Xaa = Ser, Ala, Gly or Val

<400> SEQUENCE: 68

Ser Gly Ser Leu Ser Asn Ile Gly Xaa Asn Tyr Val Ser
1               5                   10

<210> SEQ ID NO 69
<211> LENGTH: 13
<212> TYPE: PRT
<213> ORGANISM: Artificial Sequence

```
<220> FEATURE:
<223> OTHER INFORMATION: VL CDR1 defined by Chothia system
<220> FEATURE:
<221> NAME/KEY: VARIANT
<222> LOCATION: 9
<223> OTHER INFORMATION: Xaa = Ser, Ala, Gly or Val

<400> SEQUENCE: 69

Ser Gly Ser Leu Ser Asn Ile Gly Xaa Asn Tyr Val Ser
1               5                   10

<210> SEQ ID NO 70
<211> LENGTH: 8
<212> TYPE: PRT
<213> ORGANISM: Artificial Sequence
<220> FEATURE:
<223> OTHER INFORMATION: VL CDR1 defined by IMGT system
<220> FEATURE:
<221> NAME/KEY: VARIANT
<222> LOCATION: 6
<223> OTHER INFORMATION: Xaa = Ser, Ala, Gly or Val

<400> SEQUENCE: 70

Leu Ser Asn Ile Gly Xaa Asn Tyr
1               5

<210> SEQ ID NO 71
<211> LENGTH: 7
<212> TYPE: PRT
<213> ORGANISM: Artificial Sequence
<220> FEATURE:
<223> OTHER INFORMATION: VL CDR2 defined by Kabat system
<220> FEATURE:
<221> NAME/KEY: VARIANT
<222> LOCATION: 1
<223> OTHER INFORMATION: Xaa = Phe, Tyr, His, Ala, Leu, Ile or Val

<400> SEQUENCE: 71

Xaa Asn Asn Gln Arg Pro Ser
1               5

<210> SEQ ID NO 72
<211> LENGTH: 7
<212> TYPE: PRT
<213> ORGANISM: Artificial Sequence
<220> FEATURE:
<223> OTHER INFORMATION: VL CDR2 defined by Chothia system
<220> FEATURE:
<221> NAME/KEY: VARIANT
<222> LOCATION: 1
<223> OTHER INFORMATION: Xaa = Phe, Tyr, His, Ala, Leu, Ile or Val

<400> SEQUENCE: 72

Xaa Asn Asn Gln Arg Pro Ser
1               5

<210> SEQ ID NO 73
<211> LENGTH: 3
<212> TYPE: PRT
<213> ORGANISM: Artificial Sequence
<220> FEATURE:
<223> OTHER INFORMATION: VL CDR2 defined by IMGT system
<220> FEATURE:
<221> NAME/KEY: VARIANT
<222> LOCATION: 1
<223> OTHER INFORMATION: Xaa = Phe, Tyr, His, Ala, Leu, Ile or Val

<400> SEQUENCE: 73

Xaa Asn Asn
1
```

<210> SEQ ID NO 74
<211> LENGTH: 13
<212> TYPE: PRT
<213> ORGANISM: Artificial Sequence
<220> FEATURE:
<223> OTHER INFORMATION: VL CDR1 defined by Kabat system
<220> FEATURE:
<221> NAME/KEY: VARIANT
<222> LOCATION: 11
<223> OTHER INFORMATION: Xaa = Tyr, Phe, Ile, Val, Leu or Ala

<400> SEQUENCE: 74

Ser Gly Ser Leu Ser Asn Ile Gly Leu Asn Xaa Val Ser
1               5                   10

<210> SEQ ID NO 75
<211> LENGTH: 13
<212> TYPE: PRT
<213> ORGANISM: Artificial Sequence
<220> FEATURE:
<223> OTHER INFORMATION: VL CDR1 defined by Chothia system
<220> FEATURE:
<221> NAME/KEY: VARIANT
<222> LOCATION: 11
<223> OTHER INFORMATION: Xaa = Tyr, Phe, Ile, Val, Leu or Ala

<400> SEQUENCE: 75

Ser Gly Ser Leu Ser Asn Ile Gly Leu Asn Xaa Val Ser
1               5                   10

<210> SEQ ID NO 76
<211> LENGTH: 8
<212> TYPE: PRT
<213> ORGANISM: Artificial Sequence
<220> FEATURE:
<223> OTHER INFORMATION: VL CDR1 defined by IMGT system
<220> FEATURE:
<221> NAME/KEY: VARIANT
<222> LOCATION: 8
<223> OTHER INFORMATION: Xaa = Tyr, Phe, Ile, Val, Leu or Ala

<400> SEQUENCE: 76

Leu Ser Asn Ile Gly Leu Asn Xaa
1               5

<210> SEQ ID NO 77
<211> LENGTH: 22
<212> TYPE: PRT
<213> ORGANISM: Artificial Sequence
<220> FEATURE:
<223> OTHER INFORMATION: VL FR1 defined by Kabat system

<400> SEQUENCE: 77

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 78
<211> LENGTH: 15
<212> TYPE: PRT
<213> ORGANISM: Artificial Sequence
<220> FEATURE:
<223> OTHER INFORMATION: VL FR2 defined by Kabat system

<400> SEQUENCE: 78

Trp Tyr Gln Gln Leu Pro Gly Thr Ala Pro Lys Leu Leu Ile Ser

<210> SEQ ID NO 79
<211> LENGTH: 32
<212> TYPE: PRT
<213> ORGANISM: Artificial Sequence
<220> FEATURE:
<223> OTHER INFORMATION: VL FR3 defined by Kabat system
<220> FEATURE:
<221> NAME/KEY: VARIANT
<222> LOCATION: 13
<223> OTHER INFORMATION: Xaa = Thr, Asn or Tyr
<220> FEATURE:
<221> NAME/KEY: VARIANT
<222> LOCATION: 14
<223> OTHER INFORMATION: Xaa = Ser, Asn, His, Tyr, Lys or Arg

<400> SEQUENCE: 79

Gly Val Pro Asp Arg Phe Ser Gly Ser Lys Ser Gly Xaa Xaa Ala Ser
1               5                   10                  15

Leu Ala Ile Ser Gly Leu Arg Ser Glu Asp Glu Ala Asp Tyr Tyr Cys
            20                  25                  30

<210> SEQ ID NO 80
<211> LENGTH: 21
<212> TYPE: PRT
<213> ORGANISM: Artificial Sequence
<220> FEATURE:
<223> OTHER INFORMATION: VL FR4 defined by Kabat system

<400> SEQUENCE: 80

Phe Gly Gly Gly Thr Lys Leu Thr Val Leu Gly Gln Pro Lys Ala Ala
1               5                   10                  15

Pro Ser Val Thr Leu
            20

<210> SEQ ID NO 81
<211> LENGTH: 30
<212> TYPE: PRT
<213> ORGANISM: Artificial Sequence
<220> FEATURE:
<223> OTHER INFORMATION: VH FR1 defined by Kabat system

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 82
<211> LENGTH: 14
<212> TYPE: PRT
<213> ORGANISM: Artificial Sequence
<220> FEATURE:
<223> OTHER INFORMATION: VH FR2 defined by Kabat system

<400> SEQUENCE: 82

Trp Val Arg Gln Ala Pro Gly Lys Gly Leu Glu Trp Val Ser
1               5                   10

<210> SEQ ID NO 83
<211> LENGTH: 32
<212> TYPE: PRT
<213> ORGANISM: Artificial Sequence
<220> FEATURE:
<223> OTHER INFORMATION: VH FR3 defined by Kabat system

```
<400> SEQUENCE: 83

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 84
<211> LENGTH: 11
<212> TYPE: PRT
<213> ORGANISM: Artificial Sequence
<220> FEATURE:
<223> OTHER INFORMATION: VH FR4 defined by Kabat system

<400> SEQUENCE: 84

Trp Gly Gln Gly Thr Met Val Thr Val Ser Ser
1               5                   10

<210> SEQ ID NO 85
<211> LENGTH: 22
<212> TYPE: PRT
<213> ORGANISM: Artificial Sequence
<220> FEATURE:
<223> OTHER INFORMATION: VL FR1 defined by Chothia system

<400> SEQUENCE: 85

Gln Ser Val Leu Thr Gln Pro Pro Ser Ala Ser Gly Thr Pro Gly Gln
1               5                   10                  15

Arg Val Thr Ile Ser Cys
                20

<210> SEQ ID NO 86
<211> LENGTH: 15
<212> TYPE: PRT
<213> ORGANISM: Artificial Sequence
<220> FEATURE:
<223> OTHER INFORMATION: VL FR2 defined by Chothia system

<400> SEQUENCE: 86

Trp Tyr Gln Gln Leu Pro Gly Thr Ala Pro Lys Leu Leu Ile Ser
1               5                   10                  15

<210> SEQ ID NO 87
<211> LENGTH: 32
<212> TYPE: PRT
<213> ORGANISM: Artificial Sequence
<220> FEATURE:
<223> OTHER INFORMATION: VL FR3 defined by Chothia system
<220> FEATURE:
<221> NAME/KEY: VARIANT
<222> LOCATION: 13
<223> OTHER INFORMATION: Xaa = Thr, Asn or Tyr
<220> FEATURE:
<221> NAME/KEY: VARIANT
<222> LOCATION: 14
<223> OTHER INFORMATION: Xaa = Ser, Asn, His, Tyr, Lys or Arg

<400> SEQUENCE: 87

Gly Val Pro Asp Arg Phe Ser Gly Ser Lys Ser Gly Xaa Xaa Ala Ser
1               5                   10                  15

Leu Ala Ile Ser Gly Leu Arg Ser Glu Asp Glu Ala Asp Tyr Tyr Cys
                20                  25                  30

<210> SEQ ID NO 88
<211> LENGTH: 9
<212> TYPE: PRT
<213> ORGANISM: Artificial Sequence
```

```
<220> FEATURE:
<223> OTHER INFORMATION: VL FR4 defined by Chothia system

<400> SEQUENCE: 88

Phe Gly Gly Gly Thr Lys Leu Thr Val
1               5

<210> SEQ ID NO 89
<211> LENGTH: 25
<212> TYPE: PRT
<213> ORGANISM: Artificial Sequence
<220> FEATURE:
<223> OTHER INFORMATION: VH FR1 defined by Chothia system

<400> SEQUENCE: 89

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 90
<211> LENGTH: 17
<212> TYPE: PRT
<213> ORGANISM: Artificial Sequence
<220> FEATURE:
<223> OTHER INFORMATION: VH FR2 defined by Chothia system

<400> SEQUENCE: 90

Gln Trp Val Arg Gln Ala Pro Gly Lys Gly Leu Glu Trp Val Ser Tyr
1               5                   10                  15

Ile

<210> SEQ ID NO 91
<211> LENGTH: 42
<212> TYPE: PRT
<213> ORGANISM: Artificial Sequence
<220> FEATURE:
<223> OTHER INFORMATION: VH FR3 defined by Chothia system
<220> FEATURE:
<221> NAME/KEY: VARIANT
<222> LOCATION: 8
<223> OTHER INFORMATION: Xaa = Val, Gln, Thr, Ser or Asn

<400> SEQUENCE: 91

Val Thr Asn Tyr Ala Asp Ser Xaa Lys Gly Arg Phe Thr Ile Ser Arg
1               5                   10                  15

Asp Asn Ser Lys Asn Thr Leu Tyr Leu Gln Met Asn Ser Leu Arg Ala
            20                  25                  30

Glu Asp Thr Ala Val Tyr Tyr Cys Ala Arg
        35                  40

<210> SEQ ID NO 92
<211> LENGTH: 11
<212> TYPE: PRT
<213> ORGANISM: Artificial Sequence
<220> FEATURE:
<223> OTHER INFORMATION: VH FR4 defined by Chothia system

<400> SEQUENCE: 92

Trp Gly Gln Gly Thr Met Val Thr Val Ser Ser
1               5                   10

<210> SEQ ID NO 93
<211> LENGTH: 25
<212> TYPE: PRT
```

```
<213> ORGANISM: Artificial Sequence
<220> FEATURE:
<223> OTHER INFORMATION: VL FR1 defined by IMGT system
<220> FEATURE:
<221> NAME/KEY: VARIANT
<222> LOCATION: 23
<223> OTHER INFORMATION: Xaa = Ser, Arg, Asn, Asp, Glu or Gln
<220> FEATURE:
<221> NAME/KEY: VARIANT
<222> LOCATION: 25
<223> OTHER INFORMATION: Xaa = Ser, His, Asn, Thr, Asp, Arg, Leu, Phe or
      Tyr

<400> SEQUENCE: 93

Gln Ser Val Leu Thr Gln Pro Pro Ser Ala Ser Gly Thr Pro Gly Gln
1               5                   10                  15

Arg Val Thr Ile Ser Cys Xaa Gly Xaa
            20                  25

<210> SEQ ID NO 94
<211> LENGTH: 17
<212> TYPE: PRT
<213> ORGANISM: Artificial Sequence
<220> FEATURE:
<223> OTHER INFORMATION: VL FR2 defined by IMGT system

<400> SEQUENCE: 94

Val Ser Trp Tyr Gln Gln Leu Pro Gly Thr Ala Pro Lys Leu Leu Ile
1               5                   10                  15

Ser

<210> SEQ ID NO 95
<211> LENGTH: 36
<212> TYPE: PRT
<213> ORGANISM: Artificial Sequence
<220> FEATURE:
<223> OTHER INFORMATION: VL FR3 defined by IMGT system
<220> FEATURE:
<221> NAME/KEY: VARIANT
<222> LOCATION: 17
<223> OTHER INFORMATION: Xaa = Thr, Asn or Tyr
<220> FEATURE:
<221> NAME/KEY: VARIANT
<222> LOCATION: 18
<223> OTHER INFORMATION: Xaa = Ser, Asn, His, Tyr, Lys or Arg

<400> SEQUENCE: 95

Gln Arg Pro Ser Gly Val Pro Asp Arg Phe Ser Gly Ser Lys Ser Gly
1               5                   10                  15

Xaa Xaa Ala Ser Leu Ala Ile Ser Gly Leu Arg Ser Glu Asp Glu Ala
            20                  25                  30

Asp Tyr Tyr Cys
        35

<210> SEQ ID NO 96
<211> LENGTH: 10
<212> TYPE: PRT
<213> ORGANISM: Artificial Sequence
<220> FEATURE:
<223> OTHER INFORMATION: VL FR4 defined by IMGT system

<400> SEQUENCE: 96

Phe Gly Gly Gly Thr Lys Leu Thr Val Leu
1               5                   10

<210> SEQ ID NO 97
<211> LENGTH: 25
```

```
<212> TYPE: PRT
<213> ORGANISM: Artificial Sequence
<220> FEATURE:
<223> OTHER INFORMATION: VH FR1 defined by IMGT system

<400> SEQUENCE: 97

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 98
<211> LENGTH: 17
<212> TYPE: PRT
<213> ORGANISM: Artificial Sequence
<220> FEATURE:
<223> OTHER INFORMATION: VH FR2 defined by IMGT system

<400> SEQUENCE: 98

Met Gln Trp Val Arg Gln Ala Pro Gly Lys Gly Leu Glu Trp Val Ser
1               5                   10                  15

Tyr

<210> SEQ ID NO 99
<211> LENGTH: 38
<212> TYPE: PRT
<213> ORGANISM: Artificial Sequence
<220> FEATURE:
<223> OTHER INFORMATION: VH FR3 defined by IMGT system
<220> FEATURE:
<221> NAME/KEY: VARIANT
<222> LOCATION: 6
<223> OTHER INFORMATION: Xaa = Val, Gln, Thr, Ser or Asn

<400> SEQUENCE: 99

Asn Tyr Ala Asp Ser Xaa Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 100
<211> LENGTH: 11
<212> TYPE: PRT
<213> ORGANISM: Artificial Sequence
<220> FEATURE:
<223> OTHER INFORMATION: VH FR4 defined by IMGT system

<400> SEQUENCE: 100

Trp Gly Gln Gly Thr Met Val Thr Val Ser Ser
1               5                   10

<210> SEQ ID NO 101
<211> LENGTH: 110
<212> TYPE: PRT
<213> ORGANISM: Artificial Sequence
<220> FEATURE:
<223> OTHER INFORMATION: VL domain
<220> FEATURE:
<221> NAME/KEY: VARIANT
<222> LOCATION: 23
<223> OTHER INFORMATION: Xaa = Arg, Asn, Asp, Glu, Gln or His

<400> SEQUENCE: 101

Gln Ser Val Leu Thr Gln Pro Pro Ser Ala Ser Gly Thr Pro Gly Gln
```

```
                1               5                   10                  15
            Arg Val Thr Ile Ser Cys Xaa Gly Ser Leu Ser Asn Ile Gly Leu Asn
                            20                  25                  30

Tyr Val Ser Trp Tyr Gln Gln Leu Pro Gly Thr Ala Pro Lys Leu Leu
                            35                  40                  45

Ile Ser Arg Asn Asn Gln Arg Pro Ser Gly Val Pro Asp Arg Phe Ser
                            50                  55                  60

Gly Ser Lys Ser Gly Thr Ser Ala Ser Leu Ala Ile Ser Gly Leu Arg
            65                  70                  75                  80

Ser Glu Asp Glu Ala Asp Tyr Tyr Cys Ala Ala Trp Asp Asp Ser Pro
                            85                  90                  95

Pro Gly Glu Ala Phe Gly Gly Gly Thr Lys Leu Thr Val Leu
                            100                 105                 110

<210> SEQ ID NO 102
<211> LENGTH: 110
<212> TYPE: PRT
<213> ORGANISM: Artificial Sequence
<220> FEATURE:
<223> OTHER INFORMATION: VL domain
<220> FEATURE:
<221> NAME/KEY: VARIANT
<222> LOCATION: 25
<223> OTHER INFORMATION: Xaa = His, Asn, Thr, Asp, Arg, Leu, Phe or Tyr

<400> SEQUENCE: 102

Gln Ser Val Leu Thr Gln Pro Pro Ser Ala Ser Gly Thr Pro Gly Gln
            1               5                   10                  15

Arg Val Thr Ile Ser Cys Ser Gly Xaa Leu Ser Asn Ile Gly Leu Asn
                            20                  25                  30

Tyr Val Ser Trp Tyr Gln Gln Leu Pro Gly Thr Ala Pro Lys Leu Leu
                            35                  40                  45

Ile Ser Arg Asn Asn Gln Arg Pro Ser Gly Val Pro Asp Arg Phe Ser
                            50                  55                  60

Gly Ser Lys Ser Gly Thr Ser Ala Ser Leu Ala Ile Ser Gly Leu Arg
            65                  70                  75                  80

Ser Glu Asp Glu Ala Asp Tyr Tyr Cys Ala Ala Trp Asp Asp Ser Pro
                            85                  90                  95

Pro Gly Glu Ala Phe Gly Gly Gly Thr Lys Leu Thr Val Leu
                            100                 105                 110

<210> SEQ ID NO 103
<211> LENGTH: 118
<212> TYPE: PRT
<213> ORGANISM: Artificial Sequence
<220> FEATURE:
<223> OTHER INFORMATION: VH domain
<220> FEATURE:
<221> NAME/KEY: VARIANT
<222> LOCATION: 64
<223> OTHER INFORMATION: Xaa = Gln, Thr, Ser or Asn

<400> SEQUENCE: 103

Glu Val Gln Leu Leu Glu Ser Gly Gly Gly Leu Val Gln Pro Gly Gly
            1               5                   10                  15

Ser Leu Arg Leu Ser Cys Ala Ala Ser Gly Phe Thr Phe Ser Tyr Tyr
                            20                  25                  30

Tyr Met Gln Trp Val Arg Gln Ala Pro Gly Lys Gly Leu Glu Trp Val
                            35                  40                  45

Ser Tyr Ile Gly Ser Ser Gly Gly Val Thr Asn Tyr Ala Asp Ser Xaa
```

```
                    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Gly Leu Gly Asp Ala Phe Asp Ile Trp Gly Gln Gly Thr
            100                 105                 110

Met Val Thr Val Ser Ser
            115

<210> SEQ ID NO 104
<211> LENGTH: 110
<212> TYPE: PRT
<213> ORGANISM: Artificial Sequence
<220> FEATURE:
<223> OTHER INFORMATION: VL domain
<220> FEATURE:
<221> NAME/KEY: VARIANT
<222> LOCATION: 26
<223> OTHER INFORMATION: Xaa = Ile, Met, Phe or Tyr

<400> SEQUENCE: 104

Gln Ser Val Leu Thr Gln Pro Pro Ser Ala Ser Gly Thr Pro Gly Gln
 1               5                  10                  15

Arg Val Thr Ile Ser Cys Ser Gly Ser Xaa Ser Asn Ile Gly Leu Asn
                 20                  25                  30

Tyr Val Ser Trp Tyr Gln Gln Leu Pro Gly Thr Ala Pro Lys Leu Leu
             35                  40                  45

Ile Ser Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Pro
                 85                  90                  95

Pro Gly Glu Ala Phe Gly Gly Gly Thr Lys Leu Thr Val Leu
            100                 105                 110

<210> SEQ ID NO 105
<211> LENGTH: 110
<212> TYPE: PRT
<213> ORGANISM: Artificial Sequence
<220> FEATURE:
<223> OTHER INFORMATION: VL domain
<220> FEATURE:
<221> NAME/KEY: VARIANT
<222> LOCATION: 23
<223> OTHER INFORMATION: Xaa = Arg, Asn, Glu, Gln, His or Lys
<220> FEATURE:
<221> NAME/KEY: VARIANT
<222> LOCATION: 25
<223> OTHER INFORMATION: Xaa = His, Asn, Thr, Asp, Arg, Leu, Phe or Tyr

<400> SEQUENCE: 105

Gln Ser Val Leu Thr Gln Pro Pro Ser Ala Ser Gly Thr Pro Gly Gln
 1               5                  10                  15

Arg Val Thr Ile Ser Cys Xaa Gly Xaa Leu Ser Asn Ile Gly Leu Asn
                 20                  25                  30

Tyr Val Ser Trp Tyr Gln Gln Leu Pro Gly Thr Ala Pro Lys Leu Leu
             35                  40                  45

Ile Ser Arg Asn Asn Gln Arg Pro Ser Gly Val Pro Asp Arg Phe Ser
 50                  55                  60
```

```
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Pro
                 85                  90                  95

Pro Gly Glu Ala Phe Gly Gly Gly Thr Lys Leu Thr Val Leu
            100                 105                 110

<210> SEQ ID NO 106
<211> LENGTH: 110
<212> TYPE: PRT
<213> ORGANISM: Artificial Sequence
<220> FEATURE:
<223> OTHER INFORMATION: VL domain
<220> FEATURE:
<221> NAME/KEY: VARIANT
<222> LOCATION: 23
<223> OTHER INFORMATION: Xaa = Arg, Asn, Glu, Gln, His or Lys

<400> SEQUENCE: 106

Gln Ser Val Leu Thr Gln Pro Pro Ser Ala Ser Gly Thr Pro Gly Gln
 1               5                  10                  15

Arg Val Thr Ile Ser Cys Xaa Gly Ser Leu Ser Asn Ile Gly Leu Asn
                 20                  25                  30

Tyr Val Ser Trp Tyr Gln Gln Leu Pro Gly Thr Ala Pro Lys Leu Leu
             35                  40                  45

Ile Ser Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Pro
                 85                  90                  95

Pro Gly Glu Ala Phe Gly Gly Gly Thr Lys Leu Thr Val Leu
            100                 105                 110

<210> SEQ ID NO 107
<211> LENGTH: 110
<212> TYPE: PRT
<213> ORGANISM: Artificial Sequence
<220> FEATURE:
<223> OTHER INFORMATION: VL domain
<220> FEATURE:
<221> NAME/KEY: VARIANT
<222> LOCATION: 23
<223> OTHER INFORMATION: Xaa = Arg, Asn, Glu, Gln, His or Lys
<220> FEATURE:
<221> NAME/KEY: VARIANT
<222> LOCATION: 26
<223> OTHER INFORMATION: Xaa = Ile, Met, Phe or Tyr

<400> SEQUENCE: 107

Gln Ser Val Leu Thr Gln Pro Pro Ser Ala Ser Gly Thr Pro Gly Gln
 1               5                  10                  15

Arg Val Thr Ile Ser Cys Xaa Gly Ser Xaa Ser Asn Ile Gly Leu Asn
                 20                  25                  30

Tyr Val Ser Trp Tyr Gln Gln Leu Pro Gly Thr Ala Pro Lys Leu Leu
             35                  40                  45

Ile Ser Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Pro
                 85                  90                  95
```

Pro Gly Glu Ala Phe Gly Gly Gly Thr Lys Leu Thr Val Leu
            100                 105                 110

<210> SEQ ID NO 108
<211> LENGTH: 110
<212> TYPE: PRT
<213> ORGANISM: Artificial Sequence
<220> FEATURE:
<223> OTHER INFORMATION: VL domain
<220> FEATURE:
<221> NAME/KEY: VARIANT
<222> LOCATION: 25
<223> OTHER INFORMATION: Xaa = His, Asn, Thr, Asp, Arg, Leu, Phe or Tyr
<220> FEATURE:
<221> NAME/KEY: VARIANT
<222> LOCATION: 26
<223> OTHER INFORMATION: Xaa = Ile, Met, Phe or Tyr

<400> SEQUENCE: 108

Gln Ser Val Leu Thr Gln Pro Pro Ser Ala Ser Gly Thr Pro Gly Gln
1               5                   10                  15

Arg Val Thr Ile Ser Cys Ser Gly Xaa Xaa Ser Asn Ile Gly Leu Asn
            20                  25                  30

Tyr Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Pro
                85                  90                  95

Pro Gly Glu Ala Phe Gly Gly Gly Thr Lys Leu Thr Val Leu
            100                 105                 110

<210> SEQ ID NO 109
<211> LENGTH: 110
<212> TYPE: PRT
<213> ORGANISM: Artificial Sequence
<220> FEATURE:
<223> OTHER INFORMATION: VL domain
<220> FEATURE:
<221> NAME/KEY: VARIANT
<222> LOCATION: 23
<223> OTHER INFORMATION: Xaa = Arg, Asn, Asp, Glu, Gln, His or Lys
<220> FEATURE:
<221> NAME/KEY: VARIANT
<222> LOCATION: 25
<223> OTHER INFORMATION: Xaa = His, Asn, Thr, Asp, Arg, Leu, Phe or Tyr

<400> SEQUENCE: 109

Gln Ser Val Leu Thr Gln Pro Pro Ser Ala Ser Gly Thr Pro Gly Gln
1               5                   10                  15

Arg Val Thr Ile Ser Cys Xaa Gly Xaa Leu Ser Asn Ile Gly Leu Asn
            20                  25                  30

Tyr Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Pro
                85                  90                  95

```
Pro Gly Glu Ala Phe Gly Gly Gly Thr Lys Leu Thr Val Leu
            100                 105                 110
```

<210> SEQ ID NO 110
<211> LENGTH: 110
<212> TYPE: PRT
<213> ORGANISM: Artificial Sequence
<220> FEATURE:
<223> OTHER INFORMATION: VL domain
<220> FEATURE:
<221> NAME/KEY: VARIANT
<222> LOCATION: 23
<223> OTHER INFORMATION: Xaa = Arg, Asn, Asp, Glu, Gln, His or Lys
<220> FEATURE:
<221> NAME/KEY: VARIANT
<222> LOCATION: 25
<223> OTHER INFORMATION: Xaa = His, Asn, Thr, Asp, Arg, Leu, Phe or Tyr
<220> FEATURE:
<221> NAME/KEY: VARIANT
<222> LOCATION: 26
<223> OTHER INFORMATION: Xaa = Ile, Met, Phe or Tyr

<400> SEQUENCE: 110

```
Gln Ser Val Leu Thr Gln Pro Pro Ser Ala Ser Gly Thr Pro Gly Gln
1               5                   10                  15

Arg Val Thr Ile Ser Cys Xaa Gly Xaa Xaa Ser Asn Ile Gly Leu Asn
            20                  25                  30

Tyr Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Pro
                85                  90                  95

Pro Gly Glu Ala Phe Gly Gly Gly Thr Lys Leu Thr Val Leu
            100                 105                 110
```

<210> SEQ ID NO 111
<211> LENGTH: 118
<212> TYPE: PRT
<213> ORGANISM: Artificial Sequence
<220> FEATURE:
<223> OTHER INFORMATION: VH domain
<220> FEATURE:
<221> NAME/KEY: VARIANT
<222> LOCATION: 31
<223> OTHER INFORMATION: Xaa = Ser, Ala or Gly

<400> SEQUENCE: 111

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Tyr
            20                  25                  30

Tyr Met Gln Trp Val Arg Gln Ala Pro Gly Lys Gly Leu Glu Trp Val
        35                  40                  45

Ser Tyr Ile Gly Ser Ser Gly Gly Val Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Gly Asp Ala Phe Asp Ile Trp Gly Gln Gly Thr
```

```
                    100                 105                 110

Met Val Thr Val Ser Ser
            115

<210> SEQ ID NO 112
<211> LENGTH: 110
<212> TYPE: PRT
<213> ORGANISM: Artificial Sequence
<220> FEATURE:
<223> OTHER INFORMATION: VL domain
<220> FEATURE:
<221> NAME/KEY: VARIANT
<222> LOCATION: 70
<223> OTHER INFORMATION: Xaa = Asn, His, Tyr, Lys or Arg
<220> FEATURE:
<221> NAME/KEY: VARIANT
<222> LOCATION: 71
<223> OTHER INFORMATION: Xaa = Asn or Tyr

<400> SEQUENCE: 112

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Leu Asn
            20                  25                  30

Tyr Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Xaa Xaa Ala Ser Leu Ala Ile Ser Gly Leu Arg
65                  70                  75                  80

Ser Glu Asp Glu Ala Asp Tyr Tyr Cys Ala Ala Trp Asp Asp Ser Pro
                85                  90                  95

Pro Gly Glu Ala Phe Gly Gly Gly Thr Lys Leu Thr Val Leu
            100                 105                 110

<210> SEQ ID NO 113
<211> LENGTH: 110
<212> TYPE: PRT
<213> ORGANISM: Artificial Sequence
<220> FEATURE:
<223> OTHER INFORMATION: VL domain
<220> FEATURE:
<221> NAME/KEY: VARIANT
<222> LOCATION: 51
<223> OTHER INFORMATION: Xaa = Phe, Tyr, His, Ala, Leu, Ile or Val

<400> SEQUENCE: 113

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Leu Asn
            20                  25                  30

Tyr Val Ser Trp Tyr Gln Gln Leu Pro Gly Thr Ala Pro Lys Leu Leu
        35                  40                  45

Ile Ser Xaa Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Pro
                85                  90                  95

Pro Gly Glu Ala Phe Gly Gly Gly Thr Lys Leu Thr Val Leu
            100                 105                 110
```

```
<210> SEQ ID NO 114
<211> LENGTH: 110
<212> TYPE: PRT
<213> ORGANISM: Artificial Sequence
<220> FEATURE:
<223> OTHER INFORMATION: VL domain
<220> FEATURE:
<221> NAME/KEY: VARIANT
<222> LOCATION: 31
<223> OTHER INFORMATION: Xaa = Ser, Ala, Gly or Val
<220> FEATURE:
<221> NAME/KEY: VARIANT
<222> LOCATION: 51
<223> OTHER INFORMATION: Xaa = Phe, Tyr, His, Ala, Leu, Ile or Val

<400> SEQUENCE: 114

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Xaa Asn
            20                  25                  30

Tyr Val Ser Trp Tyr Gln Gln Leu Pro Gly Thr Ala Pro Lys Leu Leu
        35                  40                  45

Ile Ser Xaa Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Pro
                85                  90                  95

Pro Gly Glu Ala Phe Gly Gly Gly Thr Lys Leu Thr Val Leu
            100                 105                 110

<210> SEQ ID NO 115
<211> LENGTH: 110
<212> TYPE: PRT
<213> ORGANISM: Artificial Sequence
<220> FEATURE:
<223> OTHER INFORMATION: VL domain
<220> FEATURE:
<221> NAME/KEY: VARIANT
<222> LOCATION: 31
<223> OTHER INFORMATION: Xaa = Ser, Ala, Gly or Val

<400> SEQUENCE: 115

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Xaa Asn
            20                  25                  30

Tyr Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Pro
                85                  90                  95

Pro Gly Glu Ala Phe Gly Gly Gly Thr Lys Leu Thr Val Leu
            100                 105                 110

<210> SEQ ID NO 116
<211> LENGTH: 118
<212> TYPE: PRT
<213> ORGANISM: Artificial Sequence
```

-continued

```
<220> FEATURE:
<223> OTHER INFORMATION: VH domain
<220> FEATURE:
<221> NAME/KEY: VARIANT
<222> LOCATION: 31
<223> OTHER INFORMATION: Xaa = Ser, Ala, Gly or Val

<400> SEQUENCE: 116

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Tyr
            20                  25                  30

Tyr Met Gln Trp Val Arg Gln Ala Pro Gly Lys Gly Leu Glu Trp Val
        35                  40                  45

Ser Tyr Ile Gly Ser Ser Gly Gly Val Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Gly Asp Ala Phe Asp Ile Trp Gly Gln Gly Thr
            100                 105                 110

Met Val Thr Val Ser Ser
        115

<210> SEQ ID NO 117
<211> LENGTH: 110
<212> TYPE: PRT
<213> ORGANISM: Artificial Sequence
<220> FEATURE:
<223> OTHER INFORMATION: VL domain
<220> FEATURE:
<221> NAME/KEY: VARIANT
<222> LOCATION: 33
<223> OTHER INFORMATION: Xaa = Tyr, Phe, Ile, Val, Leu or Ala

<400> SEQUENCE: 117

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Leu Asn
            20                  25                  30

Xaa Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Pro
                85                  90                  95

Pro Gly Glu Ala Phe Gly Gly Gly Thr Lys Leu Thr Val Leu
            100                 105                 110

<210> SEQ ID NO 118
<211> LENGTH: 110
<212> TYPE: PRT
<213> ORGANISM: Artificial Sequence
<220> FEATURE:
<223> OTHER INFORMATION: VL region
<220> FEATURE:
<221> NAME/KEY: VARIANT
<222> LOCATION: 70
<223> OTHER INFORMATION: Xaa = Thr, Asn or Tyr
```

```
<220> FEATURE:
<221> NAME/KEY: VARIANT
<222> LOCATION: 71
<223> OTHER INFORMATION: Xaa = Ser, Asn, His, Tyr, Lys or Arg

<400> SEQUENCE: 118

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Leu Asn
            20                  25                  30

Tyr Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Xaa Xaa Ala Ser Leu Ala Ile Ser Gly Leu Arg
65                  70                  75                  80

Ser Glu Asp Glu Ala Asp Tyr Tyr Cys Ala Ala Trp Asp Asp Ser Pro
                85                  90                  95

Pro Gly Glu Ala Phe Gly Gly Gly Thr Lys Leu Thr Val Leu
            100                 105                 110

<210> SEQ ID NO 119
<211> LENGTH: 645
<212> TYPE: PRT
<213> ORGANISM: Homo sapiens
<220> FEATURE:
<223> OTHER INFORMATION: human neuregulin-1-beta1

<400> SEQUENCE: 119

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
        195                 200                 205

Leu Cys Lys Cys Pro Asn Glu Phe Thr Gly Asp Arg Cys Gln Asn Tyr
    210                 215                 220
```

```
Val Met Ala Ser Phe Tyr Lys His Leu Gly Ile Glu Phe Met Glu Ala
225                 230                 235                 240

Glu Glu Leu Tyr Gln Lys Arg Val Leu Thr Ile Thr Gly Ile Cys Ile
                245                 250                 255

Ala Leu Leu Val Val Gly Ile Met Cys Val Val Ala Tyr Cys Lys Thr
            260                 265                 270

Lys Lys Gln Arg Lys Lys Leu His Asp Arg Leu Arg Gln Ser Leu Arg
        275                 280                 285

Ser Glu Arg Asn Asn Met Met Asn Ile Ala Asn Gly Pro His His Pro
    290                 295                 300

Asn Pro Pro Glu Asn Val Gln Leu Val Asn Gln Tyr Val Ser Lys
305                 310                 315                 320

Asn Val Ile Ser Ser Glu His Ile Val Glu Arg Glu Ala Glu Thr Ser
                325                 330                 335

Phe Ser Thr Ser His Tyr Thr Ser Thr Ala His His Ser Thr Thr Val
            340                 345                 350

Thr Gln Thr Pro Ser His Ser Trp Ser Asn Gly His Thr Glu Ser Ile
        355                 360                 365

Leu Ser Glu Ser His Ser Val Ile Val Met Ser Ser Val Glu Asn Ser
370                 375                 380

Arg His Ser Ser Pro Thr Gly Gly Pro Arg Gly Arg Leu Asn Gly Thr
385                 390                 395                 400

Gly Gly Pro Arg Glu Cys Asn Ser Phe Leu Arg His Ala Arg Glu Thr
                405                 410                 415

Pro Asp Ser Tyr Arg Asp Ser Pro His Ser Glu Arg Tyr Val Ser Ala
            420                 425                 430

Met Thr Thr Pro Ala Arg Met Ser Pro Val Asp Phe His Thr Pro Ser
        435                 440                 445

Ser Pro Lys Ser Pro Pro Ser Glu Met Ser Pro Val Ser Ser Met
    450                 455                 460

Thr Val Ser Met Pro Ser Met Ala Val Ser Pro Phe Met Glu Glu Glu
465                 470                 475                 480

Arg Pro Leu Leu Leu Val Thr Pro Pro Arg Leu Arg Glu Lys Lys Phe
                485                 490                 495

Asp His His Pro Gln Gln Phe Ser Ser Phe His His Asn Pro Ala His
            500                 505                 510

Asp Ser Asn Ser Leu Pro Ala Ser Pro Leu Arg Ile Val Glu Asp Glu
        515                 520                 525

Glu Tyr Glu Thr Thr Gln Glu Tyr Glu Pro Ala Gln Glu Pro Val Lys
    530                 535                 540

Lys Leu Ala Asn Ser Arg Arg Ala Lys Arg Thr Lys Pro Asn Gly His
545                 550                 555                 560

Ile Ala Asn Arg Leu Glu Val Asp Ser Asn Thr Ser Ser Gln Ser Ser
                565                 570                 575

Asn Ser Glu Ser Glu Thr Glu Asp Glu Arg Val Gly Glu Asp Thr Pro
            580                 585                 590

Phe Leu Gly Ile Gln Asn Pro Leu Ala Ala Ser Leu Glu Ala Thr Pro
        595                 600                 605

Ala Phe Arg Leu Ala Asp Ser Arg Thr Asn Pro Ala Gly Arg Phe Ser
    610                 615                 620

Thr Gln Glu Glu Ile Gln Ala Arg Leu Ser Ser Val Ile Ala Asn Gln
625                 630                 635                 640
```

Asp Pro Ile Ala Val
                645